(12) United States Patent
Kobayashi et al.

(10) Patent No.: US 9,150,575 B2
(45) Date of Patent: Oct. 6, 2015

(54) PIPERIDINYLPYRAZOLOPYRIDINE DERIVATIVE

(71) Applicant: Daiichi Sankyo Company, Limited, Chuo-ku, Tokyo (JP)

(72) Inventors: Hideki Kobayashi, Toshima-ku (JP); Nobuyuki Ohkawa, Saitama (JP); Daisuke Takano, Minato-ku (JP); Hideki Kubota, Shinagawa-ku (JP); Toshio Onoda, Yokohama (JP); Toshio Kaneko, Yokohama (JP); Masami Arai, Naka-gun (JP); Naoki Terasaka, Saitama (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 14/566,460

(22) Filed: Dec. 10, 2014

(65) Prior Publication Data

US 2015/0152102 A1 Jun. 4, 2015

Related U.S. Application Data

(63) Continuation of application No. PCT/JP2013/066306, filed on Jun. 13, 2013.

(30) Foreign Application Priority Data

Jun. 14, 2012 (JP) .................... 2012-134431

(51) Int. Cl.
*C07D 401/14* (2006.01)
*A61K 31/437* (2006.01)
*C07D 471/04* (2006.01)

(52) U.S. Cl.
CPC .................... *C07D 471/04* (2013.01)

(58) Field of Classification Search
CPC ............... C07D 401/14; A61K 31/437
USPC .......................... 546/119; 514/303
See application file for complete search history.

(56) References Cited

FOREIGN PATENT DOCUMENTS

| WO | 2008/002591 A2 | 1/2008 |
| WO | 2012/028243 A1 | 3/2012 |
| WO | 2012028243 | * 3/2012 |

OTHER PUBLICATIONS

Badimon, J.J., et al., "Regression of Atherosclerotic Lesions by High Density Lipoprotein Plasma Fraction in the Cholesterol-Fed Rabbit," Journal of Clinical Investigation 85(4):1234-1241, Apr. 1990.
Balicki, R., "Studies in the Field of Nitrogen Heterocyclic Compounds. Part XI. Abnormal Cyclocondensation of Ethyl 4,4,4-Trifluoroacetoacetate With Aminopyrazoles," Polish Journal of Chemistry 57:789-797, 1983.

International Preliminary Report on Patentability mailed Dec. 16, 2014, issued in corresponding International Application No. PCT/JP2013/066306, filed Jun. 13, 2013, 6 pages.
International Search Report mailed Sep. 10, 2013, issued in corresponding International Application No. PCT/JP2013/066306, filed Jun. 13, 2013, 3 pages.
Iwata, A., et al., "Antiatherogenic Effects of Newly Developed Apolipoprotein A-I Mimetic Peptide/Phospholipid Complexes Against Aortic Plaque Burden in Watanabe-Heritable Hyperlipidemic Rabbits," Atherosclerosis 218(2):300-307, Oct. 2011.
Matsuura, F., et al., "HDL From CETP-Deficient Subjects Shows Enhanced Ability to Promote Cholesterol Efflux From Macrophages in an apoE- and ABCG1-Dependent Pathway," Journal of Clinical Investigation 116(5):1435-1442, May 2006.
Ross, R., "Cell Biology of Atherosclerosis," Annual Review of Physiology 57:791-804, 1995.
Steinberg, D., "Low Density Lipoprotein Oxidation and Its Pathobiological Significance," Journal of Biological Chemistry 272(34):20963-20966, Aug. 1997.
Yvan-Charvet, L., et al., "Inhibition of Cholesteryl Ester Transfer Protein by Torcetrapib Modestly Increases Macrophage Cholesterol Efflux to HDL," Arteriosclerosis, Thrombosis, and Vascular Biology 27(5):1132-1138, May 2007.

* cited by examiner

*Primary Examiner* — Niloofar Rahmani
(74) *Attorney, Agent, or Firm* — Christensen O'Connor Johnson Kindness PLLC

(57) ABSTRACT

A compound represented by the general formula (I) or a pharmacologically acceptable salt thereof has an excellent LCAT-activating effect and is useful as an active ingredient in a therapeutic or prophylactic agent for arteriosclerosis, arteriosclerotic heart disease, coronary heart disease (including heart failure, myocardial infarction, angina pectoris, cardiac ischemia, cardiovascular disturbance, and restenosis caused by angiogenesis), cerebrovascular disease (including stroke and cerebral infarction), peripheral vascular disease (including diabetic vascular complications), dyslipidemia, hypo-HDL-cholesterolemia, or renal disease, particularly, an anti-arteriosclerotic agent, wherein R is an optionally substituted aryl group or an optionally substituted heteroaryl group.

[Formula 1]

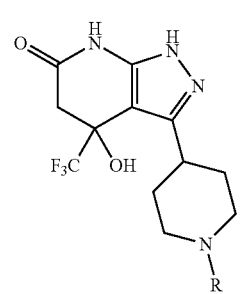

12 Claims, 1 Drawing Sheet

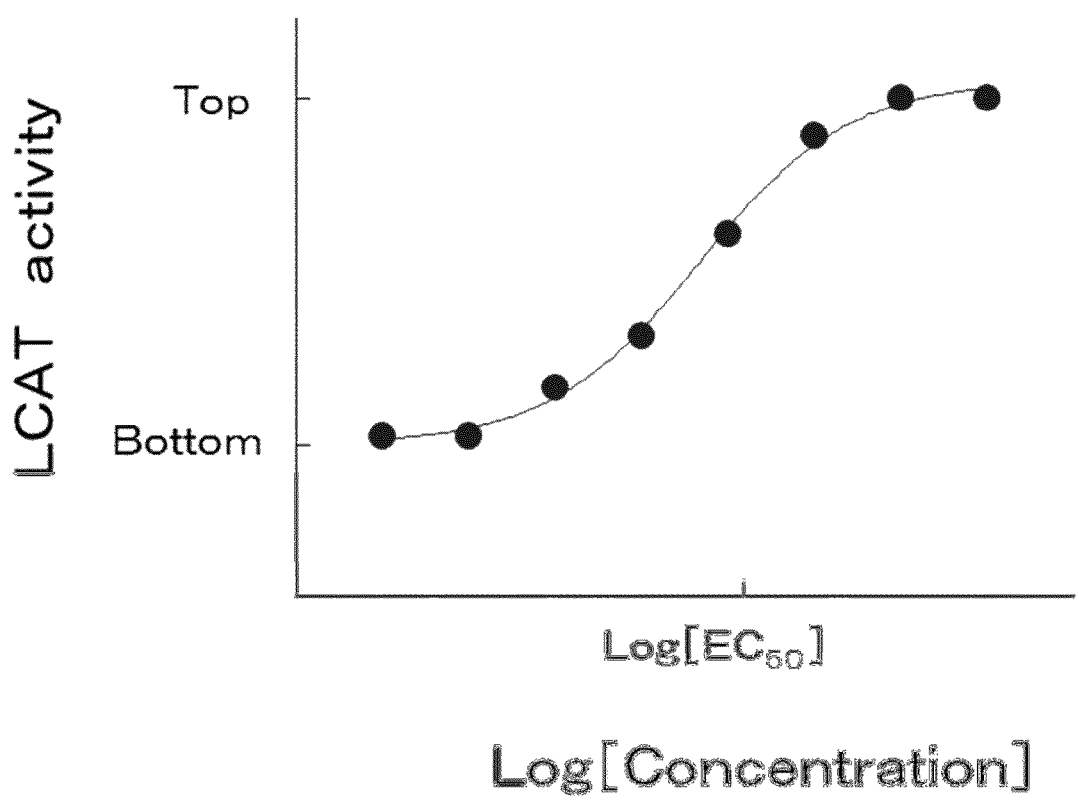

PIPERIDINYLPYRAZOLOPYRIDINE DERIVATIVE

TECHNICAL FIELD

The present invention relates to a piperidinylpyrazolopyridine derivative or a pharmacologically acceptable salt thereof which has an excellent LCAT-activating effect (preferably, reversible LCAT-activating effect).

BACKGROUND ART

Cardiovascular diseases (e.g., cardiac disease, cerebrovascular disease, and renal disease) caused by hypertension, dyslipidemia, diabetes mellitus, or the like are significant problems for developed countries. Antihypertensive, antidyslipidemic, and antidiabetic drugs are used in the treatment of the diseases hypertension, dyslipidemia, and hyperglycemia, respectively. In the clinical setting, α and β blockers, diuretics, calcium antagonists, ACE inhibitors, and A-II antagonists, etc. are used as antidyslipidemic drugs; HMG-CoA reductase inhibitors, anion exchange resins, nicotinic acid derivatives, probucol, and fibrates, etc. are used as antidyslipidemic drugs; and insulins, sulfonylureas, metformin, glitazones, and DPP4 inhibitors, etc. are used as antidiabetic drugs. These drugs contribute to the regulation of blood pressure or lipid or glucose levels in the blood. Nonetheless, even the use of these medicaments has not produced a great improvement in the death rates attributed to cardiac disease, cerebrovascular disease, and renal disease. Thus, there has been a demand for the development of better therapeutic drugs for these diseases.

A direct risk factor for cardiovascular diseases is atherosclerosis associated with thickening of the arterial wall. This thickening is caused by plaque formation resulting from the accumulation of oxidized low-density lipoprotein (hereinafter, referred to as LDL) cholesterol in macrophages and the like in the arterial wall (Non-patent Literatures 1 and 2). This plaque atherosclerosis inhibits blood flow and promotes the formation of blood clots.

The results of many epidemiologic studies indicate that serum concentrations of lipoproteins are associated with diseases such as dyslipidemia and arteriosclerosis (e.g., Non-patent Literature 3). Both an increased concentration of LDL cholesterol in the blood and a decreased concentration of high-density lipoprotein (hereinafter, referred to as HDL) cholesterol in the blood are risk factors for coronary diseases.

In peripheral tissues, HDL promotes efflux of cholesterol, which is in turn esterified by lecithin-cholesterol acetyltransferase (hereinafter, referred to as LCAT) on HDL to produce cholesteryl ester. Increased activity of LCAT promotes cholesterol efflux from macrophages (e.g., Non-patent Literatures 4 and 5). Accordingly, drugs that increase LCAT activity are considered to be useful as medicaments for the treatment or prophylaxis of diseases such as dyslipidemia and arteriosclerosis.

A peptide compound (e.g., Non-patent Literature 6) and, for example, the compound described in Patent Literature 1 as a small molecule, are known as such drugs that increase LCAT activity.

The compound described in Patent Literature 2 is known as a compound having a pyrazolopyridine skeleton. Patent Literature 2, however, makes no mention of an LCAT-activating effect, though the literature discloses an anti-LPA receptor effect.

CITATION LIST

Patent Literature

Patent Literature 1: WO2008/002591
Patent Literature 2: WO2012/028243

Non-patent Literature

Non-patent Literature 1: Ross, R., Annu. Rev. Physiol. 1995, Vol. 57, p. 791-804
Non-patent Literature 2: Steinberg, D., J. Biol. Chem. 1997, Vol. 272, p. 20963-20966
Non-patent Literature 3: Badimon, J. Clin. Invest., 1990, Vol. 85, p. 1234-1241
Non-patent Literature 4: Matsuura, F., J. Clin. Invest. 2006, Vol. 116, p. 1435-1442
Non-patent Literature 5: Yvan-Charvet, L., Arterioscler. Thromb. Vasc. Biol. 2007, Vol. 27, p. 1132-1138
Non-patent Literature 6: Iwata, A., Atherosclerosis. 2011, Vol. 218, p. 300-307

SUMMARY OF INVENTION

Technical Problem

Currently known compounds having an LCAT-activating effect are less than satisfactory in terms of safety and efficacy. Thus, there has been a strong demand for LCAT activators excellent in safety and efficacy.

Solution to Problem

The present inventors have conducted various syntheses and studies with the aim of obtaining a novel anti-arteriosclerotic drug that has an excellent LCAT-activating effect and directly promotes the efflux of cholesterol from macrophages. As a result, the present inventors have completed the present invention by finding that a pyrazolopyridine derivative having a particular structure or a pharmacologically acceptable salt thereof has an excellent LCAT-activating effect.

The present invention provides a piperidinylpyrazolopyridine derivative or a pharmacologically acceptable salt thereof which has an excellent LCAT-activating effect (preferably, reversible LCAT-activating effect), and a medicament comprising the same.

Specifically, the present invention relates to:

(1) a compound represented by the general formula (I) or a pharmacologically acceptable salt thereof:

[Formula 1]

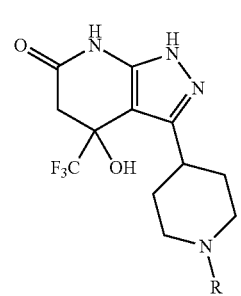

wherein R represents an optionally substituted aryl group (the substituent(s) is 1 to 3 identical or different groups selected from the group consisting of a halogen atom, a $C_{1-6}$ alkyl group, a $C_{3-7}$ cycloalkyl group, a trifluoromethyl group, a difluoromethoxy group, a trifluoromethoxy group, a cyano group, a $C_{1-6}$ alkoxy group, a $C_{3-7}$ cycloalkoxy group, a phenyl group, a $C_{2-7}$ alkoxycarbonyl group, a benzyloxycarbonyl group, a di($C_{1-6}$ alkyl)aminocarbonyl group, and a di($C_{1-6}$ alkyl)amino group) or an optionally substituted heteroaryl group (the heteroaryl is a 5- or 6-membered ring which is optionally further condensed with a benzene ring; the heteroatom(s) on the ring of the heteroaryl group is 1 or 2 nitrogen atoms, and the ring optionally further contains one nitrogen atom, oxygen atom, or sulfur atom; the substituent(s) is 1 or 2 identical or different groups selected from the group consisting of a halogen atom, a $C_{1-6}$ alkyl group, a $C_{3-7}$ cycloalkyl group, a trifluoromethyl group, a difluoromethoxy group, a trifluoromethoxy group, a cyano group, a $C_{1-6}$ alkoxy group, a $C_{3-7}$ cycloalkoxy group, a phenyl group, a $C_{2-7}$ alkoxycarbonyl group, a benzyloxycarbonyl group, a di($C_{1-6}$ alkyl)aminocarbonyl group, and a di($C_{1-6}$ alkyl)amino group; and the heteroaryl group is optionally further substituted by one optionally substituted heteroaryl group (the heteroaryl is a 5- or 6-membered ring which is optionally further condensed with a benzene ring; the heteroatom(s) on the ring of the heteroaryl group is 1 or 2 nitrogen atoms, and the ring optionally further contains one nitrogen atom, oxygen atom, or sulfur atom; and the substituent(s) is 1 or 2 identical or different groups selected from the group consisting of a halogen atom, a $C_{1-6}$ alkyl group, a trifluoromethyl group, a cyano group, and a $C_{1-6}$ alkoxy group));

(2) the compound according to (1) or a pharmacologically acceptable salt thereof, wherein R is a substituted aryl group (the substituent(s) is 1 or 2 identical or different groups selected from the group consisting of a chlorine atom, a fluorine atom, a $C_{1-3}$ alkyl group, a trifluoromethyl group, a difluoromethoxy group, a trifluoromethoxy group, a cyano group, and a $C_{1-3}$ alkoxy group);

(3) the compound according to (1) or a pharmacologically acceptable salt thereof, wherein R is a substituted phenyl group (the substituent(s) is 1 or 2 identical or different groups selected from the group consisting of a chlorine atom, a difluoromethoxy group, a trifluoromethoxy group, and a cyano group);

(4) the compound according to (1) or a pharmacologically acceptable salt thereof, wherein R is a substituted phenyl group (the substituent(s) is 1 or 2 identical or different groups selected from the group consisting of a difluoromethoxy group, a trifluoromethoxy group, and a cyano group);

(5) the compound according to (1) or a pharmacologically acceptable salt thereof, wherein R is a substituted heteroaryl group (the heteroaryl is a 5- or 6-membered ring; the heteroatom on the ring of the heteroaryl group is one nitrogen atom, and the ring optionally further contains one nitrogen atom, oxygen atom, or sulfur atom; the substituent(s) is 1 or 2 identical or different groups selected from the group consisting of a halogen atom, a $C_{1-3}$ alkyl group, a $C_{3-6}$ cycloalkyl group, a trifluoromethyl group, a difluoromethoxy group, a trifluoromethoxy group, a cyano group, a $C_{1-3}$ alkoxy group, a $C_{2-4}$ alkoxycarbonyl group, and a benzyloxycarbonyl group; and the heteroaryl group is optionally further substituted by one substituted heteroaryl group (the heteroaryl is 5- or 6-membered ring; the heteroatom on the ring of the heteroaryl group is one nitrogen atom, and the ring optionally further contains one nitrogen atom, oxygen atom, or sulfur atom; and the substituent(s) is 1 or 2 identical or different groups selected from the group consisting of a halogen atom, a $C_{2-3}$ alkyl group, a trifluoromethyl group, a cyano group, and a $C_{1-3}$ alkoxy group));

(6) the compound according to (1) or a pharmacologically acceptable salt thereof, wherein R is a substituted pyridyl, pyrimidyl, pyrazyl, pyridazyl, oxazolyl, or thiazolyl group (the substituent(s) is 1 or 2 identical or different groups selected from the group consisting of a chlorine atom, a fluorine atom, a $C_{1-3}$ alkyl group, a cyclopropyl group, a trifluoromethyl group, a difluoromethoxy group, a trifluoromethoxy group, a cyano group, a $C_{1-3}$ alkoxy group, a $C_{2-4}$ alkoxycarbonyl group, and a benzyloxycarbonyl group, and the pyridyl, pyrimidyl, pyrazyl, pyridazyl, oxazolyl, or thiazolyl group is optionally further substituted by one substituted thiazolyl group (the substituent(s) is a chlorine atom, a fluorine atom, a $C_{1-3}$ alkyl group, a trifluoromethyl group, a cyano group, or a $C_{1-3}$ alkoxy group));

(7) the compound according to (1) or a pharmacologically acceptable salt thereof, wherein R is a substituted pyridyl group (the substituent(s) is 1 or 2 identical or different groups selected from the group consisting of a chlorine atom, a trifluoromethyl group, a difluoromethoxy group, and a trifluoromethoxy group);

(8) the compound according to (1) or a pharmacologically acceptable salt thereof, wherein the compound or the salt is selected from the group consisting of:

4-hydroxy-4-(trifluoromethyl)-3-{1-[6-(trifluoromethyl)pyridin-2-yl]piperidin-4-yl}-1,4,5,7-tetrahydro-6H-pyrazolo[3,4-b]pyridin-6-one;

4-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one;

3-[1-(5-chloropyridin-2-yl)piperidin-4-yl]-4-hydroxy-4-(trifluoromethyl)-1,4,5,7-tetrahydro-6H-pyrazolo[3,4-b]pyridin-6-one;

4-hydroxy-3-{1-[6-(propan-2-yloxy)pyridazin-3-yl]piperidin-4-yl}-4-(trifluoromethyl)-1,4,5,7-tetrahydro-6H-pyrazolo[3,4-b]pyridin-6-one;

2-{4-[4-hydroxy-6-oxo-4-(trifluoromethyl)-4,5,6,7-tetrahydro-1H-pyrazolo[3,4-b]pyridin-3-yl]piperidin-1-yl}pyridine-4-carbonitrile;

5-{4-[4-hydroxy-6-oxo-4-(trifluoromethyl)-4,5,6,7-tetrahydro-1H-pyrazolo[3,4-b]pyridin-3-yl]piperidin-1-yl}pyridine-3-carbonitrile;

4-hydroxy-4-(trifluoromethyl)-3-{1-[6-(trifluoromethyl)pyridin-3-yl]piperidin-4-yl}-1,4,5,7-tetrahydro-6H-pyrazolo[3,4-b]pyridin-6-one;

4-hydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one;

3-{1-[4,4'-bis(trifluoromethyl)-2,5'-bi-1,3-thiazol-2'-yl]piperidin-4-yl}-4-hydroxy-4-(trifluoromethyl)-1,4,5,7-tetrahydro-6H-pyrazolo[3,4-b]pyridin-6-one;

3-{1-[5-(difluoromethoxy)pyridin-2-yl]piperidin-4-yl}-4-hydroxy-4-(trifluoromethyl)-1,4,5,7-tetrahydro-6H-pyrazolo[3,4-b]pyridin-6-one;

4-hydroxy-3-{1-[5-(propan-2-yloxy)pyridin-2-yl]piperidin-4-yl}-4-(trifluoromethyl)-1,4,5,7-tetrahydro-6H-pyrazolo[3,4-b]pyridin-6-one;

3-{1-[6-(difluoromethoxy)pyridin-3-yl]piperidin-4-yl}-4-hydroxy-4-(trifluoromethyl)-1,4,5,7-tetrahydro-6H-pyrazolo[3,4-b]pyridin-6-one;

3-{1-[4-(difluoromethoxy)phenyl]piperidin-4-yl}-4-hydroxy-4-(trifluoromethyl)-1,4,5,7-tetrahydro-6H-pyrazolo[3,4-b]pyridin-6-one;

5-{4-[4-hydroxy-6-oxo-4-(trifluoromethyl)-4,5,6,7-tetrahydro-1H-pyrazolo[3,4-b]pyridin-3-yl]piperidin-1-yl}-2-(trifluoromethoxy)benzonitrile;

4-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one;

4-hydroxy-3-{1-[5-(trifluoromethoxy)pyridin-2-yl]piperidin-4-yl}-4-(trifluoromethyl)-1,4,5,7-tetrahydro-6H-pyrazolo[3,4-b]pyridin-6-one;

benzyl 2-[4-(4-hydroxy-6-oxo-4-(trifluoromethyl)-4,5,6,7-tetrahydro-1H-pyrazolo[3,4-b]pyridin-3-yl)piperidin-1-yl]-5-(trifluoromethyl)pyridine-4-carboxylate;

4-hydroxy-3-{1-[2-(propan-2-yl)-6-(trifluoromethyl)pyrimidin-4-yl]piperidin-4-yl}-4-(trifluoromethyl)-1,4,5,7-tetrahydro-6H-pyrazolo[3,4-b]pyridin-6-one;

ethyl 2-{4-[4-hydroxy-6-oxo-4-(trifluoromethyl)-4,5,6,7-tetrahydro-1H-pyrazolo[3,4-b]pyridin-3-yl]piperidin-1-yl}-4-(trifluoromethyl)-1,3-oxazole-5-carboxylate;

6-{4-[4-hydroxy-6-oxo-4-(trifluoromethyl)-4,5,6,7-tetrahydro-1H-pyrazolo[3,4-b]pyridin-3-yl]piperidin-1-yl}-4-(trifluoromethyl)pyridine-3-carbonitrile; and 3-[1-(5-cyclopropylpyridin-2-yl)piperidin-4-yl]-4-hydroxy-4-(trifluoromethyl)-1,4,5,7-tetrahydro-6H-pyrazolo[3,4-b]pyridin-6-one;

(9) the compound according to (1) or a pharmacologically acceptable salt thereof, wherein the compound or the salt is selected from the group consisting of:

(−)-4-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one;

(−)-3-[1-(5-chloropyridin-2-yl)piperidin-4-yl]-4-hydroxy-4-(trifluoromethyl)-1,4,5,7-tetrahydro-6H-pyrazolo[3,4-b]pyridin-6-one; and (−)-3-{1-[4-(difluoromethoxy)phenyl]piperidin-4-yl}-4-hydroxy-4-(trifluoromethyl)-1,4,5,7-tetrahydro-6H-pyrazolo[3,4-b]pyridin-6-one;

(10) a pharmaceutical composition comprising a compound according to any one of (1) to (9) or a pharmacologically acceptable salt thereof as an active ingredient;

(11) the pharmaceutical composition according to (10), wherein the pharmaceutical composition is for the treatment or prophylaxis of arteriosclerosis, arteriosclerotic heart disease, coronary heart disease, cerebrovascular disease, peripheral vascular disease, dyslipidemia, hypo-HDL-cholesterolemia, or renal disease;

(12) the pharmaceutical composition according to (10), wherein the pharmaceutical composition is for the treatment or prophylaxis of arteriosclerosis;

(13) the pharmaceutical composition according to (10), wherein the pharmaceutical composition is for the treatment or prophylaxis of dyslipidemia;

(14) the pharmaceutical composition according to (10), wherein the pharmaceutical composition is for the treatment or prophylaxis of a disease caused by an increased concentration of LDL cholesterol in the blood;

(15) the pharmaceutical composition according to (10), wherein the pharmaceutical composition is for the treatment or prophylaxis of a disease caused by a decreased concentration of HDL cholesterol in the blood;

(16) an LCAT activator comprising a compound according to any one of (1) to (9) or a pharmacologically acceptable salt thereof as an active ingredient;

(17) a reversible LCAT activator comprising a compound according to any one of (1) to (9) or a pharmacologically acceptable salt thereof as an active ingredient;

(18) an anti-arteriosclerotic agent comprising a compound according to any one of (1) to (9) or a pharmacologically acceptable salt thereof as an active ingredient;

(19) a prophylactic or therapeutic agent for arteriosclerosis, comprising a compound according to any one of (1) to (9) or a pharmacologically acceptable salt thereof as an active ingredient;

(20) an agent for lowering the concentration of LDL cholesterol in the blood, comprising a compound according to any one of (1) to (9) or a pharmacologically acceptable salt thereof as an active ingredient;

(21) an agent for elevating the concentration of HDL cholesterol in the blood, comprising a compound according to any one of (1) to (9) or a pharmacologically acceptable salt thereof as an active ingredient;

(22) a pharmaceutical composition comprising a compound according to any one of (1) to (9) or a pharmacologically acceptable salt thereof and a pharmacologically acceptable carrier;

(23) use of a compound according to any one of (1) to (9) or a pharmacologically acceptable salt thereof for the production of a pharmaceutical composition;

(24) the use according to (23), wherein the use is for the production of a pharmaceutical composition for the treatment or prophylaxis of arteriosclerosis, arteriosclerotic heart disease, coronary heart disease, cerebrovascular disease, peripheral vascular disease, dyslipidemia, hypo-HDL-cholesterolemia, or renal disease;

(25) the use according to (23), wherein the use is for the production of a pharmaceutical composition for the treatment or prophylaxis of arteriosclerosis;

(26) the use according to (23), wherein the use is for the production of a pharmaceutical composition for the treatment or prophylaxis of dyslipidemia;

(27) the use according to (23), wherein the use is for the production of a pharmaceutical composition for the treatment or prophylaxis of a disease caused by an increased concentration of LDL cholesterol in the blood;

(28) the use according to (23), wherein the use is for the production of a pharmaceutical composition for the treatment or prophylaxis of a disease caused by a decreased concentration of HDL cholesterol in the blood;

(29) a method for activating LCAT, comprising administering an effective amount of a compound according to any one of (1) to (9) or a pharmaceutical acceptable salt thereof to a human;

(30) a method for treatment or prophylaxis of a disease, comprising administering an effective amount of a compound according to any one of (1) to (9) or a pharmacologically acceptable salt thereof to a human;

(31) the method according to (30), wherein the disease is arteriosclerosis, arteriosclerotic heart disease, coronary heart disease, cerebrovascular disease, peripheral vascular disease, dyslipidemia, hypo-HDL-cholesterolemia, or renal disease;

(32) the method according to (30), wherein the disease is arteriosclerosis;

(33) the method according to (30), wherein the disease is dyslipidemia;

(34) the method according to (30), wherein the disease is a disease caused by an increased concentration of LDL cholesterol in the blood;

(35) the method according to (30), wherein the disease is a disease caused by a decreased concentration of HDL cholesterol in the blood;

(36) the compound according to any one of (1) to (9) or a pharmacologically acceptable salt thereof for use in a method for treatment or prophylaxis of a disease;
(37) the compound according to (36) or a pharmacologically acceptable salt thereof, wherein the disease is arteriosclerosis, arteriosclerotic heart disease, coronary heart disease, cerebrovascular disease, peripheral vascular disease, dyslipidemia, hypo-HDL-cholesterolemia, or renal disease;
(38) the compound according to (36) or a pharmacologically acceptable salt thereof, wherein the disease is arteriosclerosis;
(39) the compound according to (36) or a pharmacologically acceptable salt thereof, wherein the disease is dyslipidemia;
(40) the compound according to (36) or a pharmacologically acceptable salt thereof, wherein the disease is a disease caused by an increased concentration of LDL cholesterol in the blood; and
(41) the compound according to (36) or a pharmacologically acceptable salt thereof, wherein the disease is a disease caused by a decreased concentration of HDL cholesterol in the blood.

Hereinafter, substituents in the compound (I) of the present invention will be defined.

The compound (I) of the present invention encompasses both of a compound represented by the formula (I) and a compound represented by the formula (Ix), which is a tautomer thereof:

[Formula 2]

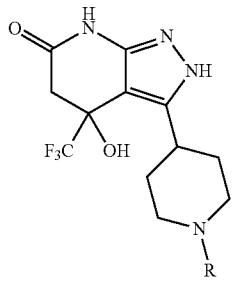

In the present application, a compound (I) including any such tautomer is also represented by the structural formula (I) and its corresponding chemical name for the sake of convenience, unless otherwise specified. The compound (I) of the present application also encompasses any isomer of an additional tautomer (amide-imide acid) of the compound (I) of the present invention. In the present application, a compound (I) including any such isomer is also represented by the structural formula (I) and its corresponding chemical name for the sake of convenience.

In the compound (I) of the present invention, the "$C_{1-6}$ alkyl group" refers to a linear or branched saturated hydrocarbon group having 1 to 6 carbon atoms. Examples thereof can include a methyl group, an ethyl group, a propyl group, an isopropyl group, a butyl group, a sec-butyl group, a tert-butyl group, an isobutyl group, a pentyl group, and a hexyl group. The $C_{1-6}$ alkyl group is preferably a linear or branched saturated hydrocarbon group having 1 to 3 carbon atoms ($C_{1-3}$ alkyl group), more preferably a methyl group or an isopropyl group.

In the compound (I) of the present invention, the "$C_{1-6}$ alkoxy group" refers to an oxygen atom bonded by the above-mentioned "$C_{1-6}$ alkyl group". Examples thereof can include a methoxy group, an ethoxy group, a propoxy group, and an isopropoxy group. The $C_{1-6}$ alkoxy group is preferably an oxygen atom bonded by the above-mentioned "$C_{1-3}$ alkyl group" ($C_{1-3}$ alkoxy group), more preferably a methoxy group or an isopropoxy group.

In the compound (I) of the present invention, the halogen atom refers to a fluorine atom, a chlorine atom, a bromine atom, or an iodine atom and is preferably a fluorine atom or a chlorine atom, more preferably a chlorine atom.

In the compound (I) of the present invention, the "$C_{2-7}$ alkoxycarbonyl group" refers to a carbonyl group bonded by the above-mentioned "$C_{1-6}$ alkoxy group" and is preferably a carbonyl group bonded by the above-mentioned "$C_{1-3}$ alkoxy group" ($C_{2-4}$ alkoxycarbonyl group). The "$C_{2-7}$ alkoxycarbonyl group" can be more preferably a methoxycarbonyl group or an ethoxycarbonyl group and is even more preferably an ethoxycarbonyl group.

In the compound (I) of the present invention, the "di($C_{1-6}$ alkyl)amino group" refers to an amino group bonded by two identical or different above-mentioned "$C_{1-6}$ alkyl groups". Examples thereof can include a dimethylamino group and a diethylamino group. The di($C_{1-6}$ alkyl)amino group is preferably a dimethylamino group.

In the compound (I) of the present invention, the "di($C_{1-6}$ alkyl)aminocarbonyl group" refers to a carbonyl group bonded by the above-mentioned "di($C_{1-6}$ alkyl)amino group". Examples thereof can include a dimethylaminocarbonyl group and a diethylaminocarbonyl group. The di($C_{1-6}$ alkyl)aminocarbonyl group is preferably a dimethylaminocarbonyl group.

In the compound (I) of the present invention, the "$C_{3-7}$ cycloalkyl group" refers to a cyclic saturated hydrocarbon group having 3 to 7 carbon atoms, such as a cyclopropyl group, a cyclobutyl group, a cyclopentyl group, or a cyclohexyl group, and is preferably a cyclic saturated hydrocarbon group having 3 to 6 carbon atoms ($C_{3-6}$ cycloalkyl group), more preferably a cyclopropyl group.

In the compound (I) of the present invention, the "$C_{3-7}$ cycloalkoxy group" refers to an oxygen atom bonded by the above-mentioned "$C_{3-7}$ cycloalkyl group". Examples thereof can include a cyclopropoxy group and a cyclobutoxy group. The $C_{3-7}$ cycloalkoxy group is preferably a cyclobutoxy group.

In the compound (I) of the present invention, the "aryl group" is, for example, a phenyl group or a naphthyl group and is preferably a phenyl group.

In the compound (I) of the present invention, the "optionally substituted aryl group (the substituent(s) is 1 to 3 identical or different groups selected from the group consisting of a halogen atom, a $C_{1-6}$ alkyl group, a $C_{3-7}$ cycloalkyl group, a trifluoromethyl group, a difluoromethoxy group, a trifluoromethoxy group, a cyano group, a $C_{1-6}$ alkoxy group, a $C_{3-7}$ cycloalkoxy group, a phenyl group, a $C_{2-7}$ alkoxycarbonyl group, a benzyloxycarbonyl group, a di($C_{1-6}$ alkyl)aminocarbonyl group, and a di($C_{1-6}$ alkyl)amino group)" is preferably an aryl group substituted by 1 or 2 identical or different groups selected from the group consisting of a chlorine atom, a fluorine atom, a $C_{1-3}$ alkyl group, a trifluoromethyl group, a difluoromethoxy group, a trifluoromethoxy group, a cyano group, and a $C_{1-3}$ alkoxy group, more preferably a phenyl group substituted by 1 or 2 identical or different groups selected from the group consisting of a fluorine atom, a chlorine atom, a methyl group, a trifluoromethyl group, a difluoromethoxy group, a trifluoromethoxy group, a cyano group, and a methoxy group, even more preferably a phenyl group substituted by 1 or 2 identical or different groups selected from the group consisting of a chlorine atom, a difluoromethoxy group, a trifluoromethoxy group, and a cyano group, particularly preferably a phenyl group substituted by 1 or 2 identical or different groups selected from the group consisting of a chlorine atom, a difluoromethoxy group, a trifluoromethoxy group, and a cyano group, most preferably a 4-(difluoromethoxy)phenyl group, a 4-(trifluoromethoxy) phenyl group, or a 3-cyano-4-(trifluoromethoxy)phenyl group.

In the compound (I) of the present invention, the "heteroaryl group (the heteroaryl is a 5- or 6-membered ring which is optionally further condensed with a benzene ring; the heteroatom(s) on the ring of the heteroaryl group is 1 or 2 nitrogen atoms; and the ring optionally further contains one nitrogen atom, oxygen atom, or sulfur atom)" can be, for example, a pyridyl group, a pyrazyl group, a pyrimidyl group, a pyridazyl group, a pyrrole group, a pyrazolyl group, an imidazolyl group, a triazolyl group, a benzoxazolyl group, a benzothiazolyl group, or a quinolyl group. The heteroaryl group is preferably a heteroaryl group (the heteroaryl is a 5- or 6-membered ring; the heteroatom on the ring of the heteroaryl group is one nitrogen atom; and the ring optionally further contains one nitrogen atom, oxygen atom, or sulfur atom), more preferably a pyridyl group, a pyrazyl group, a pyrimidyl group, a pyridazyl group, an oxazolyl group, or a thiazolyl group.

In the compound (I) of the present invention, the "optionally substituted heteroaryl group (the heteroaryl is a 5- or 6-membered ring which is optionally further condensed with a benzene ring; the heteroatom(s) on the ring of the heteroaryl group is 1 or 2 nitrogen atoms, the ring optionally further contains one nitrogen atom, oxygen atom, or sulfur atom; the substituent(s) is 1 or 2 identical or different groups selected from the group consisting of a halogen atom, a $C_{1-6}$ alkyl group, a $C_{3-7}$ cycloalkyl group, a trifluoromethyl group, a difluoromethoxy group, a trifluoromethoxy group, a cyano group, a $C_{1-6}$ alkoxy group, a $C_{3-7}$ cycloalkoxy group, a phenyl group, a $C_{2-7}$ alkoxycarbonyl group, a benzyloxycarbonyl group, a di($C_{1-6}$ alkyl)aminocarbonyl group, and a di($C_{1-6}$ alkyl)amino group; and the heteroaryl group is optionally further substituted by one optionally substituted heteroaryl group (the heteroaryl is a 5- or 6-membered ring which is optionally further condensed with a benzene ring; the heteroatom(s) on the ring of the heteroaryl group is 1 or 2 nitrogen atoms, and the ring optionally further contains one nitrogen atom, oxygen atom, or sulfur atom; and the substituent(s) is 1 or 2 identical or different groups selected from the group consisting of a halogen atom, a $C_{1-6}$ alkyl group, a trifluoromethyl group, a cyano group, and a $C_{1-6}$ alkoxy group))" is preferably a pyridyl, pyrazyl, pyrimidyl, pyridazyl, oxazolyl, or thiazolyl group substituted by 1 or 2 identical or different groups selected from the group consisting of a chlorine atom, a fluorine atom, a $C_{1-3}$ alkyl group, a cyclopropyl group, a trifluoromethyl group, a difluoromethoxy group, a trifluoromethoxy group, a cyano group, a $C_{2-3}$ alkoxy group, a $C_{2-4}$ alkoxycarbonyl group, and a benzyloxycarbonyl group and optionally further substituted by one substituted thiazolyl group (the substituent(s) is a chlorine atom, a fluorine atom, a $C_{2-3}$ alkyl group, a trifluoromethyl group, a cyano group, or a $C_{2-3}$ alkoxy group), more preferably a pyridyl, pyrazyl, pyrimidyl, or oxazolyl group substituted by 1 or 2 identical or different groups selected from the group consisting of a chlorine atom, an isopropyl group, a cyclopropyl group, a trifluoromethyl group, a difluoromethoxy group, a trifluoromethoxy group, a cyano group, an isopropoxy group, an ethoxycarbonyl group, and a benzyloxycarbonyl group, even more preferably a 5-chloropyridin-2-yl group, a 5-cyclopropylpyridin-2-yl group, a 5-(trifluoromethyl)pyridin-2-yl group, a 6-(trifluoromethyl)pyridin-3-yl group, a 2-(trifluoromethyl)pyrimidin-5-yl group, a 4-benzyloxycarbonyl-5-(trifluoromethyl)pyridin-2-yl group, a 4-(trifluoromethyl)-5-cyanopyridin-2-yl group, a 6-(difluoromethoxy)pyridin-3-yl group, a 5-(trifluoromethoxy)pyridin-2-yl group, a 4-cyanopyridin-2-yl group, a 5-cyanopyridin-3-yl group, a 5-isopropoxypyridin-2-yl group, a 5-(trifluoromethyl)pyrazin-2-yl group, a 2-isopropyl-6-(trifluoromethyl)pyrimidin-4-yl group, or a 4-(trifluoromethyl)-5-ethoxycarbonyloxazol-2-yl group.

The compound (I) of the present invention has a basic group and can therefore form an acid-addition salt with a pharmacologically acceptable acid. In the present invention, examples of the "pharmacologically acceptable salt thereof" can include: hydrohalides such as hydrofluoride, hydrochloride, hydrobromide, and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as acetate, malate, fumarate, succinate, citrate, tartrate, oxalate, and maleate; and amino acid salts such as ornithine salt, glutamate, and aspartate.

The compound (I) of the present invention or the pharmacologically acceptable salt thereof, when left in the atmosphere, may form a hydrate by absorbing water. Such hydrates are also included in the scope of the present invention.

The compound (I) of the present invention or the pharmacologically acceptable salt thereof, when left in a solvent, may form a solvate. Such solvates are also included in the scope of the present invention.

The compound (I) of the present invention has optical isomers based on the asymmetric center in the molecule. These isomers of the compound of the present invention and mixtures of these isomers are all represented by a single formula, i.e., the general formula (I), unless otherwise specified. Thus, it should be understood that even these isomers and mixtures of these isomers are all included in the scope of the present invention.

The compound (I) of the present invention may contain isotope(s) of one or more atoms constituting such a compound at a nonnatural ratio. Examples of the isotope include deuterium ($^2$H), tritium ($^3$H), iodine-125 ($^{125}$I), and carbon-14 ($^{14}$C). Alternatively, the compound may be radiolabeled with a radioisotope, for example, tritium ($^3$H), iodine-125 ($^{125}$I), or carbon-14 ($^{14}$C). Such a radiolabeled compound is useful as a therapeutic or prophylactic agent, a research reagent, for example, an assay reagent, and a diagnostic agent, for example, an in vivo diagnostic imaging agent. It should be understood that all isotopic variants of the compound of the present invention are included in the scope of the present invention, regardless of being radioactive or not.

Advantageous Effects of Invention

The compound represented by the general formula (I) of the present invention or the pharmacologically acceptable salt thereof has an excellent LCAT-activating effect and is useful as an active ingredient in a therapeutic or prophylactic agent for arteriosclerosis, arteriosclerotic heart disease, coronary heart disease (including heart failure, myocardial infarction, angina pectoris, cardiac ischemia, cardiovascular disturbance, and restenosis caused by angiogenesis), cerebrovascular disease (including stroke and cerebral infarction), peripheral vascular disease (including diabetic vascular complications), dyslipidemia, hypo-HDL-cholesterolemia, or renal disease, particularly, an anti-arteriosclerotic agent.

BRIEF DESCRIPTION OF DRAWING

FIG. 1 shows a dose-response curve for determining the 50% effective concentration ($EC_{50}$) of LCAT activation in Test Examples 1 and 2 of the present invention.

DESCRIPTION OF EMBODIMENTS

Hereinafter, typical methods for producing the compound (I) of the present invention and starting compounds for use in the production of the compound (I) of the present invention will be described. However, the present invention is not intended to be limited by these methods.

Production Method 1

Production method 1 is a method for producing the compound (I) of the present invention from compound (II).

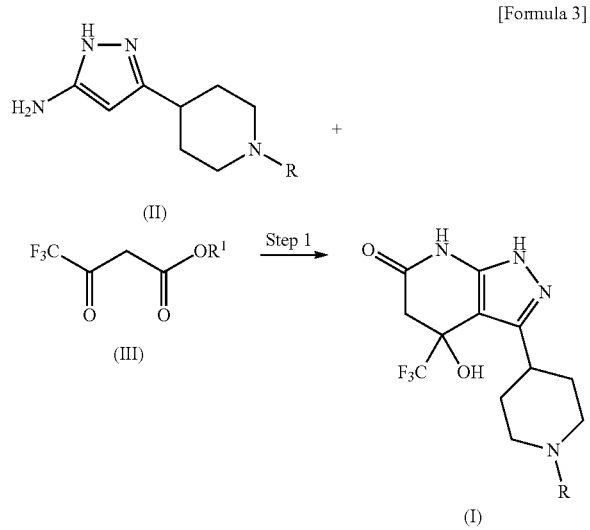

In these formulas, R is as defined above, and $R^1$ represents a methyl group or an ethyl group.

The compound (II) has compound (IIx) as a tautomer. In the present invention, the compound (II) also encompasses all isomers based on tautomers. Specifically, the compound (II) encompasses all of the compound (II), the compound (IIx), and mixtures of the compound (II) and the compound (IIx) in any arbitrary ratio. Also, a compound represented by the compound name of the compound (II) encompasses all of the compound (II), the compound (IIx), and mixtures of the compound (II) and the compound (IIx) in any arbitrary ratio.

[Formula 4]

(Step 1)

This step involves condensing compound (II) with compound (III) under heating in a solvent inert to the reaction or in the absence of a solvent to produce compound (I).

The solvent used in this step can be an organic acid such as acetic acid, formic acid, oxalic acid, methanesulfonic acid, p-toluenesulfonic acid, camphorsulfonic acid, trifluoroacetic acid, or trifluoromethanesulfonic acid; an ether such as diethyl ether, diisopropyl ether, tetrahydrofuran, dioxane, dimethoxyethane, or tert-butyl methyl ether; an alcohol such as methanol, ethanol, n-propanol, isopropanol, n-butanol, isobutanol, tert-butanol, isoamyl alcohol, octanol, cyclohexanol, 2-methoxyethanol, diethylene glycol, or glycerin; an aromatic hydrocarbon such as benzene, toluene, or xylene; or a mixed solvent thereof. The solvent is preferably an organic acid, more preferably acetic acid.

The reaction temperature of this step is usually 40° C. to 150° C., preferably 50° C. to 130° C., more preferably 60° C. to the reflux temperature of the solvent.

The reaction time of this step is usually 5 minutes to 72 hours, preferably 15 minutes to 24 hours, more preferably 30 minutes to 3 hours.

Production Method 2

The intermediate (II) of the compound of the present invention can be produced by, for example, the following method:

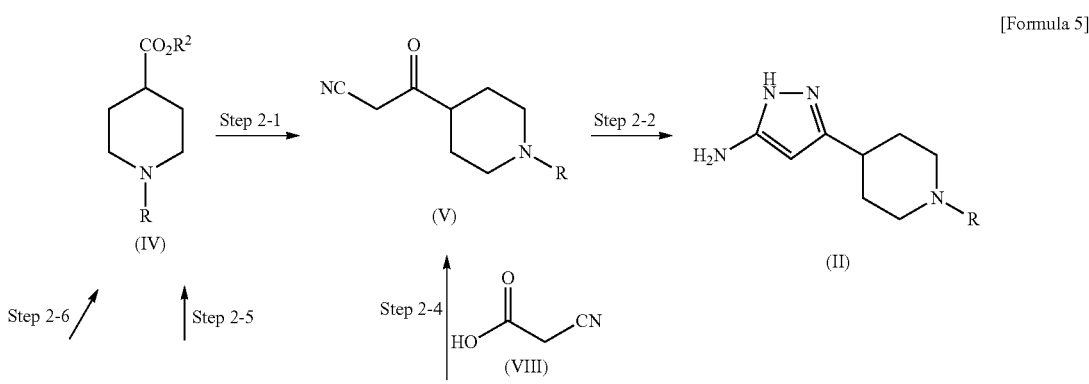

[Formula 5]

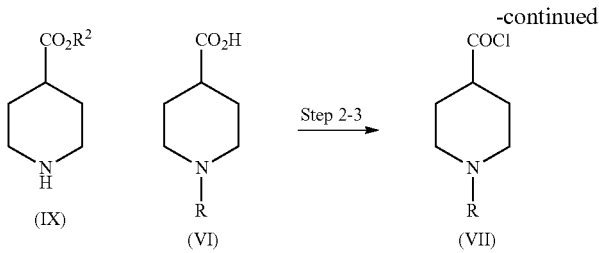

In these formulas, R is as defined above, and $R^2$ represents a methyl group or an ethyl group.

(Step 2-1)

This step involves reacting compound (IV) with acetonitrile using a base in an inert solvent to produce compound (V).

The solvent used in this step can be an ether such as diethyl ether, diisopropyl ether, tetrahydrofuran, dioxane, dimethoxyethane, or tert-butyl methyl ether; an aromatic hydrocarbon such as benzene, toluene, or xylene; an aliphatic hydrocarbon such as hexane; or a mixed solvent thereof. The solvent is preferably an ether, more preferably tetrahydrofuran.

The base used in this step can preferably be an inorganic base such as sodium hydride, sodium carbonate, potassium carbonate, or cesium carbonate; or an organic metal base such as sodium tert-butoxide, potassium tert-butoxide, or n-butyllithium. The base is more preferably sodium hydride or n-butyllithium.

The reaction temperature of this step is preferably $-100°$ C. to $0°$ C., more preferably $-78°$ C. to $-40°$ C.

The reaction time of this step is preferably 5 minutes to 3 hours, more preferably 15 minutes to 2 hours.

The compound (IV) used as a starting material in this step is commercially available or can be produced by the esterification (step 2-5) of a benzoic acid compound known in the art according to a routine method. Alternatively, the compound (IV) can be produced by the arylation or heteroarylation (step 2-6) of 4-ethoxycarbonylpiperidine known in the art according to a method mentioned later.

(Step 2-2)

This step involves reacting compound (V) with a hydrazine compound in an inert solvent to produce compound (II).

The solvent used in this step can be an alcohol such as methanol, ethanol, n-propanol, isopropanol, n-butanol, isobutanol, tert-butanol, isoamyl alcohol, octanol, cyclohexanol, 2-methoxyethanol, diethylene glycol, or glycerin; an aromatic hydrocarbon such as benzene, toluene, or xylene; or a mixed solvent thereof. The solvent is preferably an alcohol, more preferably ethanol.

The hydrazine compound used in this step can be, for example, anhydrous hydrazine, hydrazine monohydrate, hydrazine hydrochloride, hydrazine acetate, hydrazine sulfate, hydrazine nitrate, hydrazine hydrobromide, hydrazine oxalate, or hydrazine phosphate. The hydrazine compound is preferably hydrazine monohydrate or hydrazine acetate.

The reaction temperature of this step is preferably $20°$ C. to $120°$ C., more preferably $50°$ C. to the reflux temperature of the solvent.

The reaction time of this step is preferably 10 minutes to 24 hours, more preferably 1 hour to 5 hours.

(Step 2-3)

This step involves reacting the carboxy group of compound (VI) with a chlorinating agent in an inert solvent to produce compound (VII).

Reagents and reaction conditions used in this step are not particularly limited as long as they are reagents and conditions for use in usual reactions for producing an acid chloride compound from a compound having a carboxy group.

The solvent used in this step can be a halogenated hydrocarbon such as dichloromethane, chloroform, carbon tetrachloride, 1,2-dichloroethane, chlorobenzene, or dichlorobenzene; or an ether such as diethyl ether, diisopropyl ether, tetrahydrofuran, dioxane, dimethoxyethane, or tert-butyl methyl ether. The solvent is preferably dichloromethane or tetrahydrofuran.

The chlorinating agent used in this step is preferably thionyl chloride or oxalyl chloride, more preferably oxalyl chloride.

The reaction temperature of this step is preferably $-30°$ C. to $50°$ C., more preferably $-10°$ C. to $25°$ C.

The reaction time of this step is 10 minutes to 6 hours.

(Step 2-4)

This step involves reacting compound (VII) with compound (VIII) in the presence of a base in an inert solvent to produce compound (V).

The solvent used in this step is an ether such as diethyl ether, diisopropyl ether, tetrahydrofuran, dioxane, dimethoxyethane, tert-butyl methyl ether, or 1,4-dioxane. The solvent is preferably diethyl ether, tetrahydrofuran, or 1,4-dioxane, more preferably tetrahydrofuran.

The base used in this step is preferably n-butyllithium.

The reaction temperature of this step is preferably $-100°$ C. to $50°$ C., more preferably $-78°$ C. to $0°$ C.

The reaction time of this step is preferably 10 minutes to 6 hours, more preferably 30 minutes to 2 hours.

(Step 2-5)

(i) This step involves reacting compound (VI) with an alkylating agent in an inert solvent to produce compound (IV).

The solvent used in this step is an alcohol such as methanol, ethanol, n-propanol, isopropanol, n-butanol, isobutanol, tert-butanol, isoamyl alcohol, octanol, cyclohexanol, 2-methoxyethanol, diethylene glycol, or glycerin; a halogenated hydrocarbon such as dichloromethane, chloroform, carbon tetrachloride, 1,2-dichloroethane, chlorobenzene, or dichlorobenzene; an ether such as diethyl ether, diisopropyl ether, tetrahydrofuran, dioxane, dimethoxyethane, or tert-butyl methyl ether; an aromatic hydrocarbon such as benzene, toluene, or xylene; or an amide such as formamide, N,N-dimethylformamide, dimethylacetamide, N-methyl-2-pyrrolidone, or hexamethylphosphortriamide. The solvent is preferably an alcohol or an amide, more preferably methanol or N,N-dimethylformamide.

This step can be carried out in the presence of a base. Such a base can be an inorganic base such as sodium hydride, sodium carbonate, potassium carbonate, or cesium carbonate; an organic metal base such as sodium tert-butoxide, potassium tert-butoxide, or n-butyllithium; or an organic base such as triethylamine, diisopropylethylamine, 1,8-diazabicyclo

[5.4.0]-7-undecene, N-methylmorpholine, pyridine, dimethylaminopyridine, or 2,6-lutidine. The base is preferably an inorganic base, more preferably potassium carbonate.

The alkylating agent used in this step can be, for example, diazomethane, trimethylsilyldiazomethane, alkyl halide, alkyl tosylate, alkyl mesylate, or alkyl triflate and is preferably trimethylsilyldiazomethane, methyl iodide, or ethyl iodide.

The reaction temperature of this step is preferably −20° C. to 50° C., more preferably 0° C. to 30° C.

The reaction time of this step is preferably 5 minutes to 48 hours, more preferably 30 minutes to 15 hours.

(ii) Alternatively, this step involves reacting compound (VI) with an alcohol in the presence of a condensing agent and a base in an inert solvent to produce compound (IV).

The solvent used in this step is an alcohol such as methanol, ethanol, n-propanol, isopropanol, n-butanol, isobutanol, tert-butanol, isoamyl alcohol, octanol, cyclohexanol, 2-methoxyethanol, diethylene glycol, or glycerin; a halogenated hydrocarbon such as dichloromethane, chloroform, carbon tetrachloride, 1,2-dichloroethane, chlorobenzene, or dichlorobenzene; an ether such as diethyl ether, diisopropyl ether, tetrahydrofuran, dioxane, dimethoxyethane, or tert-butyl methyl ether; an aromatic hydrocarbon such as benzene, toluene, or xylene; or an amide such as formamide, N,N-dimethylformamide, dimethylacetamide, N-methyl-2-pyrrolidone, or hexamethylphosphortriamide. The solvent is preferably an alcohol or an amide, more preferably methanol, ethanol, or N,N-dimethylformamide.

The condensing agent used in this step can be a carbodiimide such as 1,3-dicyclohexylcarbodiimide, 1,3-diisopropylcarbodiimide, or 1-ethyl-3-(3-dimethylaminopropyl)carbodiimide; the above-mentioned carbodiimide combined with a base given below; the above-mentioned carbodiimide combined with a N-hydroxy compound; or 4-(4,6-dimethoxy-1,3,5-triazin-2-yl)-4-methylmorpholinium chloride. The condensing agent is preferably 1-ethyl-3-(3-dimethylaminopropyl)carbodiimide.

The base used in this step can be an inorganic base such as sodium hydride, sodium carbonate, potassium carbonate, or cesium carbonate; an organic metal base such as sodium tert-butoxide, potassium tert-butoxide, or n-butyllithium; or an organic base such as triethylamine, diisopropylethylamine, 1,8-diazabicyclo[5.4.0]-7-undecene, N-methylmorpholine, pyridine, dimethylaminopyridine, or 2,6-lutidine. The base is preferably an organic base, more preferably dimethylaminopyridine.

The reaction temperature of this step is preferably −20° C. to 50° C., more preferably −5° C. to 30° C.

The reaction time of this step is preferably 5 minutes to 48 hours, more preferably 30 minutes to 15 hours.

(Step 2-6)

(i) This step involves reacting compound (IX) with an arylating agent or a heteroarylating agent through Buchwald-Hartwig reaction using a palladium catalyst in the presence of a ligand other than the palladium catalyst and a base in an inert solvent to produce compound (IV).

The palladium catalyst, the ligand, the base, and reaction conditions used in this step are not particularly limited as long as they are reagents and conditions for use in usual Buchwald-Hartwig reactions. The reagents and the conditions are described in, for example, A. R. Muci, S. L. Buchwald, Top. Curr. Chem. 2002, Vol. 219, p. 131.

The solvent used in this step is an ether such as diethyl ether, diisopropyl ether, tetrahydrofuran, dioxane, dimethoxyethane, or tert-butyl methyl ether; or an aromatic hydrocarbon such as benzene, toluene, or xylene. The solvent is preferably toluene or dioxane, more preferably toluene.

The palladium catalyst used in this step is preferably palladium(II) acetate or palladium(0) dibenzylideneacetone.

The ligand used in this step is preferably 2-(di-tert-butylphosphino)biphenyl, tri-tert-butylphosphine, tricyclohexylphosphine, 1,3-bis(diphenylphosphino)propane, 2,2'-bis(diphenylphosphanyl)1,1'-binaphthyl, 2-(dicyclohexylphosphino)biphenyl, or 2-dicyclohexylphosphino-2'-(N,N-dimethylamino)biphenyl, more preferably 2-(di-tert-butylphosphino)biphenyl, tri-tert-butylphosphine, or 2,2'-bis(diphenylphosphanyl)1,1'-binaphthyl.

The base used in this step is preferably sodium carbonate, potassium carbonate, cesium carbonate, sodium tert-butoxide or potassium tert-butoxide, more preferably sodium tert-butoxide.

The arylating agent or the heteroarylating agent used in this step refers to a compound represented by the formula R—Cl, R—Br, or R—I and is preferably represented by the formula R—Cl or R—Br (wherein R is as defined above).

The reaction temperature of this step is preferably 20° C. to 150° C., more preferably 50° C. to the reflux temperature of the solvent.

The reaction time of this step is preferably 30 minutes to 12 hours, and more preferably 1 hour to 4 hours.

(ii) Alternatively, this step involves reacting compound (IX) with an arylating agent or a heteroarylating agent in the presence of a base in an inert solvent to produce compound (IV).

The solvent used in this step can be a halogenated hydrocarbon such as dichloromethane, chloroform, carbon tetrachloride, 1,2-dichloroethane, chlorobenzene, or dichlorobenzene; an ether such as diethyl ether, diisopropyl ether, tetrahydrofuran, dioxane, dimethoxyethane, or tert-butyl methyl ether; an aromatic hydrocarbon such as benzene, toluene, or xylene; an amide such as formamide, N,N-dimethylformamide, dimethylacetamide, N-methyl-2-pyrrolidone, or hexamethylphosphortriamide; or a sulfoxide such as dimethyl sulfoxide. The solvent is preferably an amide or a sulfoxide, more preferably N,N-dimethylformamide or dimethyl sulfoxide.

The base used in this step can be an organic base such as triethylamine, diisopropylethylamine, 1,8-diazabicyclo[5.4.0]-7-undecene, N-methylmorpholine, pyridine, dimethylaminopyridine, or 2,6-lutidine. The base is preferably triethylamine, diisopropylethylamine, 1,8-diazabicyclo[5.4.0]-7-undecene, pyridine, or dimethylaminopyridine.

The arylating agent or the heteroarylating agent used in this step refers to a compound represented by the formula R—F, R—Cl, or R—Br and is preferably a compound represented by the formula R—F or R—Cl (wherein R is as defined above).

The reaction temperature of this step is preferably 20° C. to 200° C.

In order to promote the reaction of this step, the reaction solution may be heated and may also be irradiated with microwaves.

The reaction time of this step is preferably 5 minutes to 120 hours, more preferably 10 minutes to 96 hours.

Production Method 3

The intermediate (II) of the compound of the present invention can also be produced by the following method:

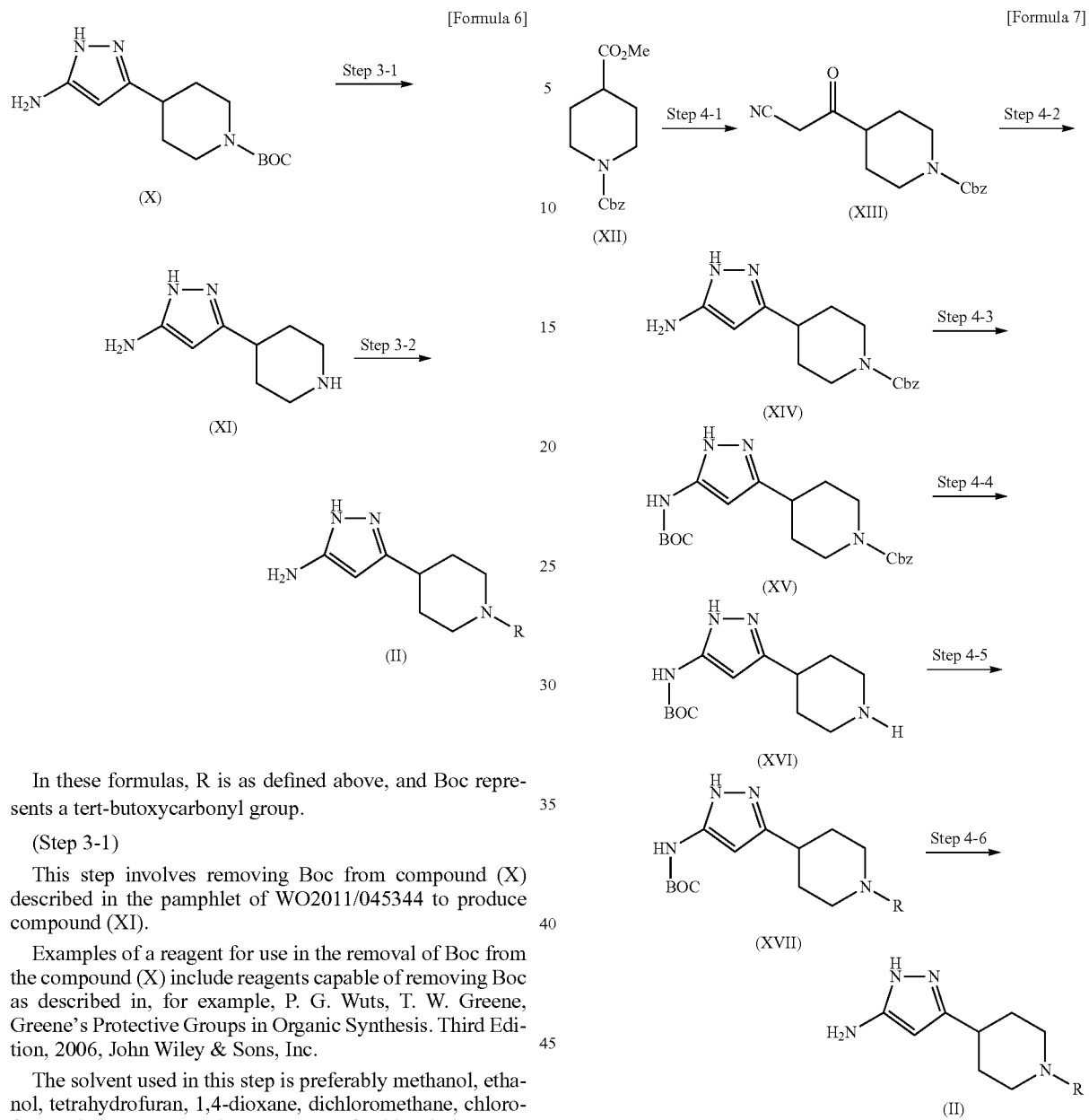

In these formulas, R is as defined above, and Boc represents a tert-butoxycarbonyl group.

(Step 3-1)

This step involves removing Boc from compound (X) described in the pamphlet of WO2011/045344 to produce compound (XI).

Examples of a reagent for use in the removal of Boc from the compound (X) include reagents capable of removing Boc as described in, for example, P. G. Wuts, T. W. Greene, Greene's Protective Groups in Organic Synthesis. Third Edition, 2006, John Wiley & Sons, Inc.

The solvent used in this step is preferably methanol, ethanol, tetrahydrofuran, 1,4-dioxane, dichloromethane, chloroform, ethyl acetate, or toluene, more preferably ethyl acetate.

The reagent used in this step is preferably hydrochloric acid or trifluoroacetic acid, more preferably hydrochloric acid.

The reaction temperature of this step is preferably 0° C. to 100° C., more preferably 0° C. to 50° C.

The reaction time of this step is preferably 5 minutes to 24 hours, more preferably 10 minutes to 6 hours.

(Step 3-2)

This step involves reacting compound (XI) with an arylating agent or a heteroarylating agent to produce compound (II).

This step can be carried out under the same conditions as in (ii) of step 2-6.

Production Method 4

The intermediate (II) of the compound of the present invention can also be produced by the following method:

In these formulas, R is as defined above; Boc represents a tert-butoxycarbonyl group; and Cbz represents a benzyloxycarbonyl group.

(Step 4-1)

This step involves reacting compound (XII) described in the pamphlet of WO2007/111323 with acetonitrile using a base in an inert solvent to produce compound (XIII).

This step can be carried out under the same conditions as in step 2-1.

(Step 4-2)

This step involves reacting compound (XIII) with a hydrazine compound in an inert solvent to produce compound (XIV).

This step can be carried out under the same conditions as in step 2-2.

(Step 4-3)

This step involves protecting a nitrogen atom on the piperidine ring of compound (XIV) with Boc to produce compound (XV) and can be carried out according to the method described in N. Suryakiran, P. Prabhakar, Y. Venkateswarlu Synth. Commun., 2008, Vol. 38, p. 177-185 or a method equivalent thereto.

The solvent used in this step is preferably dichloromethane.

The reagent used in this step is preferably bismuth trichloride.

The reaction temperature of this step is 0° C. to 100° C., more preferably 0° C. to 50° C.

The reaction time of this step is preferably 5 minutes to 6 hours, more preferably 10 minutes to 3 hours.

(Step 4-4)

This step involves removing Cbz from compound (XV) to produce compound (XVI).

Examples of a reagent for use in the removal of Cbz from the compound (XV) include reagents capable of removing Cbz as described in, for example, P. G. Wuts, T. W. Greene, Greene's Protective Groups in Organic Synthesis. Third Edition, 2006, John Wiley & Sons, Inc.

The solvent used in this step is preferably methanol, ethanol, tetrahydrofuran, 1,4-dioxane, dichloromethane, chloroform, ethyl acetate, or toluene, more preferably methanol.

The reagent used in this step is palladium-carbon, palladium hydroxide-carbon, hydrochloric acid, or trifluoroacetic acid, more preferably palladium-carbon.

The reaction temperature of this step is preferably 0° C. to 100° C., more preferably 0° C. to 50° C.

The reaction time of this step is preferably 5 minutes to 24 hours, more preferably 1 hour to 10 hours.

(Step 4-5)

This step involves reacting compound (XVI) with an arylating agent or a heteroarylating agent to produce compound (XVII).

This step can be carried out under the same conditions as in (ii) of step 2-6.

(Step 4-6)

This step involves removing Boc from compound (XVII) to produce compound (II).

This step can be carried out under the same conditions as in step 3-1.

Production Method 5

Production method 5 is a method for producing the compound (I) of the present invention from compound (X) known in the art.

[Formula 8]

In these formulas, R is as defined above, and Boc represents a tert-butoxycarbonyl group.

(Step 5-1)

This step involves condensing compound (X) described in the pamphlet of WO2011/045344 with compound (III) under heating in a solvent inert to the reaction or in the absence of a solvent to produce compound (XVIII).

This step can be carried out under the same conditions as in step 1.

(Step 5-2)

This step involves removing the Boc group from compound (XVIII) to produce compound (XIV).

This step can be carried out under the same conditions as in step 3-1.

(Step 5-3)

This step involves reacting compound (XIV) with an arylating agent or a heteroarylating agent to produce compound (I).

This step can be carried out under the same conditions as in (ii) of step 2-6. However, when the heteroarylating agent is an N-oxide compound, the reaction can be performed under the same conditions as in (ii) of step 2-6, followed by reaction with a reducing agent to produce compound (I).

The reducing agent used in the reaction is, for example, iron powder, palladium-carbon, Raney nickel, or platinum oxide and is more preferably iron powder.

The solvent used in the reaction is, for example, acetic acid, an alcohol solvent, THF, or water and is preferably acetic acid.

The reaction temperature is preferably 0° C. to 100° C., more preferably 20° C. to 100° C.

The reaction time is preferably 5 minutes to 24 hours, more preferably 1 hour to 5 hours.

If necessary, the product of each step mentioned above can be isolated as a free compound or a salt thereof from the reaction mixture after the completion of the reaction by a routine method, for example, (1) a method of directly concentrating the reaction solution, (2) a method of filtering off insoluble matter such as a catalyst and concentrating the filtrate, (3) a method of adding water and a solvent immiscible with water (e.g., dichloroethane, diethyl ether, ethyl acetate, or toluene) to the reaction solution to extract a product, or (4) a method of collecting a crystallized or precipitated product by filtration. The isolated product can be purified, if necessary, by a routine method, for example, recrystallization, reprecipitation, or various chromatography techniques. Alternatively, the product of each step may be used in the subsequent step without being isolated or purified.

The compound (I) of the present invention is isolated and purified as a free compound or a pharmacologically acceptable salt, a hydrate, or a solvate thereof. The pharmacologically acceptable salt of the compound (I) of the present invention can be produced through a salt-forming reaction of the compound (I) by a routine method. The isolation and purification are carried out by application of usual chemical operations such as extraction, concentration, distillation, crystallization, filtration, recrystallization, or various chromatography techniques.

Various isomers can be separated by exploiting differences in physicochemical properties between the isomers. For example, a racemic mixture can be converted to an optically pure isomer by, for example, fractionated crystallization for producing a diastereomer salt with an optically active base or acid or chromatography using a chiral column. Also, a diastereomeric mixture can be separated by, for example, fractionated crystallization or various chromatography techniques. Alternatively, an optically active compound can also be produced using an appropriate optically active starting material.

Examples of dosage forms of the compound represented by the general formula (I) of the present invention or the pharmacologically acceptable salt thereof can include: oral administration forms such as tablets, granules, powders, capsules, and syrups; and parenteral administration forms such as injections and suppositories. These formulations can be administered systemically or locally.

Examples of forms of oral medicaments comprising the compound represented by the general formula (I) of the present invention or the pharmacologically acceptable salt thereof include tablets, pills, granules, powders, capsules, solutions, suspension, emulsions, syrups, and elixirs. Examples of forms of parenteral medicaments comprising the compound represented by the general formula (I) of the present invention or the pharmacologically acceptable salt thereof include injections, ointments, gels, creams, patches, aerosols, inhalants, sprays, eye drops, and suppositories. The medicaments in these forms can be prepared according to a routine method using additives appropriately selected according to need from pharmaceutically acceptable additives such as excipients, binders, diluents, stabilizers, antiseptics, colorants, solubilizers, suspending agents, buffers, and wetting agents.

The dose at which the compound represented by the general formula (I) of the present invention or the pharmacologically acceptable salt thereof is administered differs depending on the symptoms, body weight, and age of a recipient (a warm-blooded animal, for example, a human), the administration method, etc. For example, in the case of oral administration, a single dose is 0.01 mg/kg body weight (preferably 0.03 mg/kg body weight) as the lower limit and 300 mg/kg body weight (preferably 100 mg/kg body weight) as the upper limit and is desirably administered one to several times a day according to the symptoms. In the case of intravenous administration, a single dose is 0.01 mg/kg body weight (preferably 0.03 mg/kg body weight) as the lower limit and 300 mg/kg body weight (preferably 100 mg/kg body weight) as the upper limit and is desirably administered one to several times a day according to the symptoms.

Hereinafter, the present invention will be described in more detail with reference to Examples, Test Examples, and Formulation Examples. However, the scope of the present invention is not intended to be limited by these. In the Examples given below, hexane represents n-hexane; THF represents tetrahydrofuran; and DMF represents N,N'-dimethylformamide.

EXAMPLES

Reference Example 1

3-Oxo-3-[1-(pyridin-2-yl)piperidin-4-yl]propanenitrile

[Formula 9]

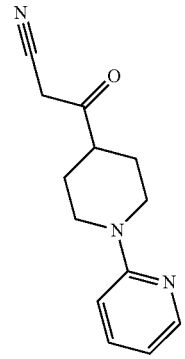

Five drops of DMF were added to a solution of 1-(pyridin-2-yl)piperidine-4-carboxylic acid (1.10 g, 5.33 mmol) in dichloromethane (20 mL), then oxalyl chloride (0.60 mL, 6.88 mmol) was added thereto at 0° C., and the mixture was stirred for 25 minutes. Then, the solvent in the reaction solution was distilled off under reduced pressure to obtain an acid chloride compound.

n-Butyllithium (2.69 M solution in hexane, 7.50 mL, 20.18 mmol) was added dropwise at −78° C. to a solution of cyanoacetic acid (800 mg, 9.41 mmol) and 2,2'-bipyridyl (5 mg, 0.03 mmol) in anhydrous THF (50 mL), and then, the mixture was stirred at the same temperature as above for 30 minutes. To the resulting reaction solution, a solution of the above-obtained acid chloride compound in anhydrous THF (10 mL) was added dropwise at −78° C., and the mixture was stirred at the same temperature as above for 1 hour. A saturated ammonium chloride aqueous solution was added to the reaction solution, followed by extraction with ethyl acetate. The obtained organic layer was washed with brine and dried over anhydrous magnesium sulfate, and the solvent was distilled off under reduced pressure. The obtained residue was purified by silica gel column chromatography [elute: hexane/ethyl acetate=100/0-40/60 (gradient)] to obtain the title compound (138 mg, yield: 11%).

$^1$H-NMR (400 MHz, CDCl$_3$) δ: 8.19-8.17 (1H, m), 7.50-7.46 (1H, m), 6.67 (1H, d, J=9 Hz), 6.65-6.61 (1H, m), 4.33

(2H, dt, J=13 Hz, 3 Hz), 3.56 (2H, s), 2.98-2.91 (2H, m), 2.81 (1H, tt, J=12 Hz, 4 Hz), 1.99 (2H, dd, J=15 Hz, 3 Hz), 1.72 (2H, dq, J=12 Hz, 4 Hz).

Reference Example 2

3-[1-(Pyridin-2-yl)piperidin-4-yl]-1H-pyrazol-5-amine

[Formula 10]

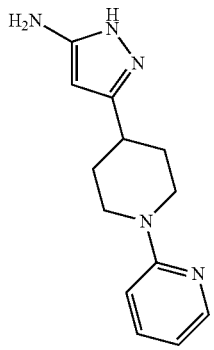

Hydrazine monohydrate (0.20 mL, 4.12 mmol) was added to a solution of 3-oxo-3-[1-(pyridin-2-yl)piperidin-4-yl]propanenitrile (138 mg, 0.60 mmol) produced in Reference Example 1 in ethanol (20 mL), and the mixture was stirred for 5 hours under heating to reflux. The reaction solution was left until reaching room temperature, and then, the solvent was distilled off under reduced pressure. The obtained residue was purified by silica gel column chromatography [elute: ethyl acetate/methanol=100/0-94/6 (gradient)] to obtain the title compound (130 mg, yield: 89%).

$^1$H-NMR (500 MHz, DMSO-d$_6$) δ: 11.18 (1H, brs), 8.09 (1H, d, J=4 Hz), 7.50 (1H, t, J=8 Hz), 6.83 (1H, d, J=9 Hz), 6.59 (1H, t, J=6 Hz), 5.18 (1H, s), 4.45 (2H, brs), 4.31 (2H, d, J=13 Hz), 2.85 (2H, t, J=13 Hz), 2.70 (1H, t, J=12 Hz), 1.87 (2H, d, J=13 Hz), 1.55-1.44 (2H, m).

Reference Example 3

3-(1-Phenylpiperidin-4-yl)-1H-pyrazol-5-amine

[Formula 11]

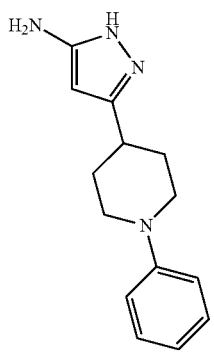

(1) 3-Oxo-3-(1-phenylpiperidin-4-yl)propanenitrile was obtained through the same reaction as in Reference Example 1 using 1-phenylpiperidine-4-carboxylic acid (1.01 g, 4.92 mmol) instead of 1-(pyridin-2-yl)piperidine-4-carboxylic acid.

(2) The title compound (648 mg, yield: 54%) was obtained through the same reaction as in Reference Example 2 using the compound obtained in (1) instead of 3-oxo-3-[1-(pyridin-2-yl)piperidin-4-yl]propanenitrile.

$^1$H-NMR (500 MHz, DMSO-d$_6$) δ: 11.19 (1H, brs), 7.23 (2H, t, J=8 Hz), 6.98 (2H, d, J=8 Hz), 6.78 (1H, t, J=7 Hz), 5.25 (1H, brs), 4.40 (1H, brs), 4.15 (1H, brs), 3.73 (2H, d, J=13 Hz), 2.75 (2H, td, J=12 Hz, 2 Hz), 2.68-2.58 (1H, m), 1.98-1.91 (2H, m), 1.67 (2H, dq, J=12 Hz, 4 Hz).

Reference Example 4

3-[1-(6-Methylpyridin-2-yl)piperidin-4-yl]-1H-pyrazol-5-amine

[Formula 12]

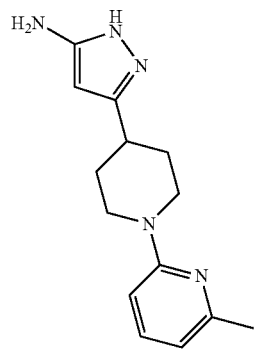

n-Butyllithium (2.69 M solution in hexane, 7.60 mL, 20.44 mmol) was added dropwise at −78° C. to a solution of anhydrous acetonitrile (1.10 mL, 21.01 mmol) in anhydrous tetrahydrofuran (50 mL). After stirring at the same temperature as above for 20 minutes, a solution of ethyl 1-(6-methylpyridin-2-yl)piperidine-4-carboxylate (compound described in the pamphlet of WO2010/097576, 1.70 g, 6.85 mmol) in anhydrous THF (10 mL) was added dropwise thereto at −78° C., and the mixture was stirred at the same temperature as above for 30 minutes. A saturated ammonium chloride aqueous solution was added to the reaction solution, followed by extraction with ethyl acetate. The obtained organic layer was washed with brine and dried over anhydrous magnesium sulfate, and the solvent was distilled off under reduced pressure.

Hydrazine monohydrate (1.00 mL, 20.58 mmol) was added to a solution of the obtained residue in ethanol (50 mL), and the mixture was stirred for 3 hours under heating to reflux. The reaction solution was left at room temperature, and then, the solvent was distilled off under reduced pressure. The obtained residue was purified by silica gel column chromatography [elute: ethyl acetate/methanol=100/0-94/6 (gradient)] to obtain the title compound (1.52 g, yield: 86%).

$^1$H-NMR (400 MHz, DMSO-d$_6$) δ: 11.13 (1H, brs), 7.39 (1H, t, J=8 Hz), 6.61 (1H, d, J=8 Hz), 6.46 (1H, d, J=7 Hz), 5.19 (1H, brs), 4.45-4.23 (4H, m), 2.81 (2H, t, J=12 Hz), 2.68 (1H, brs), 2.29 (3H, s), 1.88 (2H, d, J=13 Hz), 1.50 (2H, dq, J=12 Hz, 4 Hz).

Reference Example 5

3-[1-(5-Methylpyridin-2-yl)piperidin-4-yl]-1H-pyrazol-5-amine

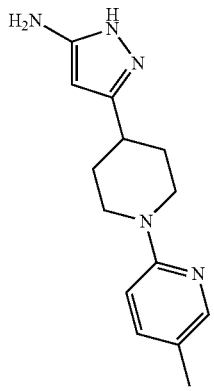

[Formula 13]

The title compound (480 mg, yield: 45%) was obtained through reaction in the same way as the method described in Reference Example 4 using ethyl 1-(5-methylpyridin-2-yl)piperidine-4-carboxylate (compound described in the pamphlet of WO2010/097576, 1.02 g, 4.11 mmol) instead of ethyl 1-(6-methylpyridin-2-yl)piperidine-4-carboxylate.

$^1$H-NMR (500 MHz, DMSO-$d_6$) δ: 11.11 (1H, brs), 7.93 (1H, s), 7.35 (1H, dd, J=9 Hz, 2 Hz), 6.76 (1H, d, J=9 Hz), 5.18 (1H, s), 4.41 (2H, brs), 4.23 (2H, d, J=13 Hz), 2.80 (2H, td, J=13 Hz, 2 Hz), 2.67 (1H, t, J=11 Hz), 2.13 (3H, s), 1.86 (2H, d, J=12 Hz), 1.50 (2H, dq, J=12 Hz, 4 Hz).

Reference Example 6

3-[1-(4-Methylpyridin-2-yl)piperidin-4-yl]-1H-pyrazol-5-amine

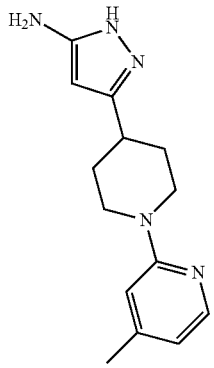

[Formula 14]

The title compound (1.07 g, yield: 69%) was obtained through reaction in the same way as the method described in Reference Example 4 using ethyl 1-(4-methylpyridin-2-yl)piperidine-4-carboxylate (compound described in the pamphlet of WO2010/097576, 1.49 g, 6.00 mmol) instead of ethyl 1-(6-methylpyridin-2-yl)piperidine-4-carboxylate.

$^1$H-NMR (500 MHz, DMSO-$d_6$) δ: 11.12 (1H, brs), 7.95 (1H, d, J=5 Hz), 6.67 (1H, s), 6.44 (1H, d, J=4 Hz), 5.19 (1H, brs), 4.49-4.26 (4H, m), 2.84 (2H, t, J=12 Hz), 2.70 (1H, brs), 2.21 (3H, s), 1.87 (2H, d, J=12 Hz), 1.54-1.44 (2H, m).

Reference Example 7

3-[1-(3-Methylpyridin-2-yl)piperidin-4-yl]-1H-pyrazol-5-amine

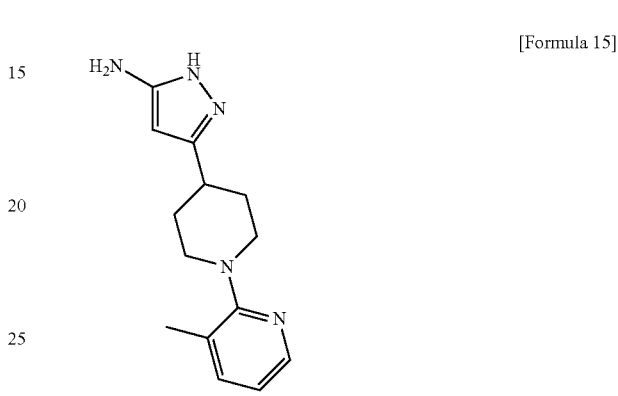

[Formula 15]

The title compound (2.20 g, yield: 80%) was obtained through reaction in the same way as the method described in Reference Example 4 using ethyl 1-(3-methylpyridin-2-yl)piperidine-4-carboxylate (compound described in the pamphlet of WO2010/097576, 2.64 g, 10.64 mmol) instead of ethyl 1-(6-methylpyridin-2-yl)piperidine-4-carboxylate.

$^1$H-NMR (500 MHz, DMSO-$d_6$) δ: 8.09 (1H, d, J=5 Hz), 7.48 (1H, d, J=7 Hz), 6.90 (1H, dd, J=7 Hz, 5 Hz), 5.24 (1H, s), 3.41 (2H, d, J=13 Hz), 2.76 (2H, t, J=12 Hz), 2.61 (1H, t, J=12 Hz), 2.24 (3H, s), 1.92 (2H, d, J=12 Hz), 1.69 (2H, tt, J=18 Hz, 6 Hz).

Reference Example 8

3-{1-[6-(Trifluoromethyl)pyridin-2-yl]piperidin-4-yl}-1H-pyrazol-5-amine

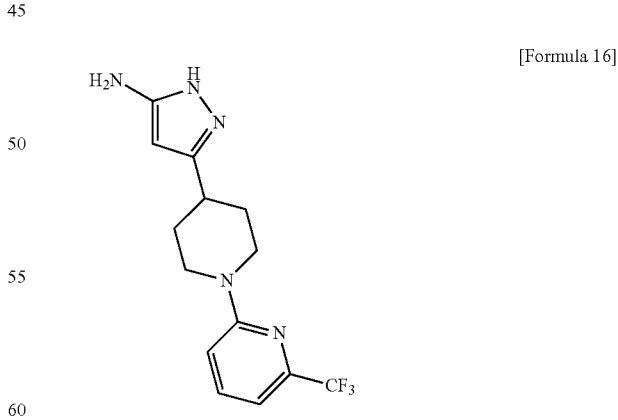

[Formula 16]

The title compound (1.10 g, yield: 98%) was obtained through reaction in the same way as the method described in Reference Example 4 using methyl 1-[6-(trifluoromethyl)pyridin-2-yl]piperidine-4-carboxylate (1.04 g, 3.61 mmol) instead of ethyl 1-(6-methylpyridin-2-yl) piperidine-4-carboxylate.

$^1$H-NMR (500 MHz, DMSO-d$_6$) δ: 11.15 (1H, brs), 7.72 (1H, t, J=8 Hz), 7.14 (1H, d, J=9 Hz), 6.99 (1H, d, J=7 Hz), 5.21 (1H, brs), 4.36 (3H, d, J=12 Hz), 2.95 (2H, t, J=12 Hz), 2.75 (1H, brs), 1.91 (2H, d, J=12 Hz), 1.51 (2H, dq, J=12 Hz, 4 Hz).

Reference Example 9

Methyl 1-[5-(trifluoromethyl)pyridin-2-yl]piperidine-4-carboxylate

[Formula 17]

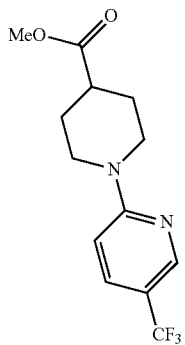

Methyl iodide (0.30 mL, 4.82 mmol) was added to a solution of 1-[5-(trifluoromethyl)pyridin-2-yl]piperidine-4-carboxylic acid (1.00 g, 3.65 mmol) and potassium carbonate (800 mg, 5.79 mmol) in DMF (10 mL), and the mixture was stirred at room temperature for 6 hours. Water was added to the reaction solution, followed by extraction with diethyl ether twice. The obtained organic layer was washed with brine and dried over anhydrous magnesium sulfate, and the solvent was distilled off under reduced pressure. The obtained residue was purified by silica gel column chromatography [elute: hexane/ethyl acetate=100/0-60/40 (gradient)] to obtain the title compound (1.03 g, yield: 98%).

$^1$H-NMR (500 MHz, CDCl$_3$) δ: 8.38 (1H, s), 7.61 (1H, dd, J=9 Hz, 2 Hz), 6.65 (1H, d, J=9 Hz), 4.33-4.28 (2H, m), 3.71 (3H, s), 3.10-3.05 (2H, m), 2.61 (1H, tt, J=11 Hz, 4 Hz), 2.04-1.98 (2H, m), 1.80-1.71 (2H, m).

Reference Example 10

3-{1-[5-(Trifluoromethyl)pyridin-2-yl]piperidin-4-yl}-1H-pyrazol-5-amine

[Formula 18]

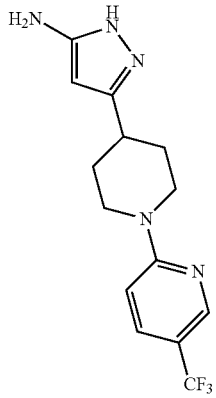

n-Butyllithium (2.69 M solution in hexane, 4.00 mL, 10.8 mmol) was added dropwise at −78° C. to a solution of anhydrous acetonitrile (0.60 mL, 11.5 mmol) in anhydrous THF (30 mL), and then, the mixture was stirred at the same temperature as above for 20 minutes. Then, a solution of methyl 1-[5-(trifluoromethyl)pyridin-2-yl]piperidine-4-carboxylate (1.03 g, 3.57 mmol) produced in Reference Example 9 in anhydrous THF (10 mL) was added dropwise thereto at −78° C., and the mixture was stirred at the same temperature as above for 30 minutes. A saturated ammonium chloride aqueous solution was added to the reaction solution, followed by extraction with ethyl acetate three times. The obtained organic layer was washed with brine and dried over anhydrous magnesium sulfate, and the solvent was distilled off under reduced pressure.

Hydrazine monohydrate (1.00 mL, 20.6 mmol) was added to a solution of the obtained residue in ethanol (30 mL), and the mixture was stirred for 3 hours under heating to reflux. The reaction solution was left at room temperature, and then, the solvent was distilled off under reduced pressure. The obtained residue was purified by silica gel column chromatography [elute: ethyl acetate/methanol=100/0-94/6 (gradient)] to obtain the title compound (880 mg, yield: 79%).

$^1$H-NMR (500 MHz, DMSO-d$_6$) δ: 11.14 (1H, brs), 8.39 (1H, s), 7.76 (1H, dd, J=9 Hz, 2 Hz), 6.98 (1H, d, J=9 Hz), 5.20 (1H, brs), 4.51-4.25 (4H, m), 3.01 (2H, t, J=12 Hz), 2.78 (1H, brs), 1.90 (2H, d, J=12 Hz), 1.49 (2H, dq, J=12 Hz, 4 Hz).

Reference Example 11

3-{1-[3-(Trifluoromethyl)pyridin-2-yl]piperidin-4-yl}-1H-pyrazol-5-amine

[Formula 19]

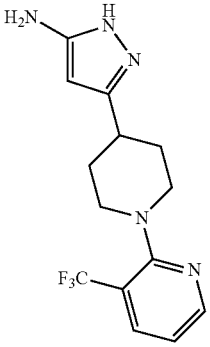

The title compound (765 mg, yield: 81%) was obtained through reaction in the same way as the method described in Reference Example 4 using ethyl 1-[3-(trifluoromethyl)pyridin-2-yl]piperidine-4-carboxylate (1.00 g, 3.31 mmol) instead of ethyl 1-(6-methylpyridin-2-yl) piperidine-4-carboxylate.

$^1$H-NMR (400 MHz, DMSO-d$_6$) δ: 11.15 (1H, brs), 8.51 (1H, dd, J=5 Hz, 1 Hz), 8.05 (1H, dd, J=8 Hz, 2 Hz), 7.16 (1H, dd, J=8 Hz, 5 Hz), 5.21 (1H, brs), 4.45 (2H, brs), 3.52 (2H, d, J=13 Hz), 2.95 (2H, t, J=11 Hz), 2.71-2.60 (1H, m), 1.92 (2H, d, J=11 Hz), 1.65 (2H, dq, J=12 Hz, 3 Hz).

Reference Example 12

3-{1-[3-Chloro-5-(trifluoromethyl)pyridin-2-yl]piperidin-4-yl}-1H-pyrazol-5-amine

[Formula 20]

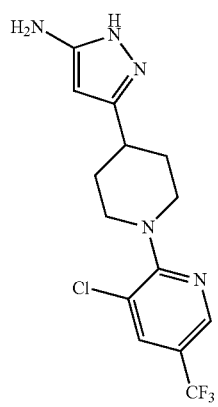

The title compound (1.16 g, yield: 57%) was obtained through reaction in the same way as the method described in Reference Example 4 using ethyl 1-[3-chloro-5-(trifluoromethyl)pyridin-2-yl]piperidine-4-carboxylate (2.00 g, 5.94 mmol) instead of ethyl 1-(6-methylpyridin-2-yl)piperidine-4-carboxylate.

$^1$H-NMR (500 MHz, DMSO-d$_6$) δ: 11.15 (1H, brs), 8.54 (1H, s), 8.17 (1H, d, J=2 Hz), 5.21 (1H, brs), 4.55-4.36 (2H, m), 4.02 (2H, d, J=14 Hz), 3.11-2.96 (2H, m), 2.73 (1H, t, J=12 Hz), 1.93 (2H, t, J=11 Hz), 1.67 (2H, dq, J=12 Hz, 3 Hz).

Reference Example 13

Ethyl 1-(3-chloropyridin-2-yl)piperidine-4-carboxylate

[Formula 21]

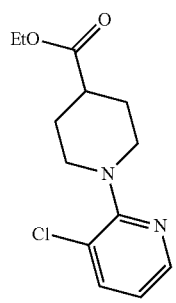

Sodium tert-butoxide (0.936 g, 9.74 mmol), 2,2'-bis(diphenylphosphino)-1,1'-binaphthyl (0.364 g, 0.585 mmol), and tris(dibenzylideneacetone)dipalladium(0) (0.178 g, 0.195 mmol) were added to a solution of ethyl piperidine-4-carboxylate (2.45 g, 15.6 mmol) and 2-bromo-3-chloropyridine (1.50 g, 7.79 mmol) in toluene (30 mL) under a nitrogen atmosphere, and the mixture was stirred for 4 hours under heating to reflux. A saturated ammonium chloride aqueous solution was added to the reaction solution, followed by extraction with ethyl acetate twice. The obtained organic layer was washed with brine and then dried over anhydrous sodium sulfate, and the solvent was distilled off under reduced pressure. The obtained residue was purified by silica gel column chromatography [elute: hexane/ethyl acetate=90/10] to obtain the title compound (0.813 g, yield: 39%).

$^1$H-NMR (400 MHz, CDCl$_3$) δ: 8.17 (1H, dd, J=5 Hz, 2 Hz), 7.58 (1H, dd, J=8 Hz, 2 Hz), 6.83 (1H, dd, J=8 Hz, 5 Hz), 4.17 (2H, q, J=7 Hz), 3.81-3.76 (2H, m), 2.92-2.85 (2H, m), 2.54-2.45 (1H, m), 2.05-1.85 (4H, m), 1.28 (3H, t, J=7 Hz).

Reference Example 14

3-[1-(3-Chloropyridin-2-yl)piperidin-4-yl]-1H-pyrazol-5-amine

[Formula 22]

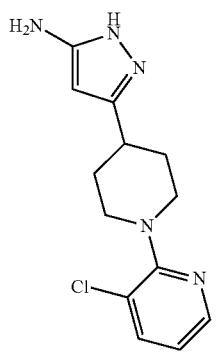

The title compound (667 mg, yield: 79%) was obtained through reaction in the same way as the method described in Reference Example 4 using ethyl 1-(3-chloropyridin-2-yl)piperidine-4-carboxylate (813 mg, 3.03 mmol) produced in Reference Example 13 instead of ethyl 1-(6-methylpyridin-2-yl)piperidine-4-carboxylate.

$^1$H-NMR (400 MHz, CDCl$_3$) δ: 8.19 (1H, dd, J=5 Hz, 2 Hz), 7.60 (1H, dd, J=8 Hz, 2 Hz), 6.85 (1H, dd, J=8 Hz, 5 Hz), 5.53 (1H, s), 3.90-3.85 (2H, m), 2.95-2.88 (2H, m), 2.80-2.71 (1H, m), 2.06-2.00 (2H, m), 1.93-1.82 (2H, m).

Reference Example 15

Ethyl 1-(6-methoxypyridin-2-yl)piperidine-4-carboxylate

[Formula 23]

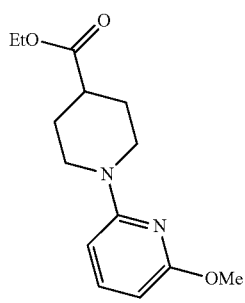

Diisopropylethylamine (2.16 mL, 12.7 mmol) was added to a solution of ethyl piperidine-4-carboxylate (2.00 g, 12.7 mmol) and 2-chloro-6-methoxypyridine (1.48 mL, 12.7 mmol) in DMF (10 mL), and the mixture was stirred while irradiated with microwaves at 150° C. for 3 hours using Initiator® manufactured by Biotage Japan Ltd. Water was added to the reaction solution, followed by extraction with ethyl acetate. The obtained organic layer was dried over anhydrous sodium sulfate, and the solvent was distilled off under reduced pressure. The obtained residue was purified by silica gel column chromatography [elute: hexane/ethyl acetate=90/10] to obtain the title compound (365 mg, yield: 11%).

$^1$H-NMR (400 MHz, CDCl$_3$) δ: 7.39 (1H, t, J=8 Hz), 6.18 (1H, d, J=8 Hz), 6.05 (1H, d, J=8 Hz), 4.25-4.19 (2H, m), 4.15 (2H, q, J=7 Hz), 3.86 (3H, s), 2.97-2.89 (2H, m), 2.55-2.47 (1H, m), 2.00-1.94 (2H, m), 1.81-1.71 (2H, m), 1.27 (3H, t, J=7 Hz).

Reference Example 16

3-[1-(6-Methoxypyridin-2-yl)piperidin-4-yl]-1H-pyrazol-5-amine

[Formula 24]

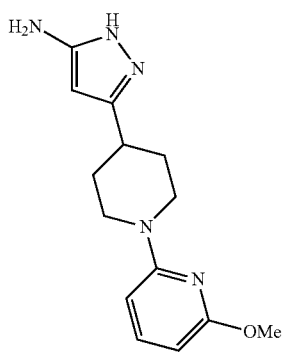

The title compound (386 mg, yield: 75%) was obtained through reaction in the same way as the method described in Reference Example 4 using ethyl 1-(6-methoxypyridin-2-yl)piperidine-4-carboxylate (500 mg, 1.89 mmol) produced in Reference Example 15 instead of ethyl 1-(6-methylpyridin-2-yl)piperidine-4-carboxylate.

$^1$H-NMR (500 MHz, CD$_3$OD) δ: 7.40 (1H, t, J=8 Hz), 6.28 (1H, d, J=8 Hz), 6.01 (1H, d, J=8 Hz), 5.44 (1H, s), 4.39-4.33 (2H, m), 3.82 (3H, s), 2.92-2.85 (2H, m), 2.81-2.75 (1H, m), 1.98-1.91 (2H, m), 1.71-1.61 (2H, m).

Reference Example 17

Ethyl 1-[4-(trifluoromethyl)pyridin-2-yl]piperidine-4-carboxylate

[Formula 25]

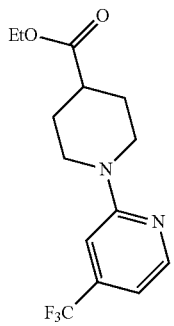

The title compound (1.12 g, yield: 42%) was obtained through reaction in the same way as the method described in Reference Example 13 using 2-bromo-4-(trifluoromethyl)pyridine (2.00 g, 8.85 mmol) instead of 2-bromo-3-chloropyridine.

$^1$H-NMR (500 MHz, CDCl$_3$) δ: 8.29 (1H, d, J=5 Hz), 6.81 (1H, s), 6.75 (1H, d, J=5 Hz), 4.28-4.25 (2H, m), 4.16 (2H, q, J=7 Hz), 3.06-3.01 (2H, m), 2.60-2.54 (1H, m), 2.04-1.99 (2H, m), 1.81-1.72 (2H, m), 1.27 (3H, t, J=7 Hz).

Reference Example 18

3-{1-[4-(Trifluoromethyl)pyridin-2-yl]piperidin-4-yl}-1H-pyrazol-5-amine

[Formula 26]

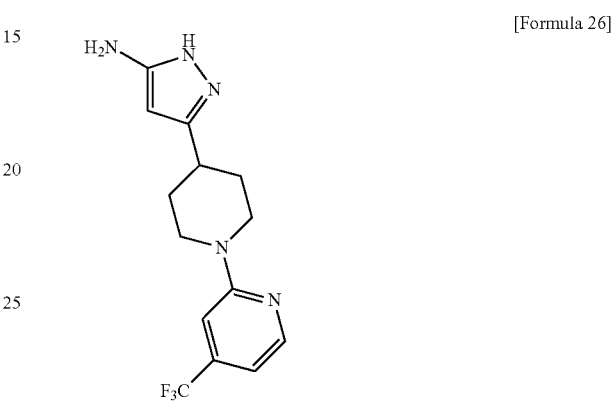

The title compound (1.02 g, yield: 89%) was obtained through reaction in the same way as the method described in Reference Example 4 using ethyl 1-[4-(trifluoromethyl)pyridin-2-yl]piperidine-4-carboxylate (1.12 g, 3.70 mmol) produced in Reference Example 17 instead of ethyl 1-(6-methylpyridin-2-yl)piperidine-4-carboxylate.

$^1$H-NMR (400 MHz, CDCl$_3$) δ: 8.29 (1H, d, J=5 Hz), 6.82 (1H, s), 6.76 (1H, d, J=5 Hz), 5.47 (1H, s), 4.44-4.37 (2H, m), 3.03-2.95 (2H, m), 2.88-2.79 (1H, m), 2.07-1.99 (2H, m), 1.75-1.64 (2H, m).

Reference Example 19

Ethyl 1-(5-chloropyridin-2-yl)piperidine-4-carboxylate

[Formula 27]

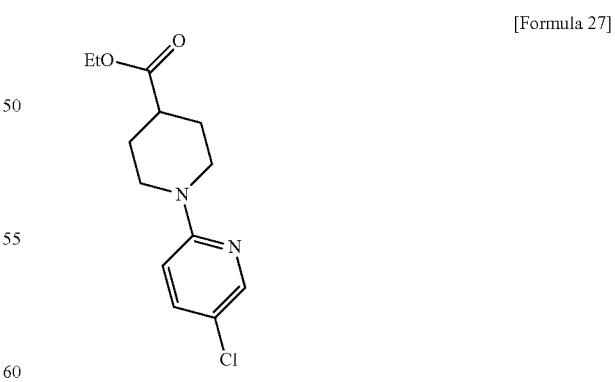

Sodium t-butoxide (1.25 g, 13.0 mmol), 2,2-bis(diphenylphosphino)-1,1-binaphthyl (0.485 g, 0.779 mmol), and tris(dibenzylideneacetone)dipalladium(0) (0.238 g, 0.260 mmol) were added to a solution of ethyl piperidine-4-carboxylate (2.00 g, 10.4 mmol) and 2-bromo-5-chloropyridine (2.00 g, 10.4 mmol) in toluene (50 mL), and the mixture was stirred for 1 hour under heating to reflux. A saturated ammonium chloride aqueous solution was added to the reaction solution, followed by extraction with toluene twice. The obtained organic layer was washed with brine and then dried over anhydrous sodium sulfate, and the solvent was distilled off under reduced pressure. The obtained residue was purified by silica gel column chromatography [elute: hexane/ethyl acetate=85/15] to obtain the title compound (1.47 g, yield: 53%).

$^1$H-NMR (500 MHz, CDCl$_3$) δ: 8.10 (1H, d, J=3 Hz), 7.40 (1H, dd, J=9 Hz, 3 Hz), 6.60 (1H, d, J=9 Hz), 4.18-4.10 (4H, m), 2.99-2.93 (2H, m), 2.55-2.49 (1H, m), 2.01-1.96 (2H, m), 1.80-1.71 (2H, m), 1.26 (3H, t, J=7 Hz).

Reference Example 20

3-[1-(5-Chloropyridin-2-yl)piperidin-4-yl]-1H-pyrazol-5-amine

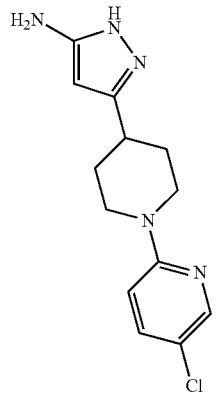

[Formula 28]

n-Butyllithium (2.69 M solution in hexane, 6.10 mL, 16.4 mmol) was added dropwise at −78° C. to a solution of anhydrous acetonitrile (0.71 mL, 17.0 mmol) in anhydrous THF (60 mL), and then, the mixture was stirred at the same temperature as above for 20 minutes. Then, a solution of ethyl 1-(5-chloropyridin-2-yl)piperidine-4-carboxylate (1.47 g, 5.47 mmol) produced in Reference Example 19 in anhydrous THF (10 mL) was added dropwise thereto at −78° C., and the mixture was stirred at the same temperature as above for 30 minutes. A saturated ammonium chloride aqueous solution was added to the reaction solution, followed by extraction with an acetic acid-methanol mixed solution twice. The organic layer was dried over anhydrous magnesium sulfate, and the solvent was distilled off under reduced pressure.

Hydrazine monohydrate (0.795 mL, 16.4 mmol) was added to a solution of the obtained residue in ethanol (20 mL), and the mixture was stirred at 50° C. for 2 hours. The reaction solution was left at room temperature, and then, the solvent was distilled off under reduced pressure. The obtained residue was suspended in ethyl acetate. Insoluble matter was filtered off, and the solvent in the filtrate was distilled off under reduced pressure. The obtained residue was purified by silica gel column chromatography [elute: ethyl acetate/methanol=95/5-93/7 (gradient)] to obtain the title compound (0.484 g, yield: 32%).

$^1$H-NMR (400 MHz, CDCl$_3$) δ: 8.11 (1H, d, J=3 Hz), 7.41 (1H, dd, J=9 Hz, 3 Hz), 6.62 (1H, d, J=9 Hz), 5.47 (1H, s), 4.32-4.26 (2H, m), 2.97-2.89 (2H, m), 2.84-2.75 (1H, m), 2.03-1.98 (2H, m), 1.74-1.64 (2H, m).

Reference Example 21

Ethyl 1-(5-fluoropyridin-2-yl)piperidine-4-carboxylate

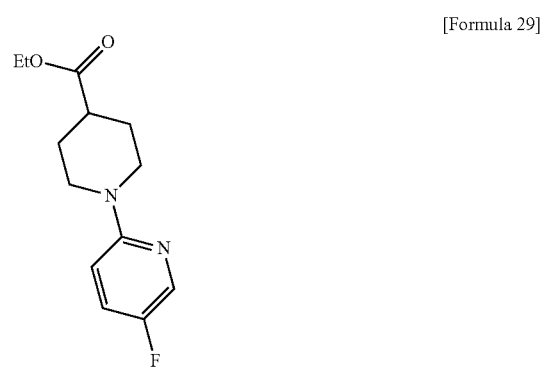 [SMILES: CCOC(=O)C1CCN(c2ccc(F)cn2)CC1]

[Formula 29]

The title compound (2.24 g, yield: 67%) was obtained through reaction in the same way as the method described in Reference Example 13 using 2-bromo-5-fluoropyridine (2.35 g, 13.4 mmol) instead of 2-bromo-3-chloropyridine.

$^1$H-NMR (500 MHz, CDCl$_3$) δ: 8.04 (1H, d, J=3 Hz), 7.26-7.22 (1H, m), 6.63 (1H, dd, J=9 Hz, 3 Hz), 4.18-4.08 (4H, m), 2.96-2.89 (2H, m), 2.54-2.47 (1H, m), 2.02-1.97 (2H, m), 1.82-1.73 (2H, m), 1.27 (3H, t, J=7 Hz).

Reference Example 22

3-[1-(5-Fluoropyridin-2-yl)piperidin-4-yl]-1H-pyrazol-5-amine

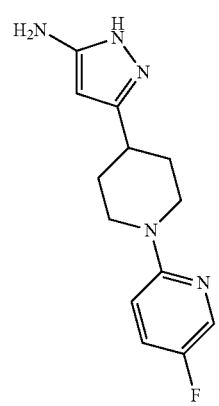

[Formula 30]

The title compound (1.46 g, yield: 63%) was obtained through reaction in the same way as the method described in Reference Example 4 using ethyl 1-(5-fluoropyridin-2-yl)piperidine-4-carboxylate (2.24 g, 8.88 mmol) produced in Reference Example 21 instead of ethyl 1-(6-methylpyridin-2-yl)piperidine-4-carboxylate.

$^1$H-NMR (400 MHz, CD$_3$OD) δ: 7.97 (1H, d, J=3 Hz), 7.40-7.34 (1H, m), 6.84 (1H, dd, J=9 Hz, 3 Hz), 5.44 (1H, s), 4.26-4.20 (2H, m), 2.94-2.87 (2H, m), 2.81-2.73 (1H, m), 2.00-1.93 (2H, m), 1.73-1.62 (2H, m).

Reference Example 23

Ethyl 1-(quinolin-2-yl)piperidine-4-carboxylate

[Formula 31]

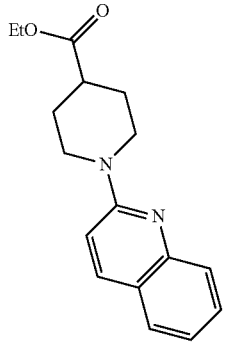

1-Ethyl-3-(3-dimethylaminopropyl)carbodiimide hydrochloride (1.79 g, 9.34 mmol) was added to a solution of 1-(quinolin-2-yl)piperidine-4-carboxylic acid hydrochloride (1.14 g, 3.89 mmol), N,N-dimethyl-4-aminopyridine (1.42 g, 11.6 mmol), and ethanol (546 μL, 9.34 mmol) in dichloromethane (20 mL), and the mixture was stirred overnight at room temperature. Then, the solvent in the reaction solution was distilled off under reduced pressure. A solution of the obtained residue in ethyl acetate was washed with water twice and brine once and dried over anhydrous sodium sulfate, and then, the solvent was distilled off under reduced pressure. The obtained residue was purified by silica gel column chromatography [elute: hexane/ethyl acetate=95/5-60/40 (gradient)] to obtain the title compound (1.07 g, yield: 96%).

$^1$H-NMR (CDCl$_3$) δ: 7.88 (1H, d, J=9 Hz), 7.69 (1H, d, J=8 Hz), 7.59 (1H, dd, J=8 Hz, 1 Hz), 7.55-7.50 (1H, m), 7.25-7.19 (1H, m), 7.00 (1H, d, J=9 Hz), 4.50-4.43 (2H, m), 4.16 (2H, q, J=7 Hz), 3.15-3.06 (2H, m), 2.62-2.54 (1H, m), 2.08-2.00 (2H, m), 1.86-1.75 (2H, m), 1.27 (3H, t, J=7 Hz).

Reference Example 24

3-[1-(Quinolin-2-yl)piperidin-4-yl]-1H-pyrazol-5-amine

[Formula 32]

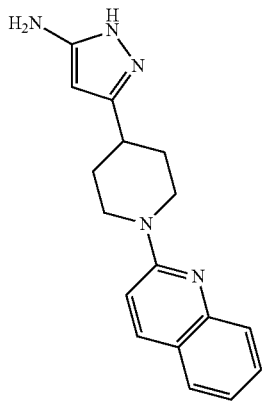

The title compound (1.01 g, yield: 98%) was obtained through reaction in the same way as the method described in Reference Example 4 using ethyl 1-(quinolin-2-yl)piperidine-4-carboxylate (1.00 g, 3.52 mmol) produced in Reference Example 23 instead of ethyl 1-(6-methylpyridin-2-yl)piperidine-4-carboxylate.

$^1$H-NMR (400 MHz, DMSO-d$_6$) δ: 8.94 (1H, br s), 8.01 (1H, d, J=9 Hz), 7.68 (1H, d, J=8 Hz), 7.56-7.48 (2H, m), 7.27 (1H, d, J=9 Hz), 7.25-7.18 (1H, m), 5.20 (1H, s), 4.61-4.54 (2H, m), 4.13 (2H, brs), 3.04-2.89 (2H, m), 2.83-2.73 (1H, m), 1.96-1.90 (2H, m), 1.60-1.50 (2H, m).

Reference Example 25

Ethyl 1-[6-(propan-2-yloxy)pyridazin-3-yl]piperidine-4-carboxylate

[Formula 33]

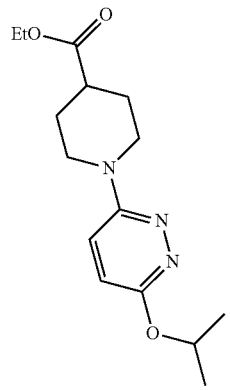

The title compound (3.05 g, yield: 67%) was obtained through reaction in the same way as the method described in Reference Example 13 using 3-chloro-6-(propan-2-yloxy)pyridazine (compound described in the pamphlet of WO2009/119537, 2.70 g, 15.6 mmol) instead of 2-bromo-3-chloropyridine.

$^1$H-NMR (500 MHz, CDCl$_3$) δ: 7.02 (1H, d, J=10 Hz), 6.77 (1H, d, J=10 Hz), 5.44-5.37 (1H, m), 4.15 (2H, q, J=7 Hz), 4.12-4.07 (2H, m), 3.03-2.97 (2H, m), 2.56-2.48 (1H, m), 2.03-1.98 (2H, m), 1.85-1.77 (2H, m), 1.37 (6H, d, J=6 Hz), 1.27 (3H, t, J=7 Hz).

Reference Example 26

3-{1-[6-(Propan-2-yloxy)pyridazin-3-yl]piperidin-4-yl}-1H-pyrazol-5-amine

[Formula 34]

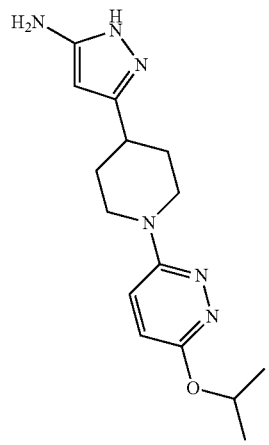

The title compound (2.53 g, yield: 80%) was obtained through reaction in the same way as the method described in Reference Example 4 using ethyl 1-[6-(propan-2-yloxy)pyridazin-3-yl]piperidine-4-carboxylate (3.05 g, 10.4 mmol) produced in Reference Example 25 instead of ethyl 1-(6-methylpyridin-2-yl)piperidine-4-carboxylate.

$^1$H-NMR (400 MHz, CD$_3$OD) δ: 7.35 (1H, d, J=10 Hz), 6.91 (1H, d, J=10 Hz), 5.45 (1H, s), 5.27-5.20 (1H, m), 4.21-4.16 (2H, m), 3.02-2.94 (2H, m), 2.85-2.75 (1H, m), 2.03-1.96 (2H, m), 1.77-1.67 (2H, m), 1.35 (6H, d, J=6 Hz).

Reference Example 27

Benzyl 4-(5-amino-1H-pyrazol-3-yl)piperidine-1-carboxylate

[Formula 35]

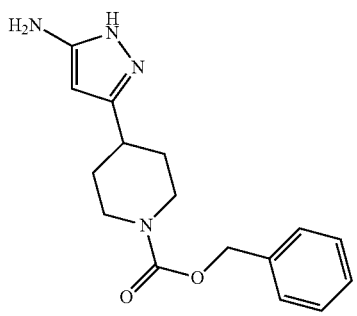

The title compound (10.38 g, yield: 61%) was obtained through reaction in the same way as the method described in Reference Example 4 using 1-benzyl 4-methyl piperidine-1,4-dicarboxylate (compound described in the pamphlet of WO2007/111323, 15.80 g, 56.98 mmol) instead of ethyl 1-(6-methylpyridin-2-yl)piperidine-4-carboxylate.

$^1$H-NMR (400 MHz, CDCl$_3$) δ: 7.39-7.29 (5H, m), 5.44 (1H, s), 5.14 (2H, s), 4.65 (2H, brs), 4.32-4.17 (2H, m), 2.97-2.83 (2H, m), 2.77-2.68 (1H, m), 1.97-1.86 (2H, m), 1.66-1.52 (2H, m).

Reference Example 28

Benzyl 4-{5-[(tert-butoxycarbonyl)amino]-1H-pyrazol-3-yl}piperidine-1-carboxylate

[Formula 36]

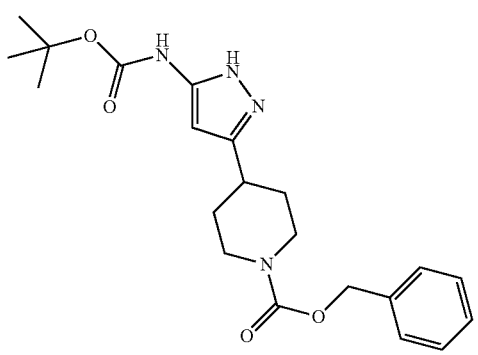

Reference Example 28 was carried out according to the method described in the literature (Synth. Commun., 2008, Vol. 38, p. 177-185). Bismuth trichloride (0.543 g, 1.73 mmol) was added to a solution of benzyl 4-(5-amino-1H-pyrazol-3-yl)piperidine-1-carboxylate (10.35 g, 34.4 mmol) produced in Reference Example 27 and di-tert-butyl dicarbonate (11.29 g, 51.7 mmol) in dichloromethane (105 mL), and the mixture was stirred at room temperature for 1 hour. A saturated sodium bicarbonate aqueous solution was added to the reaction solution, followed by extraction with ethyl acetate. The obtained organic layer was washed with brine and dried over anhydrous sodium sulfate, and the solvent was distilled off under reduced pressure. The obtained residue was purified by silica gel column chromatography [elute: hexane/ethyl acetate=60/40-40/60 (gradient)] to obtain the title compound (12.26 g, yield: 89%).

$^1$H-NMR (400 MHz, CDCl$_3$) δ: 7.39-7.28 (5H, m), 5.28-5.22 (3H, m), 5.14 (2H, s), 4.34-4.15 (2H, m), 2.95-2.71 (3H, m), 1.95-1.84 (2H, m), 1.71-1.49 (2H, m), 1.64 (9H, s).

Reference Example 29 tert-Butyl [3-(piperidin-4-yl)-1H-pyrazol-5-yl]carbamate

[Formula 37]

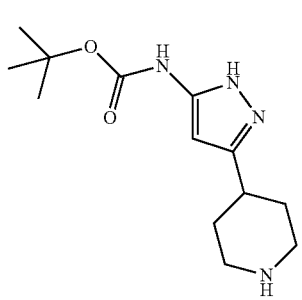

10% palladium-carbon (M type, wet product, 2.50 g) was added to a solution of benzyl 4-{5-[(tert-butoxycarbonyl)amino]-1H-pyrazol-3-yl}piperidine-1-carboxylate (12.25 g, 30.59 mmol) produced in Reference Example 28 in methanol (130 mL), and the mixture was stirred at room temperature for 8 hours under a hydrogen atmosphere. The catalyst in the reaction solution was filtered off, and the solvent in the obtained filtrate was distilled off under reduced pressure to obtain the title compound (8.50 g).

MS (ESI) m/z: 267 (M+H)$^+$.

Reference Example 30 tert-Butyl {3-[1-(5-cyanopyridin-2-yl)piperidin-4-yl]-1H-pyrazol-5-yl}carbamate

[Formula 38]

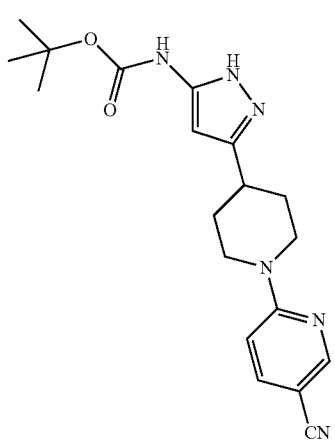

N,N-Diisopropylethylamine (1.18 mL, 6.76 mmol) was added to a solution of tert-butyl (3-piperidin-4-yl-1H-pyrazol-5-yl)carbamate (0.600 g, 2.25 mmol) produced in Reference Example 29 and 2-chloro-5-cyanopyridine (0.468 g, 3.38 mmol) in N-methylpyrrolidinone (12 mL), and the mixture was stirred at room temperature for 71 hours. Water was added to the reaction solution, followed by extraction with ethyl acetate. The obtained organic layer was washed with brine and dried over anhydrous sodium sulfate, and the solvent was distilled off under reduced pressure. The obtained residue was purified by silica gel column chromatography [elute: hexane/ethyl acetate=60/40-40/60 (gradient)] to obtain the title compound (0.387 g, yield: 49%).

$^1$H-NMR (400 MHz, CDCl$_3$) δ: 8.41-8.39 (1H, m), 7.59 (1H, dd, J=9 Hz, 2 Hz), 6.64-6.60 (1H, m), 5.28-5.22 (3H, m), 4.51-4.45 (2H, m), 3.07-2.99 (2H, m), 2.95-2.87 (1H, m), 2.05-1.99 (2H, m), 1.69-1.60 (2H, m), 1.65 (9H, s).

Reference Example 31

6-(5-Amino-1H-pyrazol-3-yl)piperidin-1-yl]pyridine-3-carbonitrile

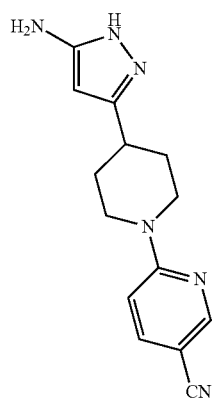

[Formula 39]

Trifluoroacetic acid (4 mL) was added to a solution of tert-butyl {3-[1-(5-cyanopyridin-2-yl)piperidin-4-yl]-1H-pyrazol-5-yl}carbamate (0.381 g, 1.03 mmol) produced in Reference Example 30 in dichloromethane (8 mL), and the mixture was stirred at room temperature for 16 hours. The reaction solution was neutralized by the addition of a 1 N sodium hydroxide aqueous solution, followed by extraction with ethyl acetate. The obtained organic layer was washed with brine and dried over anhydrous sodium sulfate, and the solvent was distilled off under reduced pressure. The obtained residue was purified by silica gel column chromatography [elute: ethyl acetate/methanol=90/10] to obtain the title compound (0.211 g, yield: 76%).

$^1$H-NMR (400 MHz, DMSO-d$_6$) δ: 11.12 (1H, brs), 8.47-8.45 (1H, m), 7.81 (1H, dd, J=9 Hz, 2 Hz), 6.97-6.93 (1H, m), 5.18 (1H, s), 4.56-4.32 (4H, m), 3.08-2.99 (2H, m), 2.83-2.72 (1H, m), 1.94-1.86 (2H, m), 1.53-1.43 (2H, m).

Reference Example 32

2-[4-(5-Amino-1H-pyrazol-3-yl)piperidin-1-yl]pyridine-4-carbonitrile

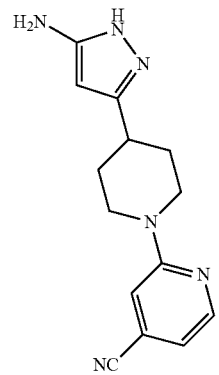

[Formula 40]

A crude product of tert-butyl {3-[1-(4-cyanopyridin-2-yl)piperidin-4-yl]-1H-pyrazol-5-yl}carbamate was obtained through reaction at 60° C. for 2 hours and further at 100° C. for 6.5 hours in the same way as the method described in Reference Example 30 using 2-chloro-4-cyanopyridine (0.390 g, 2.82 mmol) instead of 2-chloro-5-cyanopyridine.

The title compound (0.119 g, yield: 24%) was obtained through reaction in the same way as the method described in Reference Example 31 using the above-obtained crude product instead of tert-butyl {3-[1-(5-cyanopyridin-2-yl)piperidin-4-yl]-1H-pyrazol-5-yl}carbamate.

$^1$H-NMR (400 MHz, DMSO-d$_6$) δ: 11.13 (1H, brs), 8.27 (1H, dd, J=5 Hz, 1 Hz), 7.33-7.31 (1H, m), 6.89 (1H, dd, J=5 Hz, 1 Hz), 5.18 (1H, s), 4.45 (2H, brs), 4.41-4.34 (2H, m), 3.00-2.91 (2H, m), 2.79-2.71 (1H, m), 1.92-1.85 (2H, m), 1.53-1.44 (2H, m).

Reference Example 33

3-(Piperidin-4-yl)-1H-pyrazol-5-amine hydrochloride

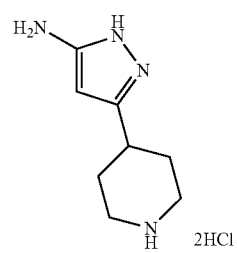

[Formula 41]

Hydrochloric acid (4 M solution in dioxane, 31.7 mL, 127 mmol) was added dropwise to a solution of tert-butyl 4-(5-amino-1H-pyrazol-3-yl)piperidine-1-carboxylate (compound described in the pamphlet of WO2011/045344, 13.5 g, 50.7 mmol) in ethyl acetate (60 mL) under ice cooling, and the mixture was stirred at room temperature for 3 hours. Ethyl acetate (40 mL) was added to the reaction solution, and the mixture was stirred for 10 minutes. Then, the obtained precipitate was collected by filtration to obtain the title compound (12.5 g, yield: 100%).

$^1$H-NMR (400 MHz, DMSO-d$_6$) δ: 9.06-8.85 (2H, m), 5.71 (1H, s), 3.34-3.26 (2H, m), 3.03-2.91 (3H, m), 2.11-2.03 (2H, m), 1.85-1.73 (2H, m).

Reference Example 34

3-[1-(6-Chloropyridazin-3-yl)piperidin-4-yl]-1H-pyrazol-5-amine

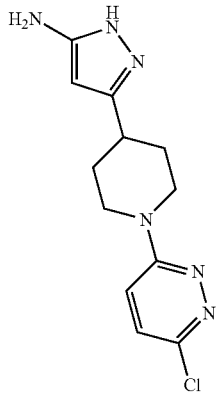 [SMILES: N#Cc1ncc(N2CCC(c3cc(N)[nH]n3)CC2)cc1F]

[Formula 42]

1,8-Diazabicyclo[5.4.0]-7-undecene (0.750 mL, 5.02 mmol) was added to a suspension of 3-(piperidin-4-yl)-1H-pyrazol-5-amine hydrochloride (0.400 g, 1.67 mmol) produced in Reference Example 33 in dimethyl sulfoxide (4 mL), and the mixture was stirred at room temperature for 10 minutes. Then, 3,6-dichloropyridazine (0.249 g, 1.67 mmol) was added thereto, and the mixture was stirred at room temperature for 1 hour and at 60° C. for 4 hours. After cooling to room temperature, water was added to the reaction solution, followed by extraction with ethyl acetate. The obtained organic layer was washed with brine and dried over anhydrous sodium sulfate, and the solvent was distilled off under reduced pressure. The obtained residue was purified by silica gel column chromatography [elute: ethyl acetate/methanol=95/5-90/10 (gradient)] to obtain the title compound (0.330 g, yield: 71%).

$^1$H-NMR (400 MHz, DMSO-$d_6$) δ: 11.13 (1H, br s), 7.49 (1H, d, J=10 Hz), 7.41 (1H, d, J=10 Hz), 5.19 (1H, brs), 4.43 (2H, brs), 4.39-4.31 (2H, m), 3.05-2.98 (2H, m), 2.81-2.73 (1H, m), 1.94-1.87 (2H, m), 1.58-1.49 (2H, m).

Reference Example 35

5-[4-(5-Amino-1H-pyrazol-3-yl)piperidin-1-yl]pyridine-3-carbonitrile

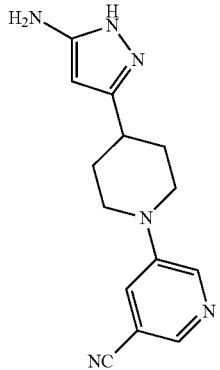

[Formula 43]

The title compound (0.167 g, yield: 37%) was obtained through reaction in the same way as the method described in Reference Example 34 using 5-fluoropyridine-3-carbonitrile (0.204 g, 1.67 mmol) instead of 3,6-dichloropyridazine.

$^1$H-NMR (400 MHz, DMSO-$d_6$) δ: 11.13 (1H, brs), 8.59 (1H, d, J=3 Hz), 8.28 (1H, d, J=2 Hz), 7.78 (1H, dd, J=3 Hz, 2 Hz), 5.20 (1H, brs), 4.45 (2H, brs), 3.94-3.87 (2H, m), 2.93-2.85 (2H, m), 2.73-2.64 (1H, m), 1.94-1.87 (2H, m), 1.65-1.55 (2H, m).

Reference Example 36

5-[4-(5-Amino-1H-pyrazol-3-yl)piperidin-1-yl]-3-fluoropyridine-2-carbonitrile

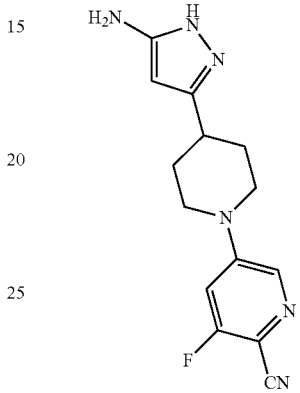

The title compound (0.276 g, yield: 58%) was obtained through reaction at room temperature for 3 hours in the same way as the method described in Reference Example 34 using 3,5-difluoropyridine-2-carbonitrile (0.234 g, 1.67 mmol) instead of 3,6-dichloropyridazine.

$^1$H-NMR (DMSO-$d_6$) δ: 11.13 (1H, brs), 8.32-8.30 (1H, m), 7.40 (1H, dd, J=14 Hz, 2 Hz), 5.19 (1H, s), 4.47 (2H, brs), 4.11-4.04 (2H, m), 3.13-3.05 (2H, m), 2.82-2.74 (1H, m), 1.95-1.87 (2H, m), 1.62-1.51 (2H, m).

Reference Example 37

5-[4-(5-Amino-1H-pyrazol-3-yl)piperidin-1-yl]pyridine-2-carbonitrile

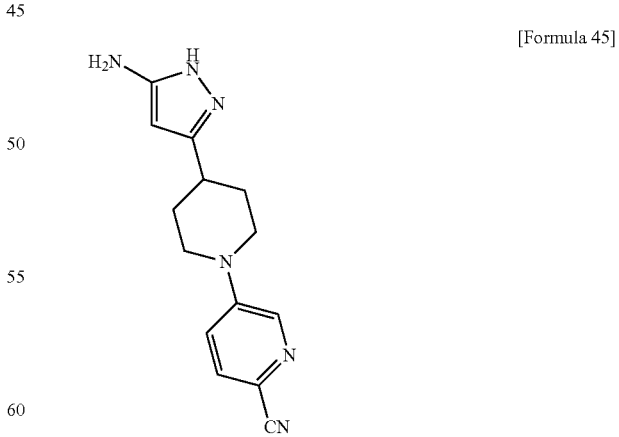

[Formula 45]

Reaction was performed at room temperature for 18 hours in the same way as the method described in Reference Example 34 using 5-fluoropyridine-2-carbonitrile (0.133 g, 1.09 mmol) instead of 3,6-dichloropyridazine. Water was added to the reaction solution, followed by extraction with ethyl acetate twice. Then, the organic layer was washed with water and brine. The obtained organic layer was dried over anhydrous sodium sulfate, and the solvent was distilled off under reduced pressure. A mixed solvent of ethyl acetate and hexane was added to the obtained residue, and the precipitate was collected by filtration to obtain the title compound (0.121 g, yield: 54%).

$^1$H-NMR (400 MHz, DMSO-$d_6$) δ: 11.17 (1H, brs), 8.43 (1H, d, J=3 Hz), 7.72 (1H, d, J=9 Hz), 7.38 (1H, dd, J=9 Hz, 3 Hz), 5.21 (1H, br s), 4.36 (2H, brs), 4.07-3.97 (2H, m), 3.05-2.95 (2H, m), 2.80-2.68 (1H, m), 1.94-1.86 (2H, m), 1.63-1.51 (2H, m).

Reference Example 38

6-[4-(5-Amino-1H-pyrazol-3-yl)piperidin-1-yl]-2-methylpyridine-3-carbonitrile

[Formula 46]

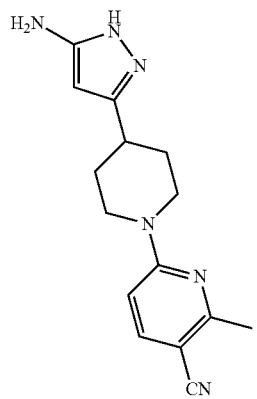

The title compound (0.458 g, yield: 78%) was obtained through reaction at room temperature for 4 hours in the same way as the method described in Reference Example 34 using 6-chloro-2-methylpyridine-3-carbonitrile (0.319 g, 2.09 mmol) instead of 3,6-dichloropyridazine.

$^1$H-NMR (400 MHz, CD$_3$OD) δ: 7.61 (1H, d, J=9 Hz), 6.68 (1H, d, J=9 Hz), 5.43 (1H, s), 4.61-4.53 (2H, m), 3.08-3.00 (2H, m), 2.92-2.83 (1H, m), 2.50 (3H, s), 2.00-1.94 (2H, m), 1.67-1.54 (2H, m).

Reference Example 39

6-[4-(5-Amino-1H-pyrazol-3-yl)piperidin-1-yl]-2-chloropyridine-3-carbonitrile

[Formula 47]

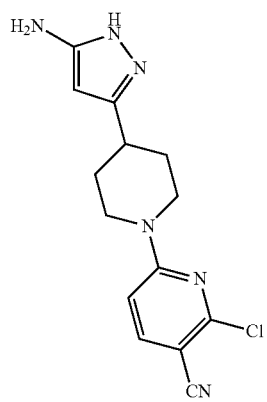

The title compound (0.245 g, yield: 65%) was obtained through reaction in the same way as the method described in Reference Example 34 using 2,6-dichloropyridine-3-carbonitrile (0.217 g, 1.25 mmol) instead of 3,6-dichloropyridazine.

$^1$H-NMR (400 MHz, CD$_3$OD) δ: 7.71 (1H, d, J=9 Hz), 6.80 (1H, d, J=9 Hz), 5.44 (1H, s), 4.55-4.46 (2H, m), 3.14-3.07 (2H, m), 2.94-2.83 (1H, m), 2.05-1.96 (2H, m), 1.68-1.56 (2H, m).

Reference Example 40

6-[4-(5-Amino-1H-pyrazol-3-yl)piperidin-1-yl]-2-carbonitrile

[Formula 48]

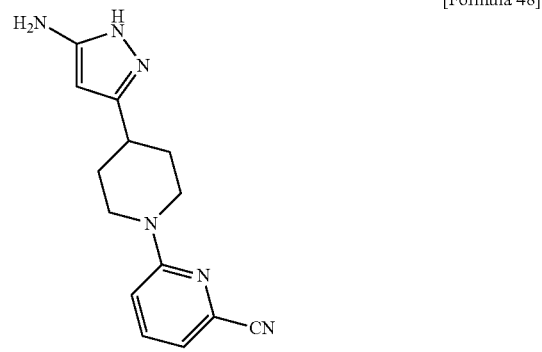

The title compound (0.150 g, yield: 51%) was obtained through reaction in the same way as the method described in Reference Example 34 using 6-chloropyridine-2-carbonitrile (0.152 g, 1.10 mmol) instead of 3,6-dichloropyridazine.

$^1$H-NMR (400 MHz, DMSO-$d_6$) δ: 11.12 (1H, brs), 7.67 (1H, dd, J=9 Hz, 7 Hz), 7.21 (1H, d, J=9 Hz), 7.15 (1H, d, J=7 Hz), 5.19 (1H, s), 4.42 (2H, br s), 4.35-4.28 (2H, m), 3.00-2.90 (2H, m), 2.79-2.70 (1H, m), 1.93-1.87 (2H, m), 1.55-1.44 (2H, m).

Reference Example 41

3-[4-(5-Amino-1H-pyrazol-3-yl)piperidin-1-yl]benzonitrile

[Formula 49]

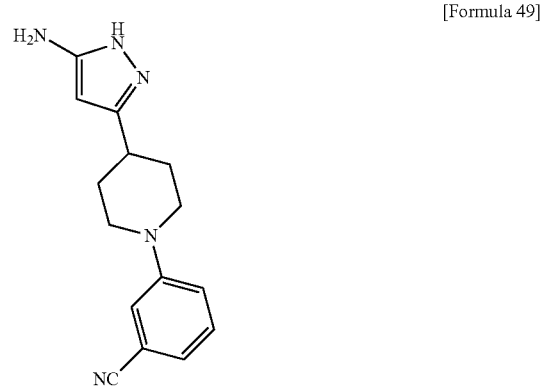 [SMILES: N#Cc1cccc(N2CCC(c3cc(N)[nH]n3)CC2)c1]

The title compound (49.0 mg, yield: 44%) was obtained through reaction at 130° C. for 3 hours in the same way as the method described in Reference Example 34 using 3-fluorobenzonitrile (253 mg, 2.09 mmol) instead of 3,6-dichloropyridazine.

¹H-NMR (400 MHz, CD₃OD) δ: 7.38-7.34 (1H, m), 7.29-7.25 (2H, m), 7.10-7.07 (1H, m), 5.46 (1H, s), 3.86-3.80 (2H, m), 2.90-2.82 (2H, m), 2.79-2.70 (1H, m), 2.05-1.97 (2H, m), 1.82-1.71 (2H, m).

Reference Example 42

3-[1-(1,3-Benzoxazol-2-yl)piperidin-4-yl]-1H-pyrazol-5-amine

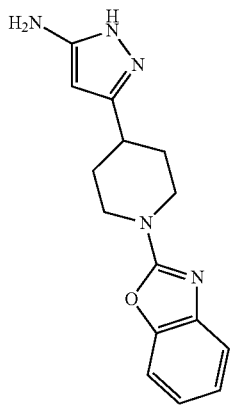

[Formula 50]

The title compound (0.93 g, yield: 85%) was obtained through reaction in the same way as the method described in Reference Example 4 using ethyl 1-(1,3-benzoxazol-2-yl)piperidine-4-carboxylate (1.00 g, 3.84 mmol) instead of ethyl 1-(6-methylpyridin-2-yl)piperidine-4-carboxylate.

¹H-NMR (DMSO-d₆) δ: 11.16 (1H, brs), 7.39 (1H, d, J=8 Hz), 7.28 (1H, d, J=8 Hz), 7.14 (1H, td, J=8 Hz, 1 Hz), 7.00 (1H, td, J=7 Hz, 1 Hz), 5.21 (1H, brs), 4.39 (1H, brs), 4.20-4.13 (2H, m), 3.22-3.20 (2H, m), 2.84-2.69 (1H, m), 1.96-1.90 (2H, m), 1.66-1.54 (2H, m).

Reference Example 43

3-[1-(1,3-Benzothiazol-2-yl)piperidin-4-yl]-1H-pyrazol-5-amine

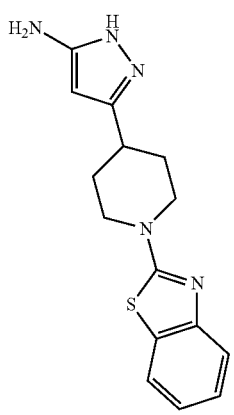

[Formula 51]

The title compound (0.58 g, yield: 54%) was obtained through reaction in the same way as the method described in Reference Example 4 using ethyl 1-(1,3-benzothiazol-2-yl)piperidine-4-carboxylate (1.00 g, 3.62 mmol) instead of ethyl 1-(6-methylpyridin-2-yl)piperidine-4-carboxylate.

¹H-NMR (DMSO-d₆) δ: 11.18 (1H, brs), 7.75 (1H, dd, J=8 Hz, 1 Hz), 7.44 (1H, dd, J=8 Hz, 1 Hz), 7.27 (1H, td, J=8 Hz, 1 Hz), 7.05 (1H, td, J=8 Hz, 1 Hz), 5.21 (1H, s), 4.40 (1H, br s), 4.09-4.02 (2H, m), 3.25 (2H, m), 2.78 (1H, m), 1.98-1.91 (2H, m), 1.68-1.56 (2H, m).

Reference Example 44

3-[1-(6-Methylpyrazin-2-yl)piperidin-4-yl]-1H-pyrazol-5-amine

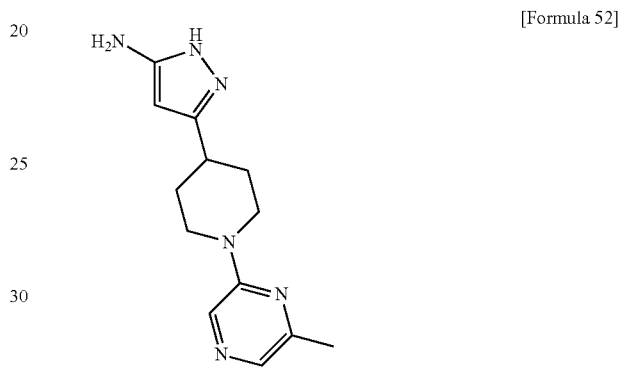

[Formula 52]

The title compound (0.99 g, yield: 95%) was obtained through reaction in the same way as the method described in Reference Example 4 using ethyl 1-(6-methylpyrazin-2-yl)piperidine-4-carboxylate (1.00 g, 4.01 mmol) instead of ethyl 1-(6-methylpyridin-2-yl)piperidine-4-carboxylate.

¹H-NMR (DMSO-d₆) δ: 11.15 (1H, brs), 8.12 (1H, s), 7.69 (1H, s), 5.21 (1H, s), 4.45-4.25 (3H, m), 2.92 (2H, td, J=13 Hz, 2 Hz), 2.82-2.66 (1H, m), 2.29 (3H, s), 1.91-1.89 (2H, m), 1.57-1.46 (2H, m).

Reference Example 45

3-[1-(Pyridin-3-yl)piperidin-4-yl]-1H-pyrazol-5-amine

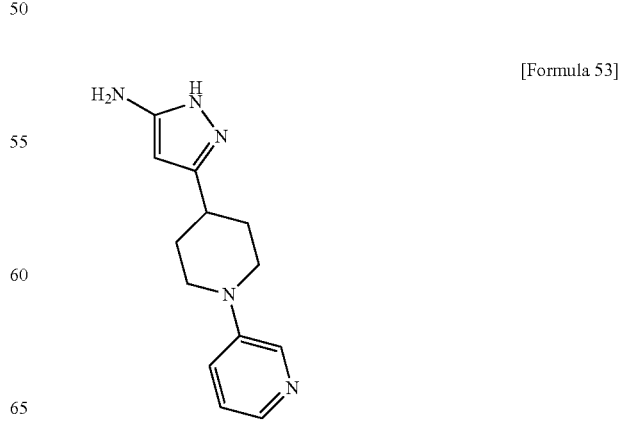

[Formula 53]

The title compound (397 mg, yield: 81%) was obtained through reaction in the same way as the method described in Reference Example 4 using ethyl 1-(pyridin-3-yl)piperidine-4-carboxylate (compound described in the pamphlet of WO2005/19200, 0.470 g, 2.01 mmol) instead of ethyl 1-(6-methylpyridin-2-yl)piperidine-4-carboxylate.

$^1$H-NMR (400 MHz, DMSO-d$_6$) δ: 11.14 (1H, brs), 8.32-8.29 (1H, m), 7.96 (1H, dd, J=5 Hz, 1 Hz), 7.35-7.30 (1H, m), 7.21-7.17 (1H, m), 5.21 (1H, s), 4.45 (2H, brs), 3.82-3.73 (2H, m), 2.83-2.73 (2H, m), 2.69-2.57 (1H, m), 1.96-1.87 (2H, m), 1.70-1.57 (2H, m).

Reference Example 46

Ethyl 1-(6-methoxypyridazin-3-yl)piperidine-4-carboxylate

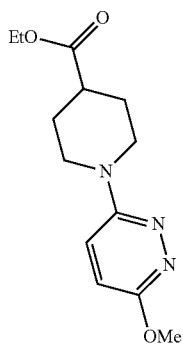

[Formula 54]

The title compound (7.23 g, yield: 66%) was obtained through reaction in the same way as the method described in Reference Example 13 using 3-chloro-6-methoxypyridazine (6.00 g, 41.5 mmol) instead of 2-bromo-3-chloropyridine.

$^1$H-NMR (400 MHz, CDCl$_3$) δ: 7.04 (1H, d, J=10 Hz), 6.84 (1H, d, J=10 Hz), 4.15 (2H, q, J=7 Hz. 2 Hz), 4.14-4.09 (2H, m), 4.03 (3H, s), 3.07-2.99 (2H, m), 2.57-2.50 (1H, m), 2.05-1.99 (2H, m), 1.86-1.77 (2H, m), 1.26 (3H, t, J=7 Hz).

Reference Example 47

3-[1-(6-Methoxypyridazin-3-yl)piperidin-4-yl]-1H-pyrazol-5-amine

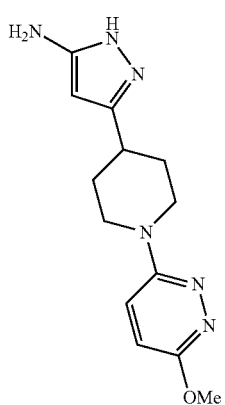

[Formula 55]

The title compound (4.82 g, yield: 65%) was obtained through reaction in the same way as the method described in Reference Example 4 using ethyl 1-(6-methoxypyridazin-3-yl)piperidine-4-carboxylate (7.22 g, 27.2 mmol) produced in Reference Example 46 instead of ethyl 1-(6-methylpyridin-2-yl)piperidine-4-carboxylate.

$^1$H-NMR (400 MHz, DMSO-d$_6$) δ: 11.14 (1H, brs), 7.40 (1H, d, J=10 Hz), 7.00 (1H, d, J=10 Hz), 5.19 (1H, s), 4.41 (2H, brs), 4.22-4.14 (2H, m), 3.89 (3H, s), 2.95-2.84 (2H, m), 2.76-2.64 (1H, m), 1.94-1.83 (2H, m), 1.62-1.49 (2H, m).

Reference Example 48

3-[1-(1,3-Thiazol-2-yl)piperidin-4-yl]-1H-pyrazol-5-amine

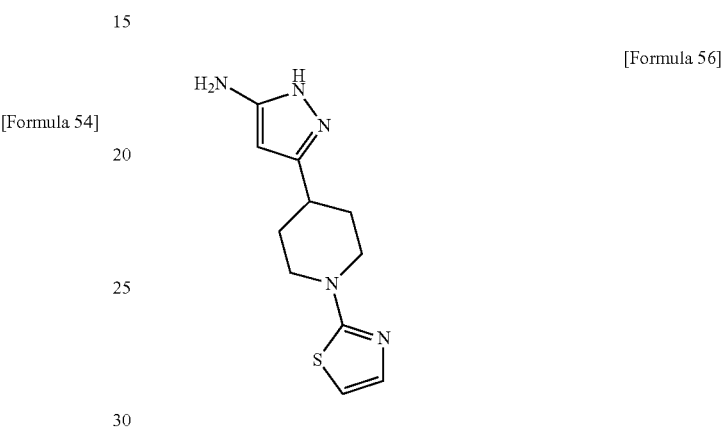

[Formula 56]

The title compound (4.73 g, yield: 92%) was obtained through reaction in the same way as the method described in Reference Example 4 using ethyl 1-(1,3-thiazol-2-yl)piperidine-4-carboxylate (compound described in the pamphlet of WO2011/41152, 4.93 g, 20.5 mmol) instead of ethyl 1-(6-methylpyridin-2-yl)piperidine-4-carboxylate.

$^1$H-NMR (400 MHz, CDCl$_3$) δ: 7.19 (1H, d, J=4 Hz), 6.57 (1H, d, J=4 Hz), 5.47 (1H, s), 5.00 (2H, brs), 4.10-4.02 (2H, m), 3.16-3.06 (2H, m), 2.83-2.74 (1H, m), 2.06-1.98 (2H, m), 1.85-1.72 (2H, m).

Reference Example 49

3-[1-(4-Methoxypyrimidin-2-yl)piperidin-4-yl]-1H-pyrazol-5-amine

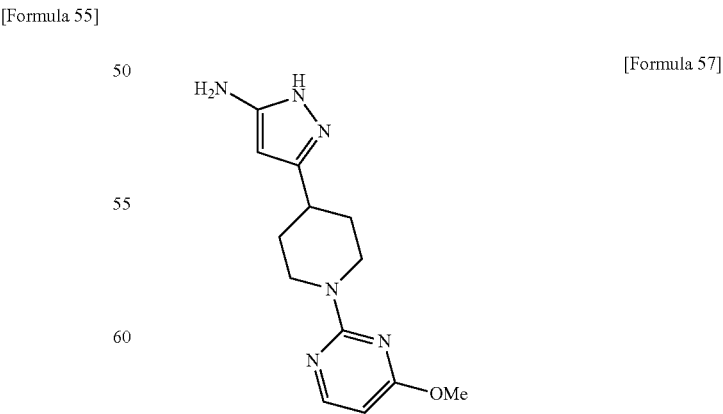

[Formula 57]

The title compound (0.549 g, yield: 100%) was obtained through reaction in the same way as the method described in Reference Example 4 using methyl 1-(4-methoxypyrimidin- 2-yl)piperidine-4-carboxylate (0.500 g, 1.99 mmol) instead of ethyl 1-(6-methylpyridin-2-yl)piperidine-4-carboxylate.

$^1$H-NMR (400 MHz, CDCl$_3$) δ: 8.05 (1H, d, J=6 Hz), 5.98 (1H, d, J=6 Hz), 5.47 (1H, s), 4.87-4.76 (2H, m), 4.72 (2H, brs), 3.89 (3H, s), 3.01-2.92 (2H, m), 2.87-2.78 (1H, m), 2.03-1.96 (2H, m), 1.69-1.58 (2H, m).

Reference Example 50

Ethyl 1-(6-methoxypyridin-3-yl)piperidine-4-carboxylate

[Formula 58]

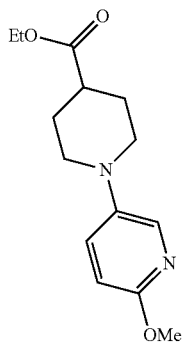

The title compound (0.906 g, yield: 65%) was obtained through reaction in the same way as the method described in Reference Example 13 using 5-bromo-2-methoxypyridine (1.000 g, 5.319 mmol) instead of 2-bromo-3-chloropyridine.

$^1$H-NMR (400 MHz, CDCl$_3$) δ: 7.81-7.78 (1H, m), 7.29 (1H, dd, J=9 Hz, 3 Hz), 6.67 (1H, dd, J=9 Hz, 1 Hz), 4.16 (2H, q, J=7 Hz), 3.89 (3H, s), 3.47-3.41 (2H, m), 2.77-2.69 (2H, m), 2.45-2.36 (1H, m), 2.08-1.99 (2H, m), 1.96-1.84 (2H, m), 1.27 (3H, t, J=7 Hz).

Reference Example 51

3-[1-(6-Methoxypyridin-3-yl)piperidin-4-yl]-1H-pyrazol-5-amine

[Formula 59]

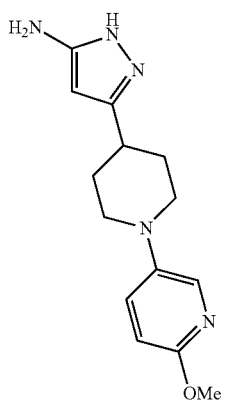

The title compound (0.917 g, yield: 99%) was obtained through reaction in the same way as the method described in Reference Example 4 using ethyl 1-(6-methoxypyridin-3-yl) piperidine-4-carboxylate (0.900 g, 3.41 mmol) produced in Reference Example 50 instead of ethyl 1-(6-methylpyridin-2-yl)piperidine-4-carboxylate.

$^1$H-NMR (400 MHz, DMSO-d$_6$) δ: 11.15 (1H, brs), 7.80-7.78 (1H, m), 7.45 (1H, dd, J=9 Hz, 3 Hz), 6.70 (1H, dd, J=9 Hz, 1 Hz), 5.22 (1H, brs), 4.37 (2H, brs), 3.77 (3H, s), 3.57-3.51 (2H, m), 2.70-2.63 (2H, m), 2.60-2.52 (1H, m), 1.95-1.88 (2H, m), 1.72-1.62 (2H, m).

Reference Example 52

Methyl 1-(4-cyanophenyl)piperidine-4-carboxylate

[Formula 60]

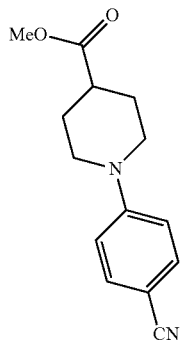

(Trimethylsilyl)diazomethane (2.0 M solution in hexane, 2.7 mL, 5.40 mmol) was added to a mixed solution of 1-(4-cyanophenyl)piperidine-4-carboxylic acid (1.13 g, 4.91 mmol) in THF (13 mL) and methanol (6.5 mL) (2:1, v/v), and the mixture was stirred at room temperature for 1 hour. Acetic acid (appropriate amount) was added to the reaction solution to stop the reaction. Then, the solvent was distilled off under reduced pressure. A saturated sodium bicarbonate aqueous solution was added to the obtained residue, followed by extraction with ethyl acetate. The obtained organic layer was washed with brine and dried over anhydrous sodium sulfate, and the solvent was distilled off under reduced pressure. The obtained residue was purified by silica gel column chromatography [elute: hexane/ethyl acetate=80/20] to obtain the title compound (1.06 g, yield: 88%).

$^1$H-NMR (400 MHz, CDCl$_3$) δ: 7.50-7.46 (2H, m), 6.88-6.84 (2H, m), 3.83-3.76 (2H, m), 3.71 (3H, s), 3.02-2.94 (2H, m), 2.60-2.51 (1H, m), 2.06-1.99 (2H, m), 1.88-1.77 (2H, m).

Reference Example 53

4-[4-(5-Amino-1H-pyrazol-3-yl)piperidin-1-yl]benzonitrile

[Formula 61]

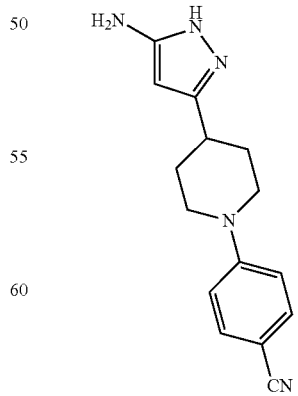

The title compound (1.000 g, yield: 87%) was obtained through reaction in the same way as the method described in Reference Example 4 using methyl 1-(4-cyanophenyl)piperidine-4-carboxylate (1.052 g, 4.306 mmol) produced in Reference Example 52 instead of ethyl 1-(6-methylpyridin-2-yl)piperidine-4-carboxylate.

$^1$H-NMR (400 MHz, DMSO-$d_6$) δ: 11.14 (1H, brs), 7.57-7.52 (2H, m), 7.05-7.00 (2H, m), 5.19 (1H, brs), 4.35 (2H, brs), 3.99-3.90 (2H, m), 2.99-2.89 (2H, m), 2.78-2.65 (1H, m), 1.94-1.84 (2H, m), 1.62-1.49 (2H, m).

Reference Example 54

3-[1-(5-Methoxypyridin-2-yl)piperidin-4-yl]-1H-pyrazol-5-amine

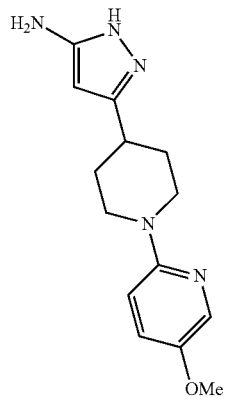

[Formula 62]

The title compound (0.821 g, yield: 94%) was obtained through reaction in the same way as the method described in Reference Example 4 using ethyl 1-(5-methoxypyridin-2-yl)piperidine-4-carboxylate (compound described in the pamphlet of US2011/53948, 0.847 g, 3.20 mmol) instead of ethyl 1-(6-methylpyridin-2-yl)piperidine-4-carboxylate.

$^1$H-NMR (400 MHz, DMSO-$d_6$) δ: 11.10 (1H, brs), 7.87-7.85 (1H, m), 7.23 (1H, dd, J=9 Hz, 3 Hz), 6.82 (1H, d, J=9 Hz), 5.18 (1H, brs), 4.40 (2H, brs), 4.18-4.09 (2H, m), 3.72 (3H, s), 2.81-2.72 (2H, m), 2.69-2.58 (1H, m), 1.91-1.82 (2H, m), 1.59-1.47 (2H, m).

Reference Example 55

3-[1-(4-Methoxypyridin-2-yl)piperidin-4-yl]-1H-pyrazol-5-amine

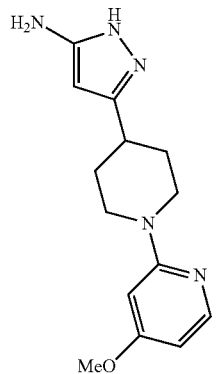

[Formula 63]

The title compound (0.723 g, yield: 99%) was obtained through reaction in the same way as the method described in Reference Example 4 using ethyl 1-(4-methoxypyridin-2-yl)piperidine-4-carboxylate (compound described in the pamphlet of WO2010/97576, 0.704 g, 2.66 mmol) instead of ethyl 1-(6-methylpyridin-2-yl)piperidine-4-carboxylate.

$^1$H-NMR (DMSO-$d_6$) δ: 11.11 (1H, brs), 7.91 (1H, d, J=6 Hz), 6.28 (1H, d, J=2 Hz), 6.24 (1H, dd, J=6 Hz, 2 Hz), 5.18 (1H, s), 4.43 (2H, brs), 4.34-4.26 (2H, m), 3.77 (3H, s), 2.87-2.79 (2H, m), 2.73-2.64 (1H, m), 1.90-1.83 (2H, m), 1.55-1.44 (2H, m).

Reference Example 56

Ethyl 1-(5-methoxypyridin-3-yl)piperidine-4-carboxylate

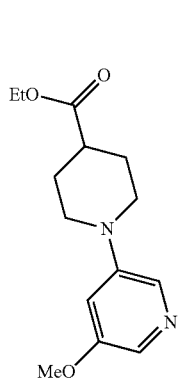

[Formula 64]

The title compound (1.010 g, yield: 72%) was obtained through reaction in the same way as the method described in Reference Example 13 using 3-bromo-5-methoxypyridine (1.000 g, 5.32 mmol) instead of 2-bromo-3-chloropyridine.

$^1$H-NMR (CDCl$_3$) δ: 7.96 (1H, d, J=2 Hz), 7.81 (1H, d, J=2 Hz), 6.71-6.69 (1H, m), 4.16 (2H, q, J=7 Hz), 3.84 (3H, s), 3.68-3.62 (2H, m), 2.90-2.82 (2H, m), 2.50-2.43 (1H, m), 2.07-2.00 (2H, m), 1.91-1.82 (2H, m), 1.27 (3H, t, J=7 Hz).

Reference Example 57

3-[1-(5-Methoxypyridin-3-yl)piperidin-4-yl]-1H-pyrazol-5-amine

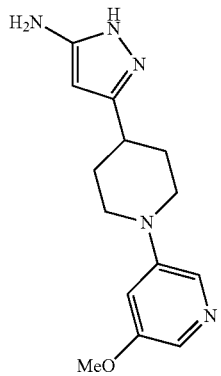

[Formula 65]

The title compound (0.881 g, yield: 85%) was obtained through reaction in the same way as the method described in Reference Example 4 using ethyl 1-(5-methoxypyridin-3-yl)piperidine-4-carboxylate (1.003 g, 3.80 mmol) produced in Reference Example 56 instead of ethyl 1-(6-methylpyridin-2-yl)piperidine-4-carboxylate.

¹H-NMR (DMSO-d₆) δ: 11.14 (1H, brs), 7.92 (1H, d, J=2 Hz), 7.70 (1H, d, J=2 Hz), 6.87-6.84 (1H, m), 5.21 (1H, s), 4.45 (2H, brs), 3.82-3.75 (2H, m), 3.79 (3H, s), 2.83-2.75 (2H, m), 2.67-2.59 (1H, m), 1.95-1.88 (2H, m), 1.68-1.58 (2H, m).

Reference Example 58

3-{1-[6-(Trifluoromethyl)pyridin-3-yl]piperidin-4-yl}-1H-pyrazol-5-amine

[Formula 66]

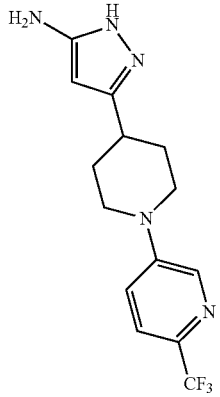

The title compound (0.343 g, yield: 66%) was obtained through reaction at room temperature for 92 hours in the same way as the method described in Reference Example 34 using 5-fluoro-2-(trifluoromethyl)pyridine (0.276 g, 1.67 mmol) instead of 3,6-dichloropyridazine.

¹H-NMR (DMSO-d₆) δ: 11.14 (1H, brs), 8.43 (1H, d, J=3 Hz), 7.61 (1H, d, J=9 Hz), 7.44 (1H, dd, J=9 Hz, 3 Hz), 5.20 (1H, s), 4.41 (2H, brs), 4.00-3.93 (2H, m), 2.99-2.91 (2H, m), 2.76-2.67 (1H, m), 1.96-1.89 (2H, m), 1.66-1.56 (2H, m).

Reference Example 59

6-[4-(5-Amino-1H-pyrazol-3-yl)piperidin-1-yl]-4-methylpyridine-3-carbonitrile

[Formula 67]

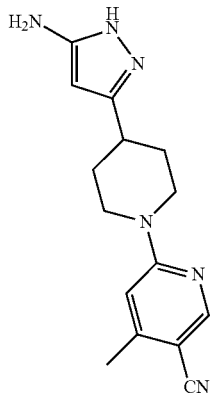

The title compound (0.410 g, yield: 87%) was obtained through reaction at room temperature for 67 hours in the same way as the method described in Reference Example 34 using 6-chloro-4-methylpyridine-3-carbonitrile (0.255 g, 1.67 mmol) instead of 3,6-dichloropyridazine.

¹H-NMR (DMSO-d₆) δ: 11.12 (1H, brs), 8.37 (1H, s), 6.89 (1H, s), 5.18 (1H, s), 4.54-4.39 (4H, m), 3.06-2.98 (2H, m), 2.83-2.75 (1H, m), 2.33 (3H, s), 1.92-1.86 (2H, m), 1.52-1.42 (2H, m).

Example 1

4-Hydroxy-3-(1-phenylpiperidin-4-yl)-4-(trifluoromethyl)-1,4,5,7-tetrahydro-6H-pyrazolo[3,4-b]pyridin-6-one

[Formula 68]

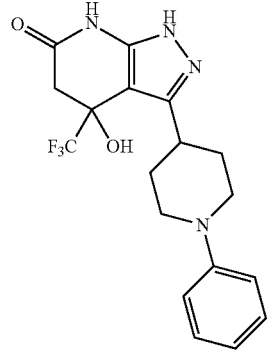

Ethyl trifluoroacetoacetate (1.50 g, 8.15 mmol) was added to a solution of 3-(1-phenylpiperidin-4-yl)-1H-pyrazol-5-amine (648 mg, 2.67 mmol) produced in Reference Example 3 in acetic acid (10 mL), and the mixture was stirred at 60° C. for 2 hours and 30 minutes. A saturated sodium bicarbonate aqueous solution was added to the reaction solution, followed by extraction with ethyl acetate. The obtained organic layer was washed with brine and dried over anhydrous magnesium sulfate, and the solvent was distilled off under reduced pressure. The obtained residue was purified by silica gel column chromatography [NH-silica gel column, elute: ethyl acetate/methanol=100/0-96/4 (gradient)] and further purified by silica gel chromatography [elute: hexane/ethyl acetate=60/40-0/100 (gradient)] to obtain the title compound (430 mg, yield: 42%).

¹H-NMR (400 MHz, DMSO-d₆) δ: 12.29 (1H, s), 10.51 (1H, s), 7.21 (2H, dd, J=9 Hz, 7 Hz), 6.96 (2H, d, J=8 Hz), 6.77 (1H, t, J=7 Hz), 6.72 (1H, s), 3.79 (2H, d, J=10 Hz), 3.16-3.07 (1H, m), 2.90 (1H, d, J=16 Hz), 2.72 (1H, d, J=16 Hz), 2.69-2.61 (2H, m), 1.96-1.72 (4H, m);

MS (ESI) m/z: 381 (M+H)⁺.

Example 2

4-Hydroxy-3-[1-(pyridin-2-yl)piperidin-4-yl]-4-(trifluoromethyl)-1,4,5,7-tetrahydro-6H-pyrazolo[3,4-b]pyridin-6-one

[Formula 69]

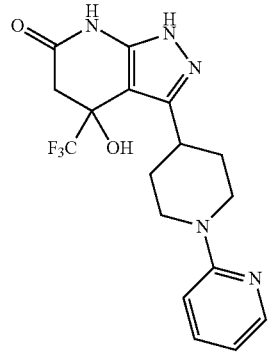

Reaction was performed in the same way as the method described in Example 1 using 3-[1-(pyridin-2-yl)piperidin-4-yl]-1H-pyrazol-5-amine (130 mg, 0.53 mmol) produced in Reference Example 2 instead of 3-(1-phenylpiperidin-4-yl)-1H-pyrazol-5-amine. The obtained residue was purified by silica gel column chromatography [NH-silica gel column, elute: ethyl acetate/methanol=100/0-88/12 (gradient)] and further purified by silica gel column chromatography [elute: hexane/ethyl acetate=60/40-0/100 (gradient)] to obtain the title compound (35 mg, yield: 17%).

$^1$H-NMR (500 MHz, DMSO-$d_6$) δ: 12.24 (1H, s), 10.50 (1H, s), 8.10 (1H, d, J=5 Hz), 7.53-7.49 (1H, m), 6.85 (1H, d, J=9 Hz), 6.74 (1H, s), 6.60 (1H, dd, J=7 Hz, 5 Hz), 4.45 (2H, d, J=13 Hz), 3.28-3.17 (1H, m), 2.90 (1H, d, J=16 Hz), 2.81-2.69 (3H, m), 1.92-1.62 (4H, m);

MS (ESI) m/z: 382 (M+H)$^+$.

Example 3

4-Hydroxy-3-[1-(6-methylpyridin-2-yl)piperidin-4-yl]-4-(trifluoromethyl)-1,4,5,7-tetrahydro-6H-pyrazolo[3,4-b]pyridin-6-one

[Formula 70]

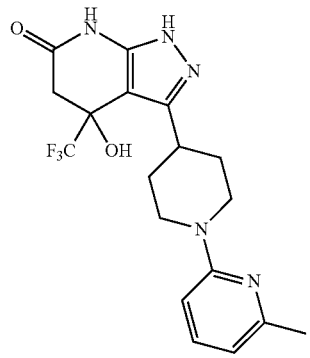

The title compound (900 mg, yield: 39%) was obtained through reaction in the same way as the method described in Example 1 using 3-[1-(6-methylpyridin-2-yl)piperidin-4-yl]-1H-pyrazol-5-amine (1.52 g, 5.91 mmol) produced in Reference Example 4 instead of 3-(1-phenylpiperidin-4-yl)-1H-pyrazol-5-amine.

$^1$H-NMR (400 MHz, DMSO-$d_6$) δ: 12.24 (1H, s), 10.51 (1H, s), 7.40 (1H, dd, J=9 Hz, 7 Hz), 6.74 (1H, s), 6.63 (1H, d, J=9 Hz), 6.47 (1H, d, J=7 Hz), 4.46 (2H, d, J=13 Hz), 3.26-3.17 (1H, m), 3.17 (3H, s), 2.90 (1H, d, J=16 Hz), 2.77-2.68 (3H, m), 1.91-1.64 (4H, m);

MS (ESI) m/z: 396 (M+H)$^+$.

Example 4

4-Hydroxy-3-[1-(5-methylpyridin-2-yl)piperidin-4-yl]-4-(trifluoromethyl)-1,4,5,7-tetrahydro-6H-pyrazolo[3,4-b]pyridin-6-one

[Formula 71]

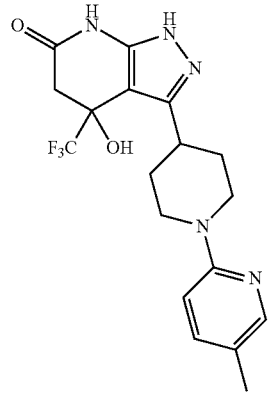

Reaction was performed in the same way as the method described in Example 1 using 3-[1-(5-methylpyridin-2-yl)piperidin-4-yl]-1H-pyrazol-5-amine (480 mg, 1.87 mmol) produced in Reference Example 5 instead of 3-(1-phenylpiperidin-4-yl)-1H-pyrazol-5-amine. The obtained residue was purified by silica gel column chromatography [elute: ethyl acetate/hexane=50/50-0/100 (gradient)] and recrystallized from ethyl acetate to obtain the title compound (183 mg, yield: 25%).

$^1$H-NMR (500 MHz, DMSO-$d_6$) δ: 12.25 (1H, s), 10.52 (1H, s), 7.98 (1H, d, J=2 Hz), 7.39 (1H, dd, J=9 Hz, 2 Hz), 6.81 (1H, d, J=9 Hz), 6.75 (1H, s), 4.40 (2H, d, J=10 Hz), 3.28-3.19 (1H, m), 2.92 (1H, d, J=17 Hz), 2.79-2.72 (3H, m), 2.17 (3H, s), 1.92-1.65 (4H, m);

MS (ESI) m/z: 396 (M+H)$^+$.

Example 5

4-Hydroxy-3-[1-(4-methylpyridin-2-yl)piperidin-4-yl]-4-(trifluoromethyl)-1,4,5,7-tetrahydro-6H-pyrazolo[3,4-b]pyridin-6-one

[Formula 72]

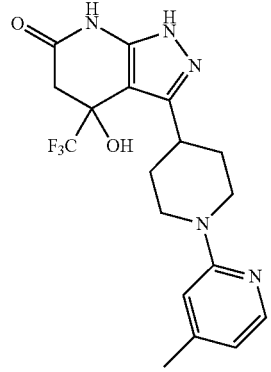

The title compound (570 mg, yield: 35%) was obtained through reaction in the same way as the method described in Example 1 using 3-[1-(4-methylpyridin-2-yl)piperidin-4-yl]-1H-pyrazol-5-amine (1.07 g, 4.16 mmol) produced in Reference Example 6 instead of 3-(1-phenylpiperidin-4-yl)-1H-pyrazol-5-amine.

¹H-NMR (500 MHz, DMSO-d₆) δ: 12.22 (1H, s), 10.50 (1H, s), 7.96 (1H, d, J=5 Hz), 6.73 (1H, s), 6.69 (1H, s), 6.45 (1H, d, J=5 Hz), 4.48-4.41 (2H, m), 3.18-3.15 (1H, m), 2.89 (1H, d, J=17 Hz), 2.80-2.70 (3H, m), 2.21 (3H, s), 1.90-1.63 (4H, m);
MS (ESI) m/z: 396 (M+H)⁺.

Example 6

4-Hydroxy-3-[1-(3-methylpyridin-2-yl)piperidin-4-yl]-4-(trifluoromethyl)-1,4,5,7-tetrahydro-6H-pyrazolo[3,4-b]pyridin-6-one

[Formula 73]

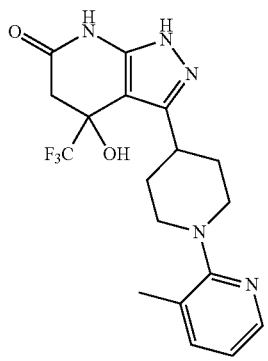

Reaction was performed in the same way as the method described in Example 1 using 3-[1-(3-methylpyridin-2-yl)piperidin-4-yl]-1H-pyrazol-5-amine (2.15 g, 8.36 mmol) produced in Reference Example 7 instead of 3-(1-phenylpiperidin-4-yl)-1H-pyrazol-5-amine. The obtained residue was purified by silica gel column chromatography [elute: hexane/ethyl acetate=50/50-0/100 (gradient)] and washed with a methanol-ethyl acetate mixed solvent to obtain the title compound (1.08 g, yield: 33%).

¹H-NMR (500 MHz, DMSO-d₆) δ: 12.32 (1H, s), 10.50 (1H, s), 8.10 (1H, dd, J=5 Hz, 1 Hz), 7.50 (1H, d, J=6 Hz), 6.91 (1H, dd, J=7 Hz, 5 Hz), 6.72 (1H, s), 3.50 (2H, d, J=10 Hz), 3.13 (1H, t, J=12 Hz), 2.90 (1H, d, J=16 Hz), 2.75-2.63 (3H, m), 2.27 (3H, s), 1.96-1.74 (4H, m);
MS (ESI) m/z: 396 (M+H)⁺.

Example 7

4-Hydroxy-4-(trifluoromethyl)-3-{1-[6-(trifluoromethyl)pyridin-2-yl]piperidin-4-yl}-1,4,5,7-tetrahydro-6H-pyrazolo[3,4-b]pyridin-6-one

[Formula 74]

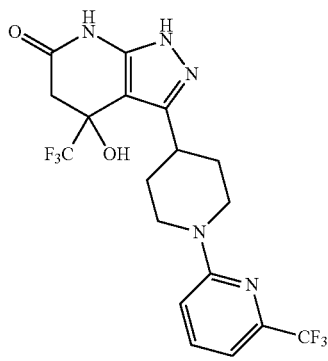

The title compound (810 mg, yield: 51%) was obtained through reaction in the same way as the method described in Example 1 using 3-{1-[6-(trifluoromethyl)pyridin-2-yl]piperidin-4-yl}-1H-pyrazol-5-amine (1.10 g, 3.53 mmol) produced in Reference Example 8 instead of 3-(1-phenylpiperidin-4-yl)-1H-pyrazol-5-amine.

¹H-NMR (500 MHz, DMSO-d₆) δ: 12.25 (1H, s), 10.53 (1H, s), 7.76 (1H, t, J=8 Hz), 7.18 (1H, d, J=9 Hz), 7.02 (1H, d, J=7 Hz), 6.78 (1H, s), 4.52 (2H, d, J=12 Hz), 3.29 (1H, brs), 2.96-2.86 (3H, m), 2.75 (1H, d, J=17 Hz), 1.94 (1H, d, J=12 Hz), 1.79-1.65 (3H, m);
MS (ESI) m/z: 450 (M+H)⁺.

Example 8

4-Hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one

[Formula 75]

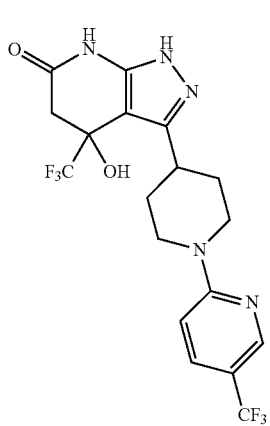

Ethyl trifluoroacetoacetate (1.50 g, 8.15 mmol) was added to a solution of 3-{1-[5-(trifluoromethyl)pyridin-2-yl]piperidin-4-yl}-1H-pyrazol-5-amine (880 mg, 2.83 mmol) produced in Reference Example 10 in acetic acid (10 mL), and the mixture was stirred at 60° C. for 2 hours. A saturated sodium bicarbonate aqueous solution was added to the reaction solution, followed by extraction with ethyl acetate three times. The obtained organic layer was washed with brine and dried over anhydrous magnesium sulfate, and the solvent was distilled off under reduced pressure. The obtained residue was purified by silica gel column chromatography [NH-silica gel column, elute: ethyl acetate/methanol=100/0-96/4 (gradient)] and further purified by silica gel column chromatography [elute: hexane/ethyl acetate=60/40-0/100 (gradient)] to obtain the title compound (610 mg, yield: 48%).

¹H-NMR (500 MHz, DMSO-d₆) δ: 12.20 (1H, s), 10.50 (1H, s), 8.42 (1H, s), 7.79 (1H, dd, J=9 Hz, 2 Hz), 7.00 (1H, d, J=9 Hz), 6.75 (1H, s), 4.58 (2H, s), 2.98-2.87 (4H, m), 2.73 (1H, d, J=17 Hz), 1.90 (1H, d, J=12 Hz), 1.75-1.60 (3H, m);
MS (ESI) m/z: 450 (M+H)⁺.

Example 9

4-Hydroxy-4-(trifluoromethyl)-3-{1-[3-(trifluoromethyl)pyridin-2-yl]piperidin-4-yl}-1,4,5,7-tetrahydro-6H-pyrazolo[3,4-b]pyridin-6-one

[Formula 76]

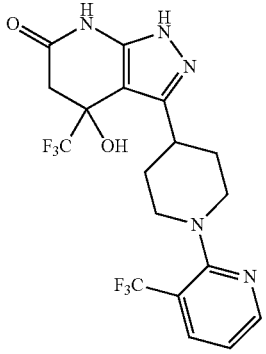

The title compound (440 mg, yield: 40%) was obtained through reaction in the same way as the method described in Example 1 using 3-{1-[3-(trifluoromethyl)pyridin-2-yl]piperidin-4-yl}-1H-pyrazol-5-amine (765 mg, 2.46 mmol) produced in Reference Example 11 instead of 3-(1-phenylpiperidin-4-yl)-1H-pyrazol-5-amine.

$^1$H-NMR (500 MHz, DMSO-$d_6$) δ: 12.34 (1H, s), 10.50 (1H, s), 8.53 (1H, d, J=4 Hz), 8.06 (1H, dd, J=8 Hz, 2 Hz), 7.17 (1H, dd, J=7 Hz, 5 Hz), 6.73 (1H, s), 3.65-3.57 (2H, m), 3.16 (1H, t, J=12 Hz), 2.94-2.87 (3H, m), 2.73 (1H, d, J=17 Hz), 1.97-1.73 (4H, m);
MS (ESI) m/z: 450 (M+H)$^+$.

Example 10

3-{1-[3-Chloro-5-(trifluoromethyl)pyridin-2-yl]piperidin-4-yl}-4-hydroxy-4-(trifluoromethyl)-1,4,5,7-tetrahydro-6H-pyrazolo[3,4-b]pyridin-6-one

[Formula 77]

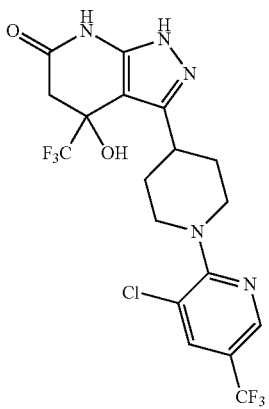

The title compound (703 mg, yield: 43%) was obtained through reaction in the same way as the method described in Example 1 using 3-{1-[3-chloro-5-(trifluoromethyl)pyridin-2-yl]piperidin-4-yl}-1H-pyrazol-5-amine (1.16 g, 3.36 mmol) produced in Reference Example 12 instead of 3-(1-phenylpiperidin-4-yl)-1H-pyrazol-5-amine.

$^1$H-NMR (500 MHz, DMSO-$d_6$) δ: 12.31 (1H, s), 10.51 (1H, s), 8.57 (1H, dd, J=2 Hz, 1 Hz), 8.19 (1H, d, J=2 Hz), 6.76 (1H, s), 4.20-4.12 (2H, m), 3.30-3.21 (1H, m), 2.98-2.87 (3H, m), 2.73 (1H, d, J=17 Hz), 1.98-1.75 (4H, m);
MS (FAB) m/z: 484 (M+H)$^+$.

Example 11

3-[1-(3-Chloropyridin-2-yl)piperidin-4-yl]-4-hydroxy-4-(trifluoromethyl)-1,4,5,7-tetrahydro-6H-pyrazolo[3,4-b]pyridin-6-one

[Formula 78]

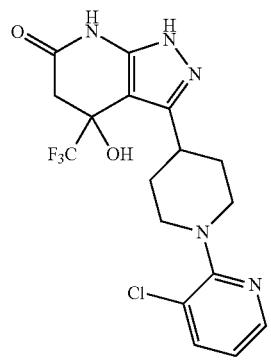

The title compound (165 mg, yield: 17%) was obtained through reaction in the same way as the method described in Example 1 using 3-[1-(3-chloropyridin-2-yl)piperidin-4-yl]-1H-pyrazol-5-amine (667 mg, 2.40 mmol) produced in Reference Example 14 instead of 3-(1-phenylpiperidin-4-yl)-1H-pyrazol-5-amine.

$^1$H-NMR (400 MHz, DMSO-$d_6$) δ: 12.33 (1H, s), 10.51 (1H, s), 8.23 (1H, dd, J=5 Hz, 2 Hz), 7.80 (1H, dd, J=8 Hz, 2 Hz), 7.00 (1H, dd, J=8 Hz, 5 Hz), 6.74 (1H, s), 3.88-3.81 (2H, m), 3.21-3.12 (1H, m), 2.90 (1H, d, J=16 Hz), 2.82-2.69 (3H, m), 1.98-1.86 (3H, m), 1.80-1.74 (1H, m);
MS (ESI) m/z: 416 (M+H)$^+$.

Example 12

4-Hydroxy-3-[1-(6-methoxypyridin-2-yl)piperidin-4-yl]-4-(trifluoromethyl)-1,4,5,7-tetrahydro-6H-pyrazolo[3,4-b]pyridin-6-one

[Formula 79]

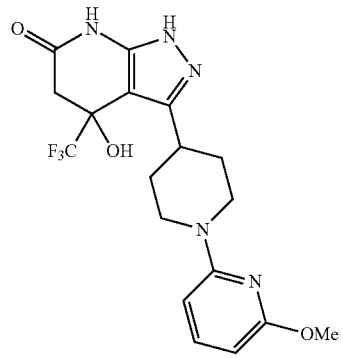

The title compound (324 mg, yield: 56%) was obtained through reaction in the same way as the method described in Example 1 using 3-[1-(6-methoxypyridin-2-yl)piperidin-4-yl]-1H-pyrazol-5-amine (0.386 g, 1.41 mmol) produced in Reference Example 16 instead of 3-(1-phenylpiperidin-4-yl)-1H-pyrazol-5-amine.

¹H-NMR (400 MHz, DMSO-d₆) δ: 12.27 (1H, s), 10.51 (1H, s), 7.73 (1H, d, J=9 Hz), 6.75 (1H, s), 6.54 (1H, s), 6.42 (1H, d, J=9 Hz), 4.48-4.38 (2H, m), 3.76 (3H, s), 3.28-3.20 (1H, m), 2.92-2.70 (4H, m), 1.92-1.86 (1H, m), 1.78-1.67 (3H, m);

MS (ESI) m/z: 412 (M+H)⁺.

Example 13

4-Hydroxy-4-(trifluoromethyl)-3-{1-[4-(trifluoromethyl)pyridin-2-yl]piperidin-4-yl}-1,4,5,7-tetrahydro-6H-pyrazolo[3,4-b]pyridin-6-one

[Formula 80]

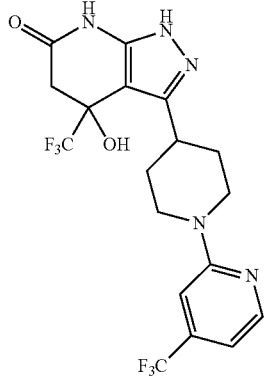

The title compound (0.645 g, yield: 44%) was obtained through reaction in the same way as the method described in Example 1 using 3-{1-[4-(trifluoromethyl)pyridin-2-yl]piperidin-4-yl}-1H-pyrazol-5-amine (1.02 g, 3.28 mmol) produced in Reference Example 18 instead of 3-(1-phenylpiperidin-4-yl)-1H-pyrazol-5-amine.

¹H-NMR (400 MHz, DMSO-d₆) δ: 12.21 (1H, s), 10.50 (1H, s), 8.33 (1H, d, J=5 Hz), 7.12 (1H, s), 6.85 (1H, d, J=5 Hz), 6.75 (1H, s), 4.61-4.52 (2H, m), 3.33-3.23 (1H, m), 2.95-2.85 (3H, m), 2.73 (1H, d, J=16 Hz), 1.92-1.86 (1H, m), 1.77-1.60 (3H, m);

MS (ESI) m/z: 450 (M+H)⁺.

Example 14

3-[1-(5-Chloropyridin-2-yl)piperidin-4-yl]-4-hydroxy-4-(trifluoromethyl)-1,4,5,7-tetrahydro-6H-pyrazolo[3,4-b]pyridin-6-one

[Formula 81]

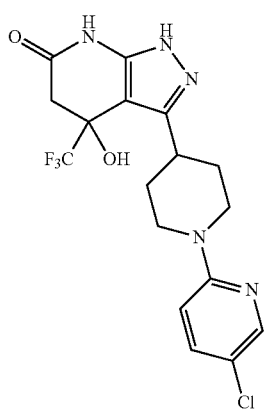

Ethyl trifluoroacetoacetate (1.28 g, 6.97 mmol) was added to a solution of 3-[1-(5-chloropyridin-2-yl)piperidin-4-yl]-1H-pyrazol-5-amine (0.484 g, 1.74 mmol) produced in Reference Example 20 in acetic acid (8 mL), and the mixture was stirred at 60° C. for 1.5 hours. A saturated sodium bicarbonate aqueous solution was added to the reaction solution, followed by extraction with ethyl acetate twice. The obtained organic layer was washed with brine and dried over anhydrous magnesium sulfate, and the solvent was distilled off under reduced pressure. The obtained residue was purified by silica gel column chromatography [NH-silica gel column, elute: ethyl acetate/methanol=100/0-95/5 (gradient)] and further purified by silica gel column chromatography [elute: hexane/ethyl acetate=20/80-0/100 (gradient)] to obtain the title compound (0.283 g, yield: 39%).

¹H-NMR (400 MHz, DMSO-d₆) δ: 12.23 (1H, s), 10.51 (1H, s), 8.11 (1H, d, J=3 Hz), 7.59 (1H, dd, J=9 Hz, 3 Hz), 6.91 (1H, d, J=9 Hz), 6.75 (1H, s), 4.46-4.38 (2H, m), 3.28-3.20 (1H, m), 2.93-2.79 (3H, m), 2.72 (1H, d, J=16 Hz), 1.89-1.83 (1H, m), 1.75-1.61 (3H, m);

MS (ESI) m/z: 416 (M+H)⁺.

Example 15

3-[1-(5-Fluoropyridin-2-yl)piperidin-4-yl]-4-hydroxy-4-(trifluoromethyl)-1,4,5,7-tetrahydro-6H-pyrazolo[3,4-b]pyridin-6-one

[Formula 82]

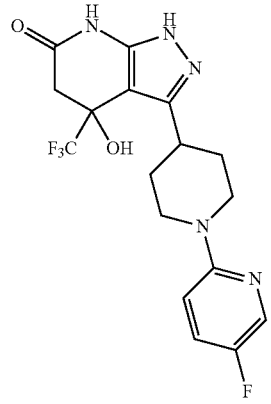

Reaction was performed in the same way as the method described in Example 1 using 3-[1-(5-fluoropyridin-2-yl)piperidin-4-yl]-1H-pyrazol-5-amine (1.46 g, 5.59 mmol) produced in Reference Example 22 instead of 3-(1-phenylpiperidin-4-yl)-1H-pyrazol-5-amine. The obtained residue was purified by silica gel column chromatography [NH-silica gel, elute: ethyl acetate/methanol=100/0-95/5 (gradient)]. Ethyl acetate was added to the obtained crude product, and the resulting suspension was stirred. The precipitate was collected by filtration to obtain the title compound (0.647 g, yield: 29%).

¹H-NMR (400 MHz, DMSO-d₆) δ: 12.23 (1H, s), 10.50 (1H, s), 8.09 (1H, d, J=3 Hz), 7.50 (1H, ddd, J=10 Hz, 7 Hz, 2 Hz), 6.90 (1H, dd, J=10 Hz, 3 Hz), 6.73 (1H, s), 4.39-4.33 (2H, m), 3.25-3.16 (1H, m), 2.90 (1H, d, J=16 Hz), 2.82-2.68 (3H, m), 1.90-1.84 (1H, m), 1.80-1.63 (3H, m);

MS (ESI) m/z: 400 (M+H)⁺.

Example 16

4-Hydroxy-3-[1-(quinolin-2-yl)piperidin-4-yl]-4-(trifluoromethyl)-1,4,5,7-tetrahydro-6H-pyrazolo[3,4-b]pyridin-6-one

[Formula 83]

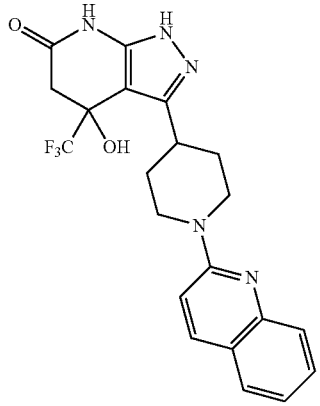

The title compound (415 mg, yield: 28%) was obtained through reaction in the same way as the method described in Example 1 using 3-[1-(quinolin-2-yl)piperidin-4-yl]-1H-pyrazol-5-amine (1.01 g, 3.44 mmol) produced in Reference Example 24 instead of 3-(1-phenylpiperidin-4-yl)-1H-pyrazol-5-amine.

$^1$H-NMR (500 MHz, DMSO-$d_6$) δ: 12.21 (1H, s), 10.49 (1H, s), 8.03 (1H, d, J=9 Hz), 7.69 (1H, d, J=8 Hz), 7.57-7.49 (2H, m), 7.29 (1H, d, J=9 Hz), 7.22-7.17 (1H, m), 6.75 (1H, s), 4.76-4.69 (2H, m), 3.18-3.13 (1H, m), 2.96-2.86 (3H, m), 2.73 (1H, d, J=16 Hz), 1.97-1.89 (1H, m), 1.80-1.67 (3H, m);
MS (ESI) m/z: 432 (M+H)$^+$.

Example 17

4-Hydroxy-3-{1-[6-(propan-2-yloxy)pyridazin-3-yl]piperidin-4-yl}-4-(trifluoromethyl)-1,4,5,7-tetrahydro-6H-pyrazolo[3,4-b]pyridin-6-one

[Formula 84]

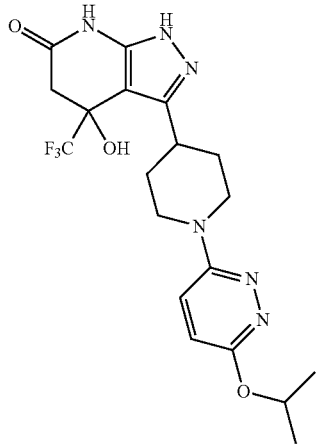

Reaction was performed in the same way as the method described in Example 1 using 3-{1-[6-(propan-2-yloxy)pyridazin-3-yl]piperidin-4-yl}-1H-pyrazol-5-amine (2.53 g, 8.37 mmol) produced in Reference Example 26 instead of 3-(1-phenylpiperidin-4-yl)-1H-pyrazol-5-amine. Ethanol was added to the obtained residue, and the resulting suspension was stirred at 70° C. for 2 hours. After cooling to room temperature, the resulting precipitate was collected by filtration to obtain the title compound (1.16 g, yield: 32%).

$^1$H-NMR (400 MHz, DMSO-$d_6$) δ: 12.25 (1H, s), 10.50 (1H, s), 7.40 (1H, d, J=10 Hz), 6.94 (1H, d, J=10 Hz), 6.73 (1H, s), 5.28-5.21 (1H, m), 4.35-4.28 (2H, m), 3.28-3.18 (1H, m), 2.93-2.77 (3H, m), 2.73 (1H, d, J=16 Hz), 1.91-1.67 (4H, m), 1.31 (6H, d, J=6 Hz);
MS (ESI) m/z: 441 (M+H)$^+$.

Example 18

4-Hydroxy-3-{1-[6-(propan-2-yloxy)pyridazin-3-yl]piperidin-4-yl}-4-(trifluoromethyl)-1,4,5,7-tetrahydro-6H-pyrazolo[3,4-b]pyridin-6-one hydrochloride

[Formula 85]

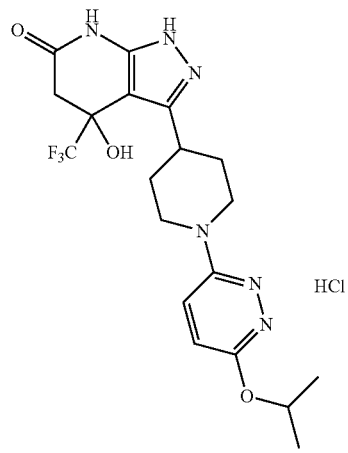

1 N hydrochloric acid (0.295 mL, 0.295 mmol) was added dropwise at room temperature to a suspension of 4-hydroxy-3-{1-[6-(propan-2-yloxy)pyridazin-3-yl]piperidin-4-yl}-4-(trifluoromethyl)-1,4,5,7-tetrahydro-6H-pyrazolo[3,4-b]pyridin-6-one (100 mg, 0.227 mmol) produced in Example 17 in ethanol (2 mL). Then, the solvent in the reaction solution was distilled off under reduced pressure. THF was added to the obtained residue, and the resulting suspension was stirred. The resulting precipitate was collected by filtration to obtain the title compound (88.0 mg, 81%).

$^1$H-NMR (400 MHz, DMSO-$d_6$) δ: 12.29 (1H, s), 10.55 (1H, s), 8.06-7.99 (1H, m), 7.60-7.52 (1H, m), 6.82 (1H, s), 5.15-5.09 (1H, m), 4.37-4.30 (2H, m), 3.39-3.32 (1H, m), 3.30-3.19 (2H, m), 2.92 (1H, d, J=16 Hz), 2.73 (1H, d, J=16 Hz), 2.01-1.95 (1H, m), 1.89-1.74 (3H, m), 1.36 (6H, d, J=6 Hz);
MS (ESI) m/z: 441 (M+H)$^+$.

Example 19

5-{4-[4-Hydroxy-6-oxo-4-(trifluoromethyl)-4,5,6,7-tetrahydro-1H-pyrazolo[3,4-b]pyridin-3-yl]piperidin-1-yl}pyridine-2-carbonitrile

[Formula 86]

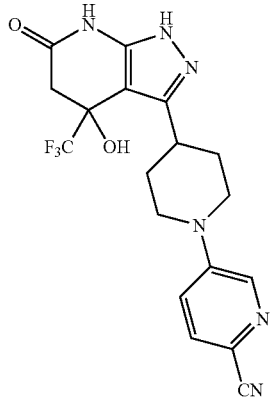

Reaction was performed in the same way as the method described in Example 1 using 5-[4-(5-amino-1H-pyrazol-3-yl)piperidin-1-yl]pyridine-2-carbonitrile (121 mg, 0.451 mmol) produced in Reference Example 37 instead of 3-(1-phenylpiperidin-4-yl)-1H-pyrazol-5-amine. Ethanol (2 mL) was added to the reaction solution, and the resulting suspension was stirred for 30 minutes. The resulting precipitate was collected by filtration to obtain the title compound (68.5 mg, yield: 37%).

$^1$H-NMR (400 MHz, DMSO-d$_6$) δ: 12.24 (1H, s), 10.51 (1H, s), 8.45 (1H, d, J=3 Hz), 7.75 (1H, d, J=9 Hz), 7.40 (1H, dd, J=9 Hz, 3 Hz), 6.75 (1H, s), 4.20-4.11 (2H, m), 3.32-3.22 (1H, m), 3.02-2.86 (3H, m), 2.73 (1H, d, J=16 Hz), 1.93-1.86 (1H, m), 1.83-1.68 (3H, m);
MS (ESI) m/z: 407 (M+H)$^+$.

Example 20

6-{4-[4-Hydroxy-6-oxo-4-(trifluoromethyl)-4,5,6,7-tetrahydro-1H-pyrazolo[3,4-b]pyridin-3-yl]piperidin-1-yl}-2-methylpyridine-3-carbonitrile

[Formula 87]

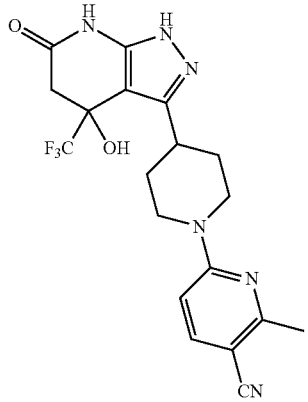

The title compound (0.195 g, yield: 29%) was obtained through reaction in the same way as the method described in Example 19 using 6-[4-(5-amino-1H-pyrazol-3-yl)piperidin-1-yl]-2-methylpyridine-3-carbonitrile (0.458 g, 1.62 mmol) produced in Reference Example 38 instead of 5-[4-(5-amino-1H-pyrazol-3-yl)piperidin-1-yl]pyridine-2-carbonitrile.

$^1$H-NMR (400 MHz, DMSO-d$_6$) δ: 12.20 (1H, s), 10.51 (1H, s), 7.77 (1H, d, J=9 Hz), 6.81 (1H, d, J=9 Hz), 6.76 (1H, s), 4.65-4.58 (2H, m), 3.33-3.25 (1H, m), 2.97-2.87 (3H, m), 2.73 (1H, d, J=16 Hz), 2.47 (3H, s), 1.94-1.88 (1H, m), 1.76-1.58 (3H, m);
MS (ESI) m/z: 421 (M+H)$^+$.

Example 21

2-Chloro-6-{4-[4-hydroxy-6-oxo-4-(trifluoromethyl)-4,5,6,7-tetrahydro-1H-pyrazolo[3,4-b]pyridin-3-yl]piperidin-1-yl}pyridine-3-carbonitrile

[Formula 88]

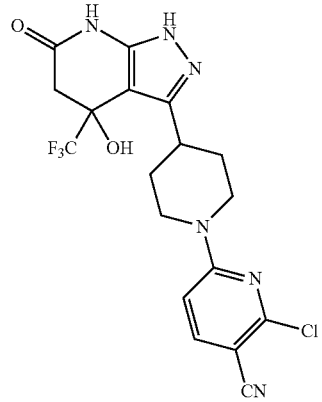

The title compound (0.131 g, yield: 37%) was obtained through reaction in the same way as the method described in Example 19 using 6-[4-(5-amino-1H-pyrazol-3-yl)piperidin-1-yl]-2-chloropyridine-3-carbonitrile (0.245 g, 0.809 mmol) produced in Reference Example 39 instead of 5-[4-(5-amino-1H-pyrazol-3-yl)piperidin-1-yl]pyridine-2-carbonitrile.

$^1$H-NMR (400 MHz, DMSO-d$_6$) δ: 12.20 (1H, s), 10.52 (1H, s), 7.95 (1H, d, J=9 Hz), 6.99 (1H, d, J=9 Hz), 6.77 (1H, s), 4.56-4.47 (2H, m), 3.37-3.28 (1H, m), 3.08-2.98 (2H, m), 2.90 (1H, d, J=16 Hz), 2.73 (1H, d, J=16 Hz), 1.95-1.90 (1H, m), 1.78-1.60 (3H, m);
MS (ESI) m/z: 441 (M+H)$^+$.

Example 22

6-{4-[4-Hydroxy-6-oxo-4-(trifluoromethyl)-4,5,6,7-tetrahydro-1H-pyrazolo[3,4-b]pyridin-3-yl]piperidin-1-yl}pyridine-2-carbonitrile

[Formula 89]

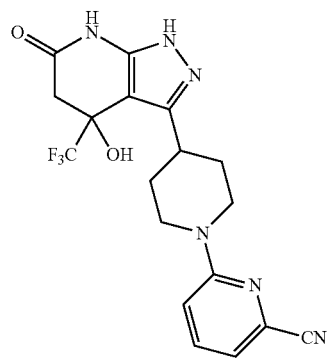

Reaction was performed for 2 hours in the same way as the method described in Example 1 using 6-[4-(5-amino-1H- pyrazol-3-yl)piperidin-1-yl]-2-carbonitrile (0.150 g, 0.559 mmol) produced in Reference Example 40 instead of 3-(1-phenylpiperidin-4-yl)-1H-pyrazol-5-amine. The obtained residue was purified by silica gel column chromatography [elute: hexane/ethyl acetate=40/60-20/80 (gradient)] to obtain the title compound (0.112 g, yield: 49%).

$^1$H-NMR (400 MHz, DMSO-$d_6$) δ: 12.22 (1H, s), 10.51 (1H, s), 7.69 (1H, dd, J=9 Hz, 7 Hz), 7.23 (1H, d, J=9 Hz), 7.17 (1H, d, J=7 Hz), 6.76 (1H, s), 4.50-4.43 (2H, m), 3.32-3.23 (1H, m), 2.94-2.84 (3H, m), 2.73 (1H, d, J=17 Hz), 1.93-1.87 (1H, m), 1.76-1.61 (3H, m);

MS (ESI) m/z: 407 (M+H)$^+$.

Example 23

3-{4-[4-Hydroxy-6-oxo-4-(trifluoromethyl)-4,5,6,7-tetrahydro-1H-pyrazolo[3,4-b]pyridin-3-yl]piperidin-1-yl}benzonitrile

[Formula 90]

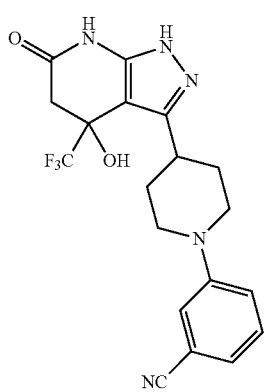

The title compound (41.5 mg, yield: 42%) was obtained through reaction in the same way as the method described in Example 22 using 3-[4-(5-amino-1H-pyrazol-3-yl)piperidin-1-yl]benzonitrile (65.0 mg, 0.243 mmol) produced in Reference Example 41 instead of 6-[4-(5-amino-1H-pyrazol-3-yl)piperidin-1-yl]-2-carbonitrile.

$^1$H-NMR (400 MHz, DMSO-$d_6$) δ: 12.28 (1H, s), 10.52 (1H, s), 7.41-7.35 (2H, m), 7.32-7.29 (1H, m), 7.15-7.12 (1H, m), 6.74 (1H, s), 3.97-3.91 (2H, m), 3.21-3.12 (1H, m), 2.90 (1H, d, J=16 Hz), 2.81-2.68 (3H, m), 1.94-1.69 (4H, m);

MS (ESI) m/z: 406 (M+H)$^+$.

Example 24

3-[1-(1,3-Benzoxazol-2-yl)piperidin-4-yl]-4-hydroxy-4-(trifluoromethyl)-1,4,5,7-tetrahydro-6H-pyrazolo[3,4-b]pyridin-6-one

[Formula 91]

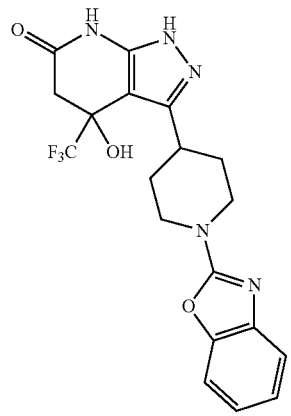

The title compound (0.50 g, yield: 36%) was obtained through reaction in the same way as the method described in Example 1 using 3-[1-(1,3-benzoxazol-2-yl)piperidin-4-yl]-1H-pyrazol-5-amine (0.93 g, 3.28 mmol) produced in Reference Example 42 instead of 3-(1-phenylpiperidin-4-yl)-1H-pyrazol-5-amine.

$^1$H-NMR (DMSO-$d_6$) δ: 12.25 (1H, s), 10.51 (1H, s), 7.42 (1H, d, J=8 Hz), 7.30 (1H, d, J=8 Hz), 7.16 (1H, td, J=8 Hz, 1 Hz), 7.02 (1H, td, J=7 Hz, 1 Hz), 6.77 (1H, s), 4.27-4.25 (2H, m), 3.32-3.25 (1H, m), 3.21-3.13 (2H, m), 2.90 (1H, d, J=17 Hz), 2.73 (1H, d, J=17 Hz), 1.98-1.70 (4H, m);

MS (ESI) m/z: 422 (M+H)$^+$.

Example 25

3-[1-(1,3-Benzothiazol-2-yl)piperidin-4-yl]-4-hydroxy-4-(trifluoromethyl)-1,4,5,7-tetrahydro-6H-pyrazolo[3,4-b]pyridin-6-one

[Formula 92]

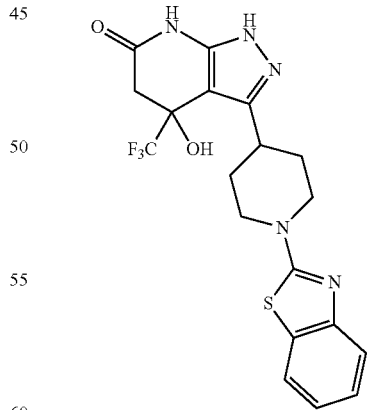

Reaction was performed in the same way as the method described in Example 1 using 3-[1-(1,3-benzothiazol-2-yl)piperidin-4-yl]-1H-pyrazol-5-amine (0.58 g, 1.94 mmol) produced in Reference Example 43 instead of 3-(1-phenylpiperidin-4-yl)-1H-pyrazol-5-amine. The obtained residue was purified by silica gel column chromatography [NH-silica gel column, elute: ethyl acetate/methanol=97/3-80/20 (gradient)] to obtain the title compound (0.40 g, yield: 47%).

$^1$H-NMR (DMSO-$d_6$) δ: 12.27 (1H, s), 10.52 (1H, s), 7.76 (1H, dd, J=8 Hz, 1 Hz), 7.46-7.45 (1H, m), 7.30-7.25 (1H, m), 7.09-7.04 (1H, m), 6.78 (1H, s), 4.20-4.11 (2H, m), 3.32-3.18 (3H, m), 2.90 (1H, d, J=16 Hz), 2.73 (1H, d, J=16 Hz), 1.98-1.73 (4H, m);

MS (ESI) m/z: 438 (M+H)$^+$.

Example 26

4-Hydroxy-3-[1-(6-methylpyrazin-2-yl)piperidin-4-yl]-4-(trifluoromethyl)-1,4,5,7-tetrahydro-6H-pyrazolo[3,4-b]pyridin-6-one

[Formula 93]

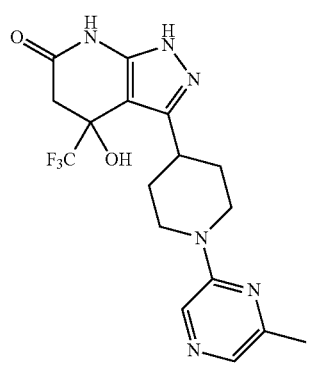

Reaction was performed in the same way as the method described in Example 1 using 3-[1-(6-methylpyrazin-2-yl)piperidin-4-yl]-1H-pyrazol-5-amine (0.99 g, 3.83 mmol) produced in Reference Example 44 instead of 3-(1-phenylpiperidin-4-yl)-1H-pyrazol-5-amine. The obtained residue was purified by silica gel column chromatography [elute: ethyl acetate/methanol=100/0-90/10 (gradient)] to obtain the title compound (571 mg, yield: 38%).

$^1$H-NMR (DMSO-$d_6$) δ: 12.23 (1H, s), 10.51 (1H, s), 8.14 (1H, s), 7.70 (1H, s), 6.75 (1H, s), 4.51-4.49 (2H, m), 3.31-3.21 (1H, m), 2.93-2.81 (3H, m), 2.73 (1H, d, J=16 Hz), 2.30 (3H, s), 1.94-1.61 (4H, m);

MS (ESI) m/z: 397 (M+H)$^+$.

Example 27

4-Hydroxy-3-[1-(pyridin-3-yl)piperidin-4-yl]-4-(trifluoromethyl)-1,4,5,7-tetrahydro-6H-pyrazolo[3,4-b]pyridin-6-one

[Formula 94]

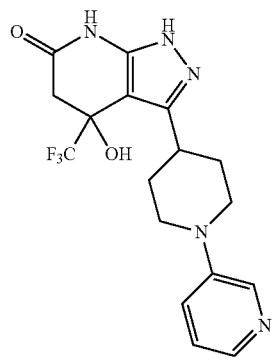

The title compound (103 mg, yield: 17%) was obtained through reaction in the same way as the method described in Example 1 using 3-[1-(pyridin-3-yl)piperidin-4-yl]-1H-pyrazol-5-amine (0.393 g, 1.62 mmol) produced in Reference Example 45 instead of 3-(1-phenylpiperidin-4-yl)-1H-pyrazol-5-amine.

$^1$H-NMR (400 MHz, DMSO-$d_6$) δ: 12.30 (1H, s), 10.51 (1H, s), 8.33 (1H, d, J=3 Hz), 7.98 (1H, dd, J=5 Hz, 1 Hz), 7.37-7.33 (1H, m), 7.21 (1H, dd, J=9 Hz, 5 Hz), 6.73 (1H, s), 3.91-3.84 (2H, m), 3.19-3.11 (1H, m), 2.90 (1H, d, J=16 Hz), 2.77-2.72 (2H, m), 2.73 (1H, d, J=16 Hz), 1.95-1.72 (4H, m);

MS (ESI) m/z: 382 (M+H)$^+$.

Example 28

4-Hydroxy-3-[1-(6-methoxypyridazin-3-yl)piperidin-4-yl]-4-(trifluoromethyl)-1,4,5,7-tetrahydro-6H-pyrazolo[3,4-b]pyridin-6-one

[Formula 95]

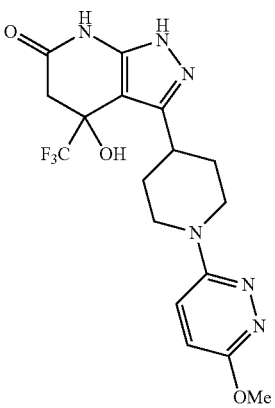

Reaction was performed in the same way as the method described in Example 1 using 3-[1-(6-methoxypyridazin-3-yl)piperidin-4-yl]-1H-pyrazol-5-amine (4.81 g, 17.5 mmol) produced in Reference Example 47 instead of 3-(1-phenylpiperidin-4-yl)-1H-pyrazol-5-amine. Then, the solvent in the reaction solution was distilled off under reduced pressure, followed by azeotropy with toluene twice. Ethanol (100 mL) was added to the obtained solid, and the resulting suspension was stirred at 60° C. for 1 hour. After cooling to room temperature, the solid was collected by filtration. Ethanol (100 mL) was added thereto again, and the mixture was further stirred at 100° C. for 3 hours. After cooling to room temperature, the solid was collected by filtration. The obtained solid was resuspended in ethanol (100 mL) again, and the suspension was stirred at 100° C. for 2 hours. After cooling to room temperature, the solid was collected by filtration to obtain the title compound (2.04 g, yield: 28%).

$^1$H-NMR (400 MHz, DMSO-$d_6$) δ: 12.24 (1H, s), 10.50 (1H, s), 7.42 (1H, d, J=10 Hz), 7.03 (1H, d, J=10 Hz), 6.73 (1H, s), 4.36-4.29 (2H, m), 3.90 (3H, s), 3.27-3.20 (1H, m), 2.93-2.79 (3H, m), 2.73 (1H, d, J=16 Hz), 1.91-1.68 (4H, m);

MS (ESI) m/z: 413 (M+H)$^+$.

Example 29

4-Hydroxy-3-[1-(1,3-thiazol-2-yl)piperidin-4-yl]-4-(trifluoromethyl)-1,4,5,7-tetrahydro-6H-pyrazolo[3,4-b]pyridin-6-one

[Formula 96]

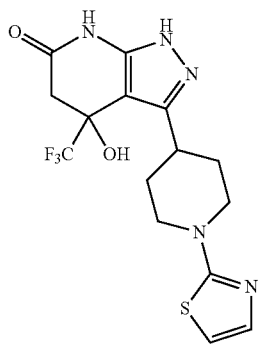

The title compound (0.086 g, yield: 13%) was obtained through reaction in the same way as the method described in Example 1 using 3-[1-(1,3-thiazol-2-yl)piperidin-4-yl]-1H-pyrazol-5-amine (0.438 g, 1.76 mmol) produced in Reference Example 48 instead of 3-(1-phenylpiperidin-4-yl)-1H-pyrazol-5-amine.

$^1$H-NMR (400 MHz, DMSO-$d_6$) δ: 12.28 (1H, s), 10.51 (1H, s), 7.15 (1H, d, J=4 Hz), 6.81 (1H, d, J=4 Hz), 6.75 (1H, s), 4.05-3.96 (2H, m), 3.27-3.17 (1H, m), 3.08-2.98 (2H, m), 2.89 (1H, d, J=17 Hz), 2.72 (1H, d, J=17 Hz), 1.94-1.70 (4H, m);

MS (ESI) m/z: 388 (M+H)$^+$.

Example 30

4-Hydro-3-[1-(4-methoxypyrimidin-2-yl)piperidin-4-yl]-4-(trifluoromethyl)-1,4,5,7-tetrahydro-6H-pyrazolo[3,4-b]pyridin-6-one

[Formula 97]

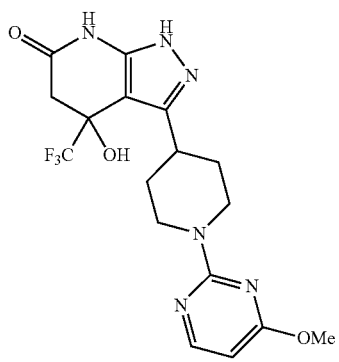

The title compound (0.305 g, yield: 38%) was obtained through reaction in the same way as the method described in Example 1 using 3-[1-(4-methoxypyrimidin-2-yl)piperidin-4-yl]-1H-pyrazol-5-amine (0.536 g, 1.95 mmol) produced in Reference Example 49 instead of 3-(1-phenylpiperidin-4-yl)-1H-pyrazol-5-amine.

$^1$H-NMR (400 MHz, DMSO-$d_6$) δ: 12.18 (1H, s), 10.49 (1H, s), 8.09 (1H, d, J=6 Hz), 6.74 (1H, s), 6.05 (1H, d, J=6 Hz), 4.85-4.77 (2H, m), 3.84 (3H, s), 3.32-3.22 (1H, m), 2.93-2.81 (3H, m), 2.72 (1H, d, J=17 Hz), 1.92-1.85 (1H, m), 1.75-1.57 (3H, m);

MS (ESI) m/z: 413 (M+H)$^+$.

Example 31

6-{4-[4-Hydroxy-6-oxo-4-(trifluoromethyl)-4,5,6,7-tetrahydro-1H-pyrazolo[3,4-b]pyridin-3-yl]piperidin-1-yl}pyridine-3-carbonitrile

[Formula 98]

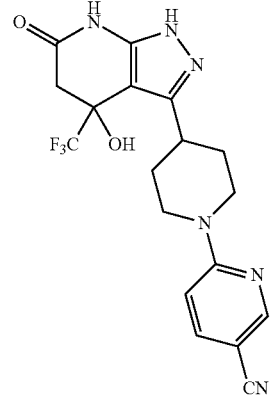

Reaction was performed in the same way as the method described in Example 1 using 6-(5-amino-1H-pyrazol-3-yl)piperidin-1-yl]pyridine-3-carbonitrile (0.206 g, 0.768 mmol) produced in Reference Example 31 instead of 3-(1-phenylpiperidin-4-yl)-1H-pyrazol-5-amine. The obtained residue was purified by silica gel column chromatography [NH-silica gel, elute: ethyl acetate]. The precipitate was collected by filtration and washed with ethyl acetate to obtain the title compound (0.037 g, yield: 12%).

$^1$H-NMR (400 MHz, DMSO-$d_6$) δ: 12.20 (1H, s), 10.50 (1H, s), 8.50-8.48 (1H, m), 7.84 (1H, dd, J=9 Hz, 2 Hz), 7.00-6.96 (1H, m), 6.75 (1H, s), 4.65-4.56 (2H, m), 3.37-3.29 (1H, m), 3.01-2.93 (2H, m), 2.89 (1H, d, J=17 Hz), 2.72 (1H, d, J=17 Hz), 1.94-1.87 (1H, m), 1.77-1.60 (3H, m);

MS (ESI) m/z: 407 (M+H)$^+$.

Example 32

4-Hydroxy-3-[1-(6-methoxypyridin-3-yl)piperidin-4-yl]-4-(trifluoromethyl)-1,4,5,7-tetrahydro-6H-pyrazolo[3,4-b]pyridin-6-one

[Formula 99]

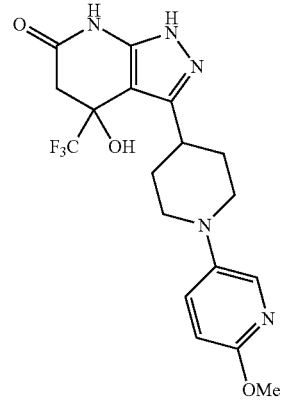

The title compound (0.345 g, yield: 25%) was obtained through reaction in the same way as the method described in Example 1 using 3-[1-(6-methoxypyridin-3-yl)piperidin-4-yl]-1H-pyrazol-5-amine (0.913 g, 3.34 mmol) produced in Reference Example 51 instead of 3-(1-phenylpiperidin-4-yl)-1H-pyrazol-5-amine.

$^1$H-NMR (400 MHz, DMSO-$d_6$) δ: 12.30 (1H, s), 10.51 (1H, s), 7.82-7.80 (1H, m), 7.47 (1H, dd, J=9 Hz, 3 Hz), 6.73-6.70 (2H, m), 3.78 (3H, s), 3.65-3.59 (2H, m), 3.12-3.04 (1H, m), 2.89 (1H, d, J=16 Hz), 2.72 (1H, d, J=16 Hz), 2.66-2.59 (2H, m), 1.96-1.81 (3H, m), 1.78-1.72 (1H, m);

MS (ESI) m/z: 412 (M+H)$^+$.

Example 33

2-{4-[4-Hydroxy-6-oxo-4-(trifluoromethyl)-4,5,6,7-tetrahydro-1H-pyrazolo[3,4-b]pyridin-3-yl]piperidin-1-yl}pyridine-4-carbonitrile

[Formula 100]

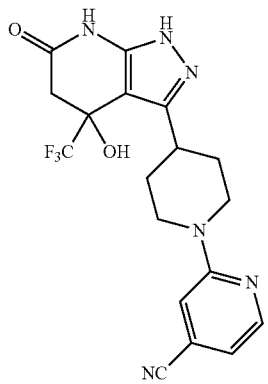

Reaction was performed in the same way as the method described in Example 1 using 2-[4-(5-amino-1H-pyrazol-3-yl)piperidin-1-yl]pyridine-4-carbonitrile (0.114 g, 0.425 mmol) produced in Reference Example 32 instead of 3-(1-phenylpiperidin-4-yl)-1H-pyrazol-5-amine. The obtained residue was purified by thin-layer silica gel column chromatography [elute: ethyl acetate/methanol=92/8] and further purified by silica gel column chromatography [elute: hexane/ethyl acetate=50/50-0/100 (gradient)] to obtain the title compound (0.080 g, yield: 46%).

$^1$H-NMR (400 MHz, DMSO-$d_6$) δ: 12.20 (1H, s), 10.50 (1H, s), 8.29 (1H, dd, J=5 Hz, 1 Hz), 7.37-7.34 (1H, m), 6.91 (1H, dd, J=5 Hz, 1 Hz), 6.74 (1H, s), 4.56-4.48 (2H, m), 3.32-3.25 (1H, m), 2.93-2.85 (3H, m), 2.73 (1H, d, J=16 Hz), 1.91-1.85 (1H, m), 1.75-1.59 (3H, m);

MS (ESI) m/z: 407 (M+H)$^+$.

Example 34

3-[1-(6-Chloropyridazin-3-yl)piperidin-4-yl]-4-hydroxy-4-(trifluoromethyl)-1,4,5,7-tetrahydro-6H-pyrazolo[3,4-b]pyridin-6-one

[Formula 101]

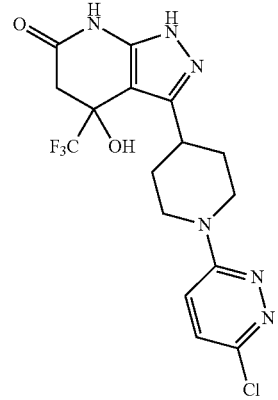

The title compound (0.158 g, yield: 33%) was obtained through reaction in the same way as the method described in Example 1 using 3-[1-(6-chloropyridazin-3-yl)piperidin-4-yl]-1H-pyrazol-5-amine (0.323 g, 1.16 mmol) produced in Reference Example 34 instead of 3-(1-phenylpiperidin-4-yl)-1H-pyrazol-5-amine.

$^1$H-NMR (400 MHz, DMSO-$d_6$) δ: 12.20 (1H, s), 10.49 (1H, s), 7.52 (1H, d, J=10 Hz), 7.43 (1H, d, J=10 Hz), 6.73 (1H, s), 4.52-4.45 (2H, m), 3.35-3.26 (1H, m), 3.00-2.85 (3H, m), 2.72 (1H, d, J=16 Hz), 1.93-1.86 (1H, m), 1.81-1.65 (3H, m);

MS (ESI) m/z: 417 (M+H)$^+$.

Example 35

4-{4-[4-Hydroxy-6-oxo-4-(trifluoromethyl)-4,5,6,7-tetrahydro-1H-pyrazolo[3,4-b]pyridin-3-yl]piperidin-1-yl}benzonitrile

[Formula 102]

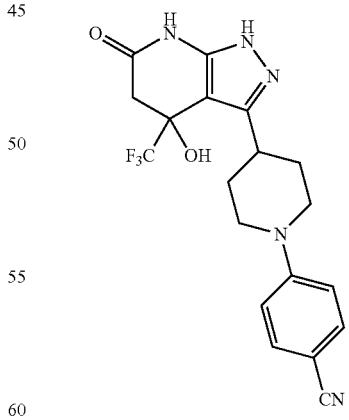

Reaction was performed in the same way as the method described in Example 1 using 4-[4-(5-amino-1H-pyrazol-3-yl)piperidin-1-yl]benzonitrile (0.994 g, 3.72 mmol) produced in Reference Example 53 instead of 3-(1-phenylpiperidin-4-yl)-1H-pyrazol-5-amine. Then, ethanol (60 mL) was added to the reaction solution, and the precipitate was collected by filtration. Ethanol (50 mL) was added to the obtained solid, and the resulting suspension was stirred at 100° C. for 2 hours. After cooling to room temperature, the precipitate was collected by filtration to obtain the title compound (0.668 g, yield: 44%).

$^1$H-NMR (400 MHz, DMSO-d$_6$) δ: 12.23 (1H, s), 10.48 (1H, s), 7.59-7.54 (2H, m), 7.06-7.02 (2H, m), 6.71 (1H, s), 4.12-4.02 (2H, m), 3.29-3.19 (1H, m), 2.94-2.84 (3H, m), 2.72 (1H, d, J=17 Hz), 1.93-1.67 (4H, m);

MS (ESI) m/z: 406 (M+H)$^+$.

Example 36

4-Hydroxy-3-[1-(5-methoxypyridin-2-yl)piperidin-4-yl]-4-(trifluoromethyl)-1,4,5,7-tetrahydro-6H-pyrazolo[3,4-b]pyridin-6-one

[Formula 103]

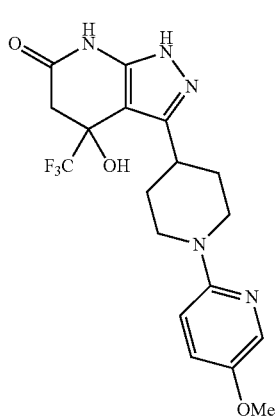

The title compound (0.460 g, yield: 38%) was obtained through reaction in the same way as the method described in Example 1 using 3-[1-(5-methoxypyridin-2-yl)piperidin-4-yl]-1H-pyrazol-5-amine (0.815 g, 2.98 mmol) produced in Reference Example 54 instead of 3-(1-phenylpiperidin-4-yl)-1H-pyrazol-5-amine.

$^1$H-NMR (400 MHz, DMSO-d$_6$) δ: 12.22 (1H, s), 10.47 (1H, s), 7.87 (1H, d, J=3 Hz), 7.25 (1H, dd, J=9 Hz, 3 Hz), 6.83 (1H, d, J=9 Hz), 6.69 (1H, s), 4.31-4.23 (2H, m), 3.73 (3H, s), 3.21-3.12 (1H, m), 2.88 (1H, d, J=17 Hz), 2.75-2.63 (3H, m), 1.91-1.65 (4H, m);

MS (ESI) m/z: 412 (M+H)$^+$.

Example 37

5-{4-[4-Hydroxy-6-oxo-4-(trifluoromethyl)-4,5,6,7-tetrahydro-1H-pyrazolo[3,4-b]pyridin-3-yl]piperidin-1-yl}pyridine-3-carbonitrile

[Formula 104]

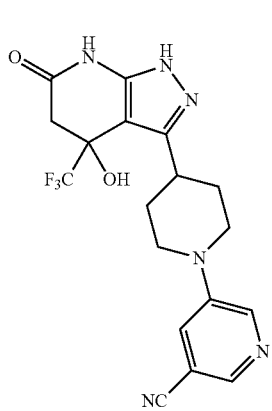

The title compound (0.080 g, yield: 33%) was obtained through reaction in the same way as the method described in Example 1 using 5-[4-(5-amino-1H-pyrazol-3-yl)piperidin-1-yl]pyridine-3-carbonitrile (0.161 g, 0.600 mmol) produced in Reference Example 35 instead of 3-(1-phenylpiperidin-4-yl)-1H-pyrazol-5-amine.

$^1$H-NMR (400 MHz, DMSO-d$_6$) δ: 12.25 (1H, s), 10.50 (1H, s), 8.61 (1H, d, J=3 Hz), 8.30 (1H, d, J=2 Hz), 7.81-7.79 (1H, m), 6.73 (1H, s), 4.07-3.99 (2H, m), 3.25-3.17 (1H, m), 2.92-2.82 (3H, m), 2.73 (1H, d, J=16 Hz), 1.93-1.69 (4H, m);

MS (ESI) m/z: 407 (M+H)$^+$.

Example 38

3-Fluoro-5-{4-[4-hydroxy-6-oxo-4-(trifluoromethyl)-4,5,6,7-tetrahydro-1H-pyrazolo[3,4-b]pyridin-3-yl]piperidin-1-yl}pyridine-2-carbonitrile

[Formula 105]

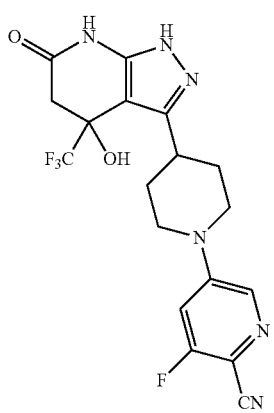

The title compound (0.128 g, yield: 32%) was obtained through reaction in the same way as the method described in Example 35 using 5-[4-(5-amino-1H-pyrazol-3-yl)piperidin-1-yl]-3-fluoropyridine-2-carbonitrile (0.270 g, 0.943 mmol) produced in Reference Example 36 instead of 4-[4-(5-amino-1H-pyrazol-3-yl)piperidin-1-yl]benzonitrile.

$^1$H-NMR (400 MHz, DMSO-d$_6$) δ: 12.21 (1H, s), 10.50 (1H, s), 8.36-8.33 (1H, m), 7.44 (1H, dd, J=14 Hz, 2 Hz), 6.74 (1H, s), 4.25-4.16 (2H, m), 3.35-3.26 (1H, m), 3.11-3.01 (2H, m), 2.88 (1H, d, J=16 Hz), 2.73 (1H, d, J=16 Hz), 1.93-1.86 (1H, m), 1.84-1.68 (3H, m);

MS (ESI) m/z: 425 (M+H)$^+$.

Example 39

4-Hydroxy-3-[1-(4-methoxypyridin-2-yl)piperidin-4-yl]-4-(trifluoromethyl)-1,4,5,7-tetrahydro-6H-pyrazolo[3,4-b]pyridin-6-one

[Formula 106]

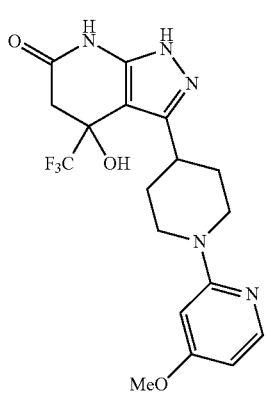

The title compound (0.407 g, yield: 38%) was obtained as a white solid through reaction in the same way as the method described in Example 1 using 3-[1-(4-methoxypyridin-2-yl)piperidin-4-yl]-1H-pyrazol-5-amine (0.716 g, 2.62 mmol) produced in Reference Example 55 instead of 3-(1-phenylpiperidin-4-yl)-1H-pyrazol-5-amine.

$^{1}$H-NMR (DMSO-$d_6$) δ: 12.22 (1H, s), 10.49 (1H, s), 7.92 (1H, d, J=6 Hz), 6.72 (1H, s), 6.30 (1H, d, J=2 Hz), 6.25 (1H, dd, J=6 Hz, 2 Hz), 4.48-4.41 (2H, m), 3.78 (3H, s), 3.26-3.18 (1H, m), 2.89 (1H, d, J=17 Hz), 2.79-2.70 (3H, m), 1.90-1.84 (1H, m), 1.78-1.62 (3H, m);

MS (ESI) m/z: 412 (M+H)$^+$.

Example 40

4-Hydroxy-3-[1-(5-methoxypyridin-3-yl)piperidin-4-yl]-4-(trifluoromethyl)-1,4,5,7-tetrahydro-6H-pyrazolo[3,4-b]pyridin-6-one

[Formula 107]

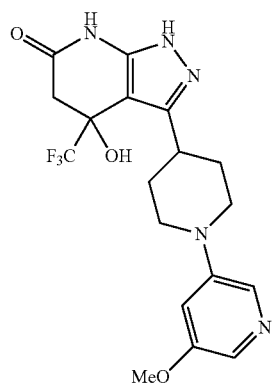

The title compound (0.495 g, yield: 38%) was obtained through reaction in the same way as the method described in Example 1 using 3-[1-(5-methoxypyridin-3-yl)piperidin-4-yl]-1H-pyrazol-5-amine (0.870 g, 3.18 mmol) produced in Reference Example 57 instead of 3-(1-phenylpiperidin-4-yl)-1H-pyrazol-5-amine.

$^{1}$H-NMR (DMSO-$d_6$) δ: 12.28 (1H, s), 10.50 (1H, s), 7.94 (1H, d, J=2 Hz), 7.71 (1H, d, J=2 Hz), 6.89-6.87 (1H, m), 6.72 (1H, s), 3.93-3.86 (2H, m), 3.80 (3H, s), 3.20-3.11 (1H, m), 2.89 (1H, d, J=16 Hz), 2.79-2.70 (3H, m), 1.94-1.71 (4H, m);

MS (ESI) m/z: 412 (M+H)$^+$.

Example 41

4-Hydroxy-4-(trifluoromethyl)-3-{1-[6-(trifluoromethyl)pyridin-3-yl]piperidin-4-yl}-1,4,5,7-tetrahydro-6H-pyrazolo[3,4-b]pyridin-6-one

[Formula 108]

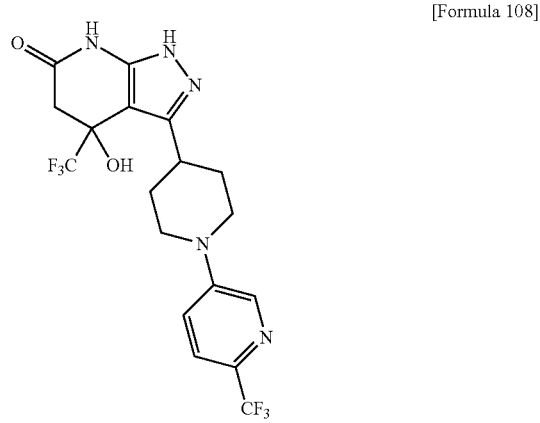 [SMILES: O=C1CC(O)(C(F)(F)F)c2c(C3CCN(c4ccc(C(F)(F)F)nc4)CC3)n[nH]c2N1]

The title compound (0.228 g, yield: 47%) was obtained through reaction in the same way as the method described in Example 1 using 3-{1-[6-(trifluoromethyl)pyridin-3-yl]piperidin-4-yl}-1H-pyrazol-5-amine (0.338 g, 1.09 mmol) produced in Reference Example 58 instead of 3-(1-phenylpiperidin-4-yl)-1H-pyrazol-5-amine.

$^{1}$H-NMR (DMSO-$d_6$) δ: 12.26 (1H, s), 10.50 (1H, s), 8.45 (1H, d, J=3 Hz), 7.64 (1H, d, J=9 Hz), 7.46 (1H, dd, J=9 Hz, 3 Hz), 6.74 (1H, s), 4.14-4.05 (2H, m), 3.30-3.21 (1H, m), 2.97-2.86 (3H, m), 2.73 (1H, d, J=17 Hz), 1.94-1.70 (4H, m);

MS (ESI) m/z: 450 (M+H)$^+$.

Example 42

6-{4-[4-Hydroxy-6-oxo-4-(trifluoromethyl)-4,5,6,7-tetrahydro-1H-pyrazolo[3,4-b]pyridin-3-yl]piperidin-1-yl}-4-methylpyridine-3-carbonitrile

[Formula 109]

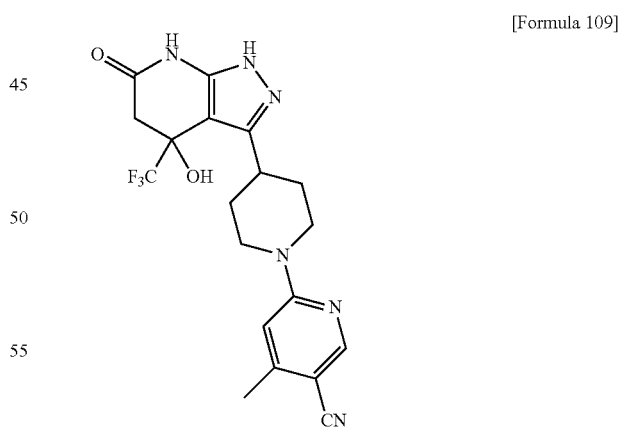

The title compound (0.179 g, yield: 30%) was obtained through reaction in the same way as the method described in Example 35 using 6-[4-(5-amino-1H-pyrazol-3-yl)piperidin-1-yl]-4-methylpyridine-3-carbonitrile (0.405 g, 1.43 mmol) produced in Reference Example 59 instead of 3-(1-phenylpiperidin-4-yl)-1H-pyrazol-5-amine.

$^{1}$H-NMR (DMSO-$d_6$) δ: 12.19 (1H, s), 10.49 (1H, s), 8.40 (1H, s), 6.92 (1H, s), 6.74 (1H, s), 4.65-4.55 (2H, m), 3.36-

3.27 (1H, m), 3.00-2.86 (3H, m), 2.73 (1H, d, J=16 Hz), 2.34 (3H, s), 1.93-1.87 (1H, m), 1.76-1.58 (3H, m);
MS (ESI) m/z: 421 (M+H)$^+$.

Reference Example 60

4-Hydroxy-3-(piperidin-4-yl)-4-(trifluoromethyl)-1,4,5,7-tetrahydro-6H-pyrazolo[3,4-b]pyridin-6-one hydrochloride

[Formula 110]

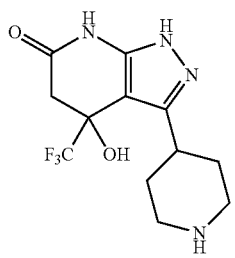

A solid (1.27 g, yield: 71%) was obtained through reaction in the same way as the method described in Example 1 using tert-butyl 4-(5-amino-1H-pyrazol-3-yl)piperidine-1-carboxylate (compound described in the pamphlet of WO2011/045344, 1 g, 4.42 mmol) instead of 3-(1-phenylpiperidin-4-yl)-1H-pyrazol-5-amine.

A solution of 4 N hydrochloric acid in dioxane (0.742 mL, 2.97 mmol) was added at 0° C. to a solution of the obtained solid (400 mg, 0.989 mmol) in 1,4-dioxane (1 mL), and the mixture was stirred at room temperature for 80 minutes. Hexane was added to the reaction solution, and the obtained precipitate was collected by filtration to obtain the title compound (366 mg, quantitative).

$^1$H-NMR (DMSO-d$_6$) δ: 10.55 (1H, s), 9.00-8.89 (1H, m), 8.67-8.51 (1H, m), 6.85 (1H, br s), 3.41-3.29 (2H, m), 3.27-3.15 (1H, m), 3.05-2.87 (2H, m), 2.92 (1H, d, J=16 Hz), 2.73 (1H, d, J=16 Hz), 2.11-1.72 (4H, m).

Example 43

4-Hydroxy-4-(trifluoromethyl)-3-{1-[6-(trifluoromethyl)pyridazin-3-yl]piperidin-4-yl}-1,4,5,7-tetrahydro-6H-pyrazolo[3,4-b]pyridin-6-one

[Formula 111]

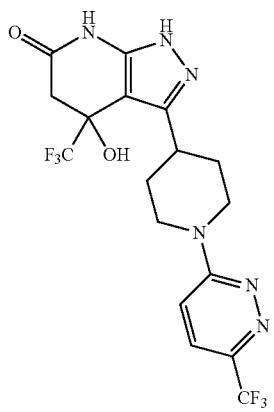

N,N-Diisopropylethylamine (59.8 μL, 0.352 mmol) and 3-chloro-6-(trifluoromethyl)pyridazine (80.2 mg, 0.439 mmol) were added to a solution of 4-hydroxy-3-(piperidin-4-yl)-4-(trifluoromethyl)-1,4,5,7-tetrahydro-6H-pyrazolo[3,4-b]pyridin-6-one hydrochloride (100 mg, 0.293 mmol) produced in Reference Example 60 in dimethyl sulfoxide (0.5 mL), and the mixture was stirred overnight at room temperature. The reaction solution was diluted with ethyl acetate, washed with water, a saturated ammonium chloride aqueous solution, and brine in this order, and dried over anhydrous sodium sulfate, and the solvent was distilled off under reduced pressure. The obtained residue was purified by silica gel column chromatography [elute: ethyl acetate/methanol=100/0-90/10 (gradient)] to obtain the title compound (39.8 mg, yield: 30%).

$^1$H-NMR (DMSO-d$_6$) δ: 12.21 (1H, s), 10.51 (1H, s), 7.81 (1H, d, J=10 Hz), 7.46 (1H, d, J=10 Hz), 6.76 (1H, s), 4.72-4.61 (2H, m), 3.42-3.34 (1H, m), 3.12-3.01 (2H, m), 2.90 (1H, d, J=17 Hz), 2.73 (1H, d, J=17 Hz), 1.98-1.89 (1H, m), 1.80-1.65 (3H, m);
MS (ESI) m/z: 451 (M+H)$^+$.

Example 44

4-Hydroxy-4-(trifluoromethyl)-3-{1-[5-(trifluoromethyl)pyrimidin-2-yl]piperidin-4-yl}-1,4,5,7-tetrahydro-6H-pyrazolo[3,4-b]pyridin-6-one

[Formula 112]

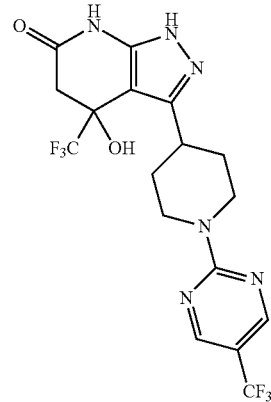

The title compound (45.2 mg, yield: 34%) was obtained through reaction in the same way as the method described in Example 43 using 2-chloro-5-(trifluoromethyl)pyrimidine (80.3 mg, 0.440 mmol) instead of 3-chloro-6-(trifluoromethyl)pyridazine.

$^1$H-NMR (DMSO-d$_6$) δ: 12.18 (1H, s), 10.50 (1H, s), 8.73-8.71 (2H, m), 6.76 (1H, s), 4.92-4.81 (2H, m), 3.39-3.33 (1H, m), 3.07-2.97 (2H, m), 2.90 (1H, d, J=17 Hz), 2.73 (1H, d, J=17 Hz), 1.97-1.90 (1H, m), 1.80-1.58 (3H, m);
MS (ESI) m/z: 451 (M+H)$^+$.

Reference Example 61

Ethyl 1-[6-(trifluoromethyl)pyrimidin-4-yl]piperidine-4-carboxylate

[Formula 113]

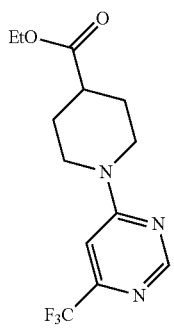

The title compound (1.06 g, yield: 90%) was obtained through reaction in the same way as the method described in Reference Example 9 using 1-[6-(trifluoromethyl)pyrimidin-4-yl]piperidine-4-carboxylic acid (1.07 g, 3.89 mmol) instead of 1-[5-(trifluoromethyl)pyridin-2-yl]piperidine-4-carboxylic acid and ethyl iodide (0.42 mL, 5.22 mmol) instead of methyl iodide.

$^1$H-NMR (400 MHz, CDCl$_3$) δ: 8.62 (1H, s), 6.78 (1H, s), 4.09 (2H, q, J=7 Hz), 3.18-3.11 (2H, m), 2.61 (1H, tt, J=11 Hz, 4 Hz), 2.04-1.97 (3H, m), 1.77-1.68 (2H, m), 1.24 (3H, t, J=7 Hz).

Reference Example 62

3-{1-[6-(Trifluoromethyl)pyrimidin-4-yl]piperidin-4-yl}-1H-pyrazol-5-amine

[Formula 114]

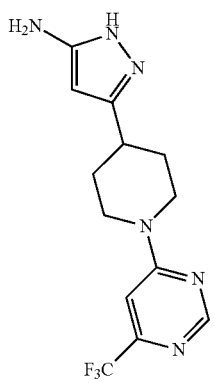

The title compound (512 mg, yield: 47%) was obtained through reaction in the same way as the method described in Reference Example 4 using ethyl 1-[6-(trifluoromethyl)pyrimidin-4-yl]piperidine-4-carboxylate (1.06 g, 3.50 mmol) produced in Reference Example 61 instead of ethyl 1-(6-methylpyridin-2-yl)piperidine-4-carboxylate.

$^1$H-NMR (400 MHz, DMSO-d$_6$) δ: 11.12 (1H, brs), 8.90 (1H, br s), 8.57 (1H, s), 7.25 (1H, s), 5.17 (1H, brs), 4.34 (1H, brs), 4.13-4.04 (2H, m), 3.14-3.00 (2H, m), 2.79 (1H, brs), 1.92-1.84 (2H, m), 1.46 (2H, dq, J=12 Hz, 4 Hz).

Example 45

4-Hydroxy-4-(trifluoromethyl)-3-{1-[6-(trifluoromethyl)pyrimidin-4-yl]piperidin-4-yl}-1,4,5,7-tetrahydro-6H-pyrazolo[3,4-b]pyridin-6-one

[Formula 115]

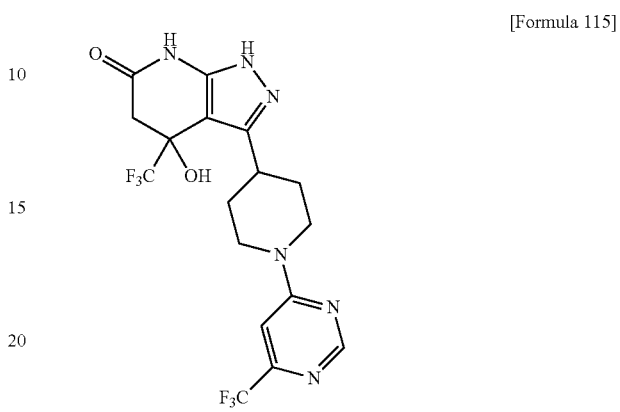

The title compound (335 mg, yield: 45%) was obtained through reaction in the same way as the method described in Example 1 using 3-{1-[6-(trifluoromethyl)pyrimidin-4-yl]piperidin-4-yl}-1H-pyrazol-5-amine (512 mg, 1.64 mmol) produced in Reference Example 62 instead of 3-(1-phenylpiperidin-4-yl)-1H-pyrazol-5-amine.

$^1$H-NMR (400 MHz, DMSO-d$_6$) δ: 12.19 (1H, s), 10.52 (1H, s), 8.64 (1H, s), 7.33 (1H, s), 6.79 (1H, s), 3.68-3.36 (3H, m), 3.03 (2H, brs), 2.90 (1H, d, J=17 Hz), 2.73 (1H, d, J=16 Hz), 1.93 (1H, d, J=11 Hz), 1.75-1.59 (3H, m);

MS (ESI) m/z: 451 (M+H)$^+$.

Example 46

4-Hydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one

[Formula 116]

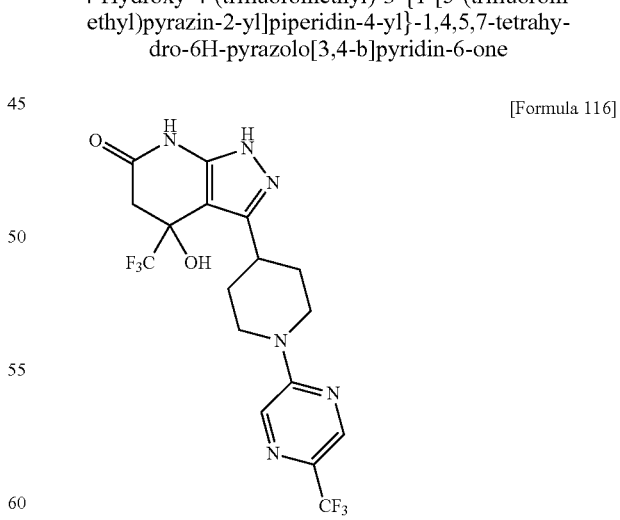

The title compound (141 mg, yield: 76%) was obtained through reaction in the same way as the method described in Example 43 using 2-chloro-5-(trifluoromethyl)pyrazine (135 mg, 0.440 mmol) instead of 3-chloro-6-(trifluoromethyl)pyridazine.

¹H-NMR (DMSO-d₆) δ: 12.20 (1H, s), 10.52 (1H, s), 8.50 (2H, m), 6.77 (1H, s), 4.64-4.61 (2H, m), 3.42-3.35 (1H, m), 3.05 (2H, t, J=14 Hz), 2.90 (1H, d, J=17 Hz), 2.73 (1H, d, J=16 Hz), 1.92 (1H, d, J=12 Hz), 1.79-1.65 (3H, m);
MS (ESI) m/z: 451 (M+H)⁺.

Example 47

4-Hydroxy-4-(trifluoromethyl)-3-{1-[5-(trifluoromethyl)-1,3,4-thiadiazol-2-yl]piperidin-4-yl}-1,4,5,7-tetrahydro-6H-pyrazolo[3,4-b]pyridin-6-one

[Formula 117]

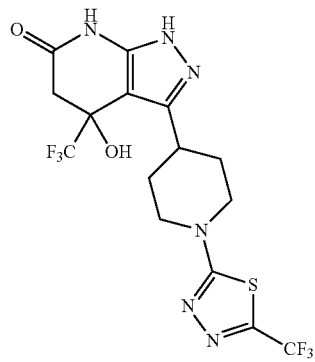

The title compound (145 mg, yield: 69%) was obtained through reaction in the same way as the method described in Example 43 using 2-chloro-5-(trifluoromethyl)-1,3,4-thiadiazole (140 mg, 0.742 mmol) instead of 3-chloro-6-(trifluoromethyl)pyridazine.
¹H-NMR (400 MHz, DMSO-d₆) δ: 12.28 (1H, s), 10.54 (1H, s), 6.80 (1H, s), 4.04 (2H, dd, J=13 Hz, 6 Hz), 3.44-3.30 (3H, m), 2.90 (1H, d, J=17 Hz), 2.73 (1H, d, J=16 Hz), 1.96-1.76 (4H, m);
MS (ESI) m/z: 457 (M+H)⁺.

Example 48

4-Hydroxy-4-(trifluoromethyl)-3-{1-[4-(trifluoromethyl)-1,3-thiazol-2-yl]piperidin-4-yl}-1,4,5,7-tetrahydro-6H-pyrazolo[3,4-b]pyridin-6-one (hereinafter, referred to as compound 48-a)

[Formula 118]

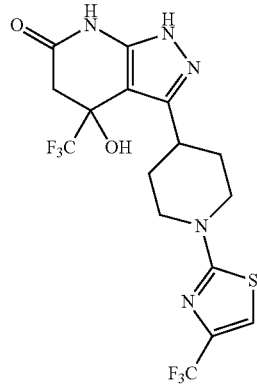

and 3-{1-[4,4'-bis(trifluoromethyl)-2,5'-bi-1,3-thiazol-2'-yl]piperidin-4-yl}-4-hydroxy-4-(trifluoromethyl)-1,4,5,7-tetrahydro-6H-pyrazolo[3,4-b]pyridin-6-one (hereinafter, referred to as compound 48-b)

[Formula 119]

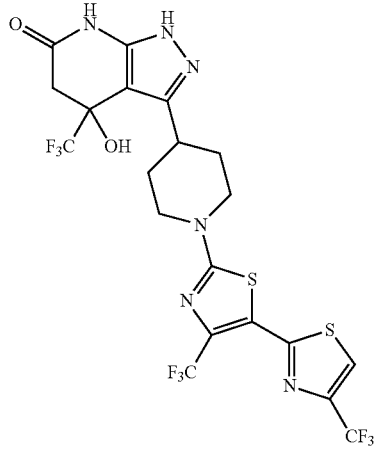

Copper(II) chloride (2.90 g, 21.57 mmol) was added to a solution of 2-amino-4-(trifluoromethyl)thiazole (3.05 g, 18.14 mmol) in acetonitrile (80 mL), then isoamyl nitrite (3.60 mL, 27.04 mmol) was added dropwise thereto at 0° C., and the mixture was stirred at room temperature for 1 hour and at 50° C. for 2 hours. Then, the solvent in the reaction solution was distilled off under reduced pressure. The obtained residue was purified by silica gel column chromatography [elute: hexane/ethyl acetate=100/0-70/30 (gradient)] to obtain an oil (1.12 g).
4-Hydroxy-3-(piperidin-4-yl)-4-(trifluoromethyl)-1,4,5,7-tetrahydro-6H-pyrazolo[3,4-b]pyridin-6-one (62 mg, 0.18 mmol) produced in Reference Example 60 and N,N-diisopropylethylamine (40 μL, 0.24 mmol) were added to a solution of the obtained oil (55 mg) in dimethyl sulfoxide (2 mL), and the mixture was stirred at room temperature for 5 hours and further at 0° C. for 2 hours and 30 minutes. The reaction solution was diluted with ethyl acetate, washed with water and brine, and dried over anhydrous magnesium sulfate, and the solvent was distilled off under reduced pressure. The obtained residue was purified by silica gel column chromatography [elute: hexane/ethyl acetate=70/30-10/90 (gradient)] to obtain the title compound 48-a (6 mg, yield: 6%) and compound 48-b (18 mg, yield: 16%).
Compound 48-a
¹H-NMR (400 MHz, DMSO-d₆) δ: 12.29 (1H, s), 10.53 (1H, s), 7.54 (1H, s), 6.79 (1H, s), 4.05-3.96 (2H, m), 3.40-3.20 (1H, m), 3.14 (2H, t, J=12 Hz), 2.90 (1H, d, J=16 Hz), 2.73 (1H, d, J=16 Hz), 1.94-1.74 (4H, m);
MS (ESI) m/z: 456 (M+H)⁺.
Compound 48-b
¹H-NMR (400 MHz, DMSO-d₆) δ: 12.27 (1H, s), 10.54 (1H, s), 8.61 (1H, s), 6.80 (9H, s), 4.10 (2H, d, J=13 Hz), 3.33-3.18 (3H, m), 2.90 (1H, d, J=16 Hz), 2.73 (1H, d, J=16 Hz), 1.99-1.74 (4H, m);
MS (ESI) m/z: 607 (M+H)⁺.

Example 49

(−)-4-Hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one and (+)-4-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one

[Formula 120]

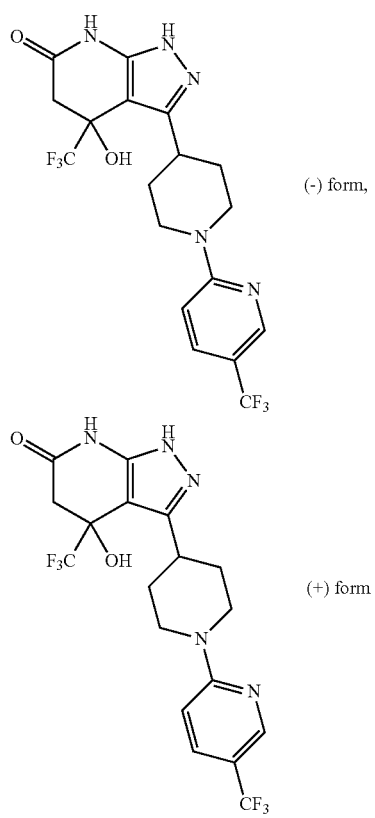

A mixed solution of 4-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one (180 mg, 0.401 mmol) produced in Example 8 in THF and hexane (1/1) (60 mL) was purified in 6 divided portions by flash LC [SP1; manufactured by Biotage Japan Ltd., column: Chiralflash IA (30 mm i.d.×100 mm); manufactured by Daicel Corporation, elute: THF/hexane=50/50, flow rate: 10 mL/min] to obtain each of a compound eluted first (hereinafter, referred to as compound 49-1) (83.0 mg, yield: 46%) and a compound eluted second (hereinafter, referred to as compound 49-2) (81.5 mg, yield: 45%).

The optical purity of each compound was measured by HPLC [column: Chiralpak IA (4.6 mm i.d.×150 mm); manufactured by Daicel Corporation, elute: THF/hexane=50/50].

Compound 49-1:
Optical purity: 99% or higher (retention time: 3.4 min);
$[\alpha]_D^{25} = -10°$ (DMF, c=1.04).

Compound 49-2:
Optical purity: 99% or higher (retention time: 6.0 min)
$[\alpha]_D^{25} = +10°$ (DMF, c=1.02).

Example 50

(−)-3-[1-(5-Chloropyridin-2-yl)piperidin-4-yl]-4-hydroxy-4-(trifluoromethyl)-1,4,5,7-tetrahydro-6H-pyrazolo[3,4-b]pyridin-6-one and (+)-3-[1-(5-chloropyridin-2-yl)piperidin-4-yl]-4-hydroxy-4-(trifluoromethyl)-1,4,5,7-tetrahydro-6H-pyrazolo[3,4-b]pyridin-6-one

[Formula 121]

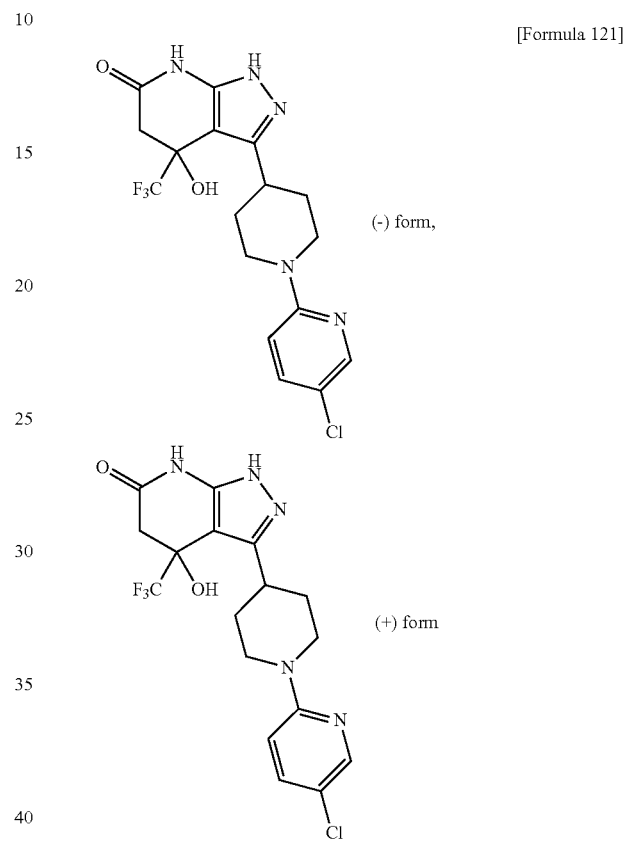

A mixed solution of 3-[1-(5-chloropyridin-2-yl)piperidin-4-yl]-4-hydroxy-4-(trifluoromethyl)-1,4,5,7-tetrahydro-6H-pyrazolo[3,4-b]pyridin-6-one (220 mg, 0.529 mmol) produced in Example 14 in ethyl acetate (2 mL) and methanol (2 mL) was adsorbed onto a silica gel, and then, the solvent was distilled off under reduced pressure. The obtained residue was packed in a column and purified by flash LC [SP1; manufactured by Biotage Japan Ltd., column: Chiralflash IA (30 mm i.d.×100 mm); manufactured by Daicel Corporation, elute: 2-propanol (hereinafter, referred to as IPA)/hexane=20/80-30/70 (gradient), flow rate: 12 mL/min] to obtain each of a compound eluted first (hereinafter, referred to as compound 50-1) (93.0 mg, yield: 42%) and a compound eluted second (hereinafter, referred to as compound 50-2) (91.0 mg, yield: 41%).

The optical purity of each compound was measured by HPLC [column: Chiralpak IA (4.6 mm i.d.×150 mm); manufactured by Daicel Corporation, elute: IPA/hexane=40/60].

Compound 50-1:
Optical purity: 99% or higher (retention time: 3.7 min);
$[\alpha]_D^{25} = -14°$ (DMF, c=1.01).

Compound 50-2:
Optical purity: 99% or higher (retention time: 7.3 min)
$[\alpha]_D^{25} = +14°$ (DMF, c=1.00).

Reference Example 63

Ethyl 1-[5-(difluoromethoxy)pyridin-2-yl]piperidine-4-carboxylate

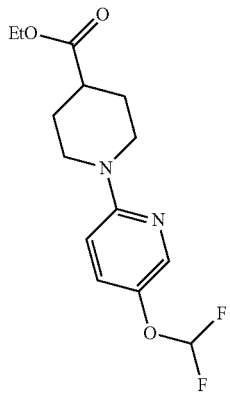

[Formula 122]

The title compound (544 mg, yield: 41%) was obtained through reaction in the same way as the method described in Reference Example 13 using 2-bromo-5-(difluoromethoxy) pyridine (compound described in J. Med. Chem., 2010, Vol. 53, p. 8421-8439, 1.00 g, 4.46 mmol) instead of 2-bromo-3-chloropyridine.

$^1$H-NMR (400 MHz, CDCl$_3$) δ: 8.08 (1H, d, J=3 Hz), 7.34 (1H, dd, J=9, 3 Hz), 6.67 (1H, d, J=9 Hz), 6.42 (1H, t, J=74 Hz), 4.22-4.17 (2H, m), 4.18 (2H, q, J=7 Hz), 3.04-2.97 (2H, m), 2.59-2.52 (1H, m), 2.06-2.00 (2H, m), 1.84-1.75 (2H, m), 1.29 (3H, t, J=7 Hz).

Reference Example 64

3-{1-[5-(Difluoromethoxy)pyridin-2-yl]piperidin-4-yl}-1H-pyrazol-5-amine

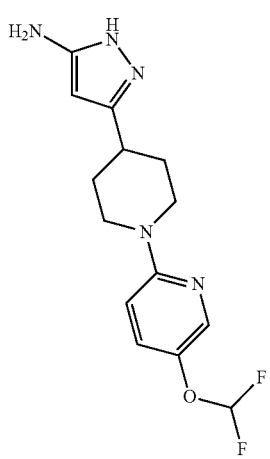

[Formula 123]

The title compound (462 mg, yield: 85%) was obtained through reaction in the same way as the method described in Reference Example 4 using ethyl 1-[5-(difluoromethoxy)pyridin-2-yl]piperidine-4-carboxylate (526 mg, 1.75 mmol) produced in Reference Example 63 instead of ethyl 1-(6-methylpyridin-2-yl)piperidine-4-carboxylate.

$^1$H-NMR (400 MHz, DMSO-d$_6$) δ: 11.12 (1H, brs), 8.00 (1H, d, J=3 Hz), 7.42 (1H, dd, J=9, 3 Hz), 7.03 (1H, t, J=74 Hz), 6.89 (1H, d, J=9 Hz), 5.18 (1H, brs), 4.39 (2H, brs), 4.30-4.22 (2H, m), 2.92-2.84 (2H, m), 2.74-2.66 (1H, m), 1.91-1.85 (2H, m), 1.56-1.46 (2H, m).

Example 51

3-{1-[5-(Difluoromethoxy)pyridin-2-yl]piperidin-4-yl}-4-hydroxy-4-(trifluoromethyl)-1,4,5,7-tetrahydro-6H-pyrazolo[3,4-b]pyridin-6-one

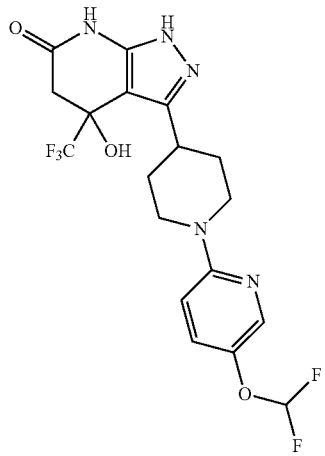

[Formula 124]

The title compound (300 mg, yield: 45%) was obtained through reaction in the same way as the method described in Example 1 using 3-{1-[5-(difluoromethoxy)pyridin-2-yl]piperidin-4-yl}-1H-pyrazol-5-amine (458 mg, 1.48 mmol) produced in Reference Example 64 instead of 3-(1-phenylpiperidin-4-yl)-1H-pyrazol-5-amine.

$^1$H-NMR (400 MHz, DMSO-d$_6$) δ: 12.22 (1H, s), 10.49 (1H, s), 8.02 (1H, d, J=3 Hz), 7.44 (1H, dd, J=9, 3 Hz), 7.05 (1H, t, J=74 Hz), 6.91 (1H, d, J=9 Hz), 6.72 (1H, s), 4.44-4.36 (2H, m), 3.27-3.19 (1H, m), 2.92-2.86 (1H, m), 2.84-2.77 (2H, m), 2.72 (1H, d, J=16 Hz), 1.91-1.85 (1H, m), 1.79-1.63 (3H, m);

MS (ESI) m/z: 448 (M+H)$^+$.

Reference Example 65

Ethyl 1-[5-(propan-2-yloxy)pyridin-2-yl]piperidine-4-carboxylate

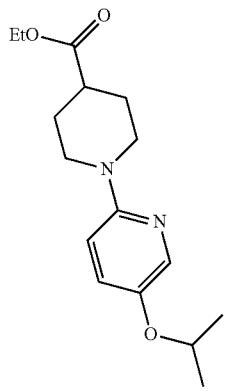

[Formula 125]

The title compound (803 mg, yield: 59%) was obtained through reaction in the same way as the method described in Reference Example 13 using 2-bromo-5-(propan-2-yloxy) pyridine (compound described in the pamphlet of WO2009/81789, 1.00 g, 4.63 mmol) instead of 2-bromo-3-chloropyridine.

¹H-NMR (400 MHz, CDCl₃) δ: 7.91 (1H, d, J=3 Hz), 7.18-7.13 (1H, m), 6.66 (1H, d, J=9 Hz), 4.41-4.33 (1H, m), 4.15 (2H, q, J=7 Hz), 4.10-4.05 (2H, m), 2.95-2.86 (2H, m), 2.52-2.45 (1H, m), 2.04-1.98 (2H, m), 1.85-1.75 (2H, m), 1.30 (6H, d, J=6 Hz), 1.26 (3H, t, J=7 Hz).

Reference Example 66

3-{1-[5-(Propan-2-yloxy)pyridin-2-yl]piperidin-4-yl}-1H-pyrazol-5-amine

[Formula 126]

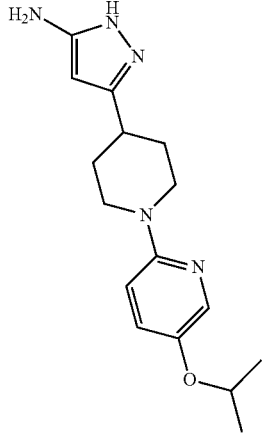

The title compound (726 mg, yield: 89%) was obtained through reaction in the same way as the method described in Reference Example 4 using ethyl 1-[5-(propan-2-yloxy)pyridin-2-yl]piperidine-4-carboxylate (796 mg, 2.72 mmol) produced in Reference Example 65 instead of ethyl 1-(6-methylpyridin-2-yl)piperidine-4-carboxylate.

¹H-NMR (400 MHz, DMSO-d₆) δ: 11.13 (1H, brs), 7.82 (1H, d, J=3 Hz), 7.22 (1H, dd, J=9, 3 Hz), 6.80 (1H, d, J=9 Hz), 5.20 (1H, brs), 4.46-4.38 (1H, m), 4.33 (2H, brs), 4.18-4.10 (2H, m), 2.81-2.73 (2H, m), 2.69-2.59 (1H, m), 1.91-1.84 (2H, m), 1.58-1.48 (2H, m), 1.22 (6H, d, J=6 Hz).

Example 52

4-Hydroxy-3-{1-[5-(propan-2-yloxy)pyridin-2-yl]piperidin-4-yl}-4-(trifluoromethyl)-1,4,5,7-tetrahydro-6H-pyrazolo[3,4-b]pyridin-6-one

[Formula 127]

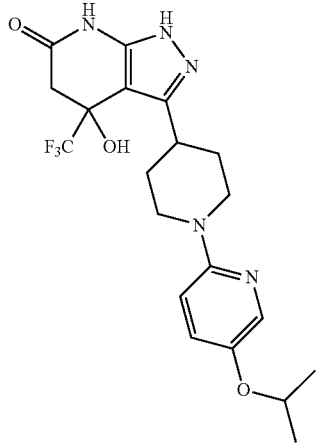

The title compound (377 mg, yield: 36%) was obtained through reaction in the same way as the method described in Example 1 using 3-{1-[5-(propan-2-yloxy)pyridin-2-yl]piperidin-4-yl}-1H-pyrazol-5-amine (721 mg, 2.39 mmol) produced in Reference Example 66 instead of 3-(1-phenylpiperidin-4-yl)-1H-pyrazol-5-amine.

¹H-NMR (400 MHz, DMSO-d₆) δ: 12.24 (1H, s), 10.48 (1H, s), 7.84 (1H, d, J=3 Hz), 7.24 (1H, dd, J=9, 3 Hz), 6.81 (1H, d, J=9 Hz), 6.71 (1H, s), 4.47-4.39 (1H, m), 4.31-4.24 (2H, m), 3.20-3.13 (1H, m), 2.89 (1H, d, J=16 Hz), 2.73-2.65 (2H, m), 2.72 (1H, d, J=16 Hz), 1.91-1.85 (1H, m), 1.82-1.65 (3H, m), 1.23 (6H, d, J=6 Hz);

MS (ESI) m/z: 440 (M+H)⁺.

Reference Example 67

Ethyl 1-[5-(trifluoromethyl)pyridin-3-yl]piperidine-4-carboxylate

[Formula 128]

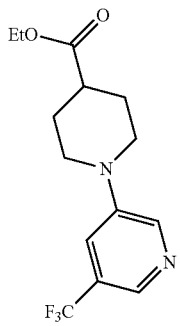

The title compound (1.02 g, yield: 76%) was obtained through reaction in the same way as the method described in Reference Example 13 using 3-bromo-5-(trifluoromethyl)pyridine (1.00 g, 4.43 mmol) instead of 2-bromo-3-chloropyridine.

¹H-NMR (400 MHz, CDCl₃) δ: 8.45 (1H, d, J=3 Hz), 8.31-8.29 (1H, m), 7.34-7.32 (1H, m), 4.18 (2H, q, J=7 Hz), 3.75-3.69 (2H, m), 2.99-2.92 (2H, m), 2.55-2.48 (1H, m), 2.10-2.05 (2H, m), 1.93-1.84 (2H, m), 1.28 (3H, t, J=7 Hz).

Reference Example 68

3-{1-[5-(Trifluoromethyl)pyridin-3-yl]piperidin-4-yl}-1H-pyrazol-5-amine

[Formula 129]

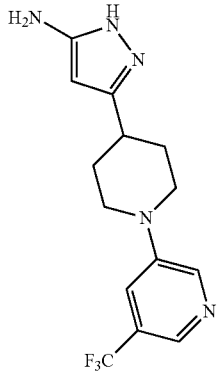

The title compound (608 mg, yield: 59%) was obtained through reaction in the same way as the method described in Reference Example 4 using ethyl 1-[5-(trifluoromethyl)pyridin-3-yl]piperidine-4-carboxylate (1.01 g, 3.33 mmol) produced in Reference Example 67 instead of ethyl 1-(6-methylpyridin-2-yl)piperidine-4-carboxylate.

$^1$H-NMR (400 MHz, DMSO-$d_6$) δ: 11.15 (1H, brs), 8.59 (1H, d, J=3 Hz), 8.26-8.24 (1H, m), 7.57-7.55 (1H, m), 5.21 (1H, brs), 4.46 (2H, brs), 3.97-3.90 (2H, m), 2.94-2.86 (2H, m), 2.72-2.64 (1H, m), 1.96-1.90 (2H, m), 1.67-1.57 (2H, m).

Example 53

4-Hydroxy-4-(trifluoromethyl)-3-{1-[5-(trifluoromethyl)pyridin-3-yl]piperidin-4-yl}-1,4,5,7-tetrahydro-6H-pyrazolo[3,4-b]pyridin-6-one

[Formula 130]

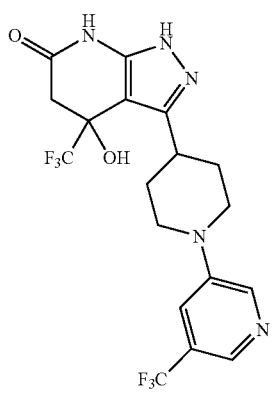

The title compound (353 mg, yield: 41%) was obtained through reaction in the same way as the method described in Example 1 using 3-{1-[5-(trifluoromethyl)pyridin-3-yl]piperidin-4-yl}-1H-pyrazol-5-amine (602 mg, 1.93 mmol) produced in Reference Example 68 instead of 3-(1-phenylpiperidin-4-yl)-1H-pyrazol-5-amine.

$^1$H-NMR (400 MHz, DMSO-$d_6$) δ: 12.27 (1H, s), 10.50 (1H, s), 8.61 (1H, d, J=3 Hz), 8.27-8.25 (1H, m), 7.60-7.57 (1H, m), 6.74 (1H, s), 4.09-4.03 (2H, m), 3.25-3.17 (1H, m), 2.92-2.83 (3H, m), 2.73 (1H, d, J=16 Hz), 1.96-1.71 (4H, m); MS (ESI) m/z: 450 (M+H)$^+$.

Reference Example 69

Ethyl 1-[6-(difluoromethoxy)pyridin-3-yl]piperidine-4-carboxylate

[Formula 131]

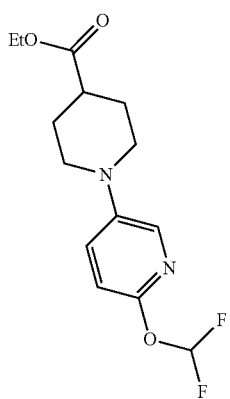

The title compound (361 mg, yield: 27%) was obtained through reaction in the same way as the method described in Reference Example 13 using 5-bromo-2-(difluoromethoxy)pyridine (compound described in J. Med. Chem., 2010, Vol. 53, p. 8421-8439, 1.00 g, 4.46 mmol) instead of 2-bromo-3-chloropyridine.

$^1$H-NMR (400 MHz, CDCl$_3$) δ: 7.83-7.79 (1H, m), 7.38-7.32 (1H, m), 7.33 (1H, t, J=74 Hz), 6.82 (1H, d, J=9 Hz), 4.17 (2H, q, J=7 Hz), 3.55-3.49 (2H, m), 2.85-2.76 (2H, m), 2.49-2.40 (1H, m), 2.10-2.01 (2H, m), 1.95-1.83 (2H, m), 1.28 (3H, t, J=7 Hz).

Reference Example 70

3-{1-[6-(Difluoromethoxy)pyridin-3-yl]piperidin-4-yl}-1H-pyrazol-5-amine

[Formula 132]

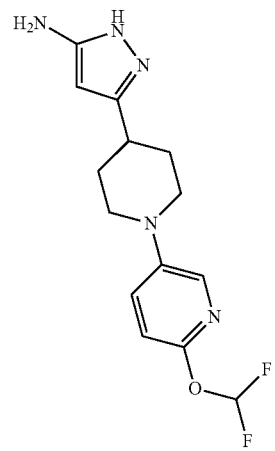

The title compound (323 mg, yield: 88%) was obtained through reaction in the same way as the method described in Reference Example 4 using ethyl 1-[6-(difluoromethoxy)pyridin-3-yl]piperidine-4-carboxylate (355 mg, 1.18 mmol) produced in Reference Example 69 instead of ethyl 1-(6-methylpyridin-2-yl)piperidine-4-carboxylate.

$^1$H-NMR (400 MHz, DMSO-$d_6$) δ: 11.15 (1H, brs), 7.89 (1H, d, J=3 Hz), 7.57 (1H, dd, J=9, 3 Hz), 7.54 (1H, t, J=74 Hz), 6.94 (1H, d, J=9 Hz), 5.22 (1H, brs), 4.37 (2H, brs), 3.71-3.65 (2H, m), 2.79-2.71 (2H, m), 2.65-2.56 (1H, m), 1.96-1.88 (2H, m), 1.70-1.61 (2H, m).

Example 54

3-{1-[6-(Difluoromethoxy)pyridin-3-yl]piperidin-4-yl}-4-hydroxy-4-(trifluoromethyl)-1,4,5,7-tetrahydro-6H-pyrazolo[3,4-b]pyridin-6-one

[Formula 133]

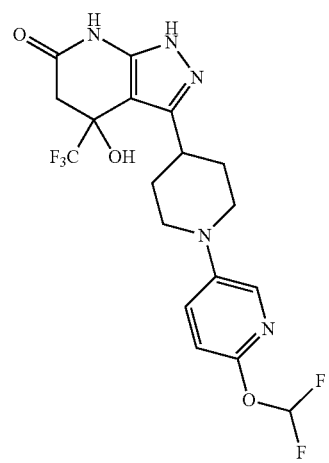

93

The title compound (180 mg, yield: 39%) was obtained through reaction in the same way as the method described in Example 1 using 3-{1-[6-(difluoromethoxy)pyridin-3-yl]piperidin-4-yl}-1H-pyrazol-5-amine (319 mg, 1.03 mmol) produced in Reference Example 70 instead of 3-(1-phenylpiperidin-4-yl)-1H-pyrazol-5-amine.

$^1$H-NMR (400 MHz, DMSO-$d_6$) δ: 12.29 (1H, s), 10.50 (1H, s), 7.91 (1H, d, J=3 Hz), 7.59 (1H, dd, J=9, 3 Hz), 7.55 (1H, t, J=74 Hz), 6.96 (1H, d, J=9 Hz), 6.72 (1H, s), 3.81-3.73 (2H, m), 3.18-3.08 (1H, m), 2.89 (1H, d, J=17 Hz), 2.76-2.66 (3H, m), 1.95-1.71 (4H, m);

MS (ESI) m/z: 448 (M+H)$^+$.

Reference Example 71

Ethyl 1-[4-(difluoromethoxy)phenyl]piperidine-4-carboxylate

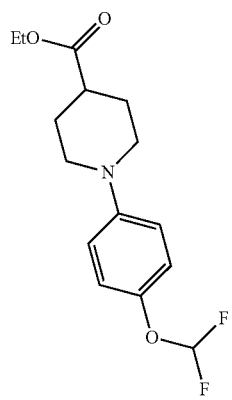

[Formula 134]

Sodium tert-butoxide (2.29 g, 23.8 mmol), palladium(II) acetate (428 mg, 1.91 mmol), and tri-tert-butylphosphine (370 μL, 1.52 mmol) were added to a solution of ethyl piperidine-4-carboxylate (3.52 mL, 22.9 mmol) and 1-bromo-4-(difluoromethoxy)benzene (4.25 g, 19.1 mmol) in toluene (122 mL), and the mixture was stirred at 80° C. for 30 minutes. Water was added to the reaction solution, followed by extraction with ethyl acetate. The obtained organic layer was washed with brine and then dried over anhydrous sodium sulfate, and the solvent was distilled off under reduced pressure. The obtained residue was purified by silica gel column chromatography [elute: hexane/ethyl acetate=100/0-90/10] to obtain the title compound (3.17 g, yield: 56%).

94

$^1$H-NMR (400 MHz, CDCl$_3$) δ: 7.07-7.00 (2H, m), 6.95-6.87 (2H, m), 6.41 (1H, t, J=75 Hz), 4.16 (2H, q, J=7 Hz), 3.61-3.55 (2H, m), 2.84-2.73 (2H, m), 2.47-2.39 (1H, m), 2.08-1.99 (2H, m), 1.95-1.83 (2H, m), 1.27 (3H, t, J=7 Hz).

Reference Example 72

3-{1-[4-(Difluoromethoxy)phenyl]piperidin-4-yl}-1H-pyrazol-5-amine

[Formula 135]

n-Butyllithium (2.69 M solution in hexane, 11.8 mL, 31.7 mmol) was added dropwise at −78° C. to a solution of anhydrous acetonitrile (1.71 mL, 32.8 mmol) in anhydrous THF (80 mL), and then, the mixture was stirred at the same temperature as above for 15 minutes. Then, a solution of ethyl 1-[4-(difluoromethoxy)phenyl]piperidine-4-carboxylate (3.17 g, 10.6 mmol) produced in Reference Example 71 in anhydrous THF (13 mL) was added dropwise thereto at −78° C., and the mixture was stirred at the same temperature as above for 30 minutes. A saturated ammonium chloride aqueous solution was added to the reaction solution, followed by extraction with ethyl acetate. The organic layer was washed with brine and dried over anhydrous magnesium sulfate, and the solvent was distilled off under reduced pressure.

Hydrazine monohydrate (1.54 mL, 31.7 mmol) was added to a solution of the obtained residue in ethanol (93 mL), and the mixture was stirred at 105° C. for 4 hours. The reaction solution was left at room temperature, and then, the solvent was distilled off under reduced pressure. The obtained residue was purified by silica gel column chromatography [elute: ethyl acetate/methanol=100/0-97.5/2.5 (gradient)] to obtain the title compound (2.98 g, yield: 91%).

$^1$H-NMR (400 MHz, DMSO-$d_6$) δ: 11.14 (1H, brs), 7.04-7.01 (2H, m), 7.04 (1H, t, J=75 Hz), 6.99-6.95 (2H, m), 5.21 (1H, brs), 4.38 (2H, brs), 3.69-3.63 (2H, m), 2.74-2.67 (2H, m), 2.63-2.54 (1H, m), 1.94-1.88 (2H, m), 1.69-1.59 (2H, m).

Example 55

3-{1-[4-(Difluoromethoxy)phenyl]piperidin-4-yl}-4-hydroxy-4-(trifluoromethyl)-1,4,5,7-tetrahydro-6H-pyrazolo[3,4-b]pyridin-6-one

[Formula 136]

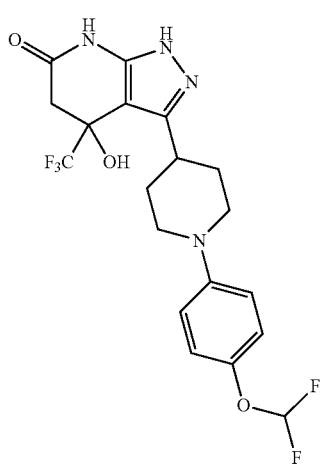

Example 56

(−)-3-{1-[4-(Difluoromethoxy)phenyl]piperidin-4-yl}-4-hydroxy-4-(trifluoromethyl)-1,4,5,7-tetrahydro-6H-pyrazolo[3,4-b]pyridin-6-one and (+)-3-{1-[4-(difluoromethoxy)phenyl]piperidin-4-yl}-4-hydroxy-4-(trifluoromethyl)-1,4,5,7-tetrahydro-6H-pyrazolo[3,4-b]pyridin-6-one

[Formula 137]

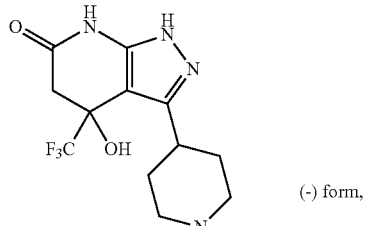

(−) form,

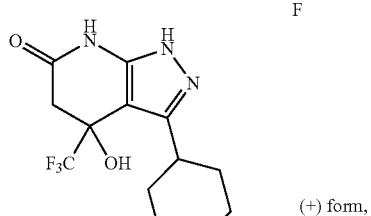

(+) form,

Ethyl trifluoroacetoacetate (5.64 mL, 38.5 mmol) was added to a solution of 3-{1-[4-(difluoromethoxy)phenyl]piperidin-4-yl}-1H-pyrazol-5-amine (2.97 g, 9.63 mmol) produced in Reference Example 72 in acetic acid (52 mL), and the mixture was stirred at 60° C. for 3 hours. The reaction solution was cooled to room temperature, and the solvent was distilled off under reduced pressure, followed by azeotropy with toluene twice. The obtained residue was purified by silica gel column chromatography [NH-silica gel column, elute: hexane/ethyl acetate=100/0-0/100 (gradient)] and further purified by silica gel column chromatography [elute: hexane/ethyl acetate=100/0-40/60 (gradient)] to obtain the title compound (1.84 g, yield: 43%).

$^1$H-NMR (400 MHz, DMSO-$d_6$) δ: 12.29 (1H, s), 10.50 (1H, s), 7.06-7.02 (2H, m), 7.05 (1H, t, J=75 Hz), 7.01-6.97 (2H, m), 6.72 (1H, s), 3.78-3.71 (2H, m), 3.14-3.07 (1H, m), 2.89 (1H, d, J=16 Hz), 2.73 (1H, d, J=16 Hz), 2.69-2.61 (2H, m), 1.94-1.72 (4H, m);

MS (ESI) m/z: 447 (M+H)$^+$.

A mixed solution of 3-{1-[4-(difluoromethoxy)phenyl]piperidin-4-yl}-4-hydroxy-4-(trifluoromethyl)-1,4,5,7-tetrahydro-6H-pyrazolo[3,4-b]pyridin-6-one (1.51 g) produced in Example 55 in ethyl acetate (32 mL) and methanol (32 mL) was adsorbed onto a silica gel (16 g), and then, the solvent was distilled off under reduced pressure. The obtained residue was packed in 8 divided portions in a column and purified by flash LC [Purif-α2; manufactured by Shoko Scientific Co., Ltd., column: Chiralflash IA (30 mm i.d.×100 mm); manufactured by Daicel Corporation, elute: IPA/hexane=30/70, flow rate: 12 mL/min] to obtain each of a compound eluted first (hereinafter, referred to as compound 56-1) (677 mg, yield: 45%) and a compound eluted second (hereinafter, referred to as compound 56-2) (667 mg, yield: 45%).

The optical purity of each compound was measured by HPLC [column: Chiralpak IA (4.6 mm i.d.×150 mm); manufactured by Daicel Corporation, elute: THF/hexane=50/50].

Compound 56-1:

Optical purity: 99% or higher (retention time: 5.6 min).

$[α]_D^{25}$=−28° (DMF, c=1.01).

Compound 56-2:
Optical purity: 99% or higher (retention time: 9.2 min).
$[\alpha]_D^{25} = +28°$ (DMF, c=1.01).

Reference Example 73

Ethyl 1-[6-(propan-2-yloxy)pyridin-3-yl]piperidine-4-carboxylate

[Formula 138]

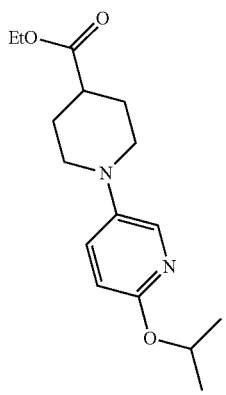

The title compound (912 mg, yield: 67%) was obtained through reaction in the same way as the method described in Reference Example 13 using 5-bromo-2-(propan-2-yloxy)pyridine (1.00 g, 4.63 mmol) instead of 2-bromo-3-chloropyridine.

$^1$H-NMR (400 MHz, CDCl$_3$) δ: 7.81-7.77 (1H, m), 7.31-7.26 (1H, m), 6.61 (1H, d, J=9 Hz), 5.23-5.15 (1H, m), 4.16 (2H, q, J=7 Hz), 3.47-3.41 (2H, m), 2.76-2.69 (2H, m), 2.44-2.37 (1H, m), 2.07-2.00 (2H, m), 1.95-1.85 (2H, m), 1.32 (6H, d, J=6 Hz), 1.27 (3H, t, J=7 Hz).

Reference Example 74

3-{1-[6-(Propan-2-yloxy)pyridin-3-yl]piperidin-4-yl}-1H-pyrazol-5-amine

[Formula 139]

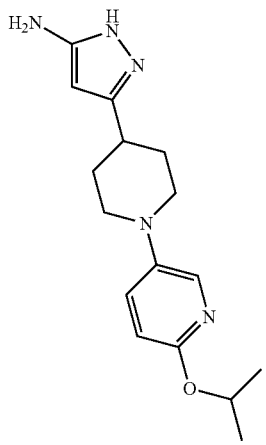

The title compound (860 mg, yield: 92%) was obtained through reaction in the same way as the method described in Reference Example 4 using ethyl 1-[6-(propan-2-yloxy)pyridin-3-yl]piperidine-4-carboxylate (909 mg, 3.11 mmol) produced in Reference Example 73 instead of ethyl 1-(6-methylpyridin-2-yl)piperidine-4-carboxylate.

$^1$H-NMR (400 MHz, DMSO-d$_6$) δ: 11.15 (1H, brs), 7.77 (1H, d, J=3 Hz), 7.41 (1H, dd, J=9, 3 Hz), 6.61 (1H, d, J=9 Hz), 5.22 (1H, brs), 5.17-5.06 (1H, m), 4.36 (2H, brs), 3.56-3.49 (2H, m), 2.70-2.48 (3H, m), 1.95-1.88 (2H, m), 1.72-1.61 (2H, m), 1.25 (6H, d, J=6 Hz).

Example 57

4-Hydroxy-3-{1-[6-(propan-2-yloxy)pyridin-3-yl]piperidin-4-yl}-4-(trifluoromethyl)-1,4,5,7-tetrahydro-6H-pyrazolo[3,4-b]pyridin-6-one

[Formula 140]

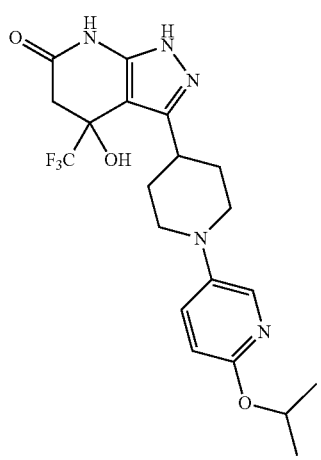

The title compound (443 mg, yield: 36%) was obtained through reaction in the same way as the method described in Example 1 using 3-{1-[6-(propan-2-yloxy)pyridin-3-yl]piperidin-4-yl}-1H-pyrazol-5-amine (856 mg, 2.84 mmol) produced in Reference Example 74 instead of 3-(1-phenylpiperidin-4-yl)-1H-pyrazol-5-amine.

$^1$H-NMR (400 MHz, DMSO-d$_6$) δ: 12.29 (1H, s), 10.50 (1H, s), 7.79 (1H, d, J=3 Hz), 7.43 (1H, dd, J=9, 3 Hz), 6.71 (1H, s), 6.63 (1H, d, J=9 Hz), 5.17-5.09 (1H, m), 3.64-3.57 (2H, m), 3.12-3.04 (1H, m), 2.89 (1H, d, J=16 Hz), 2.72 (1H, d, J=16 Hz), 2.65-2.58 (2H, m), 1.96-1.81 (3H, m), 1.78-1.72 (1H, m), 1.25 (6H, d, J=6 Hz);
MS (ESI) m/z: 440 (M+H)$^+$.

Reference Example 75

Ethyl 1-[4-(trifluoromethoxy)phenyl]piperidine-4-carboxylate

[Formula 141]

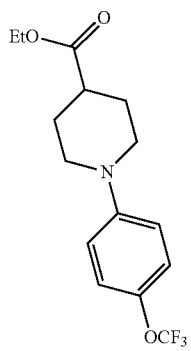

The title compound (791 mg, yield: 60%) was obtained through reaction in the same way as the method described in Reference Example 71 using 1-bromo-4-(trifluoromethoxy) benzene (1.00 g, 4.15 mmol) instead of 1-bromo-4-(difluoromethoxy)benzene.

$^1$H-NMR (400 MHz, CDCl$_3$) δ: 7.13-7.08 (2H, m), 6.93-6.87 (2H, m), 4.16 (2H, q, J=7 Hz), 3.63-3.58 (2H, m), 2.84-2.76 (2H, m), 2.47-2.40 (1H, m), 2.07-1.99 (2H, m), 1.92-1.83 (2H, m), 1.27 (3H, t, J=7 Hz).

Reference Example 76

3-{1-[4-(Trifluoromethoxy)phenyl]piperidin-4-yl}-1H-pyrazol-5-amine

[Formula 142]

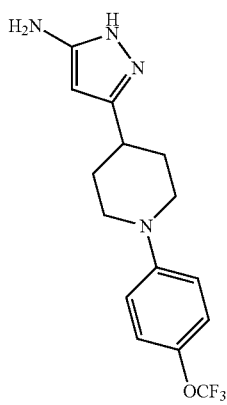

The title compound (734 mg, yield: 91%) was obtained through reaction in the same way as the method described in Reference Example 4 using ethyl 1-[4-(trifluoromethoxy) phenyl]piperidine-4-carboxylate (788 mg, 2.48 mmol) produced in Reference Example 75 instead of ethyl 1-(6-methylpyridin-2-yl)piperidine-4-carboxylate.

$^1$H-NMR (400 MHz, DMSO-d$_6$) δ: 11.15 (1H, brs), 7.19-7.14 (2H, m), 7.04-6.99 (2H, m), 5.22 (1H, brs), 4.35 (2H, brs), 3.76-3.69 (2H, m), 2.80-2.72 (2H, m), 2.67-2.56 (1H, m), 1.95-1.87 (2H, m), 1.68-1.57 (2H, m).

Example 58

4-Hydroxy-3-{1-[4-(trifluoromethoxy)phenyl]piperidin-4-yl}-4-(trifluoromethyl)-1,4,5,7-tetrahydro-6H-pyrazolo[3,4-b]pyridin-6-one

[Formula 143]

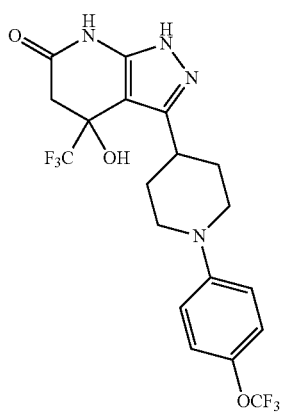

The title compound (400 mg, yield: 38%) was obtained through reaction in the same way as the method described in Example 1 using 3-{1-[4-(trifluoromethoxy)phenyl]piperidin-4-yl}-1H-pyrazol-5-amine (731 mg, 2.24 mmol) produced in Reference Example 76 instead of 3-(1-phenylpiperidin-4-yl)-1H-pyrazol-5-amine.

$^1$H-NMR (400 MHz, DMSO-d$_6$) δ: 12.29 (1H, s), 10.50 (1H, s), 7.21-7.16 (2H, m), 7.06-7.00 (2H, m), 6.72 (1H, s), 3.86-3.78 (2H, m), 3.18-3.09 (1H, m), 2.89 (1H, d, J=17 Hz), 2.76-2.66 (3H, m), 1.95-1.71 (4H, m);

MS (ESI) m/z: 465 (M+H)$^+$.

Reference Example 77

Ethyl 1-(4-ethoxyphenyl)piperidine-4-carboxylate

[Formula 144]

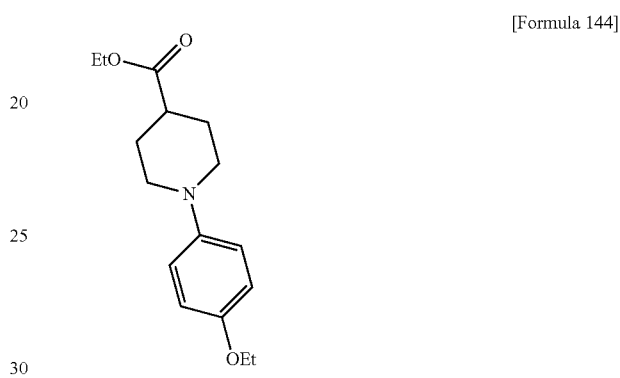

The title compound (717 mg, yield: 52%) was obtained through reaction in the same way as the method described in Reference Example 71 using 1-bromo-4-ethoxybenzene (1.00 g, 4.97 mmol) instead of 1-bromo-4-(difluoromethoxy) benzene.

$^1$H-NMR (400 MHz, CDCl$_3$) δ: 6.93-6.88 (2H, m), 6.85-6.80 (2H, m), 4.16 (2H, q, J=7 Hz), 3.98 (2H, q, J=7 Hz), 3.51-3.45 (2H, m), 2.74-2.66 (2H, m), 2.42-2.35 (1H, m), 2.07-1.98 (2H, m), 1.95-1.85 (2H, m), 1.38 (3H, t, J=7 Hz), 1.27 (3H, t, J=7 Hz).

Reference Example 78

3-[1-(4-Ethoxyphenyl)piperidin-4-yl]-1H-pyrazol-5amine

[Formula 145]

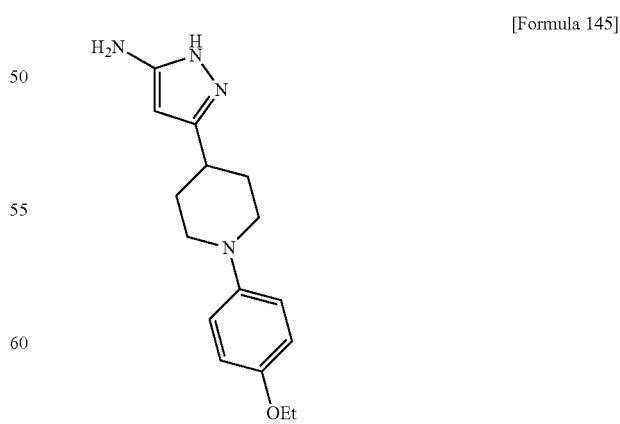

The title compound (631 mg, yield: 86%) was obtained through reaction in the same way as the method described in Reference Example 4 using ethyl 1-(4-ethoxyphenyl)piperidine-4-carboxylate (709 mg, 2.56 mmol) produced in Reference Example 77 instead of ethyl 1-(6-methylpyridin-2-yl)piperidine-4-carboxylate.

$^1$H-NMR (400 MHz, DMSO-d$_6$) δ: 11.14 (1H, brs), 6.90-6.87 (2H, m), 6.81-6.77 (2H, m), 5.22 (1H, brs), 4.36 (2H, brs), 3.93 (2H, q, J=7 Hz), 3.53-3.48 (2H, m), 2.65-2.58 (2H, m), 2.58-2.49 (1H, m), 1.93-1.88 (2H, m), 1.71-1.61 (2H, m), 1.28 (3H, t, J=7 Hz).

Example 59

3-[1-(4-Ethoxyphenyl)piperidin-4-yl]-4-hydroxy-4-(trifluoromethyl)-1,4,5,7-tetrahydro-6H-pyrazolo[3,4-b]pyridin-6-one

[Formula 146]

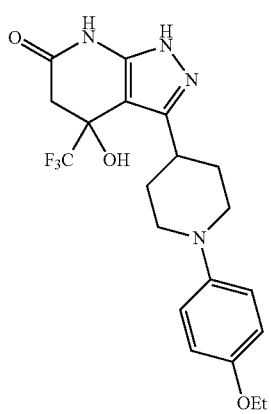

The title compound (308 mg, yield: 33%) was obtained through reaction in the same way as the method described in Example 1 using 3-[1-(4-ethoxyphenyl)piperidin-4-yl]-1H-pyrazol-5-amine (626 mg, 2.19 mmol) produced in Reference Example 78 instead of 3-(1-phenylpiperidin-4-yl)-1H-pyrazol-5-amine.

$^1$H-NMR (400 MHz, DMSO-d$_6$) δ: 12.28 (1H, s), 10.49 (1H, s), 6.92-6.88 (2H, m), 6.82-6.78 (2H, m), 6.70 (1H, s), 3.94 (2H, q, J=7 Hz), 3.62-3.55 (2H, m), 3.10-3.02 (1H, m), 2.89 (1H, d, J=16 Hz), 2.72 (1H, d, J=16 Hz), 2.60-2.52 (2H, m), 1.96-1.81 (3H, m), 1.78-1.72 (1H, m), 1.29 (3H, t, J=7 Hz).

MS (ESI) m/z: 425 (M+H)$^+$.

Reference Example 79

5-Bromo-2-(difluoromethoxy)benzonitrile

[Formula 147]

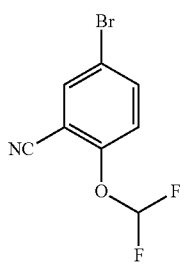

Reference Example 79 was carried out according to the method described in the pamphlet of WO2012/7868.

Sodium chloro(difluoro)acetate (9.62 g, 63.1 mmol) and cesium carbonate (12.3 g, 37.9 mmol) were added to a mixed solution of 5-bromo-2-hydroxybenzonitrile (5.00 g, 25.2 mmol) in DMF (50 mL) and water (5 mL), and the mixture was stirred at 100° C. for 30 minutes. Water was added to the reaction solution, followed by extraction with ethyl acetate. The obtained organic layer was washed with brine and then dried over anhydrous sodium sulfate, and the solvent was distilled off under reduced pressure. The obtained residue was purified by silica gel column chromatography [elute: hexane/ethyl acetate=100/0-98/2] to obtain the title compound (3.83 g, yield: 61%).

$^1$H-NMR (400 MHz, CDCl$_3$) δ: 7.80 (1H, d, J=3 Hz), 7.72 (1H, dd, J=9, 3 Hz), 7.25-7.22 (1H, m), 6.64 (1H, t, J=71 Hz).

Reference Example 80

Ethyl 1-[3-cyano-4-(difluoromethoxy)phenyl]piperidine-4-carboxylate

[Formula 148]

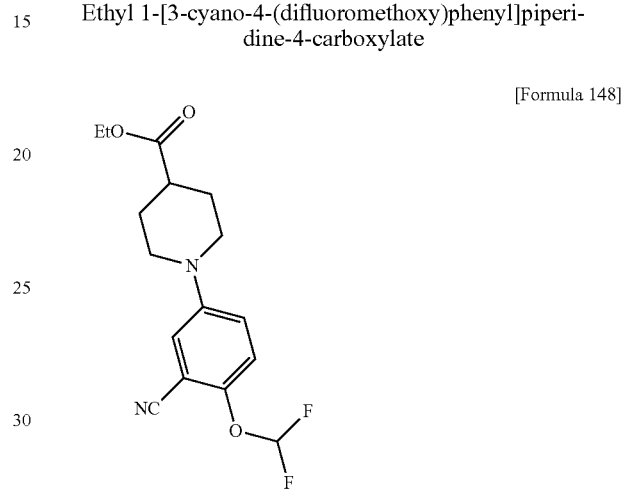

The title compound (442 mg, yield: 23%) was obtained through reaction in the same way as the method described in Reference Example 71 using 5-bromo-2-(difluoromethoxy)benzonitrile (1.50 g, 6.05 mmol) produced in Reference Example 79 instead of 1-bromo-4-(difluoromethoxy)benzene.

$^1$H-NMR (CDCl$_3$) δ: 7.20-7.17 (1H, m), 7.12-7.09 (2H, m), 6.54 (1H, t, J=72 Hz), 4.17 (2H, q, J=7 Hz), 3.62-3.57 (2H, m), 2.89-2.82 (2H, m), 2.50-2.44 (1H, m), 2.08-2.02 (2H, m), 1.91-1.81 (2H, m), 1.28 (3H, t, J=7 Hz).

Reference Example 81

5-[4-(Cyanoacetyl)piperidin-1-yl]-2-(difluoromethoxy)benzonitrile

[Formula 149]

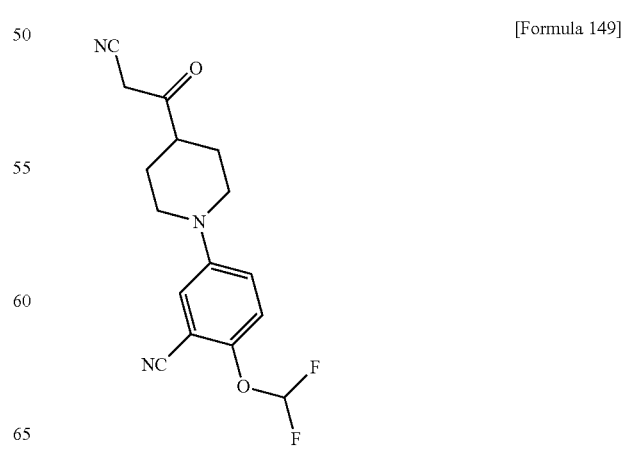

n-Butyllithium (2.69 M solution in hexane, 1.50 mL, 4.04 mmol) was added dropwise at −78° C. to a solution of anhydrous acetonitrile (218 μL, 4.18 mmol) in anhydrous THF (7 mL). After stirring at the same temperature as above for 15 minutes, a solution of ethyl 1-[3-cyano-4-(difluoromethoxy) phenyl]piperidine-4-carboxylate (437 mg, 1.35 mmol) produced in Reference Example 80 in anhydrous THF (6 mL) was added dropwise thereto at −78° C., and the mixture was stirred at the same temperature as above for 30 minutes. A saturated ammonium chloride aqueous solution was added to the reaction solution, followed by extraction with ethyl acetate. The obtained organic layer was washed with brine and dried over anhydrous sodium sulfate, and the solvent was distilled off under reduced pressure. The obtained residue was purified by silica gel column chromatography [elute: hexane/ethyl acetate=100/0-60/40] to obtain the title compound (147 mg, yield: 34%).

$^1$H-NMR (400 MHz, CDCl$_3$) δ: 7.22-7.19 (1H, m), 7.12-7.09 (2H, m), 6.55 (1H, t, J=72 Hz), 3.70-3.64 (2H, m), 3.55 (2H, s), 2.90-2.83 (2H, m), 2.80-2.73 (1H, m), 2.08-2.02 (2H, m), 1.87-1.78 (2H, m).

Reference Example 82

5-[4-(5-Amino-1H-pyrazol-3-yl)piperidin-1-yl]-2-(difluoromethoxy)benzonitrile

[Formula 150]

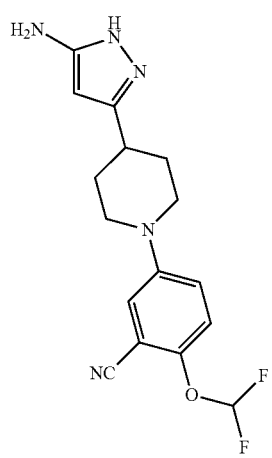

The title compound (132 mg, yield: 88%) was obtained through reaction in the same way as the method described in Reference Example 2 using 5-[4-(cyanoacetyl)piperidin-1-yl]-2-(difluoromethoxy)benzonitrile (143 mg, 0.448 mmol) produced in Reference Example 81 instead of 3-oxo-3-[1-(pyridin-2-yl)piperidin-4-yl]propanenitrile.

$^1$H-NMR (400 MHz, DMSO-d$_6$) δ: 11.13 (1H, brs), 7.41 (1H, d, J=3 Hz), 7.33 (1H, dd, J=9, 3 Hz), 7.28 (1H, d, J=9 Hz), 7.24 (1H, t, J=73 Hz), 5.20 (1H, brs), 4.42 (2H, brs), 3.81-3.75 (2H, m), 2.84-2.76 (2H, m), 2.67-2.59 (1H, m), 1.94-1.87 (2H, m), 1.65-1.55 (2H, m).

Example 60

2-(Difluoromethoxy)-5-{4-[4-hydroxy-6-oxo-4-(trifluoromethyl)-4,5,6,7-tetrahydro-1H-pyrazolo[3,4-b]pyridin-3-yl]piperidin-1-yl}benzonitrile

[Formula 151]

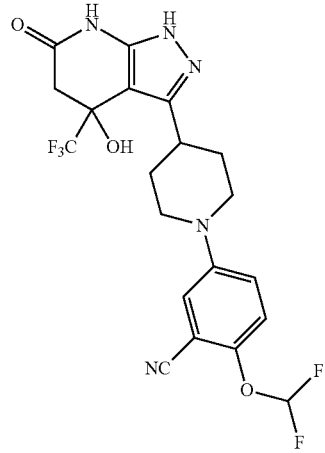

The title compound (62 mg, yield: 35%) was obtained through reaction in the same way as the method described in Example 1 using 5-[4-(5-amino-1H-pyrazol-3-yl)piperidin-1-yl]-2-(difluoromethoxy)benzonitrile (127 mg, 0.381 mmol) produced in Reference Example 82 instead of 3-(1-phenylpiperidin-4-yl)-1H-pyrazol-5-amine.

$^1$H-NMR (400 MHz, DMSO-d$_6$) δ: 12.26 (1H, s), 10.49 (1H, s), 7.43 (1H, d, J=3 Hz), 7.35 (1H, dd, J=9, 3 Hz), 7.29 (1H, d, J=9 Hz), 7.25 (1H, t, J=73 Hz), 6.72 (1H, s), 3.93-3.85 (2H, m), 3.20-3.12 (1H, m), 2.89 (1H, d, J=16 Hz), 2.79-2.72 (2H, m), 2.73 (1H, d, J=16 Hz), 1.93-1.70 (4H, m);
MS (ESI) m/z: 472 (M+H)$^+$.

Reference Example 83

Ethyl 1-[6-(cyclobutoxy)pyridin-3-yl]piperidine-4-carboxylate

[Formula 152]

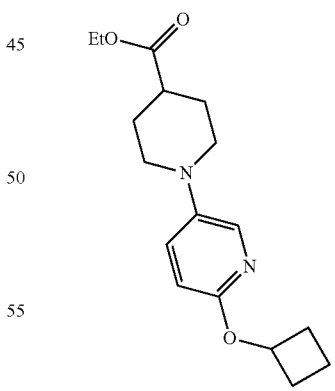

The title compound (1.29 g, yield: 64%) was obtained through reaction in the same way as the method described in Reference Example 13 using 5-bromo-2-(cyclobutoxy)pyridine (compound described in the pamphlet of WO2009/68194, 1.50 g, 6.59 mmol) instead of 2-bromo-3-chloropyridine.

$^1$H-NMR (400 MHz, CDCl$_3$) δ: 7.80-7.76 (1H, m), 7.32-7.25 (1H, m), 6.62 (1H, d, J=9 Hz), 5.13-5.04 (1H, m), 4.16

(2H, q, J=7 Hz), 3.47-3.40 (2H, m), 2.77-2.68 (2H, m), 2.49-2.36 (3H, m), 2.17-1.98 (4H, m), 1.95-1.77 (3H, m), 1.72-1.57 (1H, m), 1.27 (3H, t, J=7 Hz).

Reference Example 84

3-{1-[6-(Cyclobutoxy)pyridin-3-yl]piperidin-4-yl}-1H-pyrazol-5-amine

[Formula 153]

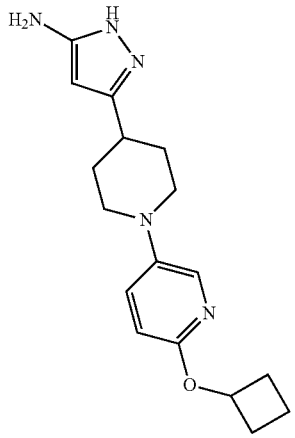

The title compound (1.18 g, yield: 90%) was obtained through reaction in the same way as the method described in Reference Example 4 using ethyl 1-[6-(cyclobutoxy)pyridin-3-yl]piperidine-4-carboxylate (1.28 g, 4.20 mmol) produced in Reference Example 83 instead of ethyl 1-(6-methylpyridin-2-yl)piperidine-4-carboxylate.

$^1$H-NMR (400 MHz, DMSO-d$_6$) δ: 11.14 (1H, brs), 7.75 (1H, d, J=3 Hz), 7.42 (1H, dd, J=9, 3 Hz), 6.64 (1H, d, J=9 Hz), 5.22 (1H, brs), 5.07-4.98 (1H, m), 4.36 (2H, brs), 3.57-3.49 (2H, m), 2.70-2.48 (3H, m), 2.40-2.30 (2H, m), 2.06-1.86 (4H, m), 1.80-1.54 (4H, m).

Example 61

3-{1-[6-(Cyclobutoxy)pyridin-3-yl]piperidin-4-yl}-4-hydroxy-4-(trifluoromethyl)-1,4,5,7-tetrahydro-6H-pyrazolo[3,4-b]pyridin-6-one

[Formula 154]

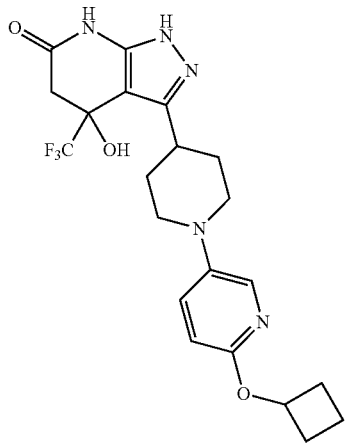

The title compound (618 mg, yield: 37%) was obtained through reaction in the same way as the method described in Example 1 using 3-{1-[6-(cyclobutoxy)pyridin-3-yl]piperidin-4-yl}-1H-pyrazol-5-amine (1.18 g, 3.75 mmol) produced in Reference Example 84 instead of 3-(1-phenylpiperidin-4-yl)-1H-pyrazol-5-amine.

$^1$H-NMR (400 MHz, DMSO-d$_6$) δ: 12.28 (1H, s), 10.48 (1H, s), 7.78 (1H, d, J=3 Hz), 7.44 (1H, dd, J=9, 3 Hz), 6.69 (1H, s), 6.66 (1H, d, J=9 Hz), 5.07-5.00 (1H, m), 3.64-3.57 (2H, m), 3.12-3.04 (1H, m), 2.89 (1H, d, J=16 Hz), 2.72 (1H, d, J=16 Hz), 2.65-2.58 (2H, m), 2.40-2.32 (2H, m), 2.05-1.71 (7H, m), 1.66-1.56 (1H, m);

MS (ESI) m/z: 452 (M+H)$^+$.

Reference Example 85

5-Bromo-2-(trifluoromethoxy)benzonitrile

[Formula 155]

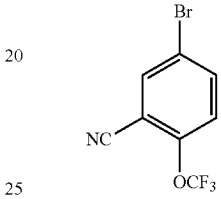

Triethylamine (1.14 mL, 8.18 mmol) and propylphosphonic anhydride (cyclic trimer) (ca. 1.7 M solution in ethyl acetate, 4.8 mL, 8.18 mmol) were added in this order to a solution of 5-bromo-2-(trifluoromethoxy)benzaldehyde (2.00 g, 7.43 mmol) and hydroxyamine hydrochloride (568 mg, 8.18 mmol) in DMF (7.5 mL), and the mixture was stirred at 100° C. for 8 hours. The reaction solution was poured to a saturated sodium bicarbonate aqueous solution, followed by extraction with ethyl acetate. The obtained organic layer was washed with brine and dried over anhydrous sodium sulfate, and the solvent was distilled off under reduced pressure. The obtained residue was purified by silica gel column chromatography [elute: hexane/ethyl acetate=100/0-98/2] to obtain the title compound (1.71 g, yield: 86%).

$^1$H-NMR (400 MHz, CDCl$_3$) δ: 7.85 (1H, d, J=3 Hz), 7.78 (1H, dd, J=9, 3 Hz), 7.31-7.27 (1H, m).

Reference Example 86

Ethyl 1-[3-cyano-4-(trifluoromethoxy)phenyl]piperidine-4-carboxylate

[Formula 156]

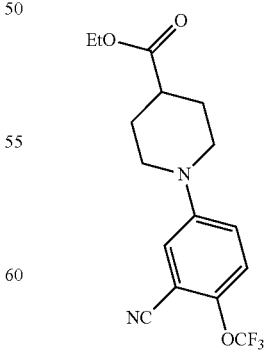

The title compound (894 mg, yield: 41%) was obtained through reaction in the same way as the method described in Reference Example 71 using 5-bromo-2-(trifluoromethoxy)

benzonitrile (1.70 g, 6.40 mmol) produced in Reference Example 85 instead of 1-bromo-4-(difluoromethoxy)benzene.

$^1$H-NMR (400 MHz, CDCl$_3$) δ: 7.25-7.21 (1H, m), 7.11-7.07 (2H, m), 4.17 (2H, q, J=7 Hz), 3.66-3.59 (2H, m), 2.93-2.85 (2H, m), 2.53-2.44 (1H, m), 2.08-2.01 (2H, m), 1.90-1.80 (2H, m), 1.28 (3H, t, J=7 Hz).

Reference Example 87

5-[4-(Cyanoacetyl)piperidin-1-yl]-2-(trifluoromethoxy)benzonitrile

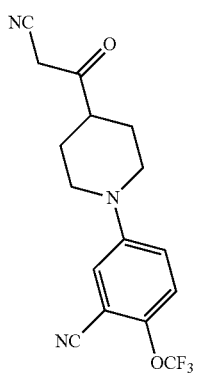

[Formula 157]

The title compound (660 mg, yield: 76%) was obtained through reaction in the same way as the method described in Reference Example 81 using ethyl 1-[3-cyano-4-(trifluoromethoxy)phenyl]piperidine-4-carboxylate (886 mg, 2.59 mmol) produced in Reference Example 86 instead of ethyl 1-[3-cyano-4-(difluoromethoxy)phenyl]piperidine-4-carboxylate.

$^1$H-NMR (400 MHz, CDCl$_3$) δ: 7.27-7.23 (1H, m), 7.12-7.09 (2H, m), 3.73-3.68 (2H, m), 3.55 (2H, s), 2.94-2.87 (2H, m), 2.83-2.76 (1H, m), 2.09-2.03 (2H, m), 1.86-1.77 (2H, m).

Reference Example 88

5-[4-(5-Amino-1H-pyrazol-3-yl)piperidin-1-yl]-2-(trifluoromethoxy)benzonitrile

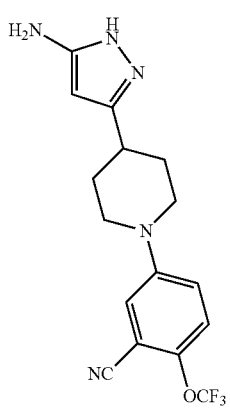

[Formula 158]

The title compound (670 mg, yield: 98%) was obtained through reaction in the same way as the method described in Reference Example 2 using 5-[4-(cyanoacetyl)piperidin-1-yl]-2-(trifluoromethoxy)benzonitrile (656 mg, 1.94 mmol) produced in Reference Example 87 instead of 3-oxo-3-[1-(pyridin-2-yl)piperidin-4-yl]propanenitrile.

$^1$H-NMR (400 MHz, DMSO-d$_6$) δ: 11.13 (1H, brs), 7.50 (1H, d, J=3 Hz), 7.45-7.42 (1H, m), 7.34 (1H, dd, J=9, 3 Hz), 5.20 (1H, s), 4.46 (2H, brs), 3.88-3.82 (2H, m), 2.91-2.83 (2H, m), 2.70-2.62 (1H, m), 1.94-1.87 (2H, m), 1.64-1.55 (2H, m).

Example 62

5-{4-[4-Hydroxy-6-oxo-4-(trifluoromethyl)-4,5,6,7-tetrahydro-1H-pyrazolo[3,4-b]pyridin-3-yl]piperidin-1-yl}-2-(trifluoromethoxy)benzonitrile

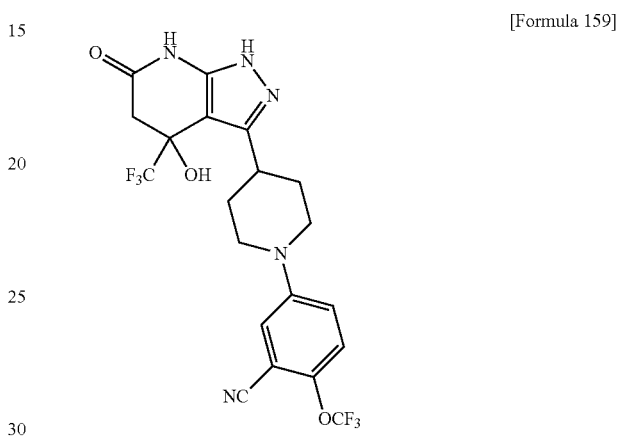

[Formula 159]

The title compound (344 mg, yield: 37%) was obtained through reaction in the same way as the method described in Example 1 using 5-[4-(5-amino-1H-pyrazol-3-yl)piperidin-1-yl]-2-(trifluoromethoxy)benzonitrile (665 mg, 1.89 mmol) produced in Reference Example 88 instead of 3-(1-phenylpiperidin-4-yl)-1H-pyrazol-5-amine.

$^1$H-NMR (400 MHz, DMSO-d$_6$) δ: 12.25 (1H, s), 10.48 (1H, s), 7.52 (1H, d, J=3 Hz), 7.47-7.43 (1H, m), 7.35 (1H, dd, J=9, 3 Hz), 6.72 (1H, s), 4.00-3.93 (2H, m), 3.23-3.16 (1H, m), 2.92-2.79 (3H, m), 2.73 (1H, d, J=16 Hz), 1.92-1.69 (4H, m);

MS (ESI) m/z: 490 (M+H)$^+$.

Reference Example 89

5-Bromo-2,3-bis(difluoromethoxy)pyridine

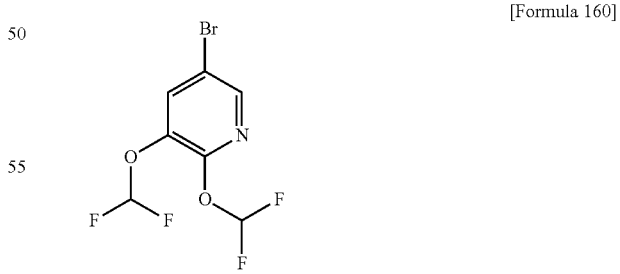

[Formula 160]

The title compound (2.02 g, yield: 33%) was obtained through reaction in the same way as the method described in Reference Example 79 using 5-bromopyridine-2,3-diol (4.00 g, 21.1 mmol) instead of 5-bromo-2-hydroxybenzonitrile.

$^1$H-NMR (400 MHz, CDCl$_3$) δ: 6.58 (1H, d, J=2 Hz), 6.23-6.21 (1H, m), 5.87 (1H, t, J=72 Hz), 5.07 (1H, t, J=73 Hz).

Reference Example 90

Ethyl 1-[5,6-bis(difluoromethoxy)pyridin-3-yl]piperidine-4-carboxylate

[Formula 161]

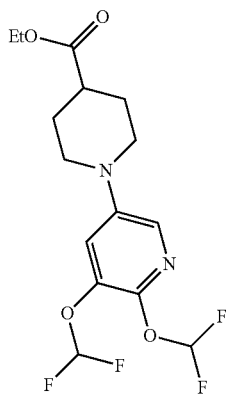

The title compound (138 mg, yield: 6%) was obtained through reaction in the same way as the method described in Reference Example 71 using 5-bromo-2,3-bis(difluoromethoxy)pyridine (1.94 g, 6.70 mmol) produced in Reference Example 89 instead of 1-bromo-4-(difluoromethoxy)benzene.

$^1$H-NMR (400 MHz, CDCl$_3$) δ: 7.72-7.69 (1H, m), 7.33 (1H, t, J=73 Hz), 7.24-7.22 (1H, m), 6.59 (1H, t, J=74 Hz), 4.17 (2H, q, J=7 Hz), 3.57-3.51 (2H, m), 2.90-2.83 (2H, m), 2.51-2.44 (1H, m), 2.11-2.04 (2H, m), 1.94-1.86 (2H, m), 1.28 (3H, t, J=7 Hz).

Reference Example 91

3-{1-[5,6-bis(Difluoromethoxy)pyridin-3-yl]piperidin-4-yl}-1H-pyrazol-5-amine

[Formula 162]

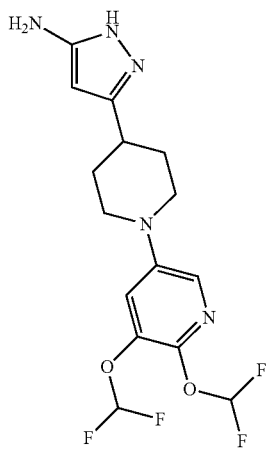

The title compound (113 mg, yield: 82%) was obtained through reaction in the same way as the method described in Reference Example 4 using ethyl 1-[5,6-bis(difluoromethoxy)pyridin-3-yl]piperidine-4-carboxylate (135 mg, 0.369 mmol) produced in Reference Example 90 instead of ethyl 1-(6-methylpyridin-2-yl)piperidine-4-carboxylate.

$^1$H-NMR (400 MHz, DMSO-d$_6$) δ: 11.16 (1H, brs), 7.78 (1H, d, J=3 Hz), 7.52 (1H, t, J=73 Hz), 7.45 (1H, d, J=3 Hz), 7.25 (1H, t, J=73 Hz), 5.21 (1H, s), 4.46 (2H, brs), 3.77-3.69 (2H, m), 2.85-2.76 (2H, m), 2.68-2.58 (1H, m), 1.96-1.89 (2H, m), 1.70-1.58 (2H, m).

Example 63

3-{1-[5,6-bis(Difluoromethoxy)pyridin-3-yl]piperidin-4-yl}-4-hydroxy-4-(trifluoromethyl)-1,4,5,7-tetrahydro-6H-pyrazolo[3,4-b]pyridin-6-one

[Formula 163]

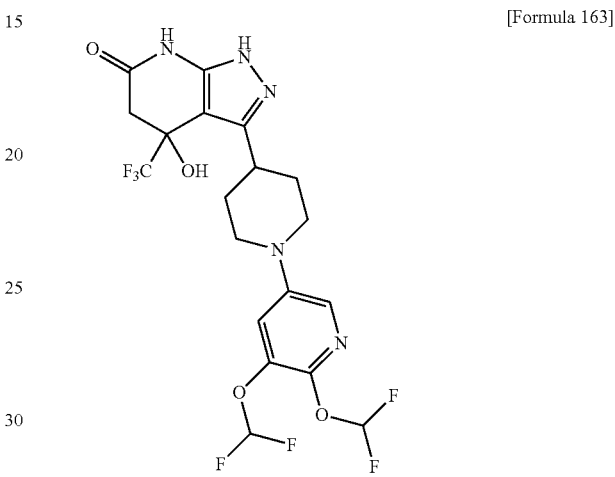

The title compound (50 mg, yield: 33%) was obtained through reaction in the same way as the method described in Example 1 using 3-{1-[5,6-bis(difluoromethoxy)pyridin-3-yl]piperidin-4-yl}-1H-pyrazol-5-amine (110 mg, 0.293 mmol) produced in Reference Example 91 instead of 3-(1-phenylpiperidin-4-yl)-1H-pyrazol-5-amine.

$^1$H-NMR (400 MHz, DMSO-d$_6$) δ: 12.28 (1H, s), 10.49 (1H, s), 7.80 (1H, d, J=3 Hz), 7.54 (1H, t, J=73 Hz), 7.48 (1H, d, J=3 Hz), 7.26 (1H, t, J=73 Hz), 6.72 (1H, s), 3.86-3.80 (2H, m), 3.19-3.11 (1H, m), 2.89 (1H, d, J=16 Hz), 2.80-2.72 (2H, m), 2.73 (1H, d, J=16 Hz), 1.95-1.72 (4H, m);

MS (ESI) m/z: 514 (M+H)$^+$.

Reference Example 92

2-Bromo-5-(prop-1-en-2-yl)pyridine

[Formula 164]

A lanthanum(III) chloride-bis(lithium chloride) complex (0.6 M solution in THF, 16.7 mL, 10 mmol) was added to a solution of 1-(6-bromopyridin-3-yl)ethanone (2 g, 10 mmol) in THF (10 mL), and the mixture was stirred at room temperature for 1 hour. Methyl magnesium bromide (1.12 M solution in THF, 10.7 mL, 12 mmol) was added thereto at 0° C., and the mixture was stirred for 1 hour. A 10% citric acid aqueous solution was added to the reaction solution, and the solvent was distilled off under reduced pressure. The residue was diluted with ethyl acetate, and insoluble matter was filtered off through Celite. After extraction with ethyl acetate twice, combined organic layers were washed with brine and dried over anhydrous sodium sulfate, and the solvent was distilled off under reduced pressure. An internal salt of (methoxycarbonylsulfamoyl)triethylammonium hydroxide (2.86 g, 12 mmol) was added to a solution of the obtained residue in THF (20 mL), and the mixture was stirred at 60° C. for 2 hours. The solvent in the reaction solution was distilled off under reduced pressure, and ethyl acetate was added to the residue. The organic layer was washed with brine and dried over anhydrous sodium sulfate, and the solvent was distilled off under reduced pressure. The obtained residue was purified by silica gel column chromatography [elute: hexane/ethyl acetate=98/2-80/20 (gradient)] to obtain the title compound (1.00 g, yield: 51%).

$^1$H-NMR (500 MHz, CDCl$_3$) δ: 8.45 (1H, dd, J=2, 1 Hz), 7.60 (1H, dd, J=8, 2 Hz), 7.43 (1H, dd, J=8, 1 Hz), 5.42-5.41 (1H, m), 5.22-5.19 (1H, m), 2.14 (3H, brs).

Reference Example 93

Ethyl 1-[5-isopropylpyridin-2-yl]piperidine-4-carboxylate

[Formula 165]

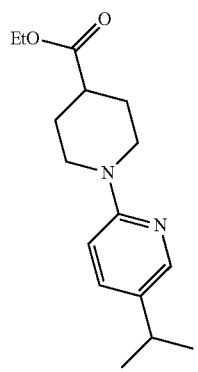

A product was obtained through reaction in the same way as the method described in Reference Example 13 using 2-bromo-5-(prop-1-en-2-yl)pyridine (1.00 g, 5.05 mmol) produced in Reference Example 92 instead of 2-bromo-3-chloropyridine.

10% palladium-carbon (300 mg) was added to a solution of the obtained product in ethanol (10 mL), and the mixture was stirred for 2 hours under a hydrogen atmosphere. The reaction solution was filtered through Celite, and the solvent in the filtrate was distilled off under reduced pressure. The obtained residue was purified by silica gel column chromatography [elute: hexane/ethyl acetate=95/5-60/40] to obtain the title compound (201 mg, yield: 14%).

$^1$H-NMR (500 MHz, CDCl$_3$) δ: 8.06 (1H, d, J=2 Hz), 7.36 (1H, dd, J=9, 2 Hz), 6.64 (1H, d, J=9 Hz), 4.20-4.15 (2H, m), 4.15 (2H, q, J=7 Hz), 2.94-2.88 (2H, m), 2.81 (1H, septet, J=7 Hz), 2.53-2.47 (1H, m), 2.03-1.96 (2H, m), 1.81-1.73 (2H, m), 1.26 (3H, t, J=7 Hz), 1.21 (6H, d, J=7 Hz).

Example 64

4-Hydroxy-3-{1-[5-isopropylpyridin-2-yl]piperidin-4-yl]-4-(trifluoromethyl)-1,4,5,7-tetrahydro-6H-pyrazolo[3,4-b]pyridin-6-one

[Formula 166]

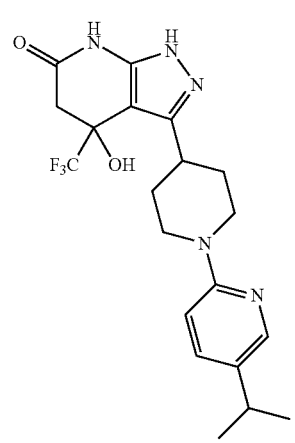

A product was obtained through reaction in the same way as the method described in Reference Example 4 using ethyl 1-[5-isopropylpyridin-2-yl]piperidine-4-carboxylate (201 mg, 0.727 mmol) produced in Reference Example 93 instead of ethyl 1-(6-methylpyridin-2-yl)piperidine-4-carboxylate. The title compound (73.4 mg, yield: 30%) was obtained through reaction in the same way as the method described in Example 1 using the obtained product instead of 3-(1-phenylpiperidin-4-yl)-1H-pyrazol-5-amine.

$^1$H-NMR (500 MHz, DMSO-d$_6$) δ: 12.24 (1H, s), 10.49 (1H, s), 7.99 (1H, d, J=2 Hz), 7.44 (1H, dd, J=9, 2 Hz), 6.81 (1H, d, J=9 Hz), 6.73 (1H, s), 4.43-4.34 (2H, m), 3.25-3.16 (1H, m), 2.89 (1H, d, J=16 Hz), 2.83-2.69 (3H, m), 2.72 (1H, d, J=16 Hz), 1.91-1.62 (4H, m), 1.17 (6H, d, J=7 Hz);
MS (ESI) m/z: 424 (M+H)$^+$.

Reference Example 94

3-{1-[2-(Trifluoromethyl)pyrimidin-5-yl]piperidin-4-yl}-1H-pyrazol-5-amine

[Formula 167]

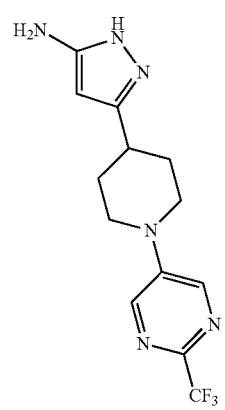

The title compound (273 mg, yield: 52%) was obtained through reaction at 80° C. in the same way as the method described in Reference Example 34 using 5-chloro-2-(trifluoromethyl)pyrimidine (310 mg, 1.70 mmol) instead of 3,6-dichloropyridazine.

¹H-NMR (500 MHz, DMSO-d₆) δ: 11.16 (1H, brs), 8.64 (2H, s), 5.21 (1H, brs), 4.50 (1H, brs), 4.06-4.02 (2H, m), 3.04-2.99 (2H, m), 2.75 (1H, brs), 1.95-1.91 (2H, m), 1.66-1.58 (2H, m).

Example 65

4-Hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one

[Formula 168]

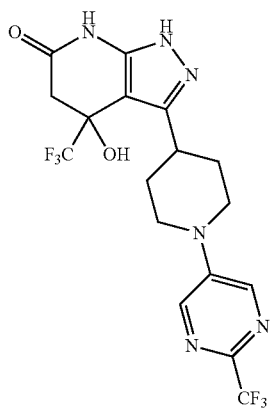

The title compound (201 mg, yield: 51%) was obtained through reaction in the same way as the method described in Example 1 using 3-{1-[2-(trifluoromethyl)pyrimidin-5-yl]piperidin-4-yl}-1H-pyrazol-5-amine (273 mg, 0.874 mmol) produced in Reference Example 94 instead of 3-(1-phenylpiperidin-4-yl)-1H-pyrazol-5-amine.

¹H-NMR (400 MHz, DMSO-d₆) δ: 12.25 (1H, s), 10.52 (1H, s), 8.67 (2H, s), 6.77 (1H, s), 4.19-4.15 (2H, m), 3.32-3.22 (1H, m), 3.03-2.88 (3H, m), 2.73 (1H, d, J=16 Hz), 1.94-1.69 (4H, m);
MS (ESI) m/z: 451 (M+H)⁺.

Reference Example 95

Ethyl 1-(2-cyclopropylpyrimidin-5-yl)piperidine-4-carboxylate

[Formula 169]

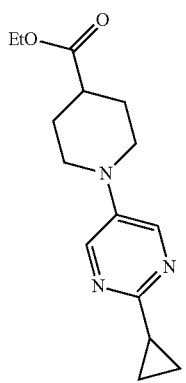

The title compound (724 mg, yield: 55%) was obtained through reaction in the same way as the method described in Reference Example 13 using 5-bromo-2-cyclopropylpyrimidine (954 mg, 4.79 mmol) instead of 2-bromo-3-chloropyridine.

¹H-NMR (400 MHz, CDCl₃) δ: 8.24 (2H, s), 4.17 (2H, q, J=7 Hz), 3.56 (2H, td, J=8, 4 Hz), 2.82 (2H, td, J=12, 3 Hz), 2.49-2.40 (1H, m), 2.20-2.13 (1H, m), 2.08-2.01 (2H, m), 1.93-1.82 (2H, m), 1.27 (3H, t, J=7 Hz), 1.03-0.97 (4H, m).

Reference Example 96

3-[1-(2-Cyclopropylpyrimidin-5-yl)piperidin-4-yl]-1H-pyrazol-5-amine

[Formula 170]

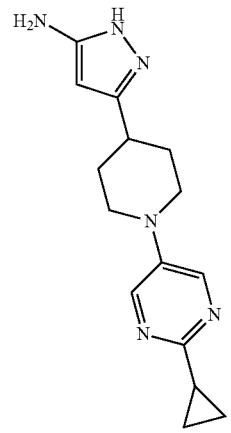

The title compound (434 mg, yield: 58%) was obtained through reaction in the same way as the method described in Reference Example 4 using ethyl 1-(2-cyclopropylpyrimidin-5-yl)piperidine-4-carboxylate (724 mg, 2.63 mmol) produced in Reference Example 95 instead of ethyl 1-(6-methylpyridin-2-yl)piperidine-4-carboxylate.

¹H-NMR (400 MHz, DMSO-d₆) δ: 11.17 (1H, brs), 8.93 (2H, s), 8.36 (2H, s), 5.21 (1H, s), 4.18-4.08 (2H, m), 3.73 (2H, d, J=13 Hz), 2.76 (2H, td, J=12, 2 Hz), 1.95-1.87 (2H, m), 1.69-1.57 (2H, m), 0.94-0.83 (4H, m).

Example 66

3-[1-(2-Cyclopropylpyrimidin-5-yl)piperidin-4-yl]-4-hydroxy-4-(trifluoromethyl)-1,4,5,7-tetrahydro-6H-pyrazolo[3,4-b]pyridin-6-one

[Formula 171]

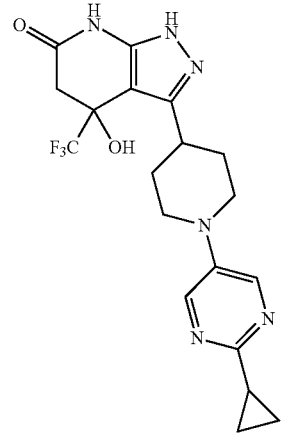

The title compound (138 mg, yield: 21%) was obtained through reaction in the same way as the method described in Example 1 using 3-[1-(2-cyclopropylpyrimidin-5-yl)piperidin-4-yl]-1H-pyrazol-5-amine (434 mg, 1.53 mmol) produced in Reference Example 96 instead of 3-(1-phenylpiperidin-4-yl)-1H-pyrazol-5-amine.

$^1$H-NMR (400 MHz, DMSO-d$_6$) δ: 12.29 (1H, s), 10.51 (1H, s), 8.37 (2H, s), 6.73 (1H, s), 3.85-3.83 (2H, m), 3.43-3.35 (1H, m), 2.92-2.87 (1H, m), 2.78-2.65 (3H, m), 2.13-2.05 (1H, m), 1.93-1.67 (4H, m), 0.95-0.83 (4H, m);

MS (ESI) m/z: 423 (M+H)$^+$.

Reference Example 97

Ethyl 1-[2-(dimethylamino)pyrimidin-5-yl]piperidine-4-carboxylate

[Formula 172]

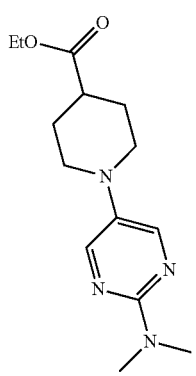

The title compound (170 mg, yield: 12%) was obtained through reaction in the same way as the method described in Reference Example 13 using 5-bromo-2-(dimethylamino)pyrimidine (1050 mg, 5.20 mmol) instead of 2-bromo-3-chloropyridine.

$^1$H-NMR (500 MHz, CDCl$_3$) δ: 8.12 (2H, s), 4.16 (2H, q, J=7 Hz), 3.33-3.12 (2H, m), 3.15 (6H, s), 2.69 (2H, td, J=12, 3 Hz), 2.42-2.34 (1H, m), 2.05-1.98 (2H, m), 1.94-1.86 (2H, m), 1.27 (3H, t, J=7 Hz).

Reference Example 98

5-[4-(5-Amino-1H-pyrazol-3-yl)piperidin-1-yl]-N,N-dimethylpyrimidin-2-amine

[Formula 173]

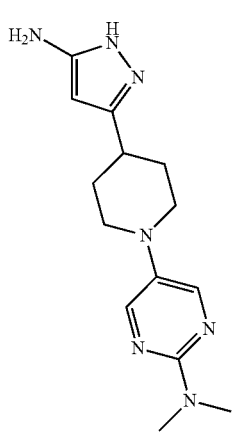

The title compound (80 mg, yield: 53%) was obtained through reaction in the same way as the method described in Reference Example 4 using ethyl 1-[2-(dimethylamino)pyrimidin-5-yl]piperidine-4-carboxylate (145 mg, 0.52 mmol) produced in Reference Example 97 instead of ethyl 1-(6-methylpyridin-2-yl)piperidine-4-carboxylate.

$^1$H-NMR (400 MHz, DMSO-d$_6$) δ: 11.16 (1H, brs), 8.18 (2H, s), 5.22 (1H, brs), 4.56-4.03 (2H, m), 3.50-3.37 (2H, m), 3.30-3.16 (1H, m), 3.08 (6H, s), 2.64-2.63 (2H, m), 1.93-1.89 (2H, m), 1.72-1.62 (2H, m).

Example 67

3-{1-[2-(Dimethylamino)pyrimidin-5-yl]piperidin-4-yl}-4-hydroxy-4-(trifluoromethyl)-1,4,5,7-tetrahydro-6H-pyrazolo[3,4-b]pyridin-6-one

[Formula 174]

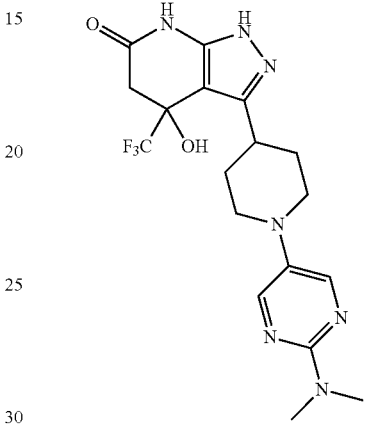

The title compound (42 mg, yield: 36%) was obtained through reaction in the same way as the method described in Example 1 using 5-[4-(5-amino-1H-pyrazol-3-yl)piperidin-1-yl]-N,N-dimethylpyrimidin-2-amine (80 mg, 0.278 mmol) produced in Reference Example 98 instead of 3-(1-phenylpiperidin-4-yl)-1H-pyrazol-5-amine.

$^1$H-NMR (400 MHz, DMSO-d$_6$) δ: 12.30 (1H, s), 10.51 (1H, s), 8.20 (2H, s), 6.72 (1H, s), 3.49-3.47 (2H, m), 3.32-3.28 (1H, m), 3.06 (6H, s), 2.89 (1H, d, J=17 Hz), 2.72 (1H, d, J=17 Hz), 2.63-2.59 (2H, m), 1.94-1.83 (3H, m), 1.75-1.72 (1H, m);

MS (ESI) m/z: 426 (M+H)$^+$.

Reference Example 99

Ethyl 1-[6-(dimethylamino)pyridin-3-yl]piperidine-4-carboxylate

[Formula 175]

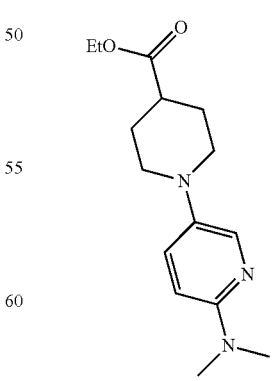

The title compound (1.45 g, yield: 51%) was obtained through reaction in the same way as the method described in Reference Example 13 using 5-bromo-2-dimethylaminopyridine (2.07 g, 10.3 mmol) instead of 2-bromo-3-chloropyridine and 2-(di-tert-butylphosphino)biphenyl (0.27 g, 0.905 mmol) instead of 2,2'-bis(diphenylphosphino)-1,1'-binaphthyl.

$^1$H-NMR (400 MHz, CDCl$_3$) δ: 7.91 (1H, d, J=3 Hz), 7.22 (1H, dd, J=9, 3 Hz), 6.51 (1H, d, J=9 Hz), 4.16 (2H, q, J=7 Hz), 3.37 (2H, dt, J=12, 4 Hz), 3.03 (6H, s), 2.68 (2H, td, J=12, 3 Hz), 2.42-2.34 (1H, m), 2.05-2.00 (2H, m), 1.94-1.85 (2H, m), 1.27 (3H, t, J=7 Hz).

Reference Example 100

5-[4-(5-Amino-1H-pyrazol-3-yl)piperidin-2-amine

[Formula 176]

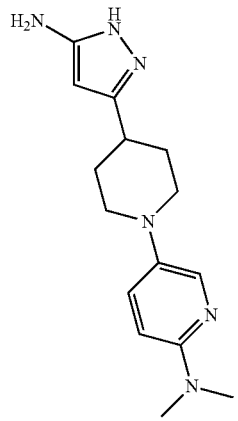

The title compound (905 mg, yield: 80%) was obtained through reaction in the same way as the method described in Reference Example 4 using ethyl 1-[6-(dimethylamino)pyridin-3-yl]piperidine-4-carboxylate (1.10 g, 3.97 mmol) produced in Reference Example 99 instead of ethyl 1-(6-methylpyridin-2-yl)piperidine-4-carboxylate.

$^1$H-NMR (400 MHz, DMSO-d$_6$) δ: 11.16 (1H, brs), 8.94 (1H, brs), 7.83 (1H, d, J=3 Hz), 7.29 (1H, dd, J=9, 3 Hz), 6.59 (1H, d, J=9 Hz), 5.23 (1H, brs), 4.37 (1H, brs), 4.12 (1H, brs), 3.51-3.37 (1H, m), 2.93 (6H, s), 2.66-2.54 (2H, m), 1.96-1.85 (2H, m), 1.72-1.62 (2H, m).

Example 68

3-{1-[6-(Dimethylamino)pyridin-3-yl]piperidin-4-yl}-4-hydroxy-4-(trifluoromethyl)-1,4,5,7-tetrahydro-6H-pyrazolo[3,4-b]pyridin-6-one

[Formula 177]

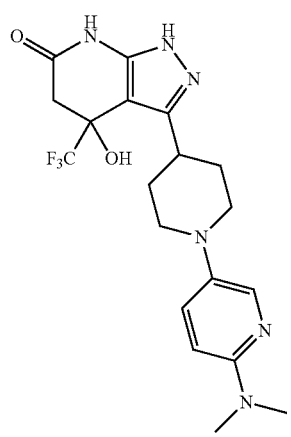

The title compound (389 mg, yield: 29%) was obtained through reaction in the same way as the method described in Example 1 using 5-[4-(5-amino-1H-pyrazol-3-yl)piperidin-2-amine (905 mg, 3.16 mmol) produced in Reference Example 100 instead of 3-(1-phenylpiperidin-4-yl)-1H-pyrazol-5-amine.

$^1$H-NMR (400 MHz, DMSO-d$_6$) δ: 12.31 (1H, s), 10.52 (1H, s), 7.85 (1H, d, J=3 Hz), 7.32 (1H, dd, J=9, 3 Hz), 6.74 (1H, s), 6.60 (1H, d, J=9 Hz), 3.50-3.40 (2H, m), 3.10-3.00 (1H, m), 2.94 (6H, s), 2.90 (1H, d, J=17 Hz), 2.72 (1H, d, J=17 Hz), 2.61-2.52 (2H, m), 1.97-1.70 (4H, m);
MS (ESI) m/z: 425 (M+H)$^+$.

Reference Example 101

5-Fluoro-N,N-dimethyl-2-(trifluoromethyl)benzamide

[Formula 178]

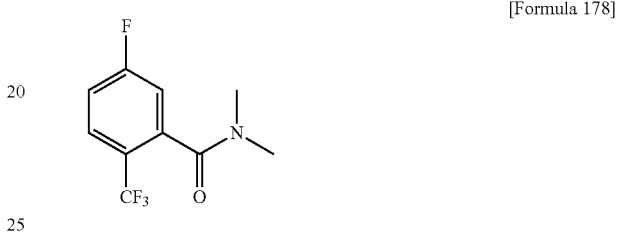

1-Ethyl-3-(3-dimethylaminopropyl)carbodiimide hydrochloride (hereinafter, referred to as EDC, 2.67 g, 13.93 mmol), 1-hydroxybenzotriazole monohydrate (140 mg, 0.91 mmol), and dimethylamine (2.0 M solution in THF, 10.0 mL, 20.0 mmol) were added at room temperature to a solution of 5-fluoro-2-(trifluoromethyl)benzoic acid (1.93 g, 9.27 mmol) in dichloromethane (50 mL), and the mixture was stirred at room temperature for 5 hours. A saturated ammonium chloride aqueous solution was added to the reaction solution, followed by extraction with dichloromethane. The obtained organic layer was washed with brine and dried over anhydrous magnesium sulfate, and the solvent was distilled off under reduced pressure. The obtained residue was purified by silica gel column chromatography [elute: hexane/ethyl acetate=100/0-60/40 (gradient)] to obtain the title compound (1.32 g, yield: 61%).

$^1$H-NMR (400 MHz, CDCl$_3$) δ: 7.71 (1H, dd, J=9, 5 Hz), 7.22-7.17 (1H, m), 7.06 (1H, dd, J=8, 2 Hz), 3.13 (3H, s), 2.82 (3H, s).

Reference Example 102

5-[4-(5-Amino-1H-pyrazol-3-yl)piperidin-1-yl]-N,N-dimethyl-2-(trifluoromethyl)benzamide

[Formula 179]

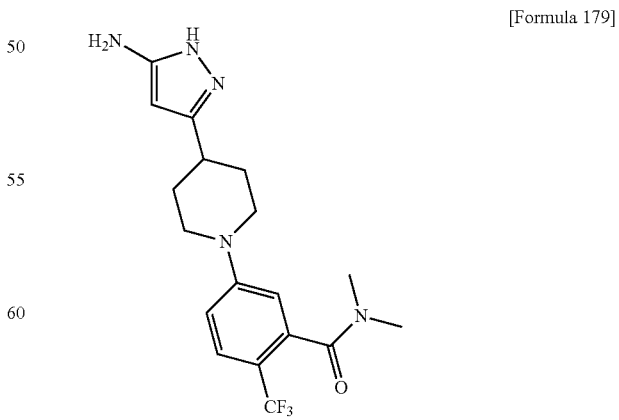

The title compound (400 mg, yield: 63%) was obtained through reaction at 80° C. in the same way as the method described in Reference Example 34 using 5-fluoro-N,N-dimethyl-2-(trifluoromethyl)benzamide (400 mg, 1.70 mmol) produced in Reference Example 101 instead of 3,6-dichloropyridazine.

¹H-NMR (400 MHz, DMSO-d₆) δ: 11.16 (1H, brs), 7.51 (1H, d, J=9 Hz), 7.06 (1H, d, J=9 Hz), 6.85 (1H, d, J=2 Hz), 5.19 (1H, brs), 4.40 (2H, brs), 3.95-3.92 (2H, m), 2.96 (3H, s), 2.94-2.88 (2H, m), 2.73 (3H, s), 2.72-2.65 (1H, m), 1.91-1.88 (2H, m), 1.62-1.52 (2H, m).

Example 69

5-{4-[4-Hydroxy-6-oxo-4-(trifluoromethyl)-4,5,6,7-tetrahydro-1H-pyrazolo[3,4-b]pyridin-3-yl]piperidin-1-yl}-N,N-dimethyl-2-(trifluoromethyl)benzamide

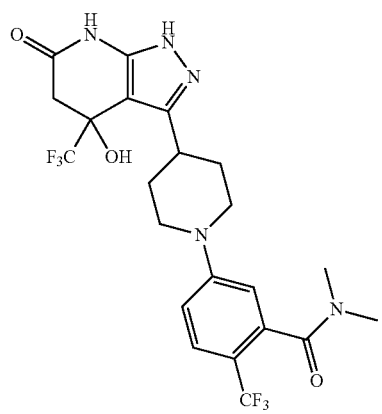

[Formula 180]

The title compound (236 mg, yield: 43%) was obtained through reaction in the same way as the method described in Example 1 using 5-[4-(5-amino-1H-pyrazol-3-yl)piperidin-1-yl]-N,N-dimethyl-2-(trifluoromethyl)benzamide (400 mg, 1.05 mmol) produced in Reference Example 102 instead of 3-(1-phenylpiperidin-4-yl)-1H-pyrazol-5-amine.

¹H-NMR (400 MHz, DMSO-d6) δ: 12.29 (1H, s), 10.53 (1H, s), 7.53 (1H, d, J=9 Hz), 7.08 (1H, d, J=7 Hz), 6.87 (1H, s), 6.81 (1H, s), 4.14-4.01 (2H, m), 3.37-3.27 (1H, m), 3.05-2.68 (10H, m), 1.92-1.67 (4H, m);
MS (ESI) m/z: 520 (M+H)⁺.

Reference Example 103

3-[1-(4-Fluorophenyl)piperidin-4-yl]-1H-pyrazol-5-amine

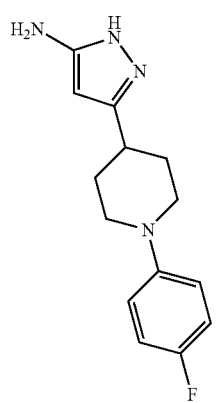

[Formula 181]

The title compound (1.44 g, yield: 84%) was obtained through reaction in the same way as the method described in Reference Example 4 using ethyl 1-(4-fluorophenyl)piperidine-4-carboxylate (compound described in the pamphlet of WO2010/97576, 1.66 g, 6.61 mmol) instead of ethyl 1-(6-methylpyridin-2-yl)piperidine-4-carboxylate.

¹H-NMR (500 MHz, DMSO-d₆) δ: 11.15 (1H, s), 7.05-6.94 (4H, m), 5.21 (1H, s), 4.40 (1H, brs), 3.62-3.59 (2H, m), 2.68 (2H, td, J=12, 2 Hz), 2.57 (1H, brs), 1.93-1.90 (2H, m), 1.70-1.60 (2H, m).

Example 70

3-[1-(4-Fluorophenyl)piperidin-4-yl]-4-hydroxy-4-(trifluoromethyl)-1,4,5,7-tetrahydro-6H-pyrazolo[3,4-b]pyridin-6-one

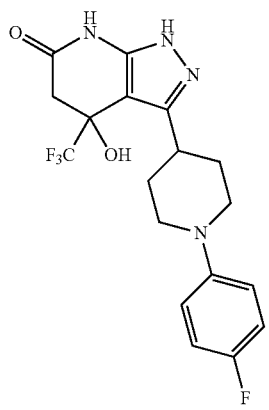

[Formula 182]

The title compound (1.14 g, yield: 52%) was obtained through reaction in the same way as the method described in Example 1 using 3-[1-(4-fluorophenyl)piperidin-4-yl]-1H-pyrazol-5-amine (1.44 g, 5.53 mmol) produced in Reference Example 103 instead of 3-(1-phenylpiperidin-4-yl)-1H-pyrazol-5-amine.

¹H-NMR (500 MHz, DMSO-d₆) δ: 12.29 (1H, s), 10.51 (1H, s), 7.06-6.97 (4H, m), 6.72 (1H, s), 3.70-3.68 (2H, m), 3.13-3.05 (1H, m), 2.89 (1H, d, J=16 Hz), 2.73 (1H, d, J=16 Hz), 2.66-2.59 (2H, m), 1.95-1.72 (4H, m);
MS (ESI) m/z: 399 (M+H)⁺.

Reference Example 104

3-[1-(3-Cyclopropyl-1,2,4-oxadiazol-5-yl)piperidin-4-yl]-1H-pyrazol-5-amine

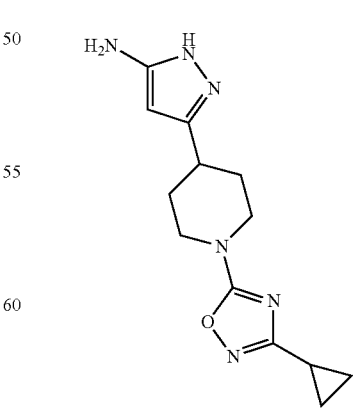

[Formula 183]

The title compound (398 mg, yield: 87%) was obtained through reaction at 100° C. in the same way as the method described in Reference Example 34 using 5-chloro-3-cyclopropyl-1,2,4-oxazole (240 mg, 1.66 mmol) instead of 3,6-dichloropyridazine.

¹H-NMR (500 MHz, DMSO-d₆) δ: 11.16 (1H, s), 5.19 (1H, s), 4.50 (1H, s), 3.94-3.91 (2H, m), 3.21-3.10 (3H, m), 2.74-2.66 (1H, m), 1.92-1.80 (2H, m), 1.68-1.47 (2H, m), 0.96-0.74 (4H, m).

Example 71

3-[1-(3-Cyclopropyl-1,2,4-oxadiazol-5-yl)piperidin-4-yl]-4-hydroxy-4-(trifluoromethyl)-1,4,5,7-tetrahydro-6H-pyrazolo[3,4-b]pyridin-6-one

[Formula 184]

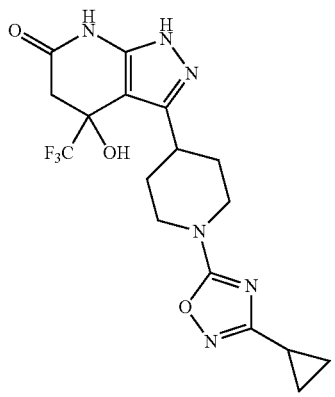

The title compound (155 mg, yield: 26%) was obtained through reaction in the same way as the method described in Example 1 using 3-[1-(3-cyclopropyl-1,2,4-oxadiazol-5-yl)piperidin-4-yl]-1H-pyrazol-5-amine (398 mg, 1.45 mmol) produced in Reference Example 104 instead of 3-(1-phenylpiperidin-4-yl)-1H-pyrazol-5-amine.

¹H-NMR (500 MHz, DMSO-d₆) δ: 12.25 (1H, s), 10.52 (1H, s), 6.78 (1H, s), 4.06-3.98 (2H, m), 3.27-3.19 (1H, m), 3.16-3.11 (2H, m), 2.89 (1H, d, J=17 Hz), 2.72 (1H, d, J=17 Hz), 1.92-1.83 (2H, m), 1.81-1.65 (3H, m), 0.97-0.79 (4H, m);

MS (ESI) m/z: 413 (M+H)⁺.

Reference Example 105

Ethyl 1-(2-tert-butylpyrimidin-5-yl)piperidine-4-carboxylate

[Formula 185]

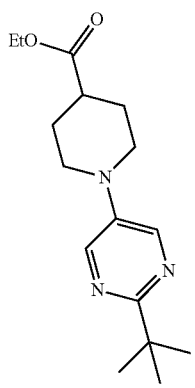

The title compound (2.19 g, yield: 65%) was obtained through reaction in the same way as the method described in Reference Example 13 using 5-bromo-2-tert-butylpyrimidine (2.50 g, 11.62 mmol) instead of 2-bromo-3-chloropyridine.

¹H-NMR (400 MHz, CDCl₃) δ: 8.35 (2H, s), 4.17 (2H, q, J=7 Hz), 3.64-3.59 (2H, m), 2.89-2.82 (2H, m), 2.50-2.43 (1H, m), 2.09-2.01 (2H, m), 1.93-1.82 (2H, m), 1.38 (9H, s), 1.27 (3H, t, J=7 Hz).

Reference Example 106

3-[1-(2-tert-Butylpyrimidin-5-yl)piperidin-4-yl]-1H-pyrazol-5-amine

[Formula 186]

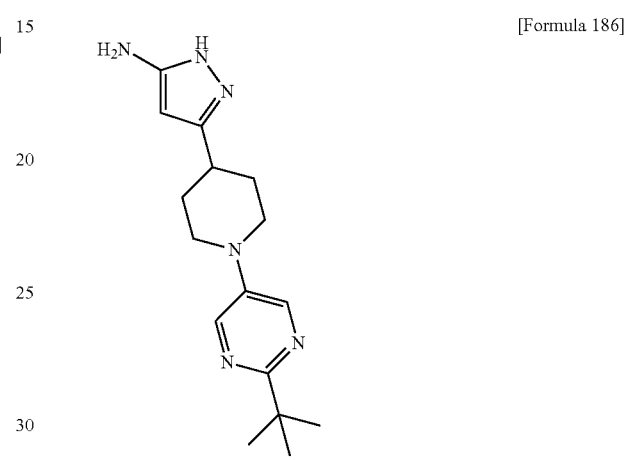

The title compound (1.84 g, yield: 81%) was obtained through reaction in the same way as the method described in Reference Example 4 using ethyl 1-(2-tert-butylpyrimidin-5-yl)piperidine-4-carboxylate (2.19 g, 7.52 mmol) produced in Reference Example 105 instead of ethyl 1-(6-methylpyridin-2-yl)piperidine-4-carboxylate.

¹H-NMR (500 MHz, DMSO-d₆) δ: 11.18 (1H, s), 8.45 (2H, s), 5.25 (1H, s), 4.36 (2H, brs), 3.80-3.77 (2H, m), 2.79 (2H, td, J=12, 2 Hz), 2.69-2.58 (1H, m), 1.94-1.91 (2H, m), 1.68-1.60 (2H, m), 1.31 (9H, s).

Example 72

3-[1-(2-tert-Butylpyrimidin-5-yl)piperidin-4-yl]-4-hydroxy-4-(trifluoromethyl)-1,4,5,7-tetrahydro-6H-pyrazolo[3,4-b]pyridin-6-one

[Formula 187]

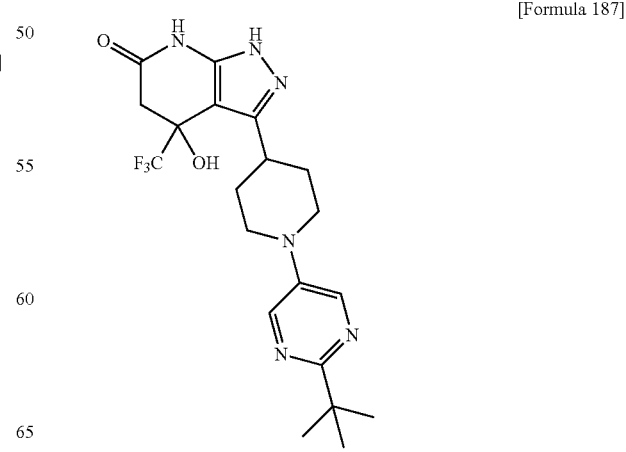

The title compound (1.65 g, yield: 61%) was obtained through reaction in the same way as the method described in Example 1 using 3-[1-(2-tert-butylpyrimidin-5-yl)piperidin-4-yl]-1H-pyrazol-5-amine (1.84 g, 6.13 mmol) produced in Reference Example 106 instead of 3-(1-phenylpiperidin-4-yl)-1H-pyrazol-5-amine.

$^1$H-NMR (500 MHz, DMSO-$d_6$) δ: 12.30 (1H, s), 10.51 (1H, s), 8.47 (2H, s), 6.74 (1H, s), 3.89-3.87 (2H, m), 3.30-3.20 (1H, m), 2.90 (1H, d, J=17 Hz), 2.79-2.70 (3H, m), 1.94-1.71 (4H, m), 1.32 (9H, s);
MS (ESI) m/z: 439 (M+H)$^+$.

Reference Example 107

Ethyl 1-(5-ethylpyridin-2-yl)piperidine-4-carboxylate

[Formula 188]

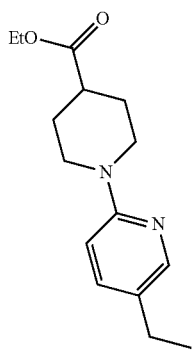

The title compound (703 mg, yield: 49%) was obtained through reaction in the same way as the method described in Reference Example 13 using 2-bromo-5-ethylpyridine (1.02 g, 5.48 mmol) instead of 2-bromo-3-chloropyridine.

$^1$H-NMR (500 MHz, CDCl$_3$) δ: 8.03 (1H, d, J=2 Hz), 7.33 (1H, dd, J=8, 2 Hz), 6.63 (1H, d, J=8 Hz), 4.20-4.09 (4H, m), 2.94-2.88 (2H, m), 2.54-2.46 (3H, m), 2.01-1.97 (2H, m), 1.82-1.74 (2H, m), 1.26 (3H, t, J=7 Hz), 1.19 (3H, t, J=8 Hz).

Reference Example 108

3-[1-(5-Ethylpyridin-2-yl)piperidin-4-yl]-1H-pyrazol-5-amine

[Formula 189]

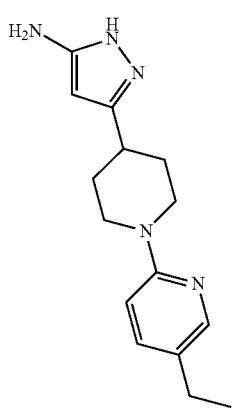

The title compound (488 mg, yield: 67%) was obtained through reaction in the same way as the method described in Reference Example 4 using ethyl 1-(5-ethylpyridin-2-yl)piperidine-4-carboxylate (703 mg, 2.68 mmol) produced in Reference Example 107 instead of ethyl 1-(6-methylpyridin-2-yl)piperidine-4-carboxylate.

$^1$H-NMR (500 MHz, DMSO-$d_6$) δ: 11.13 (1H, brs), 7.95 (1H, d, J=2 Hz), 7.38 (1H, dd, J=9, 2 Hz), 6.78 (1H, d, J=9 Hz), 5.18 (1H, s), 4.44 (2H, brs), 4.26-4.23 (2H, m), 2.81 (2H, td, J=12, 2 Hz), 2.71-2.62 (1H, m), 2.46 (2H, q, J=8 Hz), 1.88-1.85 (2H, m), 1.55-1.46 (2H, m), 1.12 (3H, t, J=8 Hz).

Example 73

3-[1-(5-Ethylpyridin-2-yl)piperidin-4-yl]-4-hydroxy-4-(trifluoromethyl)-1,4,5,7-tetrahydro-6H-pyrazolo[3,4-b]pyridin-6-one

[Formula 190]

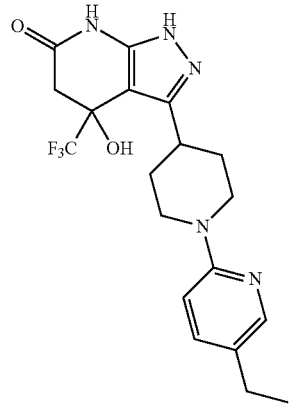

The title compound (300 mg, yield: 41%) was obtained through reaction in the same way as the method described in Example 1 using 3-[1-(5-ethylpyridin-2-yl)piperidin-4-yl]-1H-pyrazol-5-amine (488 mg, 1.80 mmol) produced in Reference Example 108 instead of 3-(1-phenylpiperidin-4-yl)-1H-pyrazol-5-amine.

$^1$H-NMR (400 MHz, DMSO-$d_6$) δ: 12.24 (1H, s), 10.50 (1H, s), 7.97 (1H, d, J=2 Hz), 7.40 (1H, dd, J=9, 2 Hz), 6.81 (1H, d, J=9 Hz), 6.73 (1H, s), 4.38 (2H, d, J=10 Hz), 3.20 (1H, t, J=12 Hz), 2.90 (1H, d, J=16 Hz), 2.78-2.68 (3H, m), 2.49-2.43 (2H, m), 1.91-1.83 (1H, m), 1.80-1.61 (3H, m), 1.13 (3H, t, J=8 Hz);
MS (ESI) m/z: 410 (M+H)$^+$.

Reference Example 109

3-[1-(5-Bromopyridin-2-yl)piperidin-4-yl]-1H-pyrazol-5-amine

[Formula 191]

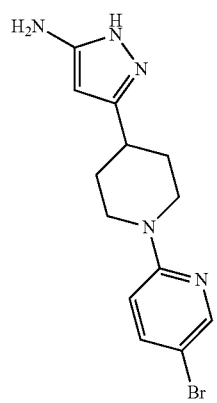

The title compound (440 mg, yield: 80%) was obtained through reaction at 80° C. in the same way as the method described in Reference Example 34 using 5-bromo-2-fluoropyridine (310 mg, 1.70 mmol) instead of 3,6-dichloropyridazine.

$^1$H-NMR (500 MHz, DMSO-$d_6$) δ: 11.12 (1H, s), 8.15 (1H, d, J=3 Hz), 7.64 (1H, dd, J=9, 3 Hz), 6.85 (1H, d, J=9 Hz), 5.18 (1H, s), 4.43 (2H, brs), 4.29-4.25 (2H, m), 2.92-2.87 (2H, m), 2.74-2.70 (1H, m), 1.89-1.85 (2H, m), 1.53-1.45 (2H, m).

Example 74

3-[1-(5-Bromopyridin-2-yl)piperidin-4-yl]-4-hydroxy-4-(trifluoromethyl)-1,4,5,7-tetrahydro-6H-pyrazolo[3,4-b]pyridin-6-one

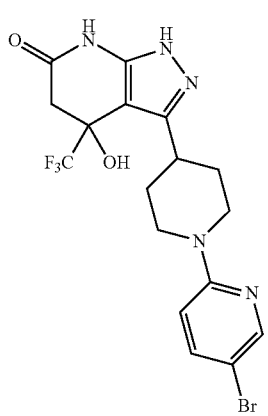

[Formula 192]

The title compound (275 mg, yield: 44%) was obtained through reaction in the same way as the method described in Example 1 using 3-[1-(5-bromopyridin-2-yl)piperidin-4-yl]-1H-pyrazol-5-amine (440 mg, 1.37 mmol) produced in Reference Example 109 instead of 3-(1-phenylpiperidin-4-yl)-1H-pyrazol-5-amine.

$^1$H-NMR (500 MHz, DMSO-d6) δ: 12.20 (1H, s), 10.48 (1H, s), 8.16 (1H, d, J=2 Hz), 7.67 (1H, dd, J=9, 2 Hz), 6.87 (1H, d, J=9 Hz), 6.73 (1H, s), 4.40 (2H, d, J=11 Hz), 3.29-3.21 (1H, m), 2.89 (1H, d, J=17 Hz), 2.86-2.79 (2H, m), 2.72 (1H, d, J=17 Hz), 1.86 (1H, d, J=11 Hz), 1.77-1.60 (3H, m);

MS (ESI) m/z: 460 (M+H)$^+$.

Reference Example 110

3-{1-[2,6-di(Propan-2-yl)pyrimidin-4-yl]piperidin-4-yl}-1H-pyrazol-5-amine

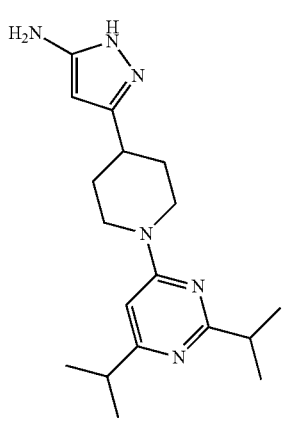

[Formula 193]

The title compound (614 mg, yield: 83%) was obtained through reaction at 85° C. in the same way as the method described in Reference Example 34 using 4-chloro-2,6-di(propan-2-yl)pyrimidine (600 mg, 3.02 mmol) instead of 3,6-dichloropyridazine.

$^1$H-NMR (500 MHz, DMSO-$d_6$) δ: 11.14 (1H, s), 6.46 (1H, s), 5.19 (1H, s), 4.53-4.36 (4H, m), 2.94-2.80 (3H, m), 2.77-2.71 (2H, m), 1.92-1.85 (2H, m), 1.50-1.42 (2H, m), 1.19 (6H, d, J=7 Hz), 1.17 (6H, d, J=7 Hz).

Example 75

3-{1-[2,6-di(Propan-2-yl)pyrimidin-4-yl]piperidin-4-yl}-4-hydroxy-4-(trifluoromethyl)-1,4,5,7-tetrahydro-6H-pyrazolo[3,4-b]pyridin-6-one

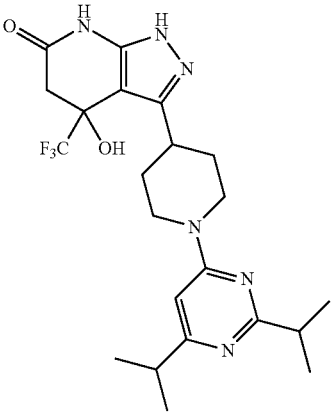

[Formula 194]

The title compound (243 mg, yield: 28%) was obtained through reaction in the same way as the method described in Example 1 using 3-{1-[2,6-di(propan-2-yl)pyrimidin-4-yl]piperidin-4-yl}-1H-pyrazol-5-amine (614 mg, 1.87 mmol) produced in Reference Example 110 instead of 3-(1-phenylpiperidin-4-yl)-1H-pyrazol-5-amine.

$^1$H-NMR (500 MHz, DMSO-d6) δ: 12.19 (1H, s), 10.50 (1H, s), 6.75 (1H, s), 6.48 (1H, s), 4.61 (2H, s), 2.91-2.71 (6H, m), 1.93-1.86 (1H, m), 1.78-1.56 (3H, m), 1.20 (6H, d, J=7 Hz), 1.18 (6H, d, J=7 Hz);

MS (ESI) m/z: 467 (M+H)$^+$.

Reference Example 111

Ethyl 1-[5-(trifluoromethoxy)pyridin-2-yl]piperidine-4-carboxylate

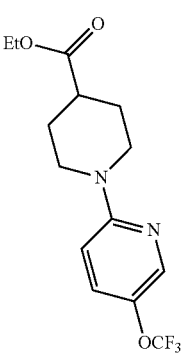

[Formula 195]

The title compound (1.07 g, yield: 74%) was obtained through reaction in the same way as the method described in Reference Example 13 using 2-bromo-5-(trifluoromethoxy)pyridine (1.10 g, 4.55 mmol) instead of 2-bromo-3-chloropyridine.

$^1$H-NMR (500 MHz, CDCl$_3$) δ: 8.09 (1H, d, J=3 Hz), 7.35-7.33 (1H, m), 6.63 (1H, d, J=9 Hz), 4.22-4.13 (4H, m), 3.03-2.96 (2H, m), 2.57-2.50 (1H, m), 2.03-1.97 (2H, m), 1.81-1.72 (2H, m), 1.27 (3H, t, J=7 Hz).

Reference Example 112

3-{1-[5-(Trifluoromethoxy)pyridin-2-yl]piperidin-4-yl}-1H-pyrazol-5-amine

[Formula 196]

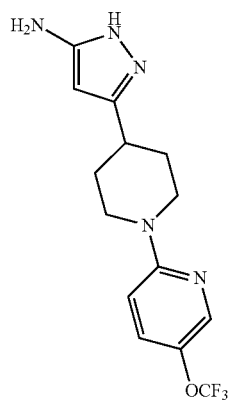

The title compound (1.13 g, yield: 130%) was obtained through reaction in the same way as the method described in Reference Example 4 using ethyl 1-[5-(trifluoromethoxy)pyridin-2-yl]piperidine-4-carboxylate (1.07 g, 3.36 mmol) produced in Reference Example 111 instead of ethyl 1-(6-methylpyridin-2-yl)piperidine-4-carboxylate.

$^1$H-NMR (500 MHz, DMSO-d$_6$) δ: 11.14 (1H, s), 8.92 (1H, s), 8.13 (1H, d, J=3 Hz), 7.57 (1H, dd, J=9, 2 Hz), 6.92 (1H, d, J=9 Hz), 5.20 (1H, s), 4.41-4.10 (4H, m), 2.95-2.90 (2H, m), 2.72 (1H, s), 1.90-1.87 (2H, m), 1.55-1.47 (2H, m).

Example 76

4-Hydroxy-3-{1-[5-(trifluoromethoxy)pyridin-2-yl]piperidin-4-yl}-4-(trifluoromethyl)-1,4,5,7-tetrahydro-6H-pyrazolo[3,4-b]pyridin-6-one

[Formula 197]

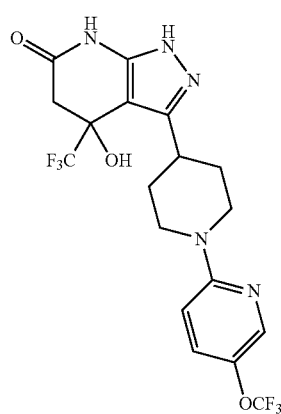

The title compound (560 mg, yield: 32%) was obtained through reaction in the same way as the method described in Example 1 using 3-{1-[5-(trifluoromethoxy)pyridin-2-yl]piperidin-4-yl}-1H-pyrazol-5-amine (1.13 g, 4.36 mmol) produced in Reference Example 112 instead of 3-(1-phenylpiperidin-4-yl)-1H-pyrazol-5-amine.

$^1$H-NMR (400 MHz, DMSO-d$_6$) δ: 12.22 (1H, s), 10.50 (1H, s), 8.15 (1H, d, J=3 Hz), 7.59 (1H, dd, J=9, 3 Hz), 6.95 (1H, d, J=9 Hz), 6.73 (1H, s), 4.47-4.43 (2H, m), 3.31-3.21 (1H, m), 2.93-2.81 (3H, m), 2.73 (1H, d, J=16 Hz), 1.91-1.85 (1H, m), 1.78-1.60 (3H, m);

MS (ESI) m/z: 382 (M+H)$^+$.

Example 77

Methyl 6-{4-[4-hydroxy-6-oxo-4-(trifluoromethyl)-4,5,6,7-tetrahydro-1H-pyrazolo[3,4-b]pyridin-3-yl]piperidin-1-yl}-3-(trifluoromethyl)pyridine-2-carboxylate

[Formula 198]

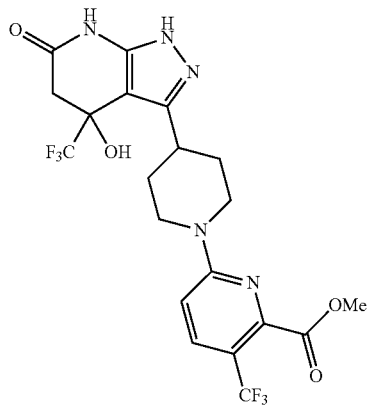

The title compound (132 mg, yield: 59%) was obtained through reaction in the same way as the method described in Example 43 using methyl 6-chloro-3-(trifluoromethyl)pyridine-2-carboxylate (160 mg, 0.668 mmol) instead of 3-chloro-6-(trifluoromethyl)pyridazine.

$^1$H-NMR (400 MHz, DMSO-d$_6$) δ: 12.21 (1H, s), 10.51 (1H, s), 7.88 (1H, d, J=9 Hz), 7.11 (1H, d, J=9 Hz), 6.77 (1H, s), 4.55 (2H, d, J=13 Hz), 3.86 (3H, s), 3.04-2.84 (4H, m), 2.72 (1H, d, J=16 Hz), 1.94-1.87 (1H, m), 1.77-1.58 (3H, m);

MS (ESI) m/z: 508 (M+H)$^+$.

Example 78

5-{4-[4-Hydroxy-6-oxo-4-(trifluoromethyl)-4,5,6,7-tetrahydro-1H-pyrazolo[3,4-b]pyridin-3-yl]piperidin-1-yl}pyrazine-2-carbonitrile

[Formula 199]

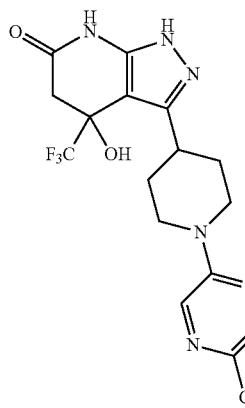

The title compound (70 mg, yield: 39%) was obtained through reaction in the same way as the method described in Example 43 using 5-chloropyrazine-2-carbonitrile (93 mg, 0.666 mmol) instead of 3-chloro-6-(trifluoromethyl)pyridazine.

¹H-NMR (400 MHz, DMSO-d₆) δ: 12.20 (1H, s), 10.53 (1H, s), 8.59 (1H, d, J=2 Hz), 8.50 (1H, d, J=2 Hz), 6.79 (1H, s), 4.65 (2H, brs), 3.33-3.27 (1H, m), 3.13-3.02 (2H, m), 2.90 (1H, d, J=16 Hz), 2.73 (1H, d, J=16 Hz), 1.98-1.91 (1H, m), 1.81-1.62 (3H, m);
MS (ESI) m/z: 406 (M−H)⁻.

Example 79

4-Hydroxy-4-(trifluoromethyl)-3-{1-[2-(trifluoromethyl)pyrimidin-4-yl]piperidin-4-yl}-1,4,5,7-tetrahydro-6H-pyrazolo[3,4-b]pyridin-6-one

[Formula 200]

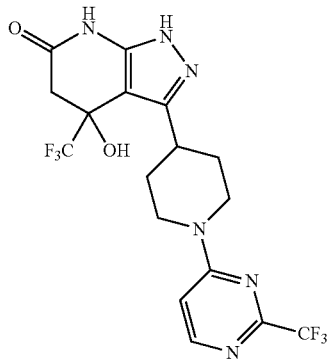

The title compound (165 mg, yield: 79%) was obtained through reaction in the same way as the method described in Example 43 using 4-chloro-2-(trifluoromethyl)pyrimidine (145 mg, 0.794 mmol) instead of 3-chloro-6-(trifluoromethyl)pyridazine.

¹H-NMR (400 MHz, DMSO-d₆) δ: 12.19 (1H, s), 10.52 (1H, s), 8.34 (1H, d, J=6 Hz), 7.12 (1H, d, J=6 Hz), 6.78 (1H, s), 4.60 (2H, brs) 3.09-2.96 (3H, m), 2.90 (1H, d, J=16 Hz), 2.73 (1H, d, J=16 Hz), 1.98-1.90 (1H, m), 1.81-1.62 (3H, m);
MS (ESI) m/z: 451 (M+H)⁺.

Example 80

4-Hydroxy-4-(trifluoromethyl)-3-{1-[4-(trifluoromethyl)pyrimidin-2-yl]piperidin-4-yl}-1,4,5,7-tetrahydro-6H-pyrazolo[3,4-b]pyridin-6-one

[Formula 201]

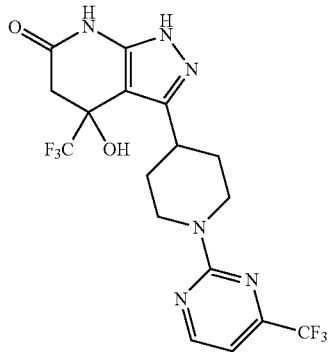

The title compound (142 mg, yield: 60%) was obtained through reaction in the same way as the method described in Example 43 using 2-chloro-4-(trifluoromethyl)pyrimidine (180 mg, 0.986 mmol) instead of 3-chloro-6-(trifluoromethyl)pyridazine.

¹H-NMR (400 MHz, DMSO-d₆) δ: 12.18 (1H, s), 10.51 (1H, s), 8.70 (1H, d, J=5 Hz), 7.01 (1H, d, J=5 Hz), 6.78 (1H, s), 4.80 (2H, brs), 3.34-3.26 (1H, m), 3.03-2.86 (3H, m), 2.73 (1H, d, J=16 Hz), 1.95-1.58 (4H, m);
MS (ESI) m/z: 451 (M+H)⁺.

Example 81

2-{4-[4-Hydroxy-6-oxo-4-(trifluoromethyl)-4,5,6,7-tetrahydro-1H-pyrazolo[3,4-b]pyridin-3-yl]piperidin-1-yl}-1,3-thiazole-5-carbonitrile

[Formula 202]

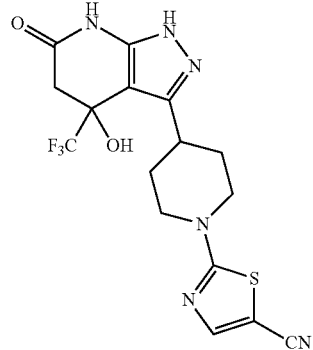

The title compound (95 mg, yield: 52%) was obtained through reaction in the same way as the method described in Example 43 using 2-chlorothiazole-5-carbonitrile (100 mg, 0.692 mmol) instead of 3-chloro-6-(trifluoromethyl)pyridazine.

¹H-NMR (400 MHz, DMSO-d₆) δ: 12.26 (1H, s), 10.53 (1H, s), 8.03 (1H, s), 6.78 (1H, s), 4.13-4.00 (2H, m), 3.33-3.21 (3H, m), 2.90 (1H, d, J=17 Hz), 2.72 (1H, d, J=16 Hz), 1.98-1.70 (4H, m);
MS (ESI) m/z: 411 (M−H)⁻.

Example 82

Methyl 2-{4-[4-hydroxy-6-oxo-4-(trifluoromethyl)-4,5,6,7-tetrahydro-1H-pyrazolo[3,4-b]pyridin-3-yl]piperidin-1-yl}-5-(trifluoromethyl)pyridine-4-carboxylate

[Formula 203]

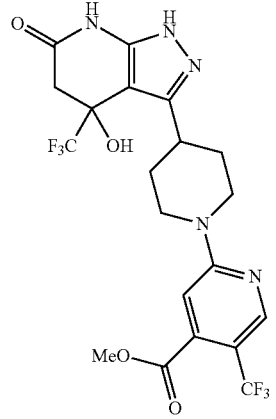

The title compound (82 mg, yield: 43%) was obtained through reaction in the same way as the method described in Example 43 using methyl 2-chloro-5-(trifluoromethyl)pyridine-4-carboxylate (128 mg, 0.376 mmol) instead of 3-chloro-6-(trifluoromethyl)pyridazine.

$^1$H-NMR (500 MHz, DMSO-d$_6$) δ: 12.19 (1H, s), 10.50 (1H, s), 8.49 (1H, s), 7.18 (1H, s), 6.75 (1H, s), 4.61 (2H, brs), 3.87 (3H, s), 3.36-3.27 (1H, m), 3.04-2.98 (2H, m), 2.89 (1H, d, J=16 Hz), 2.73 (1H, d, J=16 Hz), 1.92-1.89 (1H, m), 1.76-1.59 (3H, m);

MS (ESI) m/z: 508 (M+H)$^+$.

Reference Example 113

6-Chloro-N,N-dimethyl-3-(trifluoromethyl)pyridine-2-carboxamide

[Formula 204]

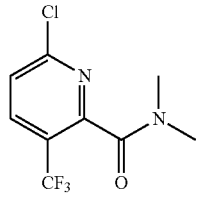

EDC (650 mg, 3.39 mmol) and dimethylamine (2.0 M solution in THF, 2.30 mL, 4.60 mmol) were added at room temperature to a solution of 6-chloro-3-(trifluoromethyl)pyridine-2-carboxylic acid (516 mg, 2.29 mmol) in dichloromethane (20 mL), and the mixture was stirred at room temperature for 4 hours. A saturated ammonium chloride aqueous solution was added to the reaction solution, followed by extraction with dichloromethane. The obtained organic layer was washed with brine and dried over anhydrous magnesium sulfate, and the solvent was distilled off under reduced pressure. The obtained residue was purified by silica gel column chromatography [elute: hexane/ethyl acetate=100/0-70/30 (gradient)] to obtain the title compound (246 mg, yield: 43%).

$^1$H-NMR (500 MHz, CDCl$_3$) δ: 8.02 (1H, d, J=8 Hz), 7.53 (1H, d, J=8 Hz), 3.18 (3H, s), 2.89 (3H, s).

Example 83

6-{4-[4-Hydroxy-6-oxo-4-(trifluoromethyl)-4,5,6,7-tetrahydro-1H-pyrazolo[3,4-b]pyridin-3-yl]piperidin-1-yl}-N,N-dimethyl-3-(trifluoromethyl)pyridine-2-carboxamide

[Formula 205]

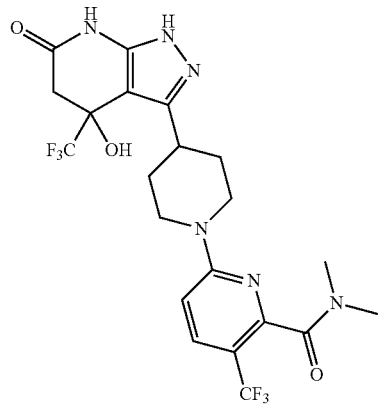

The title compound (113 mg, yield: 34%) was obtained through reaction in the same way as the method described in Example 43 using 6-chloro-N,N-dimethyl-3-(trifluoromethyl)pyridine-2-carboxamide (246 mg, 0.973 mmol) produced in Reference Example 113 instead of 3-chloro-6-(trifluoromethyl)pyridazine.

$^1$H-NMR (500 MHz, DMSO-d$_6$) δ: 12.22 (1H, s), 10.50 (1H, s), 7.84 (1H, d, J=9 Hz), 7.01 (1H, d, J=9 Hz), 6.76 (1H, s), 4.54 (2H, d, J=13 Hz), 3.33-3.27 (1H, m), 3.01-2.92 (5H, m), 2.89 (1H, d, J=17 Hz), 2.77 (3H, s), 2.73 (1H, d, J=17 Hz), 1.91-1.89 (1H, m), 1.76-1.61 (3H, m);

MS (ESI) m/z: 521 (M+H)$^+$.

Reference Example 114

2-Chloro-N,N-dimethyl-5-(trifluoromethyl)pyridine-4-carboxamide

[Formula 206]

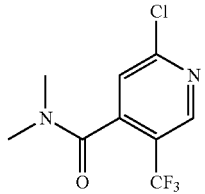

The title compound (170 mg, yield: 25%) was obtained through reaction in the same way as the method described in Reference Example 113 using 2-chloro-5-(trifluoromethyl)pyridine-4-carboxylic acid (610 mg, 2.70 mmol) instead of 6-chloro-3-(trifluoromethyl)pyridine-2-carboxylic acid.

$^1$H-NMR (400 MHz, CDCl$_3$) δ: 8.73 (1H, s), 7.33 (1H, s), 3.14 (3H, s), 2.84 (3H, s).

Example 84

2-{4-[4-Hydroxy-6-oxo-4-(trifluoromethyl)-4,5,6,7-tetrahydro-1H-pyrazolo[3,4-b]pyridin-3-yl]piperidin-1-yl}-N,N-dimethyl-5-(trifluoromethyl)pyridine-4-carboxamide

[Formula 207]

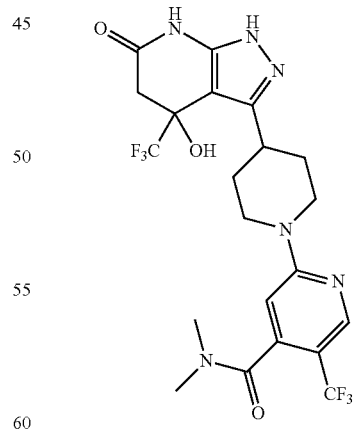

The title compound (18 mg, yield: 8%) was obtained through reaction in the same way as the method described in Example 43 using 2-chloro-N,N-dimethyl-5-(trifluoromethyl)pyridine-4-carboxamide (170 mg, 0.673 mmol) produced in Reference Example 114 instead of 3-chloro-6-(trifluoromethyl)pyridazine.

¹H-NMR (400 MHz, DMSO-d₆) δ: 12.22 (1H, s), 10.51 (1H, s), 8.45 (1H, s), 6.90 (1H, s), 6.76 (1H, s), 4.62 (2H, d, J=38 Hz), 3.33-3.30 (1H, m), 3.06-2.93 (5H, m), 2.90 (1H, d, J=17 Hz), 2.79 (3H, s), 2.73 (1H, d, J=17 Hz), 1.93-1.55 (4H, m);
MS (ESI) m/z: 521 (M+H)⁺.

Example 85

Benzyl 2-[4-(4-hydroxy-6-oxo-4-(trifluoromethyl)-4,5,6,7-tetrahydro-1H-pyrazolo[3,4-b]pyridin-3-yl)piperidin-1-yl]-5-(trifluoromethyl)pyridine-4-carboxylate

[Formula 208]

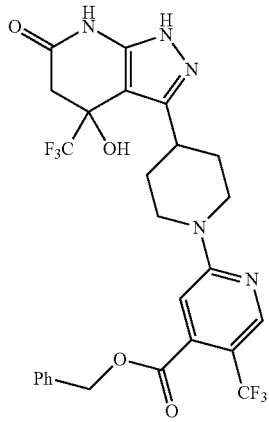

A product (2.94 g) was obtained through reaction in the same way as the method described in Reference Example 9 using 2-chloro-5-(trifluoromethyl)pyridine-4-carboxylic acid (2.00 g, 8.87 mmol) instead of 1-[5-(trifluoromethyl)pyridin-2-yl]piperidine-4-carboxylic acid and benzyl bromide (1.00 mL, 8.42 mmol) instead of methyl iodide.

The title compound (210 mg, yield: 44%) was obtained through reaction in the same way as the method described in Example 43 using the obtained product (400 mg) instead of 3-chloro-6-(trifluoromethyl)pyridazine.
¹H-NMR (500 MHz, DMSO-d₆) δ: 12.18 (1H, s), 10.50 (1H, s), 8.49 (1H, s), 7.46-7.35 (5H, m), 7.19 (1H, s), 6.76 (1H, s), 5.34 (2H, s), 4.66-4.55 (2H, m), 3.03-2.96 (3H, m), 2.89 (1H, d, J=17 Hz), 2.73 (1H, d, J=17 Hz), 1.91-1.89 (1H, m), 1.75-1.60 (3H, m);
MS (ESI) m/z: 584 (M+H)⁺.

Example 86

3-{1-[6-(Dimethylamino)-2-(trifluoromethyl)pyrimidin-4-yl]piperidin-4-yl}-4-hydroxy-4-(trifluoromethyl)-1,4,5,7-tetrahydro-6H-pyrazolo[3,4-b]pyridin-6-one

[Formula 209]

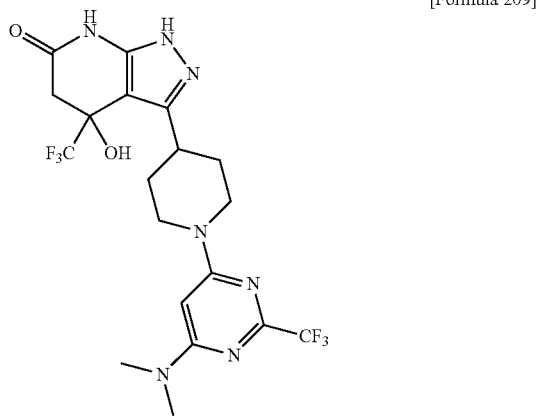

The title compound (91 mg, yield: 28%) was obtained through reaction at 80° C. in the same way as the method described in Example 43 using 6-chloro-N,N-dimethyl-2-(trifluoromethyl)pyrimidin-4-amine (150 mg, 0.665 mmol) instead of 3-chloro-6-(trifluoromethyl)pyridazine.
¹H-NMR (500 MHz, DMSO-d₆) δ: 12.20 (1H, s), 10.51 (1H, s), 6.76 (1H, s), 5.84 (1H, s), 4.52 (2H, brs), 3.31-3.24 (1H, m), 3.05 (6H, s), 2.92-2.83 (3H, m), 2.73 (1H, d, J=16 Hz), 1.90-1.88 (1H, m), 1.76-1.59 (3H, m);
MS (ESI) m/z: 494 (M+H)⁺.

Example 87

4-Hydroxy-3-{1-[2-methyl-6-(trifluoromethyl)pyrimidin-4-yl]piperidin-4-yl}-4-(trifluoromethyl)-1,4,5,7-tetrahydro-6H-pyrazolo[3,4-b]pyridin-6-one

[Formula 210]

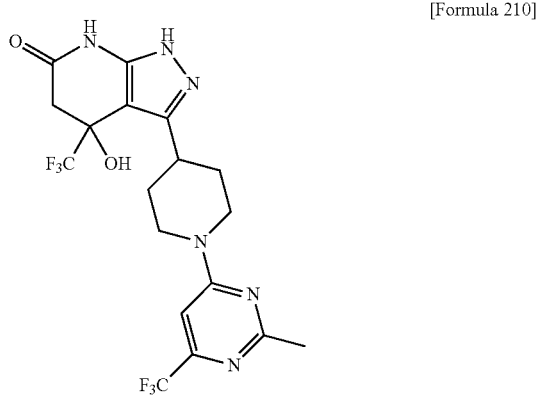 [SMILES: Cc1nc(N2CCC(c3n[nH]c4c3C(O)(C(F)(F)F)CC(=O)N4)CC2)cc(C(F)(F)F)n1]

The title compound (82 mg, yield: 27%) was obtained through reaction at 50° C. in the same way as the method described in Example 43 using 4-chloro-2-methyl-6-trifluoromethylpyrimidine (160 mg, 0.814 mmol) instead of 3-chloro-6-(trifluoromethyl)pyridazine.
¹H-NMR (500 MHz, DMSO-d₆) δ: 12.18 (1H, s), 10.52 (1H, s), 7.14 (1H, s), 6.78 (1H, s), 4.50 (2H, brs), 3.30-3.23

(1H, m), 2.98 (2H, brs), 2.90 (1H, d, J=17 Hz), 2.73 (1H, d, J=17 Hz), 2.41 (3H, s), 1.93-1.91 (1H, m), 1.79-1.58 (3H, m); MS (ESI) m/z: 465 (M+H)+.

Example 88

4-Hydroxy-3-{1-[2-(propan-2-yl)-6-(trifluoromethyl)pyrimidin-4-yl]piperidin-4-yl}-4-(trifluoromethyl)-1,4,5,7-tetrahydro-6H-pyrazolo[3,4-b]pyridin-6-one

[Formula 211]

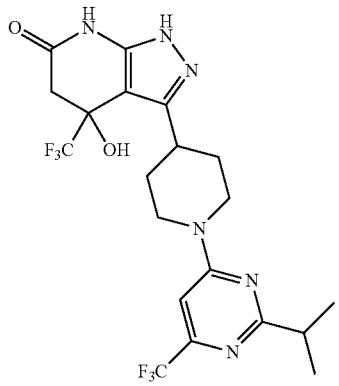

The title compound (125 mg, yield: 54%) was obtained through reaction in the same way as the method described in Example 43 using 4-chloro-2-(propan-2-yl)-6-(trifluoromethyl)pyrimidine (140 mg, 0.623 mmol) instead of 3-chloro-6-(trifluoromethyl)pyridazine.

$^1$H-NMR (500 MHz, DMSO-d$_6$) δ: 12.17 (1H, s), 10.51 (1H, s), 7.13 (1H, s), 6.78 (1H, s), 4.60 (2H, brs), 3.29-3.22 (1H, m), 3.07-2.87 (4H, m), 2.73 (1H, d, J=16 Hz), 1.94-1.92 (1H, m), 1.79-1.60 (3H, m), 1.23 (6H, d, J=7 Hz);
MS (ESI) m/z: 493 (M+H)+.

Example 89

4-Hydroxy-3-[1-(5-phenyl-1,3-thiazol-2-yl)piperidin-4-yl]-4-(trifluoromethyl)-1,4,5,7-tetrahydro-6H-pyrazolo[3,4-b]pyridin-6-one

[Formula 212]

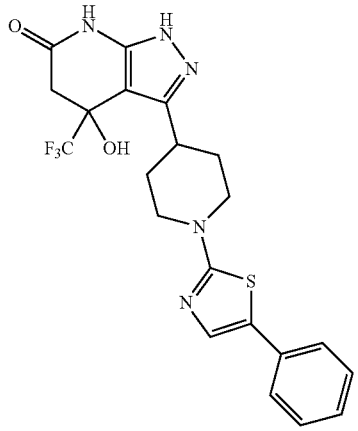

The title compound (41 mg, yield: 13%) was obtained through reaction at 100° C. in the same way as the method described in Example 43 using 2-chloro-5-phenylthiazole (150 mg, 0.767 mmol) instead of 3-chloro-6-(trifluoromethyl)pyridazine.

$^1$H-NMR (400 MHz, DMSO-d$_6$) δ: 12.30 (1H, s), 10.53 (1H, s), 7.61 (1H, s), 7.48 (2H, d, J=7 Hz), 7.36 (2H, t, J=8 Hz), 7.22 (1H, t, J=7 Hz), 6.79 (1H, s), 4.11-4.01 (2H, m), 3.29-3.22 (1H, m), 3.12 (2H, t, J=12 Hz), 2.90 (1H, d, J=16 Hz), 2.73 (1H, d, J=16 Hz), 2.00-1.71 (4H, m);
MS (ESI) m/z: 464 (M+H)+.

Example 90

4-Hydroxy-3-[1-(4-phenyl-1,3-thiazol-2-yl)piperidin-4-yl]-4-(trifluoromethyl)-1,4,5,7-tetrahydro-6H-pyrazolo[3,4-b]pyridin-6-one

[Formula 213]

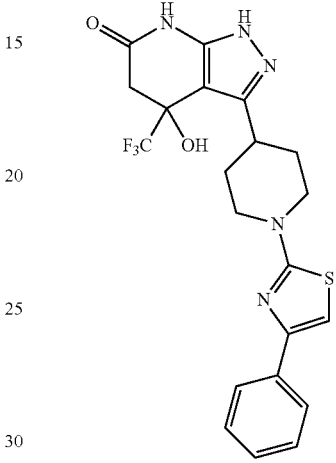

The title compound (16 mg, yield: 5%) was obtained through reaction at 100° C. in the same way as the method described in Example 43 using 2-chloro-4-phenylthiazole (145 mg, 0.741 mmol) instead of 3-chloro-6-(trifluoromethyl)pyridazine.

$^1$H-NMR (400 MHz, DMSO-d$_6$) δ: 12.28 (1H, s), 10.50 (1H, s), 7.84 (2H, d, J=7 Hz), 7.36 (2H, t, J=8 Hz), 7.29-7.22 (2H, m), 6.77 (1H, s), 4.08 (2H, d, J=12 Hz), 3.08 (3H, t, J=12 Hz), 2.88 (1H, d, J=17 Hz), 2.71 (1H, d, J=17 Hz), 1.99-1.70 (4H, m);
MS (ESI) m/z: 464 (M+H)+.

Example 91

Ethyl 2-{4-[4-hydroxy-6-oxo-4-(trifluoromethyl)-4,5,6,7-tetrahydro-1H-pyrazolo[3,4-b]pyridin-3-yl]piperidin-1-yl}-4-(trifluoromethyl)-1,3-oxazole-5-carboxylate

[Formula 214]

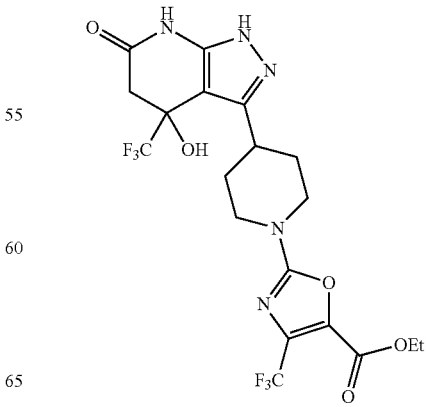

The title compound (43 mg, yield: 20%) was obtained through reaction in the same way as the method described in Example 43 using ethyl 2-chloro-4-(trifluoromethyl)-1,3-oxazole-5-carboxylate (130 mg, 0.534 mmol) instead of 3-chloro-6-(trifluoromethyl)pyridazine.
$^1$H-NMR (400 MHz, DMSO-d$_6$) δ: 12.23 (1H, s), 10.51 (1H, s), 6.77 (1H, s), 4.28 (2H, q, J=7 Hz), 4.09 (2H, d, J=13 Hz), 3.21-3.12 (3H, m), 2.87 (1H, d, J=16 Hz), 2.70 (1H, d, J=16 Hz), 1.93-1.91 (1H, m), 1.81-1.66 (3H, m), 1.25 (3H, t, J=7 Hz);
MS (ESI) m/z: 512 (M+H)$^+$.

Example 92

3-{1-[2-Cyclopropyl-6-(trifluoromethyl)pyrimidin-4-yl]piperidin-4-yl}-4-hydroxy-4-(trifluoromethyl)-1,4,5,7-tetrahydro-6H-pyrazolo[3,4-b]pyridin-6-one

[Formula 215]

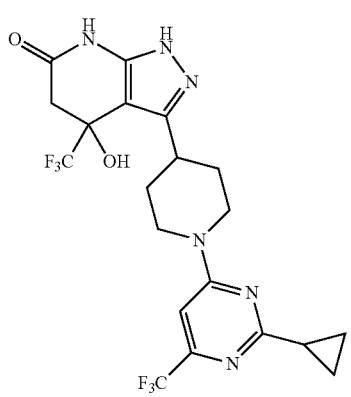

The title compound (146 mg, yield: 65%) was obtained through reaction in the same way as the method described in Example 43 using 4-chloro-2-cyclopropyl-6-(trifluoromethyl)pyrimidine (140 mg, 0.629 mmol) instead of 3-chloro-6-(trifluoromethyl)pyridazine.
$^1$H-NMR (500 MHz, DMSO-d$_6$) δ: 12.14 (1H, s), 10.48 (1H, s), 7.04 (1H, s), 6.75 (1H, s), 4.69 (2H, brs), 3.27-3.20 (1H, m), 3.01-2.87 (2H, m), 2.87 (1H, d, J=17 Hz), 2.70 (1H, d, J=17 Hz), 2.03-1.97 (1H, m), 1.89-1.87 (1H, m), 1.74-1.55 (3H, m), 0.96-0.92 (4H, m);
MS (ESI) m/z: 491 (M+H)$^+$.

Example 93

3-{1-[2-(Dimethylamino)-6-(trifluoromethyl)pyrimidin-4-yl]piperidin-4-yl}-4-hydroxy-4-(trifluoromethyl)-1,4,5,7-tetrahydro-6H-pyrazolo[3,4-b]pyridin-6-one

[Formula 216]

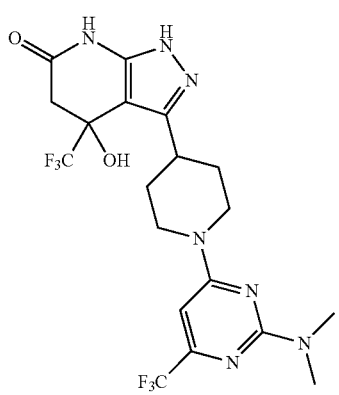

The title compound (135 mg, yield: 64%) was obtained through reaction at 50° C. in the same way as the method described in Example 43 using 4-chloro-N,N-dimethyl-6-(trifluoromethyl)pyrimidin-2-amine (140 mg, 0.621 mmol) instead of 3-chloro-6-(trifluoromethyl)pyridazine.
$^1$H-NMR (500 MHz, DMSO-d$_6$) δ: 12.18 (1H, s), 10.50 (1H, s), 6.75 (1H, s), 6.49 (1H, s), 4.58 (2H, brs), 3.33-3.26 (1H, m), 3.08 (6H, s), 2.97-2.87 (3H, m), 2.73 (1H, d, J=17 Hz), 1.91-1.88 (1H, m), 1.76-1.58 (3H, m);
MS (ESI) m/z: 491 (M+H)$^+$.

Example 94

6-{4-[4-Hydroxy-6-oxo-4-(trifluoromethyl)-4,5,6,7-tetrahydro-1H-pyrazolo[3,4-b]pyridin-3-yl]piperidin-1-yl}-3-(trifluoro)pyridine-2-carbonitrile

[Formula 217]

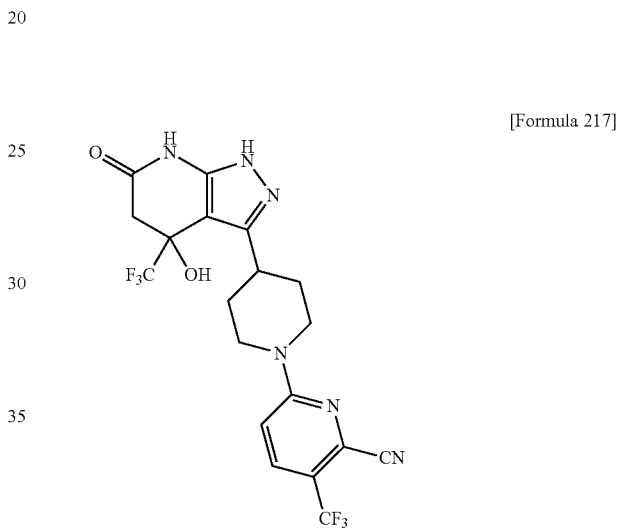

N,N-Diisopropylethylamine (89.8 µL, 0.528 mmol) and 6-fluoro-3-(trifluoromethyl)pyridine-2-carbonitrile (compound described in the pamphlet of US2008/275057, 136 mg, 0.660 mmol) were added to a solution of 4-hydroxy-3-(piperidin-4-yl)-4-(trifluoromethyl)-1,4,5,7-tetrahydro-6H-pyrazolo[3,4-b]pyridin-6-one hydrochloride (150 mg, 0.440 mmol) produced in Reference Example 60 in dimethyl sulfoxide (0.5 mL), and the mixture was stirred while irradiated with microwaves at 60° C. for 20 minutes using Initiator® manufactured by Biotage Japan Ltd. The reaction solution was poured to water, followed by extraction with ethyl acetate twice. The obtained organic layer was washed with water and brine in this order and dried over anhydrous sodium sulfate, and the solvent was distilled off under reduced pressure. The obtained residue was purified by silica gel column chromatography [elute: hexane/ethyl acetate=88/12-0/100 gradient] to obtain the title compound (43.1 mg, yield: 21%).
$^1$H-NMR (DMSO-d$_6$) δ: 12.19 (1H, s), 10.51 (1H, s), 7.99 (1H, d, J=9 Hz), 7.32 (1H, d, J=9 Hz), 6.77 (1H, s), 4.56-4.54 (2H, m), 3.38-3.27 (1H, m), 3.09-2.98 (2H, m), 2.90 (1H, d, J=17 Hz), 2.73 (1H, d, J=17 Hz), 1.97-1.60 (4H, m);
MS (ESI) m/z: 475 (M+H)$^+$.

Example 95

6-{4-[4-Hydroxy-6-oxo-4-(trifluoromethyl)-4,5,6,7-tetrahydro-1H-pyrazolo[3,4-b]pyridin-3-yl]piperidin-1-yl}-4-(trifluoromethyl)pyridine-3-carbonitrile

[Formula 218]

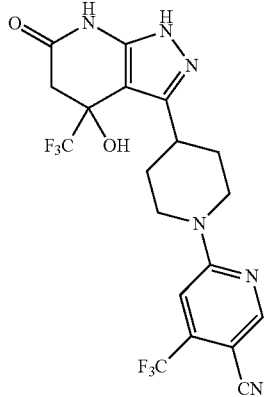

The title compound (38.4 mg, yield: 18%) was obtained through reaction in the same way as the method described in Example 94 using 6-chloro-4-(trifluoromethyl)pyridine-3-carbonitrile (compound described in the pamphlet of WO2006/68618, 136 mg, 0.66 mmol) instead of 6-fluoro-3-(trifluoromethyl)pyridine-2-carbonitrile and 1,8-diazabicyclo[5.4.0]-7-undecene (78.8 μL, 0.528 mmol) instead of N,N-diisopropylethylamine.

$^1$H-NMR (DMSO-d$_6$) δ: 12.18 (1H, s), 10.51 (1H, s), 8.72 (1H, s), 7.33 (1H, s), 6.76 (1H, s), 4.71 (2H, brs), 3.41-3.30 (1H, m), 3.14-3.02 (2H, m), 2.90 (1H, d, J=17 Hz), 2.73 (1H, d, J=17 Hz), 1.98-1.90 (1H, m), 1.80-1.60 (3H, m);
MS (ESI) m/z: 475 (M+H)$^+$.

Example 96

3-{1-[3-Fluoro-5-(trifluoromethyl)pyridin-2-yl]piperidin-4-yl}-4-hydroxy-4-(trifluoromethyl)-1,4,5,7-tetrahydro-6H-pyrazolo[3,4-b]pyridin-6-one

[Formula 219]

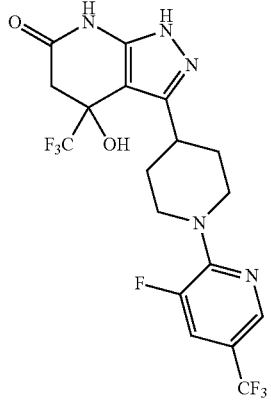

The title compound (90 mg, yield: 44%) was obtained through reaction in the same way as the method described in Example 95 using 2,3-difluoro-5-(trifluoromethyl)pyridine (121 mg, 0.66 mmol) instead of 6-chloro-4-(trifluoromethyl)pyridine-3-carbonitrile.

$^1$H-NMR (DMSO-d$_6$) δ: 12.23 (1H, s), 10.50 (1H, s), 8.39-8.35 (1H, m), 7.94 (1H, dd, J=14, 2 Hz), 6.75 (1H, s), 4.44-4.35 (2H, m), 3.35-3.25 (1H, m), 3.09-3.00 (2H, m), 2.90 (1H, d, J=17 Hz), 2.73 (1H, d, J=17 Hz), 1.96-1.71 (4H, m);
MS (ESI) m/z: 468 (M+H)$^+$.

Reference Example 115

4-Hydroxy-3-(piperidin-4-yl)-4-(trifluoromethyl)-1,4,5,7-tetrahydro-6H-pyrazolo[3,4-b]pyridin-6-one trifluoroacetate

[Formula 220]

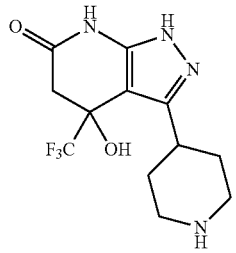

Reaction was performed in the same way as the method described in Reference Example 60 using trifluoroacetic acid (3.0 mL) instead of hydrochloric acid and methylene chloride (4.5 mL) instead of 1,4-dioxane. The reaction solution was added dropwise to diethyl ether (50 mL), and the precipitate was collected by filtration to obtain the title compound (1.31 g, yield: 60%).

$^1$H-NMR (400 MHz, DMSO-d$_6$) δ: 12.45 (1H, s), 10.57 (1H, s), 8.71 (1H, s), 8.35 (1H, s), 6.84 (1H, s), 3.41-3.19 (2H, m), 3.07-2.95 (2H, m), 2.91 (1H, d, J=16 Hz), 2.73 (1H, d, J=16 Hz), 2.06-2.03 (1H, m), 1.93-1.71 (4H, m).

Example 97

3-{1-[6-Fluoro-5-(trifluoromethyl)pyridin-2-yl]piperidin-4-yl}-4-hydroxy-4-(trifluoromethyl)-1,4,5,7-tetrahydro-6H-pyrazolo[3,4-b]pyridin-6-one

[Formula 221]

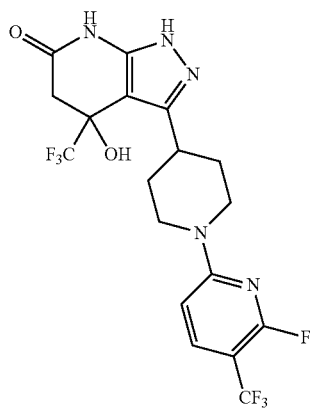

The title compound (313 mg, yield: 93%) was obtained through reaction in the same way as the method described in Example 43 using 4-hydroxy-3-(piperidin-4-yl)-4-(trifluoromethyl)-1,4,5,7-tetrahydro-6H-pyrazolo[3,4-b]pyridin-6-one trifluoroacetate (300 mg, 0.717 mmol) produced in Reference Example 115 instead of 4-hydroxy-3-(piperidin-4-yl)-4-(trifluoromethyl)-1,4,5,7-tetrahydro-6H-pyrazolo[3,4-b]

pyridin-6-one hydrochloride and 2,6-difluoro-3-(trifluoromethyl)pyridine (160 mg, 0.874 mmol) instead of 3-chloro-6-(trifluoromethyl)pyridazine.

$^1$H-NMR (500 MHz, DMSO-d$_6$) δ: 12.19 (1H, s), 10.50 (1H, s), 7.91 (1H, t, J=10 Hz), 6.86 (1H, d, J=9 Hz), 6.76 (1H, s), 4.47-4.45 (2H, m), 3.32-3.28 (1H, m), 3.01 (2H, t, J=12 Hz), 2.90 (1H, d, J=17 Hz), 2.73 (1H, d, J=17 Hz), 1.92-1.90 (1H, m), 1.78-1.59 (3H, m);

MS (ESI) m/z: 468 (M+H)$^+$.

Example 98

3-{1-[6-Chloro-5-(trifluoromethyl)pyridin-2-yl]piperidin-4-yl}-4-hydroxy-4-(trifluoromethyl)-1,4,5,7-tetrahydro-6H-pyrazolo[3,4-b]pyridin-6-one (hereinafter, referred to as compound 98-a)

[Formula 222]

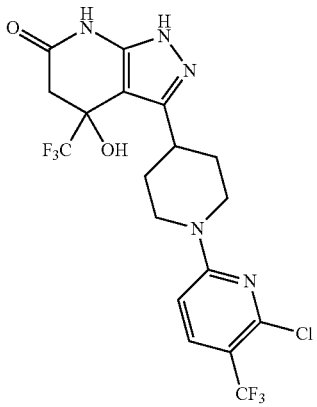

and 3-{1-[6-chloro-3-(trifluoromethyl)pyridin-2-yl]piperidin-4-yl}-4-hydroxy-4-(trifluoromethyl)-1,4,5,7-tetrahydro-6H-pyrazolo[3,4-b]pyridin-6-one (hereinafter, referred to as compound 98-b)

[Formula 223]

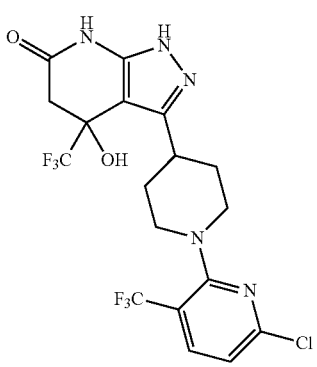

The title compound 98-a (17 mg, yield: 5%) and compound 98-b (318 mg, yield: 92%) were obtained through reaction at 50° C. in the same way as the method described in Example 97 using 2,6-dichloro-3-(trifluoromethyl)pyridine (190 mg, 0.880 mmol) instead of 2,6-difluoro-3-(trifluoromethyl)pyridine.

Compound 98-a $^1$H-NMR (400 MHz, DMSO-d$_6$) δ: 12.33 (1H, s), 10.51 (1H, s), 8.07 (1H, d, J=8 Hz), 7.15 (1H, d, J=8 Hz), 6.76 (1H, s), 3.79-3.76 (2H, m), 3.32-3.16 (1H, m), 3.02-2.86 (3H, m), 2.72 (1H, d, J=16 Hz), 2.00-1.71 (4H, m);

MS (ESI) m/z: 482 (M−H)$^−$.

Compound 98-b $^1$H-NMR (400 MHz, DMSO-d$_6$) δ: 12.20 (1H, s), 10.51 (1H, s), 7.87 (1H, d, J=9 Hz), 6.94 (1H, d, J=9 Hz), 6.79 (1H, s), 4.51-4.48 (2H, m), 3.44-3.38 (1H, m), 3.06-2.95 (2H, m), 2.90 (1H, d, J=16 Hz), 2.73 (1H, d, J=16 Hz), 1.93-1.90 (1H, m), 1.78-1.59 (3H, m);

MS (ESI) m/z: 484 (M+H)$^+$.

Reference Example 116

4-Hydroxy-3-(piperidin-4-yl)-4-(trifluoromethyl)-1,4,5,7-tetrahydro-6H-pyrazolo[3,4-b]pyridin-6-one

[Formula 224]

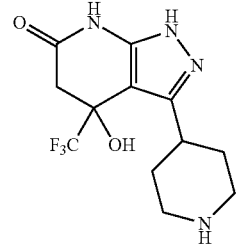

N,N-Diisopropylethylamine (9.37 mL, 55.1 mmol) was added dropwise at 0° C. to a solution of 4-hydroxy-3-(piperidin-4-yl)-4-(trifluoromethyl)-1,4,5,7-tetrahydro-6H-pyrazolo[3,4-b]pyridin-6-one trifluoroacetate (19.2 g, 45.9 mmol) produced in Reference Example 115 in ethanol (200 mL), and the mixture was stirred for 30 minutes. Dichloromethane (600 mL) was added thereto, and the mixture was stirred for 1 hour. Then, the precipitate was collected by filtration and dried under reduced pressure to obtain the title compound (12.6 g, yield: 91%).

$^1$H-NMR (DMSO-d$_6$) δ: 12.22 (1H, s), 10.46 (1H, s), 6.63 (1H, s), 3.07-2.95 (3H, m), 2.87 (1H, d, J=17 Hz), 2.71 (1H, d, J=17 Hz), 2.50-2.44 (2H, m), 1.77-1.50 (4H, m).

Example 99

3-[1-(5-Cyclopropylpyridin-2-yl)piperidin-4-yl]-4-hydroxy-4-(trifluoromethyl)-1,4,5,7-tetrahydro-6H-pyrazolo[3,4-b]pyridin-6-one

[Formula 225]

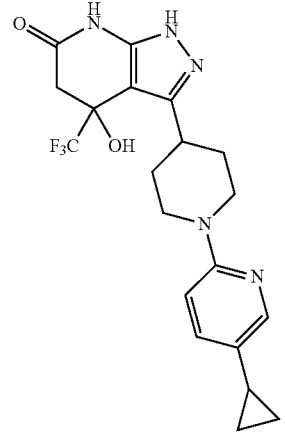

Urea hydrogen peroxide (301 mg, 3.20 mmol) and trifluoroacetic anhydride (426 μL, 3.04 mmol) were added to a solution of 5-cyclopropyl-2-fluoropyridine (compound described in the pamphlet of WO2008/76705, 209 mg, 1.52 mmol) in dichloromethane (3 mL), and the mixture was stirred overnight. The reaction solution was diluted with dichloromethane, then washed with a saturated sodium bicarbonate aqueous solution, a 10% sodium thiosulfate aqueous solution, and brine in this order, and dried over anhydrous sodium sulfate, and the solvent was distilled off under reduced pressure.

A solution of the obtained residue, 4-hydroxy-3-(piperidin-4-yl)-4-(trifluoromethyl)-1,4,5,7-tetrahydro-6H-pyrazolo[3,4-b]pyridin-6-one (385 mg, 1.27 mmol) produced in Reference Example 116, and N,N-diisopropylamine (323 μL, 1.90 mmol) in dimethyl sulfoxide (3 mL) was stirred while irradiated with microwaves at 60° C. for 1.5 hours using Initiator® manufactured by Biotage Japan Ltd. The reaction solution was poured to water, and the precipitate was collected by filtration and dried at 60° C. under reduced pressure to obtain a crude product (345 mg).

A suspension of a portion (140 mg) of the obtained crude product and iron (71.5 mg, 1.28 mmol) in acetic acid (5 mL) was stirred at 70° C. for 1 hours and 50 minutes. The solvent was distilled off under reduced pressure, and ethyl acetate was added to the residue. The resulting solid was filtered off. The filtrate was washed with a saturated sodium bicarbonate aqueous solution and brine in this order and dried over anhydrous sodium sulfate, and the solvent was distilled off under reduced pressure. The obtained residue was purified by silica gel column chromatography [NH-silica gel column, elute: ethyl acetate/methanol=95/5-80/20 (gradient)] and further purified by silica gel chromatography [elute: hexane/ethyl acetate=88/12-0/100 (gradient)] to obtain the title compound (37.2 mg, yield: 14%).

$^1$H-NMR (DMSO-d$_6$) δ: 12.22 (1H, s), 10.49 (1H, s), 7.96 (1H, d, J=2 Hz), 7.20 (1H, dd, J=9, 2 Hz), 6.77 (1H, d, J=9 Hz), 6.72 (1H, s), 4.41-4.32 (2H, m), 3.25-3.15 (1H, m), 2.89 (1H, d, J=16 Hz), 2.76-2.68 (2H, m), 2.72 (1H, d, J=16 Hz), 1.90-1.62 (4H, m), 1.30-1.20 (1H, m), 0.88-0.83 (2H, m), 0.60-0.54 (2H, m);

MS (ESI) m/z: 422 (M+H)$^+$.

Example 100

2-{4-[4-Hydroxy-6-oxo-4-(trifluoromethyl)-4,5,6,7-tetrahydro-1H-pyrazolo[3,4-b]pyridin-3-yl]piperidin-1-yl}pyridine-3-carbonitrile

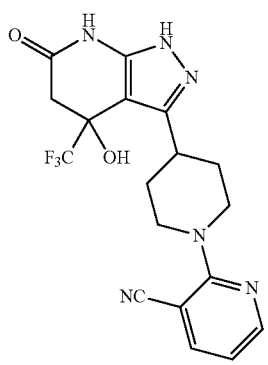

[Formula 226]

The title compound (107 mg, yield: 54%) was obtained through reaction at 60° C. in the same way as the method described in Example 43 using 4-hydroxy-3-(piperidin-4-yl)-4-(trifluoromethyl)-1,4,5,7-tetrahydro-6H-pyrazolo[3,4-b]pyridin-6-one (150 mg, 0.493 mmol) produced in Reference Example 116 instead of 4-hydroxy-3-(piperidin-4-yl)-4-(trifluoromethyl)-1,4,5,7-tetrahydro-6H-pyrazolo[3,4-b]pyridin-6-one hydrochloride and 2-fluoropyridine-3-carbonitrile (72.2 mg, 0.592 mmol) instead of 3-chloro-6-(trifluoromethyl)pyridazine.

$^1$H-NMR (DMSO-d$_6$) δ: 12.30 (1H, s), 10.51 (1H, s), 8.42 (1H, dd, J=5, 2 Hz), 8.07 (1H, dd, J=8, 2 Hz), 6.91 (1H, dd, J=8, 5 Hz), 6.75 (1H, s), 4.45-4.36 (2H, m), 3.31-3.22 (1H, m), 3.08-2.97 (2H, m), 2.90 (1H, d, J=17 Hz), 2.73 (1H, d, J=17 Hz), 1.98-1.74 (4H, m);

MS (ESI) m/z: 407 (M+H)$^+$.

Example 101

2-{4-[4-Hydroxy-6-oxo-4-(trifluoromethyl)-4,5,6,7-tetrahydro-1H-pyrazolo[3,4-b]pyridin-3-yl]piperidin-1-yl}-5-(trifluoromethyl)pyridine-3-carbonitrile

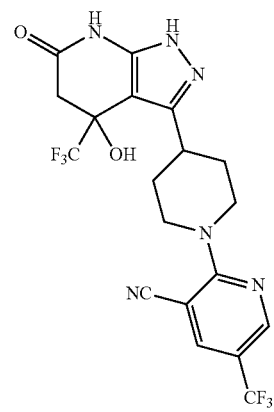

[Formula 227]

The title compound (150 mg, yield: 48%) was obtained through reaction in the same way as the method described in Example 100 using 2-fluoro-5-(trifluoromethyl)pyridine-3-carbonitrile (compound described in the pamphlet of WO2005/105092, 163 mg, 0.789 mmol) instead of 2-fluoropyridine-3-carbonitrile.

$^1$H-NMR (DMSO-d$_6$) δ: 12.27 (1H, s), 10.52 (1H, s), 8.73-8.72 (1H, m), 8.53-8.52 (1H, m), 6.77 (1H, s), 4.72-4.62 (2H, m), 3.40-3.30 (1H, m), 3.24-3.15 (2H, m), 2.91 (1H, d, J=17 Hz), 2.73 (1H, d, J=17 Hz), 2.01-1.75 (4H, m);

MS (ESI) m/z: 475 (M+H)$^+$.

Example 102

4-Hydroxy-3-{1-[4-iodo-5-(trifluoromethyl)pyridin-2-yl]piperidin-4-yl}-4-(trifluoromethyl)-1,4,5,7-tetrahydro-6H-pyrazolo[3,4-b]pyridin-6-one

[Formula 228]

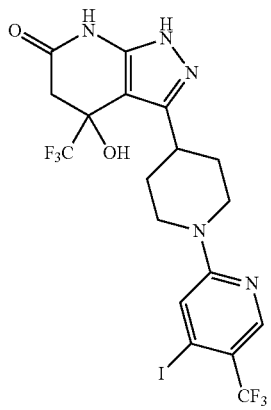

The title compound (430 mg, yield: 60%) was obtained through reaction at 60° C. in the same way as the method described in Example 100 using 2-chloro-5-(trifluoromethyl)-4-iodopyridine (380 mg, 1.24 mmol) instead of 2-fluoropyridine-3-carbonitrile.

$^1$H-NMR (500 MHz, DMSO-$d_6$) δ: 12.19 (1H, s), 10.51 (1H, s), 8.30 (1H, s), 7.55 (1H, s), 6.76 (1H, s), 4.57 (2H, brs), 3.17 (1H, s), 2.99-2.86 (3H, m), 2.73 (1H, d, J=17 Hz), 1.90-1.88 (1H, m), 1.74-1.58 (3H, m);

MS (ESI) m/z: 576 (M+H)$^+$.

Example 103

Optical isomers of 4-hydroxy-3-{1-[4-iodo-5-(trifluoromethyl)pyridin-2-yl]piperidin-4-yl}-4-(trifluoromethyl)-1,4,5,7-tetrahydro-6H-pyrazolo[3,4-b]pyridin-6-one

[Formula 229]

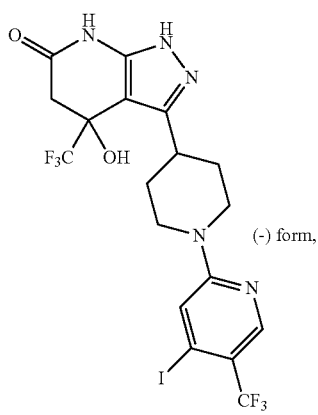
(−) form,

-continued (+) form

A mixed solution of 4-hydroxy-3-{1-[4-iodo-5-(trifluoromethyl)pyridin-2-yl]piperidin-4-yl}-4-(trifluoromethyl)-1,4,5,7-tetrahydro-6H-pyrazolo[3,4-b]pyridin-6-one (150 mg, 0.260 mmol) produced in Example 102 in IPA-hexane (3/7) (5 mL) was purified by flash LC [SP1; manufactured by Biotage Japan Ltd., column: Chiralflash IA (30 mm i.d.×100 mm); manufactured by Daicel Corporation, elute: IPA/hexane=30/70-40/60, flow rate: 12 mL/min] to obtain each of a compound eluted first (hereinafter, referred to as compound 103-1) (73 mg, yield: 49%) and a compound eluted second (hereinafter, referred to as compound 103-2) (72 mg, yield: 48%).

The optical purity of each compound was measured by HPLC [column: Chiralpak IA (4.6 mm i.d.×150 mm); manufactured by Daicel Corporation, elute: IPA/hexane=40/60].

Compound 103-1:
Optical purity: 99% or higher (retention time: 5.1 min).
Compound 103-2:
Optical purity: 99% or higher (retention time: 12.6 min).

Reference Example 117

6-Chloro-5-(trifluoromethyl)pyridine-3-carbonitrile

[Formula 230]

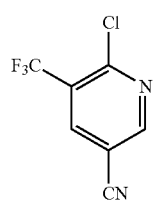

Urea hydrogen peroxide (0.815 g, 8.66 mmol) and trifluoroacetic anhydride (1.15 mL, 8.24 mmol) were added to a solution of 5-(trifluoromethyl)pyridine-3-carbonitrile (compound described in the pamphlet of WO2009/42694, 0.71 g, 4.12 mmol) in dichloromethane (10 mL), and the mixture was stirred overnight. A 10% sodium thiosulfate aqueous solution was added to the reaction solution, followed by extraction with dichloromethane twice. The organic layer was washed with brine and dried over anhydrous sodium sulfate, and the solvent was distilled off under reduced pressure. The obtained residue was purified by silica gel column chromatography [elute: hexane/ethyl acetate=88/12-0/100 (gradient)] to obtain a product.

A solution of the obtained product in phosphoryl chloride (10 mL) was stirred at 70° C. for 2 hours and further for 2 hours under reflux. The reaction solution was poured to ice, followed by extraction with dichloromethane twice. Combined organic layers were washed with brine and dried over anhydrous sodium sulfate, and the solvent was distilled off under reduced pressure. The obtained residue was purified by silica gel column chromatography [elute: hexane/ethyl acetate=99/1-90/10 (gradient)] to obtain the title compound (62 mg, yield: 7%).

$^1$H-NMR (CDCl$_3$) δ: 8.86 (1H, d, J=2 Hz), 8.28 (1H, d, J=2 Hz).

Example 104

6-{4-[4-Hydroxy-6-oxo-4-(trifluoromethyl)-4,5,6,7-tetrahydro-1H-pyrazolo[3,4-b]pyridin-3-yl]piperidin-1-yl}-5-(trifluoromethyl)pyridine-3-carbonitrile

[Formula 231]

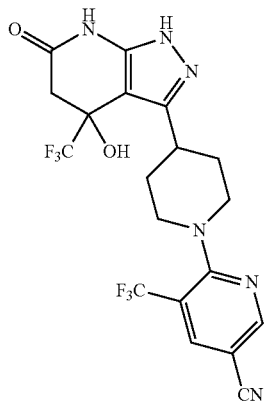

The title compound (53.6 mg, yield: 45%) was obtained through reaction in the same way as the method described in Example 100 using 6-chloro-5-(trifluoromethyl)pyridine-3-carbonitrile (62 mg, 0.300 mmol) produced in Reference Example 117 instead of 2-fluoropyridine-3-carbonitrile.

$^1$H-NMR (DMSO-d$_6$) δ: 12.28 (1H, s), 10.51 (1H, s), 8.80 (1H, d, J=2 Hz), 8.54 (1H, d, J=2 Hz), 6.76 (1H, s), 4.19-4.09 (2H, m), 3.34-3.24 (1H, m), 3.18-3.09 (2H, m), 2.90 (1H, d, J=17 Hz), 2.72 (1H, d, J=17 Hz), 1.98-1.72 (4H, m);

MS (ESI) m/z: 475 (M+H)$^+$.

Example 105

4-Hydroxy-3-[1-(6-phenylpyridazin-3-yl)piperidin-4-yl]-4-(trifluoromethyl)-1,4,5,7-tetrahydro-6H-pyrazolo[3,4-b]pyridin-6-one

[Formula 232]

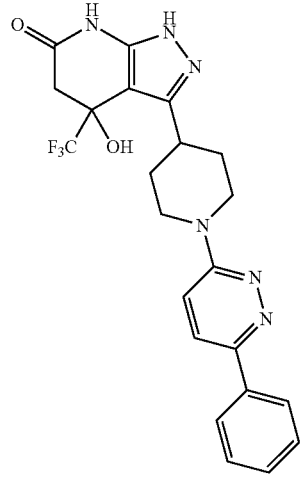

The title compound (43.6 mg, yield: 19%) was obtained through reaction at 60° C. for 2 hours and further at 100° C. for 2 hours in the same way as the method described in Example 100 using 3-chloro-6-phenylpyridazine (113 mg, 0.592 mmol) instead of 2-fluoropyridine-3-carbonitrile.

$^1$H-NMR (DMSO-d$_6$) δ: 12.25 (1H, s), 10.52 (1H, s), 8.07-8.02 (2H, m), 7.95 (1H, d, J=10 Hz), 7.52-7.39 (4H, m), 6.77 (1H, s), 4.67-4.57 (2H, m), 3.40-3.28 (1H, m), 3.04-2.87 (3H, m), 2.74 (1H, d, J=16 Hz), 1.97-1.68 (4H, m);

MS (ESI) m/z: 459 (M+H)$^+$.

Test Example 1

LCAT Activity Measurement (In Vitro)

A fraction composed of HDL3 (1.125<specific gravity<1.210 g/mL) was obtained from the plasma of a healthy person by density gradient centrifugation. The obtained fraction was dialyzed against phosphate-buffered saline (pH 7.4) and used as an enzyme source and an acceptor for LCAT. Each test drug was prepared by dissolution in dimethyl sulfoxide. [14C]Cholesterol containing DTNB (Ellman's reagent, final concentration: 0.5 mM), mercaptoethanol (final concentration: 12.5 mM), and 0.6% bovine serum albumin was added to phosphate-buffered saline (pH 7.4) containing 1 mg/mL HDL3, and the test drug was further added thereto at varying concentrations to adjust the whole amount to 80 μL. This mixture was incubated at 37° C. for approximately 16 hours. Then, a mixed solution of hexane and isopropanol (mixing ratio=3:2) was added thereto to stop the reaction. After stirring, the hexane layer was collected, and this layer was evaporated to dryness. A chloroform solution (concentration: 10 mg/mL) was added thereto, and the mixture was spotted onto a thin-layer silica gel plate and developed using a mixed solution of hexane, diethyl ether, and ethyl acetate (mixing ratio=85:15:2). The radioactivity of a portion corresponding to cholesterol oleate was measured using an imaging analyzer BAS-2500 (manufactured by Fujifilm Corp.). A sample non-supplemented with the test drug was similarly treated and assayed. The $EC_{50}$ value of LCAT activation was calculated according to the expression given below relative to LCAT activity in the sample non-supplemented with the test drug. The results are shown in Table 1.

$$Y = \text{Bottom} + \frac{(\text{Top} - \text{Bottom})}{1 + 10^{LogEC50-X}} \quad \text{[Expression 1]}$$

wherein X represents the logarithm of the concentration of the test drug;

Y represents the responsiveness (LCAT activity) of the test drug;

Top represents the maximum value (maximum plateau);

Bottom represents the minimum value (minimum plateau); and $EC_{50}$ represents the 50% effective concentration.

TABLE 1

| Test compound | $EC_{50}(\mu M)$ |
| --- | --- |
| Compound of Example 1 | 1.51 |
| Compound of Example 2 | 0.52 |
| Compound of Example 3 | 0.63 |
| Compound of Example 4 | 0.25 |
| Compound of Example 5 | 0.29 |
| Compound of Example 6 | 1.26 |
| Compound of Example 7 | 0.048 |
| Compound of Example 8 | 0.021 |
| Compound of Example 9 | 1.15 |
| Compound of Example 10 | 0.21 |
| Compound of Example 11 | 3.09 |
| Compound of Example 12 | 0.054 |
| Compound of Example 13 | 0.056 |
| Compound of Example 14 | 0.086 |
| Compound of Example 15 | 0.25 |
| Compound of Example 16 | 0.096 |
| Compound of Example 17 | 0.064 |
| Compound of Example 18 | 0.101 |
| Compound of Example 19 | 0.65 |
| Compound of Example 20 | 0.29 |
| Compound of Example 21 | 0.27 |
| Compound of Example 22 | 0.18 |
| Compound of Example 23 | 0.12 |
| Compound of Example 24 | 0.15 |
| Compound of Example 25 | 0.20 |
| Compound of Example 26 | 0.26 |
| Compound of Example 27 | 2.41 |
| Compound of Example 28 | 0.30 |
| Compound of Example 29 | 1.88 |
| Compound of Example 30 | 2.46 |
| Compound of Example 31 | 0.33 |
| Compound of Example 32 | 0.30 |
| Compound of Example 33 | 0.056 |
| Compound of Example 34 | 0.15 |
| Compound of Example 35 | 0.38 |
| Compound of Example 36 | 0.42 |
| Compound of Example 37 | 0.071 |
| Compound of Example 38 | 0.043 |
| Compound of Example 39 | 0.33 |
| Compound of Example 40 | 1.71 |
| Compound of Example 41 | 0.026 |
| Compound of Example 42 | 0.14 |
| Compound of Example 43 | 0.056 |
| Compound of Example 44 | 0.36 |
| Compound of Example 45 | 0.14 |
| Compound of Example 46 | 0.012 |
| Compound of Example 47 | 0.096 |
| Compound 48-a of Example 48 | 0.080 |
| Compound 48-b of Example 48 | 0.046 |
| Compound 49-1 of Example 49 | 0.018 |
| Compound 49-2 of Example 49 | 3.77 |
| Compound 50-1 of Example 50 | 0.045 |
| Compound of Example 51 | 0.081 |

TABLE 1-continued

| Test compound | $EC_{50}(\mu M)$ |
| --- | --- |
| Compound of Example 52 | 0.067 |
| Compound of Example 53 | 0.05 |
| Compound of Example 54 | 0.070 |
| Compound of Example 55 | 0.079 |
| Compound 56-1 of Example 56 | 0.045 |
| Compound 56-2 of Example 56 | 0.98 |
| Compound of Example 57 | 0.10 |
| Compound of Example 58 | 0.020 |
| Compound of Example 59 | 0.26 |
| Compound of Example 60 | 0.021 |
| Compound of Example 61 | 0.10 |
| Compound of Example 62 | 0.007 |
| Compound of Example 63 | 0.031 |
| Compound of Example 64 | 0.056 |
| Compound of Example 65 | 0.013 |
| Compound of Example 66 | 0.068 |
| Compound of Example 67 | 0.33 |
| Compound of Example 68 | 0.76 |
| Compound of Example 69 | 0.19 |
| Compound of Example 70 | 0.30 |
| Compound of Example 71 | 0.52 |
| Compound of Example 72 | 0.023 |
| Compound of Example 73 | 0.083 |
| Compound of Example 74 | 0.14 |
| Compound of Example 75 | 0.22 |
| Compound of Example 76 | 0.018 |
| Compound of Example 77 | 0.058 |
| Compound of Example 78 | 0.22 |
| Compound of Example 79 | 0.30 |
| Compound of Example 80 | 0.38 |
| Compound of Example 81 | 0.47 |
| Compound of Example 82 | 0.032 |
| Compound of Example 83 | 0.42 |
| Compound of Example 84 | 0.27 |
| Compound of Example 85 | 0.013 |
| Compound of Example 86 | 0.14 |
| Compound of Example 87 | 0.30 |
| Compound of Example 88 | 0.088 |
| Compound of Example 89 | 0.11 |
| Compound of Example 90 | 0.31 |
| Compound of Example 91 | 0.077 |
| Compound of Example 92 | 0.21 |
| Compound of Example 93 | 0.084 |
| Compound of Example 94 | 0.015 |
| Compound of Example 95 | 0.037 |
| Compound of Example 96 | 0.22 |
| Compound of Example 97 | 0.035 |
| Compound 98-a of Example 98 | 0.023 |
| Compound 98-b of Example 98 | 0.51 |
| Compound of Example 99 | 0.075 |
| Compound of Example 100 | 1.55 |
| Compound of Example 101 | 0.17 |
| Compound of Example 102 | 0.021 |
| Compound 103-1 of Example 103 | 0.027 |
| Compound 103-2 of Example 103 | 0.53 |
| Compound of Example 104 | 1.10 |
| Compound of Example 105 | 0.027 |

As seen from these results, the compound of the present invention has an excellent LCAT-activating effect and is useful as a medicament for the treatment or prophylaxis of diseases such as dyslipidemia and arteriosclerosis.

Test Example 2

LCAT Activity Measurement (Plasma)

The plasma of a human, a cynomolgus monkey, or a human LCAT transgenic mouse was used as an enzyme source and an acceptor for LCAT. Each test drug was prepared by dissolution in dimethyl sulfoxide. [14C]Cholesterol containing DTNB (Ellman's reagent, final concentration: 0.5 mM), mercaptoethanol (final concentration: 12.5 mM), and 0.6% bovine serum albumin was added to 5 μL of each plasma and 45 μL of PBS, and the test drug was further added thereto at varying concentrations to adjust the whole amount to 80 μL. This mixture was incubated at 37° C. for approximately 16 hours. Then, a mixed solution of hexane and isopropanol (mixing ratio=3:2) was added thereto to stop the reaction. After addition of water and stirring, the hexane layer was collected, and this layer was evaporated to dryness. A chloroform solution (concentration: 10 mg/mL) was added thereto, and the mixture was spotted onto a thin-layer silica gel plate and developed using a mixed solution of hexane, diethyl ether, and ethyl acetate (mixing ratio=85:15:2). The radioactivity of a portion corresponding to cholesterol oleate was measured using an imaging analyzer BAS-2500 (manufactured by Fujifilm Corp.). A sample non-supplemented with the test drug was similarly treated and assayed. The $EC_{50}$ value of LCAT activation was calculated according to the expression given below relative to LCAT activity in the sample non-supplemented with the test drug.

$$Y = \text{Bottom} + \frac{(\text{Top} - \text{Bottom})}{1 + 10^{LogEC50-X}} \qquad \text{[Expression 2]}$$

wherein X represents the logarithm of the concentration of the test drug;
Y represents the responsiveness (LCAT activity) of the test drug;
Top represents the maximum value (maximum plateau);
Bottom represents the minimum value (minimum plateau); and
$EC_{50}$ represents the 50% effective concentration.

Test Example 3

LCAT Activity Measurement (Ex Vivo)

LCAT activity in the plasma of a cynomolgus monkey or a human LCAT transgenic mouse receiving each test drug was measured. [14C]Cholesterol containing DTNB (Ellman's reagent, final concentration: 0.26 mM), mercaptoethanol (final concentration: 2 mM), and 0.6% bovine serum albumin was added to 25 μL of each plasma to adjust the whole amount to 40 μL. This mixture was incubated at 37° C. for 1 hour. Then, a mixed solution of hexane and isopropanol (mixing ratio=3:2) was added thereto to stop the reaction. After addition of water and stirring, the hexane layer was collected, and this layer was evaporated to dryness. A chloroform solution (concentration: 10 mg/mL) was added thereto, and the mixture was spotted onto a thin-layer silica gel plate and developed using a mixed solution of hexane, diethyl ether, and ethyl acetate (mixing ratio=85:15:2). The radioactivity of a portion corresponding to cholesterol oleate was measured using an imaging analyzer BAS-2500 (manufactured by Fujifilm Corp.). The rate of change in LCAT activation at each point in time compared with LCAT activity before administration was calculated.

Test Example 4

Drug Efficacy Test in Cynomolgus Monkeys

Each test drug was dissolved in a propylene glycol (Sigma-Aldrich Corp.)-Tween 80 (Sigma-Aldrich Corp.) mixed solution [4/1 (v/v)] or a 0.5% (w/v) methylcellulose aqueous solution, and the solution was orally administered to a cynomolgus monkey for 1 or 7 days. At 1 or 7 day of administration period, blood was collected before administration and after administration, and plasma was obtained. The content of cholesterol in the plasma was measured using a commercially available assay kit (Cholesterol-E Wako, Wako Pure Chemical Industries, Ltd.). The lipoprotein profile was analyzed by HPLC (column: LipopropakXL, manufactured by Tosoh Corp.). The contents of HDL cholesterol and non-HDL cholesterol were calculated according to the following calculation expression:

Content of HDL cholesterol=Content of cholesterol in the plasma×(Peak area of HDL cholesterol/Total sum of peaks)

Content of non-HDL cholesterol=Content of cholesterol in the plasma×(Peak area of non-HDL cholesterol/Total sum of peaks)

The rate (%) of increase in HDL level after the administration of a single dose of 10 mg/kg compared with before administration was determined from AUC before administration and 24 hours after administration. The results are shown in Table 2.

TABLE 2

| Test compound | Rate of increase in HDL level after administration of single dose |
|---|---|
| Compound of Example 7 | 334 |
| Compound of Example 8 | 531 |
| Compound of Example 10 | 526 |
| Compound 50-1 of Example 50 | 433 |
| Compound 56-1 of Example 56 | 644 |

Test Example 5

Drug Efficacy Test in Human LCAT Transgenic Mice

Each test drug was dissolved in a propylene glycol-Tween 80 mixed solution [4/1 (v/v)] or a 0.5% (w/v) methylcellulose aqueous solution, and the solution was orally administered to a human LCAT transgenic mouse for 1, 4, or 7 days. At 1, 4, or 7 day of administration period, blood was collected before administration and after administration, and plasma was obtained. The content of cholesterol in the plasma was measured using a commercially available assay kit (Cholesterol-E Wako, Wako Pure Chemical Industries, Ltd.). The lipoprotein profile was analyzed by HPLC (column: LipopropakXL, manufactured by Tosoh Corp.). The contents of HDL cholesterol and non-HDL cholesterol were calculated according to the following calculation expression:

Content of HDL cholesterol=Content of cholesterol in the plasma×(Peak area of HDL cholesterol/Total sum of peaks)

Content of non-HDL cholesterol=Content of cholesterol in the plasma×(Peak area of non-HDL cholesterol/Total sum of peaks)

As seen from these results, the compound of the present invention exhibits an excellent LCAT-activating effect and is useful as a medicament for the treatment or prophylaxis of diseases such as dyslipidemia and arteriosclerosis.

Formulation Example 1

Hard Capsule

Each standard two-piece hard gelatin capsule shell is filled with 100 mg of the compound of Example 1 in a powder form, 150 mg of lactose, 50 mg of cellulose, and 6 mg of magnesium stearate to produce a unit capsule, which is in turn washed and then dried.

Formulation Example 2

Soft Capsule

A mixture of the compound of Example 2 put in a digestible oil, for example, soybean oil, cottonseed oil, or olive oil, is prepared and injected into a gelatin shell using a positive displacement pump to obtain a soft capsule containing 100 mg of the active ingredient, which is in turn washed and then dried.

Formulation Example 3

Tablet

According to a routine method, a tablet is produced using 100 mg of the compound of Example 3, 0.2 mg of colloidal silicon dioxide, 5 mg of magnesium stearate, 275 mg of microcrystalline cellulose, 11 mg of starch, and 98.8 mg of lactose.

If desired, the tablet is coated.

Formulation Example 4

Suspension

A suspension is produced to contain 100 mg of the compound of Example 4 pulverized into a fine powder, 100 mg of sodium carboxy methyl cellulose, 5 mg of sodium benzoate, 1.0 g of a sorbitol solution (Japanese Pharmacopoeia), and 0.025 mL of vanillin in 5 mL.

Formulation Example 5

Injection

The compound of Example 6 (1.5% by weight) is stirred in 10% by weight of propylene glycol, subsequently adjusted to a fixed volume with injectable water, and then sterilized to prepare an injection.

Industrial Applicability

The compound represented by the general formula (I) of the present invention or the pharmacologically acceptable salt thereof has an excellent LCAT-activating effect and is particularly useful as an active ingredient in a therapeutic or prophylactic agent for arteriosclerosis, arteriosclerotic heart disease, coronary heart disease (including acute coronary syndromes, heart failure, myocardial infarction, angina pectoris, cardiac ischemia, cardiovascular disturbance, and restenosis caused by angiogenesis), cerebrovascular disease (including stroke and cerebral infarction), peripheral vascular disease (including peripheral arterial disease and diabetic vascular complications), dyslipidemia, LCAT deficiency, hypo-HDL-cholesterolemia, diabetes mellitus, hypertension, metabolic syndrome, Alzheimer's disease, cornea opacity, or renal disease, particularly, an anti-arteriosclerotic agent.

The invention claimed is:

1. A compound represented by the general formula (I) or a pharmacologically acceptable salt thereof:

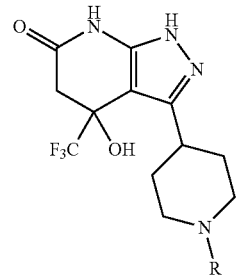

[Formula 1]

wherein R represents an optionally substituted aryl group (the substituent(s) is 1 to 3 identical or different groups selected from the group consisting of a halogen atom, a $C_{1-6}$ alkyl group, a $C_{3-7}$ cycloalkyl group, a trifluoromethyl group, a difluoromethoxy group, a trifluoromethoxy group, a cyano group, a $C_{1-6}$ alkoxy group, a $C_{3-7}$ cycloalkoxy group, a phenyl group, a $C_{2-7}$ alkoxycarbonyl group, a benzyloxycarbonyl group, a di($C_{1-6}$ alkyl)aminocarbonyl group, and a di($C_{1-6}$ alkyl)amino group) or an optionally substituted heteroaryl group (the heteroaryl is a 5- or 6-membered ring which is optionally further condensed with a benzene ring; the heteroatom(s) on the ring of the heteroaryl group is 1 or 2 nitrogen atoms, and the ring optionally further contains one nitrogen atom, oxygen atom, or sulfur atom; the substituent(s) is 1 or 2 identical or different groups selected from the group consisting of a halogen atom, a $C_{1-6}$ alkyl group, a $C_{3-7}$ cycloalkyl group, a trifluoromethyl group, a difluoromethoxy group, a trifluoromethoxy group, a cyano group, a $C_{1-6}$ alkoxy group, a $C_{3-7}$ cycloalkoxy group, a phenyl group, a $C_{2-7}$ alkoxycarbonyl group, a benzyloxycarbonyl group, a di($C_{1-6}$ alkyl)aminocarbonyl group, and a di($C_{1-6}$ alkyl)amino group; and the heteroaryl group is optionally further substituted by one optionally substituted heteroaryl group (the heteroaryl is a 5- or 6-membered ring which is optionally further condensed with a benzene ring; the heteroatom(s) on the ring of the heteroaryl group is 1 or 2 nitrogen atoms, and the ring optionally further contains one nitrogen atom, oxygen atom, or sulfur atom; and the substituent(s) is 1 or 2 identical or different groups selected from the group consisting of a halogen atom, a $C_{1-6}$ alkyl group, a trifluoromethyl group, a cyano group, and a $C_{1-6}$ alkoxy group)).

2. The compound according to claim 1 or a pharmacologically acceptable salt thereof, wherein R is a substituted aryl group (the substituent(s) is 1 or 2 identical or different groups selected from the group consisting of a chlorine atom, a fluorine atom, a $C_{1-3}$ alkyl group, a trifluoromethyl group, a difluoromethoxy group, a trifluoromethoxy group, a cyano group, and a $C_{1-3}$ alkoxy group).

3. The compound according to claim 1 or a pharmacologically acceptable salt thereof, wherein R is a substituted phenyl group (the substituent(s) is 1 or 2 identical or different groups selected from the group consisting of a chlorine atom, a difluoromethoxy group, a trifluoromethoxy group, and a cyano group).

4. The compound according to claim 1 or a pharmacologically acceptable salt thereof, wherein R is a substituted phenyl group (the substituent(s) is 1 or 2 identical or different groups selected from the group consisting of a difluoromethoxy group, a trifluoromethoxy group, and a cyano group).

5. The compound according to claim 1 or a pharmacologically acceptable salt thereof, wherein R is a substituted heteroaryl group (the heteroaryl is a 5- or 6-membered ring; the heteroatom on the ring of the heteroaryl group is one nitrogen atom, and the ring optionally further contains one nitrogen atom, oxygen atom, or sulfur atom; the substituent(s) is 1 or 2 identical or different groups selected from the group consisting of a halogen atom, a $C_{1-3}$ alkyl group, a $C_{3-6}$ cycloalkyl group, a trifluoromethyl group, a difluoromethoxy group, a trifluoromethoxy group, a cyano group, a $C_{1-3}$ alkoxy group, a $C_{2-4}$ alkoxycarbonyl group, and a benzyloxycarbonyl group; and the heteroaryl group is optionally further substituted by one substituted heteroaryl group (the heteroaryl is 5- or 6-membered ring; the heteroatom on the ring of the heteroaryl group is one nitrogen atom, and the ring optionally further contains one nitrogen atom, oxygen atom, or sulfur atom; and the substituent(s) is 1 or 2 identical or different groups selected from the group consisting of a halogen atom, a $C_{1-3}$ alkyl group, a trifluoromethyl group, a cyano group, and a $C_{1-3}$ alkoxy group)).

6. The compound according to claim 1 or a pharmacologically acceptable salt thereof, wherein R is a substituted pyridyl, pyrimidyl, pyrazyl, pyridazyl, oxazolyl, or thiazolyl group (the substituent(s) is 1 or 2 identical or different groups selected from the group consisting of a chlorine atom, a fluorine atom, a $C_{1-3}$ alkyl group, a cyclopropyl group, a trifluoromethyl group, a difluoromethoxy group, a trifluoromethoxy group, a cyano group, a $C_{1-3}$ alkoxy group, a $C_{2-4}$ alkoxycarbonyl group, and a benzyloxycarbonyl group, and the pyridyl, pyrimidyl, pyrazyl, pyridazyl, oxazolyl, or thiazolyl group is optionally further substituted by one substituted thiazolyl group (the substituent(s) is a chlorine atom, a fluorine atom, a $C_{1-3}$ alkyl group, a trifluoromethyl group, a cyano group, or a $C_{1-3}$ alkoxy group)).

7. The compound according to claim 1 or a pharmacologically acceptable salt thereof, wherein R is a substituted pyridyl group (the substituent(s) is 1 or 2 identical or different groups selected from the group consisting of a chlorine atom, a trifluoromethyl group, a difluoromethoxy group, and a trifluoromethoxy group).

8. The compound according to claim 1 or a pharmacologically acceptable salt thereof, wherein the compound is selected from the group consisting of:
  4-hydroxy-4-(trifluoromethyl)-3-{1-[6-(trifluoromethyl)pyridin-2-yl]piperidin-4-yl}-1,4,5,7-tetrahydro-6H-pyrazolo[3,4-b]pyridin-6-one;
  4-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one;
  3-[1-(5-chloropyridin-2-yl)piperidin-4-yl]-4-hydroxy-4-(trifluoromethyl)-1,4,5,7-tetrahydro-6H-pyrazolo[3,4-b]pyridin-6-one;
  4-hydroxy-3-{1-[6-(propan-2-yloxy)pyridazin-3-yl]piperidin-4-yl}-4-(trifluoromethyl)-1,4,5,7-tetrahydro-6H-pyrazolo[3,4-b]pyridin-6-one;
  2-{4-[4-hydroxy-6-oxo-4-(trifluoromethyl)-4,5,6,7-tetrahydro-1H-pyrazolo[3,4-b]pyridin-3-yl]piperidin-1-yl}pyridine-4-carbonitrile;
  5-{4-[4-hydroxy-6-oxo-4-(trifluoromethyl)-4,5,6,7-tetrahydro-1H-pyrazolo[3,4-b]pyridin-3-yl]piperidin-1-yl}pyridine-3-carbonitrile;
  4-hydroxy-4-(trifluoromethyl)-3-{1-[6-(trifluoromethyl)pyridin-3-yl]piperidin-4-yl}-1,4,5,7-tetrahydro-6H-pyrazolo[3,4-b]pyridin-6-one;
  4-hydroxy-4-(trifluoromethyl)-3-{1-[5-(trifluoromethyl)pyrazin-2-yl]piperidin-4-yl}-1,4,5,7-tetrahydro-6H-pyrazolo[3,4-b]pyridin-6-one;
  3-{1-[4,4'-bis(trifluoromethyl)-2,5'-bi-1,3-thiazol-2'-yl]piperidin-4-yl}-4-hydroxy-4-(trifluoromethyl)-1,4,5,7-tetrahydro-6H-pyrazolo[3,4-b]pyridin-6-one;
  3-{1-[5-(difluoromethoxy)pyridin-2-yl]piperidin-4-yl}-4-hydroxy-4-(trifluoromethyl)-1,4,5,7-tetrahydro-6H-pyrazolo[3,4-b]pyridin-6-one;
  4-hydroxy-3-{1-[5-(propan-2-yloxy)pyridin-2-yl]piperidin-4-yl}-4-(trifluoromethyl)-1,4,5,7-tetrahydro-6H-pyrazolo[3,4-b]pyridin-6-one;
  3-{1-[6-(difluoromethoxy)pyridin-3-yl]piperidin-4-yl}-4-hydroxy-4-(trifluoromethyl)-1,4,5,7-tetrahydro-6H-pyrazolo[3,4-b]pyridin-6-one;
  3-{1-[4-(difluoromethoxy)phenyl]piperidin-4-yl}-4-hydroxy-4-(trifluoromethyl)-1,4,5,7-tetrahydro-6H-pyrazolo[3,4-b]pyridin-6-one;
  5-{4-[4-hydroxy-6-oxo-4-(trifluoromethyl)-4,5,6,7-tetrahydro-1H-pyrazolo[3,4-b]pyridin-3-yl]piperidin-1-yl}-2-(trifluoromethoxy)benzonitrile;
  4-hydroxy-4-(trifluoromethyl)-3-{1-[2-(trifluoromethyl)pyrimidin-5-yl]piperidin-4-yl}-1,4,5,7-tetrahydro-6H-pyrazolo[3,4-b]pyridin-6-one;
  4-hydroxy-3-{1-[5-(trifluoromethoxy)pyridin-2-yl]piperidin-4-yl}-4-(trifluoromethyl)-1,4,5,7-tetrahydro-6H-pyrazolo[3,4-b]pyridin-6-one;
  benzyl 2-[4-(4-hydroxy-6-oxo-4-(trifluoromethyl)-4,5,6,7-tetrahydro-1H-pyrazolo[3,4-b]pyridin-3-yl)piperidin-1-yl]-5-(trifluoromethyl)pyridine-4-carboxylate;
  4-hydroxy-3-{1-[2-(propan-2-yl)-6-(trifluoromethyl)pyrimidin-4-yl]piperidin-4-yl}-4-(trifluoromethyl)-1,4,5,7-tetrahydro-6H-pyrazolo[3,4-b]pyridin-6-one;
  ethyl 2-{4-[4-hydroxy-6-oxo-4-(trifluoromethyl)-4,5,6,7-tetrahydro-1H-pyrazolo[3,4-b]pyridin-3-yl]piperidin-1-yl}-4-(trifluoromethyl)-1,3-oxazole-5-carboxylate;
  6-{4-[4-hydroxy-6-oxo-4-(trifluoromethyl)-4,5,6,7-tetrahydro-1H-pyrazolo[3,4-b]pyridin-3-yl]piperidin-1-yl}-4-(trifluoromethyl)pyridine-3-carbonitrile; and
  3-[1-(5-cyclopropylpyridin-2-yl)piperidin-4-yl]-4-hydroxy-4-(trifluoromethyl)-1,4,5,7-tetrahydro-6H-pyrazolo[3,4-b]pyridin-6-one.

9. The compound according to claim 1 or a pharmacologically acceptable salt thereof, wherein the compound is selected from the group consisting of:
  (−)-4-hydroxy-4-(trifluoromethyl)-3-{1-[5-(trifluoromethyl)pyridin-2-yl]piperidin-4-yl}-1,4,5,7-tetrahydro-6H-pyrazolo[3,4-b]pyridin-6-one;
  (−)-3-[1-(5-chloropyridin-2-yl)piperidin-4-yl]-4-hydroxy-4-(trifluoromethyl)-1,4,5,7-tetrahydro-6H-pyrazolo[3,4-b]pyridin-6-one; and
  (−)-3-{1-[4-(difluoromethoxy)phenyl]piperidin-4-yl}-4-hydroxy-4-(trifluoromethyl)-1,4,5,7-tetrahydro-6H-pyrazolo[3,4-b]pyridin-6-one.

10. A pharmaceutical composition comprising a compound according to claim 1 or a pharmacologically acceptable salt thereof as an active ingredient.

11. A pharmaceutical composition comprising a compound according to claim 1 or a pharmacologically acceptable salt thereof and a pharmacologically acceptable carrier.

12. A method for making a pharmaceutical composition, comprising combining a pharmacologically acceptable carrier with a compound according to claim 1 or a pharmacologically acceptable salt thereof.

* * * * *